(12) United States Patent
Aoki et al.

(10) Patent No.: US 8,497,397 B2
(45) Date of Patent: *Jul. 30, 2013

(54) SUBSTITUTED ACRYLAMIDE DERIVATIVE AND PHARMACEUTICAL COMPOSITION COMPRISING THE SAME

(75) Inventors: Kazumasa Aoki, Tokyo (JP); Koji Suda, Tokyo (JP); Toshio Kaneko, Tokyo (JP); Tomio Kimura, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/404,647

(22) Filed: Feb. 24, 2012

(65) Prior Publication Data

US 2012/0220593 A1 Aug. 30, 2012

Related U.S. Application Data

(63) Continuation of application No. 11/914,209, filed as application No. PCT/JP2006/309445 on May 11, 2006, now Pat. No. 8,143,446.

(30) Foreign Application Priority Data

May 12, 2005 (JP) ................. 2005-140019

(51) Int. Cl.
  *C07C 235/46* (2006.01)
  *A61K 31/166* (2006.01)
(52) U.S. Cl.
  USPC .......................................... 564/158; 514/616
(58) Field of Classification Search
  None
  See application file for complete search history.

(56) References Cited

U.S. PATENT DOCUMENTS

| 4,659,857 A | 4/1987 | Kuhn |
| 5,807,754 A | 9/1998 | Zambias |
| 5,852,210 A | 12/1998 | Chen et al. |
| 6,117,870 A | 9/2000 | Hosoda et al. |
| 6,881,737 B2 | 4/2005 | Buchanan et al. |
| 7,041,690 B2 | 5/2006 | Finzel et al. |
| 8,143,446 B2 | 3/2012 | Aoki et al. |
| 2005/0250819 A1 | 11/2005 | Li |
| 2009/0292024 A1* | 11/2009 | Aoki et al. .................. 514/616 |

FOREIGN PATENT DOCUMENTS

| DE | 1493184 | 4/1969 |
| EP | 0 498 424 | 8/1992 |
| EP | 0 547 545 | 6/1993 |
| GB | 1113569 | 12/1966 |
| JP | 63-166851 | 7/1988 |
| JP | 2000-204071 | 7/2000 |
| JP | 2000-510098 | 8/2000 |
| JP | 2004-277427 | 10/2004 |
| JP | 2004-277428 | 10/2004 |
| JP | 2004-277429 | 10/2004 |
| JP | 2004-292456 | 10/2004 |
| JP | 2004-300159 | 10/2004 |
| WO | WO 97/36860 | 10/1997 |
| WO | WO 00/24392 | 5/2000 |
| WO | WO 2004/002977 | 1/2004 |
| WO | WO 2004/050613 | 6/2004 |

OTHER PUBLICATIONS

Afifi et al., "Synthesis and reactions of some 2-aryl-4-arylidine-5(4)-oxazolones," Revue Roumaine de Chimie (1983), 28(8), p. 849-855.
Body, Jean-Jacques. "Current and Future Directions in Medical Therapy", Cancer supplement, vol. 88, pp. 3054-3058 (Mar. 2000).
Fautrel, Bruno, et al. "Cost of illness studies in rheumatic diseases", *Current Opinion in Rheumatology*, vol. 14, pp. 121-126 (2002).
Hoshina, H. et al. "Formation of isoquinoline and 1-azetine derivatives via novel photocyclization of substituted α-dehydrophenylalanines," Tetrahedron, vol. 56, No. 19, pp. 2941-2951 (2000).
International Search Report for PCT/JP2006/309445 dated Jul. 18, 2006.
Iqbal, Mohammad M. et al. "Osteoporosis: A Review", *Missouri Medicine*, vol. 99, No. 1, p. 99 (Jan. 2002).
Islam et al., "Reaction of 2-(*m*-tolyl)-4-arylmethylene-2-oxazolin-5-ones with amines," *Australian Journal of Chemistry* (1973), 26(8), p. 1701-1704.
Kuchar, M. et al. "Synthesis and anti-inflammatory effect of 1-ethoxycarbonylmethylimidazoline-5-one derivatives," Ceskoslovenska Farmacie, vol. 24, No. 7, pp. 287-292 (1975).
Lupsa, I. et al. "Research concerning aminolysis of unsaturated oxazolones. IV. Morpholide, piperidide, cyclohexylamide,β-hydroxytheylamide," Revista de Chimie, vol. 25, No. 2, pp. 95-101 (1974).
Romas, E. et al. "Involvement of Receptor Activator of NFκB Ligand and Tumor Necrosis Factor-α in Bone Destruction in Rheumatoid Arthritis", *Bone*, vol. 30, No. 2, pp. 340-346 (Feb. 2002).
Topuzyan, V.O. et al. "Synthesis and biological properties of N-substituted alpha, beta dehydrodipeptides", *Khimiko-Farmatsevticheskii Zhurnal*, vol. 29, No. 3, pp. 42-44 (1995).
Preliminary Amendment, U.S. Appl. No. 11/914,209 (now U.S. Patent No. 8,143,446), Nov. 12, 2007, 21 pages.
Restriction Requirement, U.S. Appl. No. 11/914,209 (now U.S. Patent No. 8,143,446), Mar. 24, 2011, 7 pages.
Response to Election Requirement, U.S. Appl. No. 11/914,209 (now U.S. Patent No. 8,143,446), Apr. 14, 2011, 19 pages.

(Continued)

Primary Examiner — Brian J Davis
(74) Attorney, Agent, or Firm — Dorsey and Whitney LLP

(57) ABSTRACT

A pharmaceutical composition comprising a compound having Formula (I) or a pharmacologically acceptable salt thereof as an active ingredient:

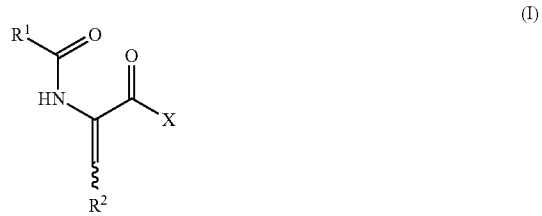

[wherein,
  $R^1$ is, for example, a $C_6$-$C_{10}$ aryl group which may be substituted with one group or more than one group selected from substituent group α; $R^2$ is, for example, a $C_6$-$C_{10}$ aryl group which may be substituted with one group or more than one group selected from substituent group α; and X is, for example, a hydroxyl group or a $C_1$-$C_6$ alkoxy group].

13 Claims, No Drawings

OTHER PUBLICATIONS

Non-Final Office Action, U.S. Appl. No. 11/914,209 (now U.S. Patent No. 8,143,446), Apr. 28, 2011, 8 pages.
Amendment and Response to Office Action, U.S. Appl. No. 11/914,209 (now U.S. Patent No. 8,143,446), Jul. 19, 2011, 14 pages.
Final Office Action, U.S. Appl. No. 11/914,209 (now U.S. Patent No. 8,143,446), Jul. 29, 2011, 7 pages.
Amendment and Response, U.S. Appl. No. 11/914,209 (now U.S. Patent No. 8,143,446), Oct. 28, 2011, 8 pages.
Advisory Action Before the Filing of an Appeal Brief, U.S. Appl. No. 11/914,209 (now U.S. Patent No. 8,143,446), Nov. 4, 2011, 3 pages.
Notice of Allowance and Fee(s) Due and Notice of Allowability, U.S. Appl. No. 11/914,209 (now U.S. Patent No. 8,143,446), Nov. 17, 2011, 7 pages.
Applicants' Interview Summary, U.S. Appl. No. 11/914,209 (now U.S. Patent No. 8,143,446), Nov. 29, 2011, 3 pages.
International Preliminary Report on Patentability, PCT Application No. PCT/JP2006/309445, English translation, Mailed Nov. 13, 2007, 7 pages.

* cited by examiner

SUBSTITUTED ACRYLAMIDE DERIVATIVE AND PHARMACEUTICAL COMPOSITION COMPRISING THE SAME

This application is a continuation application of U.S. patent application Ser. No. 11/914,209 (now U.S. Pat. No. 8,143,446), filed Dec. 3, 2008, which is a national phase application filed pursuant to 35 C.F.R. §371 of International Patent Application No. PCT/JP2006/309445, filed May 11, 2006, which claims priority to Japanese Patent Application No. 2005/140019, filed May 12, 2005, the contents of all of which are hereby incorporated by reference in their entirety.

TECHNICAL FIELD

The present invention relates to amide derivatives or pharmacologically acceptable salts thereof, which are valuable as drugs having excellent anti-osteoporosis activity, anti-inflammation activity, anti-rheumatoid arthritis activity, and anti-hypercalcemia activity and the like.

BACKGROUND ART

Previously, compounds having the following Formula (a) have been disclosed in documents below.

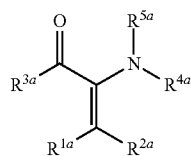

(a)

Patent Document 1 discloses compounds, for example, shown below, which are demonstrated to be valuable as anti-viral agents.

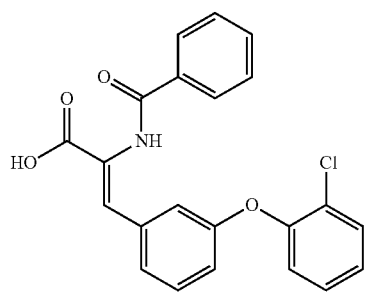

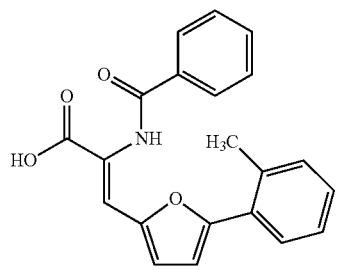

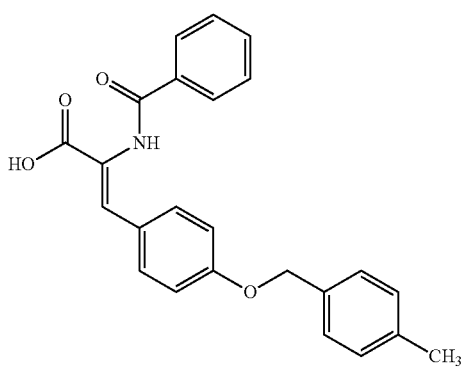

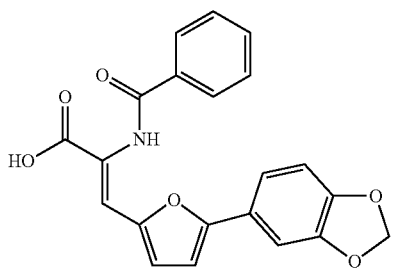

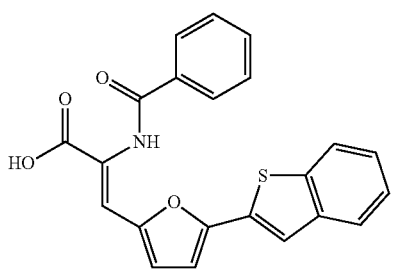

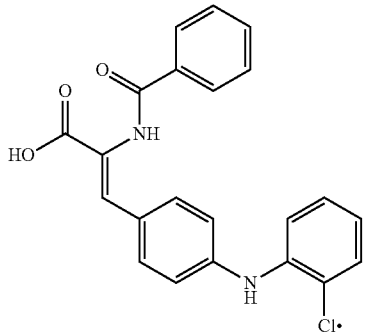

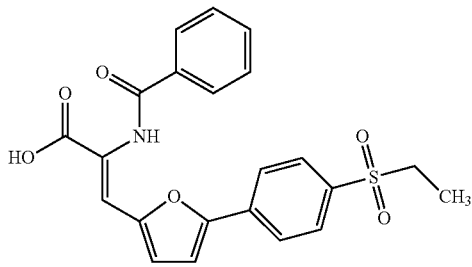

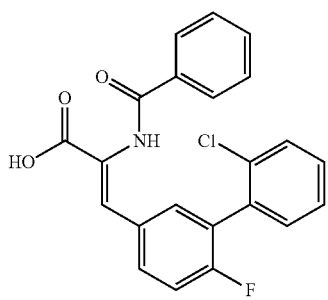

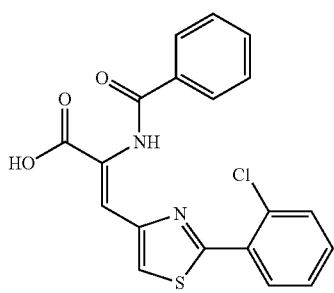

Patent Document 2 discloses compounds, for example, shown below, which are demonstrated to be valuable as therapeutic agents for Alzheimer's disease.

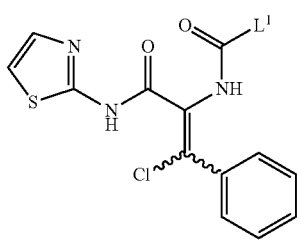

| Example | L$^1$ | Substitution position of double bond |
|---------|-------|---------------------------------------|
| 1 | 4-fluorophenyl | E |
| 2+ | 4-fluorophenyl | Z |
| 3 | 2,4-difluorophenyl | E |
| 4 | 2,4-difluorophenyl | Z |
| 5 | 3-chlorophenyl | E |
| 6 | 3-chlorophenyl | Z |
| 7 | 2-chlorophenyl | E |
| 8 | 2-chlorophenyl | Z |
| 9 | 4-methoxyphenyl | E |
| 10 | 4-methoxyphenyl | Z |

Patent Document 3 discloses compounds, for example, shown below and describes a method for synthesizing Rev-suppressing compounds and a method of screening the same.

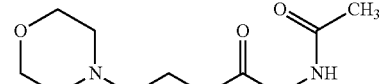

| A | B | C |
|---|---|---|
| 2,4-dichlorophenyl | phenyl | cyclohexyl |
| 2-naphthyl | α,α,α-trifluoro-m-toluyl | 1,2,3,4-tetrahydronaphth-1-yl |
| 2-naphthyl | α,α,α-trifluoro-m-toluyl | diphenylmethyl |
| 2,4-dichlorophenyl | α,α,α-trifluoro-m-toluyl | diphenylmethyl |
| 2-naphthyl | α,α,α-trifluoro-m-toluyl | 2-(p-toluyl)ethyl |
| 2-naphthyl | α,α,α-trifluoro-p-toluyl | diphenylmethyl |
| p-toluyl | 2,4-difluorophenyl | 2-hydroxyphenethyl |
| 2-naphthyl | 3-quinolinyl | (1-naphthyl)methyl |
| 2-naphthyl | α,α,α-trifluoro-p-toluyl | 4-phenylbuto-2-yl |
| 2,4-dichlorophenyl | 4-biphenylyl | diphenylmethyl |

Patent Document 4 discloses compounds, for example, shown below, which are demonstrated to be valuable as antihypertensives.

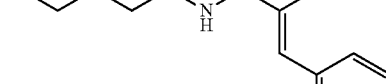

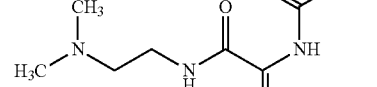

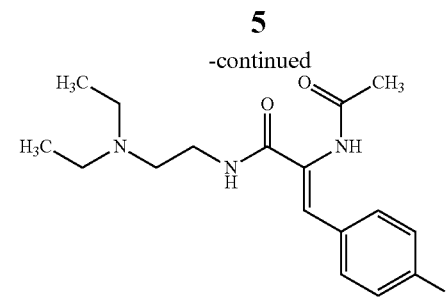
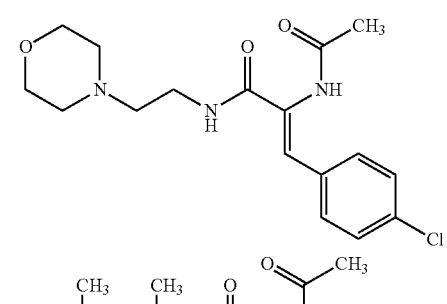
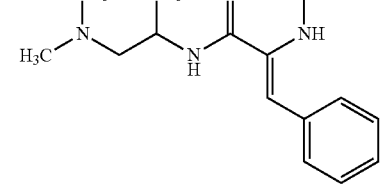
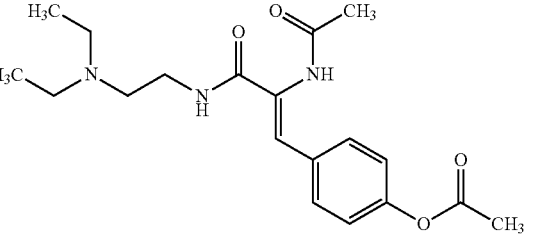
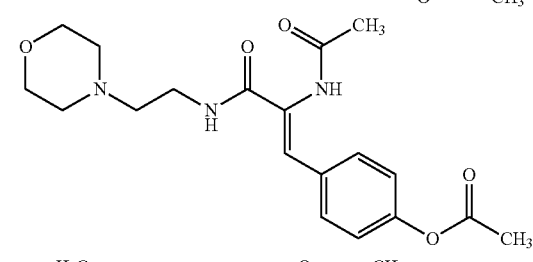
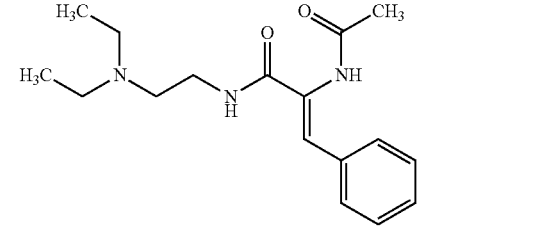
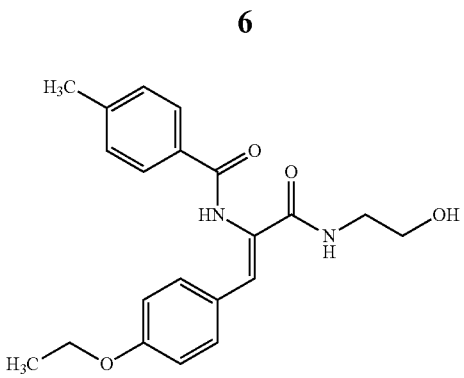
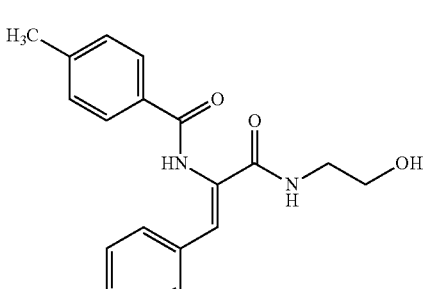
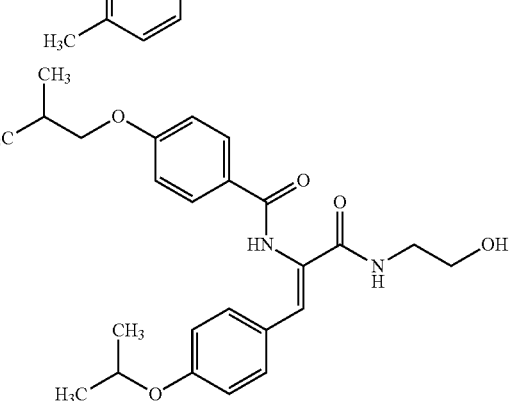
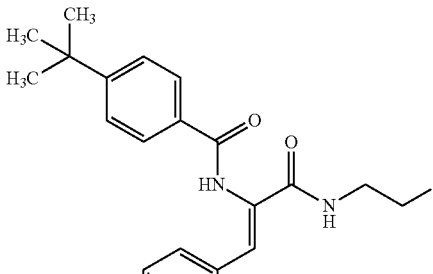
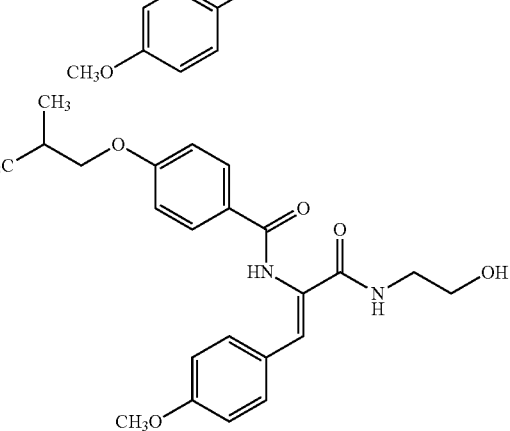
However, none of the above-mentioned Patent Documents 1 to 4 mentions activity for bone metabolic diseases and inflammation, and therefore the purposes of the uses of such compounds are quite different from those of the present invention. Furthermore, only the structures have been known for the compounds shown below, and the uses thereof are not known at all.

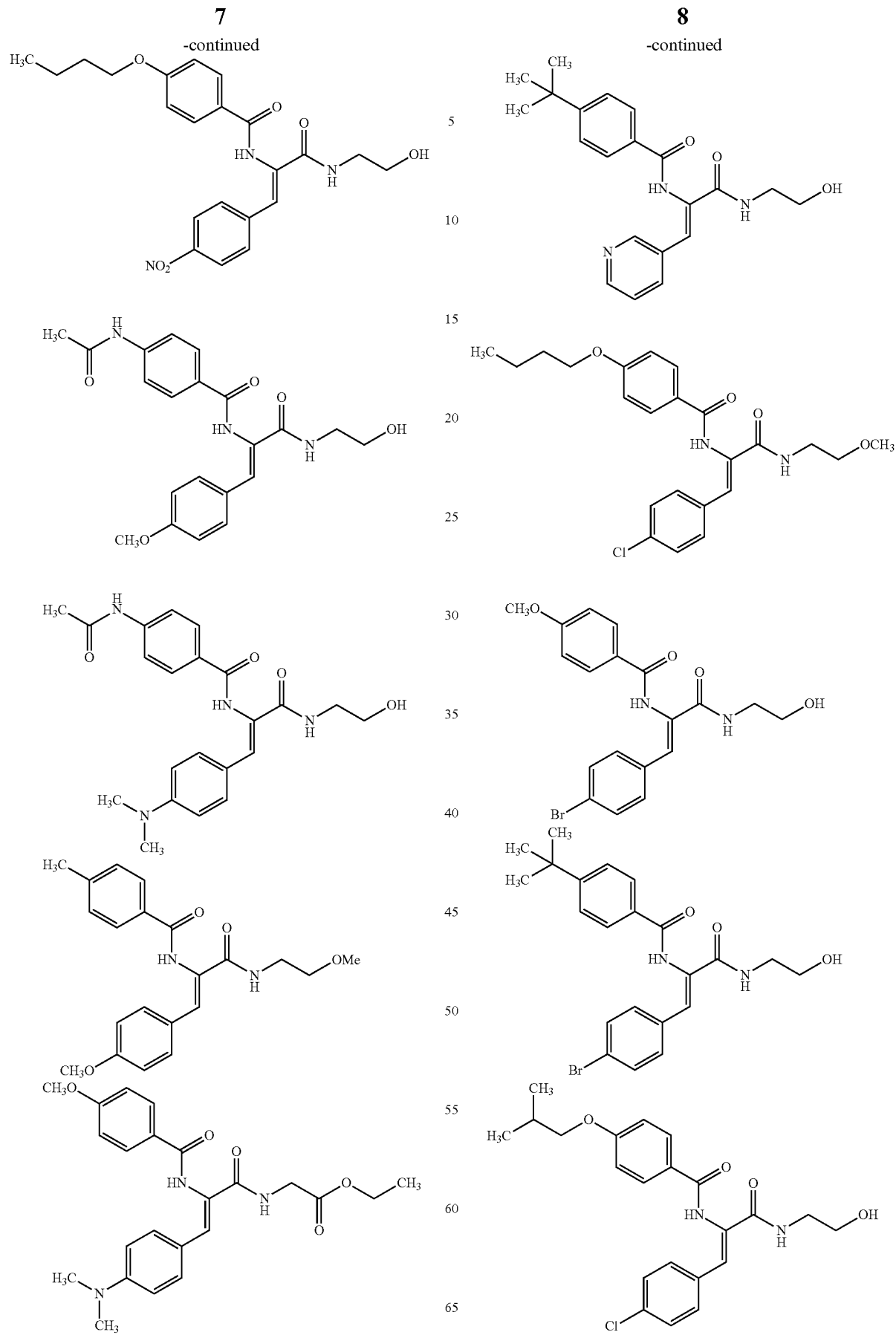

-continued

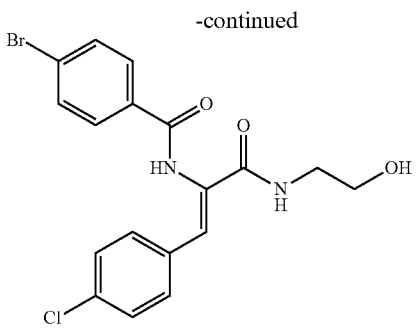

In general, in normal bone metabolism, bone resorption by osteoclasts is balanced with bone formation by osteoblasts to maintain homeostasis. It is thought that bone metabolic diseases are caused when the balance between the bone resorption and the bone formation is deteriorated. Bones retain about 99% of the total calcium in a living body and play an important role for maintaining a constant blood calcium concentration by bone formation and bone resorption. If the osteoclasts which are mainly responsible for bone resorption are abnormally formed or activated, bone resorption is accelerated to increase the blood calcium concentration, and thereby bone metabolic diseases, such as hypercalcemia, are caused.

It is known that bone metastasis of cancer causes abnormal secretion of cytokines resulting in development of hypercalcemia. In this process, bone resorption by osteoclasts is accelerated, so that the blood calcium concentration is increased (Non-Patent Document 1). Prognosis of cancer patients accompanied by cancerous hypercalcemia is generally poor.

Moreover, in rheumatoid arthritis, osteoarthritis and the like, abnormal formation or activation of osteoclasts is known as one of main causes of various symptoms in bones and joints (Non-Patent Document 2). Patients with rheumatoid arthritis, osteoarthritis, and the like suffer from severe pain, which brings considerable disadvantages to the lives of the patients.

Furthermore, when the balance between bone resorption and bone formation continuously inclines toward the bone resorption due to a decrease in secretion of female hormones after menopause or due to ageing, bone density is lowered and osteoporosis is developed. Also in this case, osteoclasts are also responsible for the bone resorption.

When aged patients with a high risk of osteoporosis suffer fractures, a possibility of becoming bedridden is high, which is a social problem (Non-Patent Document 3).

Conventionally, for these states of diseases, hormone replacement therapy using estrogen or the like has been conducted or a therapeutic agent such as a bisphosphonate or a calcitonin for suppressing the activity of osteoclasts has been administered (Non-Patent Document 4). However, none of these existing agents are satisfactory agents for essentially treating hypercalcemia or bone metabolic diseases, and thereby the development of agents having high therapeutic efficacy is desired.

[Patent Document 1]
International Publication No. WO2004/002977
[Patent Document 2]
International Publication No. WO00/24392
[Patent Document 3]
Japanese Publication of International Patent Application No. 2001-506965
[Patent Document 4]
British Patent No. 1,113,569
[Non-Patent Document 1]
Jean-Jacques Body, CANCER Supplement, vol. 88, p. 3054 (2000)
[Non-Patent Document 2]
E. Romas, et al., Bone, vol. 30, p. 340 (2002)
[Non-Patent Document 3]
Bruno Fautrel, et al., Current Opinion in Rheumatology, vol. 14, p. 121 (2002)
[Non-Patent Document 4]
Mohammad M. Iqbal, et al., Missouri Medicine, vol. 99, p. 19 (2002)

DISCLOSURE OF INVENTION

Problems to be Solved by the Invention

An object of the present invention is to provide drugs which are excellent as agents for improving, prophylaxis, or treatment of osteoporosis, inflammation, rheumatoid arthritis, hypercalcemia, and the like.

Means for Solving the Problems

The present inventors have conducted intensive studies on drugs having excellent blood calcium concentration-decreasing activity and bone mass decrease-suppressing activity and have found the fact that drugs comprising a compound having Formula (I) of the present invention (hereinafter referred to as a compound of the present invention) are low in toxicity, have excellent bone resorption-suppressing activity and blood calcium concentration-decreasing activity and bone mass decrease-suppressing activity associated therewith, and are valuable for prophylaxis or treatment of bone metabolic diseases such as osteoporosis, hypercalcemia, bone metastasis of cancer, periodontal disease, bone Paget's disease, and osteoarthritis. Thus, the present invention has been completed. The present invention is described below.

The present invention includes
a pharmaceutical composition for the suppression of bone resorption comprising a compound having Formula (I) or a pharmacologically acceptable salt thereof as an active ingredient:

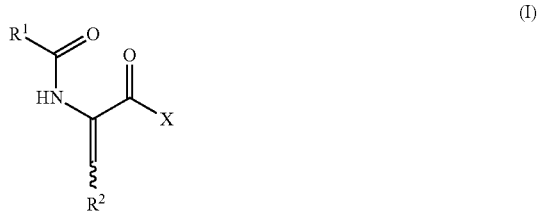

(I)

[wherein,
$R^1$ represents a $C_6$-$C_{10}$ aryl group which may be substituted with one group or more than one group selected from substituent group α or a 5- to 10-membered heteroaryl group which may be substituted with one group or more than one group selected from substituent group α;
$R^2$ represents a $C_6$-$C_{10}$ aryl group which may be substituted with one group or more than one group selected from substituent group α, a 5- to 10-membered heteroaryl group which may be substituted with one group or more than one group selected from substituent group α, or a 3- to 6-membered heterocyclyl group which may be substituted with one group or more than one group selected from substituent group α; and X represents a hydroxyl group, a $C_1$-$C_6$ alkoxy group, a $C_1$-$C_6$ alkoxy group which is substituted with a hydroxyl group, or a group having a formula $N(R^3)R^4$ (wherein $R^3$ represents a hydrogen atom, a $C_1$-$C_6$ haloalkyl group, a $C_1$-$C_6$ hydroxyalkyl group which may be protected by a hydroxyl protecting group, a $C_1$-$C_6$ alkyl group which may be substituted with one group or more than one group selected from substituent group β, a $C_1$-$C_6$ alkoxy group which may be substituted with a hydroxyl group, a $C_3$-$C_{10}$ cycloalkyl group which may be substituted with one group or more than one group selected from substituent group α, a $C_6$-$C_{10}$ aryl group which may be substituted with one group or more than one group selected from substituent group α, or a 5- to 10-membered heteroaryl group which may be substituted with one group or more than one group selected from substituent group α, and $R^4$ represents a hydrogen atom or a $C_1$-$C_6$ alkyl group; or $R^3$ and $R^4$, together with the nitrogen atom bound to $R^3$ and $R^4$, form a 3- to 6-membered heterocyclyl group which may be substituted with one group or more than one group selected from substituent group β), and substituent group α represents a group consisting of hydroxyl groups, nitro groups, cyano groups, amino groups, $C_1$-$C_6$ alkylamino groups, $C_1$-$C_6$ dialkylamino groups, $C_3$-$C_6$ cycloalkylamino groups, acetamido groups, halogen atoms, $C_1$-$C_6$ alkyl groups which may be substituted with one group or more than one group selected from substituent group β, $C_1$-$C_6$ haloalkyl groups, $C_3$-$C_{10}$ cycloalkyl groups, 3- to 6-membered heterocyclyl groups, $C_3$-$C_6$ cycloalkenyl groups, $C_6$-$C_{10}$ aryl groups which may be substituted with one group or more than one group selected from substituent group γ, 5- to 10-membered heteroaryl groups which may be substituted with one group or more than one group selected from substituent group γ, $C_1$-$C_6$ alkoxy groups which may be substituted with one group or more than one group selected from substituent group β, $C_1$-$C_6$ haloalkoxy groups, $C_1$-$C_6$ alkoxy $C_1$-$C_6$ alkoxy groups which may be substituted with one group or more than one group selected from substituent group β, $C_1$-$C_6$ alkenyloxy groups which may be substituted with one group or more than one group selected from substituent group β, $C_1$-$C_6$ alkynyloxy groups which may be substituted with one group or more than one group selected from substituent group β, $C_3$-$C_{10}$ cycloalkyloxy groups, 3- to 6-membered heterocyclyloxy groups, $C_6$-$C_{10}$ aryloxy groups which may be substituted with one group or more than one group selected from substituent group γ, $C_1$-$C_6$ alkyleneoxy groups, $C_1$-$C_6$ alkylenedioxy groups, $C_1$-$C_6$ alkylthio groups which may be substituted with one group or more than one group selected from substituent group β, $C_1$-$C_6$ haloalkylthio groups, $C_1$-$C_6$ alkylsulfonyl groups which may be substituted with one group or more than one group selected from substituent group β, $C_1$-$C_6$ haloalkylsulfonyl groups, $C_1$-$C_6$ alkylcarbonyl groups which may be substituted with one group or more than one group selected from substituent group β, $C_1$-$C_6$ haloalkylcarbonyl groups, and $C_6$-$C_{10}$ arylcarbonyl groups which may be substituted with one group or more than one group selected from substituent group γ;

substituent group β represents the group consisting of hydroxyl groups, carboxyl groups, $C_1$-$C_6$ alkoxycarbonyl groups, carbamoyl groups, cyano groups, amino groups, acetamido groups, N—$C_6$-$C_{10}$ arylacetamido groups, $C_1$-$C_6$ alkoxycarbonylamido groups, urea groups, $C_3$-$C_{10}$ cycloalkyl groups which may be substituted with one group or more than one group selected from substituent group γ, $C_3$-$C_6$ cycloalkenyl groups, 3- to 6-membered heterocyclyl groups, $C_6$-$C_{10}$ aryl groups which may be substituted with one group or more than one group selected from substituent group γ, 5- to 10-membered heteroaryl groups which may be substituted with one group or more than one group selected from substituent group γ, $C_1$-$C_6$ alkoxy groups, $C_6$-$C_{10}$ aryloxy groups which may be substituted with one group or more than one group selected from substituent group γ, and $C_3$-$C_{10}$ cycloalkyloxy groups; and substituent group γ represents a group consisting of hydroxyl groups, cyano groups, amino groups, $C_1$-$C_6$ alkylamino groups, $C_1$-$C_6$ dialkylamino groups, $C_2$-$C_6$ cyclic amino groups, halogen atoms, $C_1$-$C_6$ alkyl groups, $C_3$-$C_{10}$ cycloalkyl groups, $C_1$-$C_6$ haloalkyl groups, $C_1$-$C_6$ alkoxy groups, $C_3$-$C_{10}$ cycloalkyloxy groups, $C_1$-$C_6$ alkylenedioxy groups, and phenyl groups].

Preferred compositions as the above-mentioned composition are:

(2) the composition according to the above (1), wherein $R^1$ is a phenyl group which may be substituted with one group or more than one group selected from substituent group α or a pyridyl group which may be substituted with one group or more than one group selected from substituent group α;

(3) the composition according to the above (1), wherein R' is a phenyl group which may be substituted with one group or more than one group selected from substituent group α;

(4) the composition according to the above (1), wherein $R^1$ is a phenyl group substituted with any one group selected from the group consisting of $C_1$-$C_6$ alkoxy groups which may be substituted with one group or more than one group selected from substituent group β, $C_6$-$C_{10}$ aryloxy groups which may be substituted with one group or more than one group selected from substituent group γ, and $C_1$-$C_6$ haloalkoxy groups;

(5) the composition according to the above (1), wherein $R^1$ is a 4-isobutyloxyphenyl group, a 4-(cyclopropylmethoxy)phenyl group, a 4-(2-cyclopropylethoxy)phenyl group, a 4-(1-methylcyclopropylmethoxy)phenyl group, a 4-(3,3,3-trifluoropropyloxy)phenyl group, a 4-(4,4,4-trifluorobutyloxy)phenyl group, a 4-(2-phenylethoxy)phenyl group, a 4-(2-(4-methoxyphenyl)ethoxy)phenyl group, a 4-(2-(3-methoxyphenyl)ethoxy)phenyl group, a 4-(2-(4-chlorophenyl)ethoxy)phenyl group, a 4-(2-(4-(N,N-dimethylamino)phenyl)ethoxy)phenyl group, a 4-(4-chlorophenoxy)phenyl group, or a 4-(4-trifluoromethylphenoxy)phenyl group;

(6) the composition according to any one of the above (1) to (5), wherein $R^2$ is a $C_6$-$C_{10}$ aryl group which may be substituted with one group or more than one group selected from substituent group α;

(7) the composition according to any one of the above (1) to (5), wherein $R^2$ is a phenyl group which may be substituted with one group or more than one group selected from substituent group α;

(8) the composition according to any one of the above (1) to (5), wherein $R^2$ is a phenyl group substituted with any one group selected from the group consisting of halogen atoms, $C_1$-$C_6$ alkyl groups, $C_1$-$C_6$ haloalkyl groups, $C_3$-$C_6$ cycloalkyl groups, $C_6$ alkoxy groups, $C_3$-$C_6$ cycloalkyloxy groups, $C_1$-$C_6$ haloalkoxy groups, $C_1$-$C_6$ alkylthio groups, and 5- to 10-membered heteroaryl groups;

(9) the composition according to any one of the above (1) to (5), wherein $R^2$ is a 4-fluorophenyl group, a 4-chlorophenyl group, a 4-trifluoromethylphenyl group, a 4-isopropylphenyl group, a 4-cyclopropylphenyl group, a 4-isopropyloxyphenyl group, a 4-difluoromethoxyphenyl group, a 4-trifluoromethoxyphenyl group, a 4-(2,2,2-trifluoroethoxy)phenyl group, a 4-(2,2-difluoroethoxy)phenyl group, a 4-cyclopropyloxyphenyl group, a 4-ethoxyphenyl group, a 4-methylthiophenyl group, or a 4-(1H-pyrrol-1-yl)phenyl group;

(10) the composition according to any one of the above (1) to (9), wherein X is a group having a formula $N(R^3)R^4$ (wherein $R^3$ represents a $C_1$-$C_6$ haloalkyl group, a $C_1$-$C_6$ alkyl group which may be substituted with one group or more than one group selected from substituent group β, or a $C_1$-$C_6$ hydroxyalkyl group which may be protected by a hydroxyl protecting group, and $R^4$ represents a hydrogen atom);

(11) the composition according to any one of the above (1) to (9), wherein X is a group having a formula $N(R^3)R^4$ (where $R^3$ represents a $C_2$-$C_3$ haloalkyl group, a $C_2$-$C_3$ hydroxyalkyl group which may be protected by a hydroxyl protecting group, or a $C_1$-$C_3$ alkyl group substituted with a 1-hydroxycyclopropyl group, and $R^4$ represents a hydrogen atom);

(12) the composition according to any one of (1) to (9), wherein X is a 2-fluoroethylamino group, a 2,2-difluoroethylamino group, a 2-hydroxyethylamino group, a 1-(2-hydroxypropyl)amino group, a 1-hydroxycyclopropylmethylamino group, a 2-acetoxyethylamino group, a 2-(morpholin-4-ylacetoxy)ethylamino group, or a 2-(3-carboxypropionyloxy)ethylamino group; and

(13) the composition according to any one of the above (1) to (12), wherein the chemical structure regarding the position of the acrylamide moiety in Formula (I) is Z.

Furthermore, the present invention includes

(14) a compound having Formula (I') or a pharmacologically acceptable salt thereof:

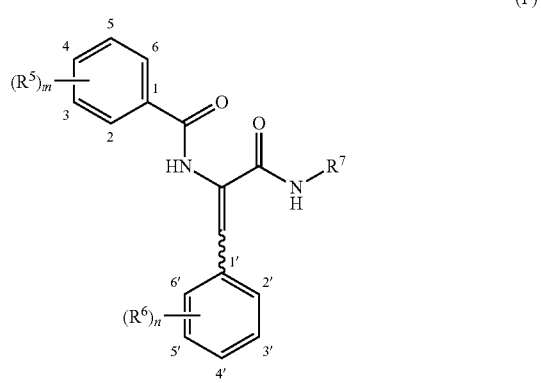

(I')

[wherein, $R^5$ and $R^6$ each independently represent a substituent on a benzene ring, the substituent being selected from substituent group α;

$R^7$ represents a hydrogen atom, a $C_1$-$C_6$ haloalkyl group, a $C_1$-$C_6$ hydroxyalkyl group which may be protected by a hydroxyl protecting group, a $C_1$-$C_6$ alkyl group which may be substituted with one group or more than one group selected from substituent group β, a $C_6$-$C_{10}$ aryl group which may be substituted with one group or more than one group selected from substituent group α, or a $C_3$-$C_{10}$ cycloalkyl group which may be substituted with one group or more than one group selected from substituent group α;

m represents an integer of 1 to 3;

n represents an integer of 1 to 3;

the numerals on each benzene ring represent the position number of each substitution;

substituent group α represents a group consisting of hydroxyl groups, nitro groups, cyano groups, amino groups, $C_1$-$C_6$ alkylamino groups, $C_1$-$C_6$ dialkylamino groups, $C_3$-$C_6$ cycloalkylamino groups, acetamido groups, halogen atoms, $C_1$-$C_6$ alkyl groups which may be substituted with one group or more than one group selected from substituent group β, $C_1$-$C_6$ haloalkyl groups, $C_3$-$C_{10}$ cycloalkyl groups, 3- to 6-membered heterocyclyl groups, $C_3$-$C_6$ cycloalkenyl groups, $C_6$-$C_{10}$ aryl groups which may be substituted with one group or more than one group selected from substituent group γ, 5- to 10-membered heteroaryl groups which may be substituted with one group or more than one group selected from substituent group γ, $C_1$-$C_6$ alkoxy groups which may be substituted with one group or more than one group selected from substituent group β, $C_1$-$C_6$ haloalkoxy groups, $C_1$-$C_6$ alkoxy $C_1$-$C_6$ alkoxy groups which may be substituted with one group or more than one group selected from substituent group β, $C_1$-$C_6$ alkenyloxy groups which may be substituted with one group or more than one group selected from substituent group β, $C_1$-$C_6$ alkynyloxy groups which may be substituted with one group or more than one group selected from substituent group β, $C_3$-$C_{10}$ cycloalkyloxy groups, 3- to 6-membered heterocyclyloxy groups, $C_6$-$C_{10}$ aryloxy groups which may be substituted with one group or more than one group selected from substituent group γ, $C_1$-$C_6$ alkyleneoxy groups, $C_1$-$C_6$ alkylenedioxy groups, $C_1$-$C_6$ alkylthio groups which may be substituted with one group or more than one group selected from substituent group β, $C_1$-$C_6$ haloalkylthio groups, $C_1$-$C_6$ alkylsulfonyl groups which may be substituted with one group or more than one group selected from substituent group β, $C_1$-$C_6$ haloalkylsulfonyl groups, $C_1$-$C_6$ alkylcarbonyl groups which may be substituted with one group or more than one group selected from substituent group β, $C_1$-$C_6$ haloalkylcarbonyl groups, and $C_6$-$C_{10}$ arylcarbonyl groups which may be substituted with one group or more than one group selected from substituent group γ;

substituent group β represents the group consisting of hydroxyl groups, carboxyl groups, $C_1$-$C_6$ alkoxycarbonyl groups, carbamoyl groups, cyano groups, amino groups, acetamido groups, N—$C_6$-$C_{10}$ arylacetamido groups, $C_1$-$C_6$ alkoxycarbonylamido groups, urea groups, $C_3$-$C_{10}$ cycloalkyl groups which may be substituted with one group or more than one group selected from substituent group γ, $C_3$-$C_6$ cycloalkenyl groups, 3- to 6-membered heterocyclyl groups, $C_6$-$C_{10}$ aryl groups which may be substituted with one group or more than one group selected from substituent group γ, 5- to 10-membered heteroaryl groups which may be substituted with one group or more than one group selected from substituent group γ, $C_1$-$C_6$ alkoxy groups, $C_6$-$C_{10}$ aryloxy groups which may be substituted with one group or more than one group selected from substituent group γ, and $C_3$-$C_{10}$ cycloalkyloxy groups; and substituent group γ represents the group consisting of hydroxyl groups, cyano groups, amino groups, $C_1$-$C_6$ alkylamino groups, $C_1$-$C_6$ dialkylamino groups, $C_2$-$C_6$ cyclic amino groups, halogen atoms, $C_1$-$C_6$ alkyl groups, $C_3$-$C_{10}$ cycloalkyl groups, $C_1$-$C_6$ haloalkyl groups, $C_1$-$C_6$ alkoxy groups, $C_3$-$C_{10}$ cycloalkyloxy groups, $C_1$-$C_6$ alkylenedioxy groups, and phenyl groups], wherein the compounds having Formula (I') are not the following compounds:

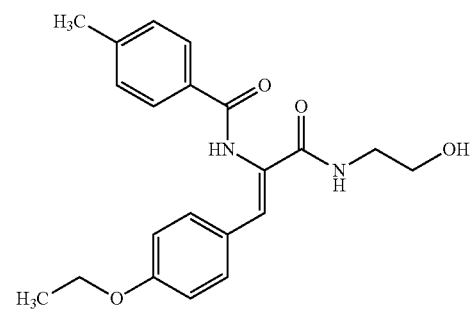

-continued
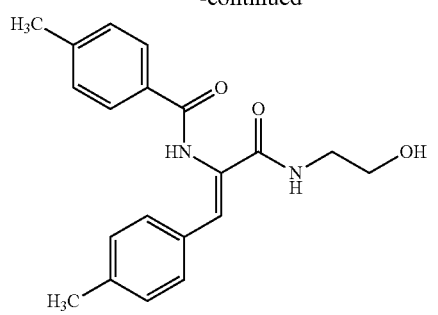
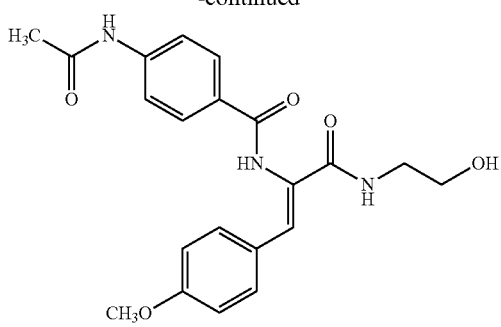
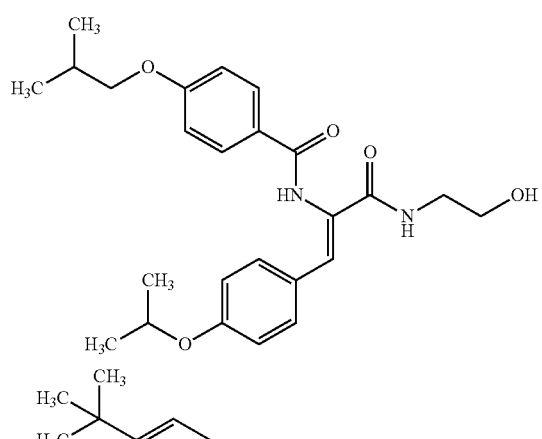
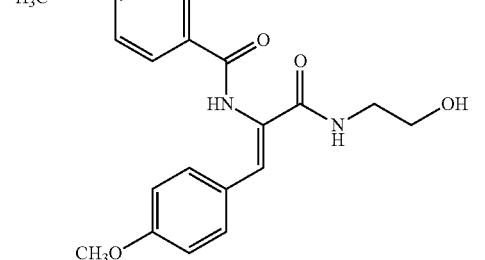
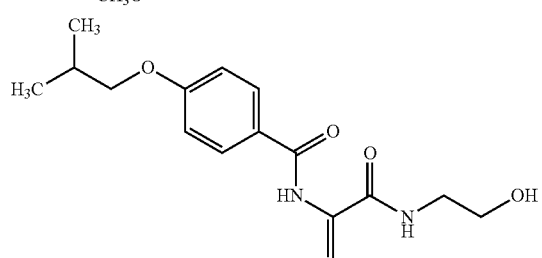
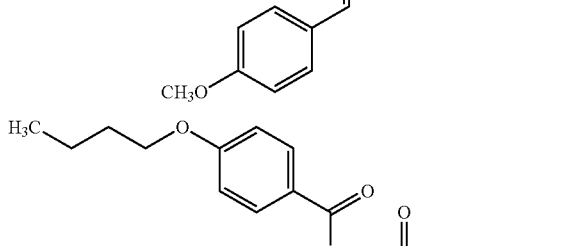
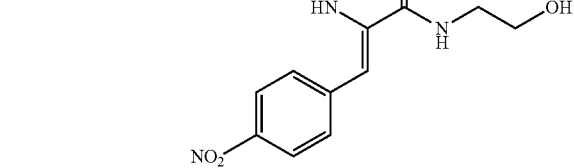
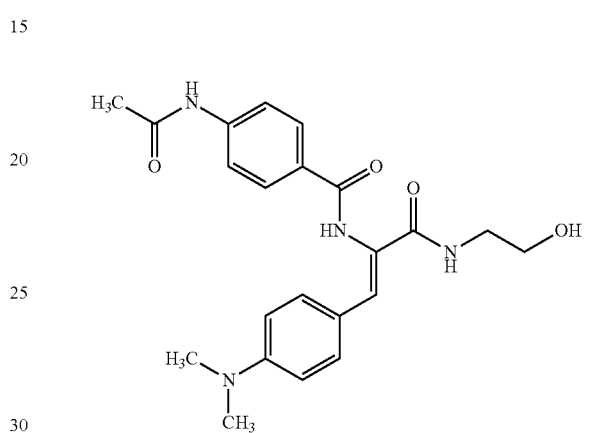
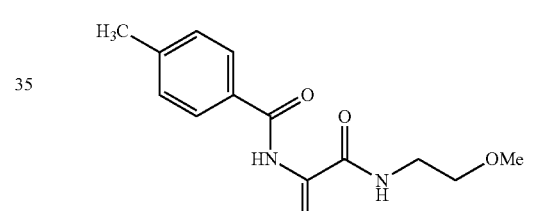
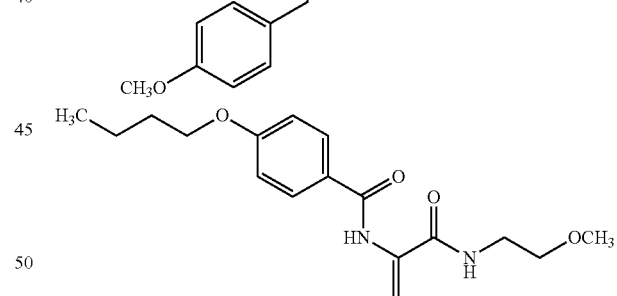
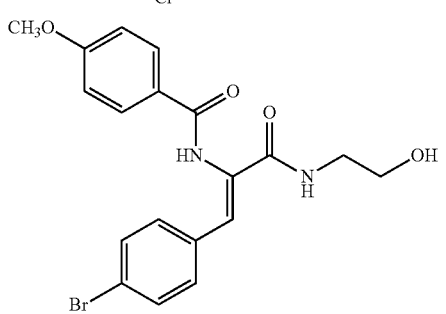

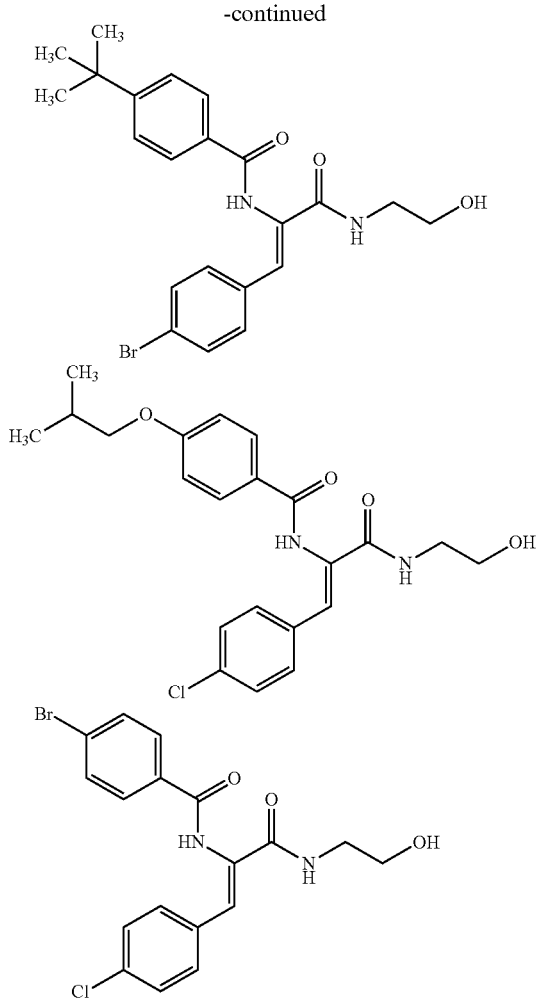

The above-mentioned compound or a pharmacologically acceptable salt thereof is preferably:

(15) the compound or a pharmacologically acceptable salt thereof according to the above (14), wherein $R^5$ is any one group selected from the group consisting of halogen atoms, $C_1$-$C_6$ alkyl groups which may be substituted with one group or more than one group selected from substituent group β, $C_1$-$C_6$ haloalkyl groups, $C_3$-$C_6$ cycloalkyl groups, $C_1$-$C_6$ alkoxy groups which may be substituted with one group or more than one group selected from substituent group β, $C_6$-$C_{10}$ aryloxy groups which may be substituted with one group or more than one group selected from substituent group γ, $C_1$-$C_6$ haloalkoxy groups, and $C_3$-$C_6$ cycloalkyloxy groups;

(16) the compound or a pharmacologically acceptable salt thereof according to the above (14), wherein $R^5$ is any one group selected from the group consisting of $C_1$-$C_6$ alkoxy groups which may be substituted with one group or more than one group selected from substituent group β, $C_6$-$C_{10}$ aryloxy groups which may be substituted with one group or more than one group selected from substituent group γ, and $C_1$-$C_6$ haloalkoxy groups;

(17) the compound or a pharmacologically acceptable salt thereof according to the above (14), wherein $R^5$ is an isobutyloxy group, a cyclopropylmethoxy group, a 2-cyclopropylethoxy group, a 1-methylcyclopropylmethoxy group, a 3,3,3-trifluoropropyloxy group, a 4,4,4-trifluorobutyloxy group, a 2-phenylethoxy group, a 2-(4-methoxyphenyl)ethoxy group, a 2-(3-methoxyphenyl)ethoxy group, a 2-(4-chlorophenyl)ethoxy group, a 2-(4-(N,N-dimethylamino)phenyl)ethoxy group, a 4-chlorophenoxy group, or a 4-trifluoromethylphenoxy group;

(18) the compound or a pharmacologically acceptable salt thereof according to any one of the above (14) to (17), wherein $R^6$ is any one group selected from the group consisting of halogen atoms, $C_1$-$C_6$ alkyl groups, $C_1$-$C_6$ haloalkyl groups, $C_3$-$C_6$ cycloalkyl groups, $C_1$-$C_6$ alkoxy groups, $C_3$-$C_6$ cycloalkyloxy groups, $C_1$-$C_6$ haloalkoxy groups, $C_1$-$C_6$ alkylthio groups, and 5- to 10-membered heteroaryl groups;

(19) the compound or a pharmacologically acceptable salt thereof according to any one of the above (14) to (17), wherein $R^6$ is a fluorine atom, a chlorine atom, a trifluoromethyl group, an isopropyl group, a cyclopropyl group, an isopropyloxy group, a difluoromethoxy group, a trifluoromethoxy group, a 2,2,2-trifluoroethoxy group, a 2,2-difluoroethoxy group, a cyclopropyloxy group, an ethoxy group, a methylthio group, or a 1H-pyrrol-1-yl group;

(20) the compound or a pharmacologically acceptable salt thereof according to any one of the above (14) to (17), wherein $R^6$ is an ethoxy group, a trifluoromethyl group, a cyclopropyl group, a cyclopropyloxy group, a difluoromethoxy group, a trifluoromethoxy group, or a 2,2-difluoroethoxy group;

(21) the compound or a pharmacologically acceptable salt thereof according to any one of the above (14) to (20), wherein $R^7$ is a $C_1$-$C_6$ haloalkyl group, a $C_1$-$C_6$ alkyl group which may be substituted with one group or more than one group selected from substituent group β, or a $C_1$-$C_6$ hydroxyalkyl group which may be protected by a hydroxyl protecting group;

(22) the compound or a pharmacologically acceptable salt thereof according to any one of the above (14) to (20), wherein $R^7$ is a $C_2$-$C_3$ haloalkyl group, a $C_2$-$C_3$ hydroxyalkyl group which may be protected by a hydroxyl protecting group, or a $C_1$-$C_3$ alkyl group substituted with 1-hydroxycyclopropyl group;

(23) the compound or a pharmacologically acceptable salt thereof according to any one of the above (14) to (20), wherein $R^7$ is a 2-fluoroethyl group, a 2,2-difluoroethyl group, a 2-hydroxyethyl group, a 2-hydroxypropyl group, a 1-hydroxycyclopropylmethyl group, a 2-acetoxyethyl group, a 2-(morpholin-4-ylacetoxy)ethyl group, or a 2-(3-carboxypropionyloxy)ethyl group;

(24) the compound or a pharmacologically acceptable salt thereof according to any one of the above (14) to (23), wherein m and n are each 1;

(25) the compound or a pharmacologically acceptable salt thereof according to the above (24), wherein $R^5$ is substituted at the 4-position of the benzene ring of Formula (I'), and $R^6$ substituted at the 4'-position of the benzene ring of Formula (I'); and

(26) a compound or its pharmacologically acceptable salt, the compound being selected from the followings:
4-(2-cyclopropylethoxy)-N-(2-(4-ethoxyphenyl)-1-{[(2-hydroxyethyl)amino]carbonyl}vinyl)benzamide,
4-(2-cyclopropylethoxy)-N-(2-[4-(cyclopropyloxy)phenyl]-1-{[(2-hydroxyethyl)amino]carbonyl}vinyl)benzamide,
4-(2-cyclopropylethoxy)-N-(2-[4-(difluoromethoxy)phenyl]-{[(2-hydroxyethyl)amino]carbonyl}vinyl)benzamide,
4-(2-cyclopropylethoxy)-N-{1-{[(2-hydroxyethyl)amino]carbonyl}-2-[4-(trifluoromethoxy)phenyl]vinyl}benzamide, 4-(2-cyclopropylethoxy)-N-(2-[4-(2,2-difluoroethoxy)phenyl]-1-{[(2-hydroxyethyl)amino]carbonyl}vinyl)benzamide, 4-(2-cyclopropylethoxy)-N-(2-(4-cyclopropylphenyl)-1-{[(2-hydroxyethyl)amino]carbonyl}vinyl)benzamide, 2-{[(2Z)-2-{[4-(2-cyclopropylethoxy)benzoyl]amino}-3-(4-cyclopropylphenyl)propen-2-oyl]amino}ethyl acetate, 2-{[(2Z)-2-{[4-(2-cyclopropylethoxy)benzoyl]amino}-3-(4-cyclopropylphenyl)propen-2-oyl]amino}ethyl succinate, 4-(2-cyclopropylethoxy)-N-{1-{[(2-hydroxyethyl)amino]carbonyl}-2-[4-(trifluoromethyl)phenyl]vinyl}benzamide, 4-(2-cyclopropylethoxy)-N-{1-{[(2-hydroxyethyl)amino]carbonyl}-2-[4-(1H-pyrrol-1-yl)-phenyl]vinyl}benzamide, N-(2-(4-chlorophenyl)-1-{[(2-hydroxyethyl)amino]carbonyl}vinyl)-4-(2-cyclopropylethoxy)benzamide, N-[1-{[(2-hydroxyethyl)amino]carbonyl}-2-(4-isopropoxyphenyl)vinyl]-4-[2-(4-methoxyphenyl)ethoxy]benzamide, N-(2-[4-(cyclopropyloxy)phenyl]-1-{[(2-hydroxyethyl)amino]carbonyl}vinyl)-4-[2-(4-methoxyphenyl)ethoxy]benzamide, N-{1-{[(2-hydroxyethyl)amino]carbonyl}-2-[4-(trifluoromethoxy)phenyl]vinyl}-4-[2-(4-methoxyphenyl)ethoxy]benzamide, N-(2-(4-cyclopropylphenyl)-1-{[(2-hydroxyethyl)amino]carbonyl}vinyl)-4-[2-(4-methoxyphenyl)ethoxy]benzamide, N-{1-{[(2-hydroxyethyl)amino]carbonyl}-2-[4-(methylthio)phenyl]vinyl}-4-[2-(4-methoxyphenyl)ethoxy]benzamide, N-(2-(4-chlorophenyl)-1-{[(2-hydroxyethyl)amino]carbonyl}vinyl)-4-[2-(4-methoxyphenyl)ethoxy]benzamide, 4-{2-[4-(dimethylamino)phenyl]ethoxy}-N-[1-{[(2-hydroxyethyl)amino]carbonyl}-2-(4-isopropoxyphenyl)vinyl]benzamide, 4-{2-[4-(dimethylamino)phenyl]ethoxy}-N-{1-{[(2-hydroxyethyl)amino]carbonyl}-2-[4-(trifluoromethoxy)phenyl]vinyl}benzamide, N-(2-(4-cyclopropylphenyl)-1-{[(2-hydroxyethyl)amino]carbonyl}vinyl)-4-{2-[4-(dimethylamino)phenyl]ethoxy}benzamide, 4-[2-(4-chlorophenyl)ethoxy]-N-(2-(4-ethoxyphenyl)-1-{[(2-hydroxyethyl)amino]carbonyl}vinyl)benzamide, 4-[2-(4-chlorophenyl)ethoxy]-N-(2-[4-(cyclopropyloxy)phenyl]-1-{[(2-hydroxyethyl)amino]carbonyl}vinyl)benzamide, 4-[2-(4-chlorophenyl)ethoxy]-N-(2-[4-(difluoromethoxy)phenyl]-1-{[(2-hydroxyethyl)amino]carbonyl}vinyl)benzamide, 4-[2-(4-chlorophenyl)ethoxy]-N-{1-{[(2-hydroxyethyl)amino]carbonyl}-2-[4-(trifluoromethoxy)phenyl]vinyl}benzamide, 4-[2-(4-chlorophenyl)ethoxy]-N-(2-(4-cyclopropylphenyl)-1-{[(2-hydroxyethyl)amino]carbonyl}vinyl)benzamide, 4-[2-(4-chlorophenyl)ethoxy]-N-(2-(4-chlorophenyl)-1-{[(2-hydroxyethyl)amino]carbonyl}vinyl)benzamide, 4-(cyclopropylmethoxy)-N-{1-{[(2-hydroxyethyl)amino]carbonyl}-2-[4-(trifluoromethoxy)phenyl]vinyl}benzamide, 4-(cyclopropylmethoxy)-N-{1-{[(2-hydroxyethyl)amino]carbonyl}-2-[4-(trifluoromethyl)phenyl]vinyl}benzamide, N-{1-{[(2-hydroxyethyl)amino]carbonyl}-2-[4-(trifluoromethoxy)phenyl]vinyl}-4-(4,4,4-trifluorobutoxy)benzamide, N-{1-{[(2-hydroxyethyl)amino]carbonyl}-2-[4-(trifluoromethyl)phenyl]vinyl}-4-(4,4,4-trifluorobutoxy)benzamide, N-{1-{[(2-hydroxyethyl)amino]carbonyl}-2-[4-(trifluoromethoxy)phenyl]vinyl}-4-(3,3,3-trifluoropropoxy)benzamide, N-{1-{[(2-hydroxyethyl)amino]carbonyl}-2-[4-(trifluoromethyl)phenyl]vinyl}-4-(3,3,3-trifluoropropoxy)benzamide, N-{1-{[(2,2-difluoroethyl)amino]carbonyl}-2-[4-(trifluoromethoxy)phenyl]vinyl}-4-(3,3,3-trifluoropropoxy)benzamide, N-{1-({[(2S)-2-hydroxypropyl]amino}carbonyl)-2-[4-(trifluoromethoxy)phenyl]vinyl}-4-(3,3,3-trifluoropropoxy)benzamide, N-(2-[4-(difluoromethoxy)phenyl]-1-{[(2-hydroxyethyl)amino]carbonyl}vinyl)-4-[4-(trifluoromethyl)phenoxy]benzamide, N-{1-{[(2-hydroxyethyl)amino]carbonyl}-2-[4-(trifluoromethoxy)phenyl]vinyl}-4-[4-(trifluoromethyl)phenoxy]benzamide, N-{1-{[(2-hydroxyethyl)amino]carbonyl}-2-[4-(trifluoromethyl)phenyl]vinyl}-4-[4-(trifluoromethyl)phenoxy]benzamide, 4-(4-chlorophenoxy)-N-{1-{[(2-hydroxyethyl)amino]carbonyl}-2-[4-(trifluoromethoxy)phenyl]vinyl}benzamide, and 4-(4-chlorophenoxy)-N-{1-{[(2-hydroxyethyl)amino]carbonyl}-2-[4-(trifluoromethyl)phenyl]vinyl}benzamide; and

(27) the compound or a pharmacologically acceptable salt thereof according to any one of the above (14) to (26), wherein the chemical structure regarding the position of the acrylamide moiety is Z.

Furthermore, the present invention provides

(28) a pharmaceutical composition comprising one or more compounds or a pharmacologically acceptable salt thereof according to any one of the above (14) to (27) as an active ingredient;

(29) the composition according to the above (28), the composition being a bone resorption-suppressing agent;

(30) the composition according to any one of the above (1) to (13), (28), and (29), the composition being used for decreasing blood calcium concentration; and

(31) the composition according to any one of the above (1) to (13), (28), and (29), the composition being used for suppressing a decrease in bone mass.

Furthermore, the present invention provides

(32) the composition according to any one of the above (1) to (13), (28), and (29), the composition being used for improving bone metabolism;

(33) the composition according to any one of the above (1) to (13), (28), and (29), the composition being used for prophylaxis or treatment of a bone metabolic disease;

(34) the composition according to the above (33), wherein the bone metabolic disease is osteoporosis;

(35) the composition according to the above (33), wherein the bone metabolic disease is hypercalcemia; and

(36) the composition according to any one of the above (1) to (13), (28), and (29), the composition being used for suppressing bone metastasis of cancer.

Furthermore, the present invention provides

(37) a method for improving bone metabolism, wherein an effective amount of a composition according to any one of the above (1) to (13), (28), and (29) is administered to a mammal;

(38) a method for the prophylaxis or treatment of a bone metabolic disease, wherein an effective amount of a composition according to any one of the above (1) to (13), (28), and (29) is administered to a mammal;

(39) a method for the prophylaxis or treatment of osteoporosis, wherein an effective amount of a composition according to any one of the above (1) to (13), (28), and (29) is administered to a mammal;

(40) a bone resorption-suppressing agent, the agent significantly decreasing serum calcium concentration of a mammal administered with the agent; and

(41) the bone resorption-suppressing agent according to the above (40), wherein the dose of the agent as an active ingredient is from 0.001 mg/kg to 100 mg/kg.

(Definition, Preferred Groups, and so on)

For substituent group α, preferred substituents are those in the group consisting of halogen atoms, $C_1$-$C_6$ alkyl groups which may be substituted with one group or more than one group selected from substituent group β, $C_1$-$C_6$ haloalkyl groups, $C_3$-$C_{10}$ cycloalkyl groups, 5- to 10-membered heteroaryl groups which may be substituted with one group or more than one group selected from substituent group γ, $C_1$-$C_6$ alkoxy groups which may be substituted with one group or more than one group selected from substituent group β, $C_1$-$C_6$ haloalkoxy groups, $C_3$-$C_{10}$ cycloalkyloxy groups, and $C_1$-$C_6$ alkylthio groups which may be substituted with one group or more than one group selected from substituent group β.

For substituent group β, preferred substituents are those in the group consisting of $C_3$-$C_{10}$ cycloalkyl groups which may be substituted with one group or more than one group selected from substituent group γ, $C_6$-$C_{10}$ aryl groups which may be substituted with one group or more than one group selected from substituent group γ, 5- to 10-membered heteroaryl groups which may be substituted with one group or more than one group selected from substituent group γ, and $C_6$-$C_{10}$ aryloxy groups which may be substituted with one group or more than one group selected from substituent group γ.

For substituent group γ, preferred substituents are those in the group consisting of hydroxyl groups, cyano groups, $C_1$-$C_6$ dialkylamino groups, halogen atoms, $C_1$-$C_6$ alkyl groups, $C_1$-$C_6$ haloalkyl groups, $C_3$-$C_{10}$ cycloalkyl groups, $C_1$-$C_6$ alkoxy groups, $C_1$-$C_6$ alkylenedioxy groups, and $C_3$-$C_{10}$ cycloalkyloxy groups.

Among the compounds having Formula (I), compounds having Formula (I') are preferred. Of the compounds having Formula (I'), the compounds in which each m and n is 1 are preferred. The compounds in which $R^5$ is a substituent at the 4-position and $R^6$ is a substituent at the 4'-position are further preferred.

The $C_6$-$C_{10}$ aryl groups of the "$C_6$-$C_{10}$ aryl group which may be substituted with one group or more than one group selected from substituent group α" in the above definitions of $R^1$, $R^2$, $R^3$, and $R^7$ and of the "$C_6$-$C_{10}$ aryl group which may be substituted with one group or more than one group selected from substituent group γ" in the definitions of substituent groups α and β may be condensed with other cyclic groups. Examples of such $C_6$-$C_{10}$ aryl groups include phenyl groups, indenyl groups, indanyl groups, naphthyl groups, and chromanyl groups, and phenyl groups are preferred.

The term "may be substituted" in the above "$C_6$-$C_{10}$ aryl group which may be substituted with one group or more than one group selected from substituent group α" preferably means substitution with one or two groups, and the term "may be substituted" in the "$C_6$-$C_{10}$ aryl group which may be substituted with one group or more than one group selected from substituent group γ" preferably means non-substitution or substitution with one group.

The 5- to 10-membered heteroaryl group of the "5- to 10-membered heteroaryl group which may be substituted with one group or more than one group selected from substituent group α" in the definitions of $R^1$, $R^2$, and $R^3$ and the 5- to 10-membered heteroaryl group of the "5- to 10-membered heteroaryl group which may be substituted with one group or more than one group selected from substituent group γ" in the definitions of substituent groups α and β are cyclic groups having 3 to 6 carbon atoms and which contain a nitrogen atom, an oxygen atom, and/or a sulfur atom. Examples of such 5- to 10-membered heteroaryl groups include furyl groups, thienyl groups, pyrrolyl groups, pyrazolyl groups, imidazolyl groups, oxazolyl groups, isoxazolyl, groups, thiazolyl groups, isothiazolyl groups, triazolyl groups, tetrazolyl groups, pyranyl groups, pyridyl groups, pyridazinyl groups, pyrimidinyl groups, and pyrazinyl groups. Among them, 5- or 6-membered heteroaryl groups are preferred. The above "5- to 10-membered heteroaryl group" may be condensed with another cyclic group such as an indolyl group, a benzofuranyl group, a benzothienyl group, a quinolyl group, an isoquinolyl group, a quinazolinyl group, a tetrahydroquinolyl group, or a tetrahydroisoquinolyl group. $R^1$ is preferably a pyridyl group, $R^2$ is preferably a pyridyl group, a triazolyl group, or a pyrrolyl group, and $R^3$ is preferably a pyridyl group. Among substituent group β, a benzothiazoyl group, a pyridyl group, and a pyrrolyl group are preferred.

The term "may be substituted" in the above "5- to 10-membered heteroaryl group which may be substituted with one group or more than one group selected from substituent group α" preferably means substitution with one or two groups, and the term "may be substituted" in the "5- to 10-membered heteroaryl group which may be substituted with one group or more than one group selected from substituent group γ" preferably means non-substitution or substitution with one group.

The "3- to 6-membered heterocyclyl groups" of the "3- to 6-membered heterocyclyl group which may be substituted with one group or more than one group selected from substituent group α" in the definition of $R^2$, the "3- to 6-membered heterocyclyl group which may be substituted with one group or more than one group selected from substituent group β" in the definitions of $R^3$ and $R^7$, and the "3- to 6-membered heterocyclyl group" in the definitions of substituent groups α and β can be, for example, an azetidinyl group, a pyrrolidinyl group, a pyrrolinyl group, an imidazolidinyl group, an imidazolinyl group, a pyrazolidinyl group, a pyrazolinyl group, an oxazolidinyl group, a thiazolidinyl group, a piperidyl group, a tetrahydropyridyl group, a dihydropyridyl group, a piperazinyl group, a morpholinyl group, a thiomorpholinyl group, a homopiperidyl group, a tetrahydrofuryl group, a tetrahydropyranyl group, a 2,5-dioxopyrrolidinyl group, and a 2,6-dioxopiperazinyl group. In substituent group β, a pyrrolidinyl group, a piperidyl group, a morpholinyl group, and a tetrahydrofuryl group are preferred.

The "3- to 6-membered heterocyclyl groups" of the "3- to 6-membered heterocyclyl group" in the definitions of substituent groups α and β may be condensed with other cyclic groups such as a 1,3-dioxo-2,3-dihydro-1H-isoindolyl group or a 2,4-dioxo-1,2,3,4-tetrahydroquinazolinyl group.

The $C_1$-$C_6$ alkoxy groups of the "$C_1$-$C_6$ alkoxy group" in the definitions of X and substituent groups β and γ and of the "$C_1$-$C_6$ alkoxy group which may be substituted with a hydroxyl group" or the "$C_1$-$C_6$ alkoxy group substituted with a hydroxyl group" in the definitions of $R^3$ and X and the $C_1$-$C_6$ alkoxy group of the "$C_1$-$C_6$ alkoxy group which may be substituted with one group or more than one group selected from substituent group β" in the definition of substituent group α can be, for example, linear or branched alkoxy groups having 1 to 6 carbon atoms; and are preferably a methoxy group, an ethoxy group, a propoxy group, an isopropoxy group, a butoxy group, or an isobutoxy group.

The term "substituted" in the above "$C_1$-$C_6$ alkoxy group substituted with a hydroxyl group" means substitution with one to three groups and, preferably, substitution with one or two groups.

The $C_1$-$C_6$ alkyl groups of the above "$C_1$-$C_6$ alkyl group" in the definitions of $R^3$, $R^4$, and substituent group γ and of the "$C_1$-$C_6$ alkyl group which may be substituted with one group or more than one group selected from substituent group β" in the definitions of $R^3$, $R^7$, and substituent group α can be, for example, linear or branched alkyl groups having 1 to 6 carbon atoms; and are preferably a methyl group, an ethyl group, a propyl group, an isopropyl group, or a butyl group.

The term "may be substituted" of the above "$C_1$-$C_6$ alkyl group which may be substituted with one group or more than one group selected from substituent group β" preferably means substitution with one or two groups.

Examples of the "hydrody protecting group" in the definitions of $R^3$ and $R^7$ include "aliphatic acyl groups", for example, alkylcarbonyl groups such as formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, icosanoyl, and henicosanoyl; aminated alkylcarbonyl groups, which are the above-mentioned alkylcarbonyl groups substituted with substituted an amino group, such as morpholin-4-ylacetyl, piperidin-1-ylacetyl, and pyrrolidin-1-ylacetyl; carboxylated alkylcarbonyl groups, such as succinoyl, glutaroyl, and azipoyl; halogeno $C_1$-$C_6$ alkylcarbonyl groups, such as chloroacetyl, dichloroacetyl, trichloroacetyl, and trifluoroacetyl; $C_1$-$C_6$ alkoxy $C_1$-$C_6$ alkylcarbonyl groups, such as methoxyacetyl; unsaturated alkylcarbonyl groups, such as (E)-2-methyl-2-butenoyl; "aromatic acyl groups", for example, arylcarbonyl groups, such as benzoyl, α-naphthoyl, and β-naphthoyl; halogeno-arylcarbonyl groups, such as 2-bromobenzoyl and 4-chlorobenzoyl; lower-alkylated arylcarbonyl groups, such as 2,4,6-trimethylbenzoyl and 4-toluoyl; lower-alkoxylated arylcarbonyl groups, such as 4-anisoyl; carboxylated arylcarbonyl groups, such as 2-carboxybenzoyl, 3-carboxybenzoyl, and 4-carboxybenzoyl; nitrated arylcarbonyl groups, such as 4-nitrobenzoyl and 2-nitrobenzoyl; lower alkoxycarbonylated arylcarbonyl groups, such as 2-(methoxycarbonyl)benzoyl; and arylated arylcarbonyl groups, such as 4-phenylbenzoyl; "tetrahydropyranyl or tetrahydrothiopyranyl groups", such as tetrahydropyran-2-yl, 3-bromotetrahydropyran-2-yl, 4-methoxytetrahydropyran-4-yl, tetrahydrothiopyran-2-yl, and 4-methoxytetrahydrothiopyran-4-yl; "tetrahydrofuranyl or tetrahydrothiofuranyl groups", such as tetrahydrofuran-2-yl and tetrahydrothiofuran-2-yl; "silyl groups", for example, tri(lower alkyl)silyl groups, such as trimethylsilyl, triethylsilyl, isopropyldimethylsilyl, t-butyldimethylsilyl, methyldiisopropylsilyl, methyldi-t-butylsilyl, and triisopropylsilyl; and tri(lower alkyl) silyl groups substituted with 1 or 2 aryl groups, such as diphenylmethylsilyl, diphenylbutylsilyl, diphenylisopropylsilyl, and phenyldiisopropylsilyl; "alkoxymethyl groups", for example, lower alkoxymethyl groups, such as methoxymethyl, 1,1-dimethyl-1-methoxymethyl, ethoxymethyl, propoxymethyl, isopropoxymethyl, butoxymethyl, and t-butoxymethyl; lower alkoxylated lower alkoxymethyl groups, such as 2-methoxyethoxymethyl; and halogeno-lower alkoxy methyl groups, such as 2,2,2-trichloroethoxymethyl and bis (2-chloroethoxy)methyl; "substituted ethyl groups", for example, lower alkoxylated ethyl groups, such as 1-ethoxyethyl and 1-(isopropoxy)ethyl; and halogenated ethyl groups, such as 2,2,2-trichloroethyl; "aralkyl groups", for example, lower alkyl groups substituted with 1 to 3 aryl groups, such as benzyl, α-naphthylmethyl, β-naphthylmethyl, diphenylmethyl, triphenylmethyl, α-naphthyldiphenylmethyl, and 9-anthrylmethyl; and lower alkyl groups substituted with 1 to 3 aryl groups the aryl ring of which is substituted with a lower alkyl, lower alkoxy, halogen, or cyano group such as 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl, methyl, and piperonyl; "alkoxycarbonyl groups", for example, lower alkoxycarbonyl groups, such as methoxycarbonyl, ethoxycarbonyl, t-butoxycarbonyl, and isobutoxycarbonyl; and lower alkoxycarbonyl groups substituted with a halogen or tri(lower alkyl)silyl group, such as 2,2,2-trichloroethoxycarbonyl and 2-trimethylsilylethoxycarbonyl; "alkenyloxycarbonyl groups", such as vinyloxycarbonyl and allyloxycarbonyl; "arylaminocarbonyl groups", such as phenylaminocarbonyl groups; and "aralkyloxycarbonyl groups in which the aryl ring may be substituted with 1 or 2 lower alkoxy or a nitro group", such as benzyloxycarbonyl, 4-methoxybenzyloxycarbonyl, 3,4-dimethoxybenzyloxycarbonyl, 2-nitrobenzyloxycarbonyl, and 4-nitrobenzyloxycarbonyl. The "protecting group for a hydroxy group" is preferably an aliphatic acyl group, more preferably an alkylcarbonyl group, an aminated alkylcarbonyl group, or a carboxylated alkylcarbonyl group, and further preferably an acetyl, morpholin-4-ylacetyl, or succinoyl group.

The $C_1$-$C_6$ hydroxyalkyl group of the "$C_1$-$C_6$ hydroxyalkyl group which may be protected by a hydroxyl protecting group" in the definitions of $R^3$ and $R^7$ can be, for example, hydroxymethyl, 2-hydroxyethyl, 3-hydroxypropyl, 4-hydroxybutyl, 5-hydroxypentyl, or 6-hydroxyhexyl; and is preferably a hydroxymethyl, 2-hydroxyethyl, or 3-hydroxypropyl group.

The $C_3$-$C_{10}$ cycloalkyl group of the "$C_3$-$C_{10}$ cycloalkyl group which may be substituted with one group or more than one group selected from substituent group α" in the definitions of $R^3$ and $R^7$ and the $C_3$-$C_{10}$ cycloalkyl groups of the "$C_3$-$C_{10}$ cycloalkyl group" in the definition of substituent group α and of the "$C_3$-$C_{10}$ cycloalkyl group which may be substituted with one group or more than one group selected from substituent group γ" in the definition of substituent group β are, for example, a cyclopropyl group, a cyclobutyl group, a cyclopentyl group, a cyclohexyl group, a cycloheptyl group, or an adamantyl group.

The term "may be substituted" in the above "$C_3$-$C_{10}$ cycloalkyl group which may be substituted with one group or more than one group selected from substituent group α" and in the "$C_3$-$C_{10}$ cycloalkyl group which may be substituted with one group or more than one group selected from substituent group γ" means unsubstituted or mono- to tri-substituted.

The "$C_1$-$C_6$ alkylamino group" in the definitions of substituent groups α and γ is an amino group substituted with one of the above-mentioned $C_1$-$C_6$ alkyl groups, such as an amino group substituted with a linear or branched alkyl group having 1 to 6 carbon atoms; and is preferably a methylamino group, an ethylamino group, a propylamino group, an isopropylamino group, or a butylamino group; and more preferably a methylamino group, an ethylamino group, or a propylamino group.

The "$C_1$-$C_6$ dialkylamino group" in the definitions of substituent groups α and γ is an amino group substituted with two of the above-mentioned $C_1$-$C_6$ alkyl groups and can be, for example, an amino group substituted with two linear or branched alkyl groups each having 1 to 6 carbon atoms; and is preferably a dimethylamino group, a diethylamino group, a dipropylamino group, a diisopropylamino group, or a dibutylamino group; and more preferably a dimethylamino group or a diethylamino group.

The "$C_3$-$C_6$ cycloalkylamino group" in the definition of substituent group α can be, for example, a cyclopropylamino group, a cyclobutylamino group, a cyclopentylamino group, or a cyclohexylamino group; and is preferably a cyclopentylamino group or a cyclohexylamino group.

The "$C_1$-$C_6$ haloalkyl group" in the definitions of $R^3$, $R^5$, $R^6$, and substituent groups α and γ is the above-mentioned $C_1$-$C_6$ alkyl group substituted with as many halogen atoms as possible. Examples of the $C_1$-$C_6$ haloalkyl group include a fluoromethyl group, a difluoromethyl group, a trifluoromethyl group, a fluoroethyl group, a difluoroethyl group, a trifluoroethyl group, a fluoropropyl group, a difluoropropyl group, a trifluoropropyl group, a fluorobutyl group, a difluorobutyl group, a trifluorobutyl group, a fluoropentyl group, a difluoropentyl group, a trifluoropentyl group, a fluorohexyl group, a difluorohexyl group, a trifluorohexyl group, a pentafluoroethyl group, a hexafluoropropyl group, a nonafluorobutyl group, a chloromethyl group, a dichloromethyl group, a trichloromethyl group, a chloroethyl group, a dichloroethyl group, a trichloroethyl group, a chloropropyl group, a dichloropropyl group, a trichloropropyl group, a chlorobutyl group, a dichlorobutyl group, a trichlorobutyl group, a chloropentyl group, a dichloropentyl group, a trichloropentyl group, a chlorohexyl group, a dichlorohexyl group, a trichlorohexyl groups, a pentachloroethyl group, a hexachloropropyl group, and a nonachlorobutyl group. The $C_1$-$C_6$ haloalkyl group is preferably a fluoromethyl group, a difluoromethyl group, a trifluoromethyl group, a fluoroethyl group, a difluoroethyl group, a trifluoroethyl group, a fluoropropyl group, a difluoropropyl group, or a trifluoropropyl group; and more preferably a fluoromethyl group, a difluoromethyl group, a trifluoromethyl group, a fluoroethyl group, a difluoroethyl group, or a trifluoroethyl group.

The "$C_3$-$C_6$ cycloalkenyl group" in the definitions of substituent groups α and β can be, for example, a cyclopropenyl group, a cyclobutenyl group, a cyclopentenyl group, or a cyclohexenyl group; and is preferably a cyclopentenyl group or a cyclohexyl group.

The "$C_1$-$C_6$ haloalkoxy group" in the definition of substituent group α is the above-mentioned $C_1$-$C_6$ haloalkyl group the alkyl terminus of which is substituted with an oxygen atom and can be, for example, a fluoromethoxy group, a difluoromethoxy group, a trifluoromethoxy group, a fluoroethoxy group, a difluoroethoxy group, a trifluoroethoxy group, a fluoropropoxy group, a difluoropropoxy group, a trifluoropropoxy group, a fluorobutoxy group, a difluorobutoxy group, a trifluorobutoxy group, a fluoropentyloxy group, a difluoropentyloxy group, a trifluoropentyloxy group, a fluorohexyloxy group, a difluorohexyloxy group, a trifluorohexyloxy group, a pentafluoroethoxy group, a hexafluoropropoxy group, a nonafluorobutoxy group, a chloromethoxy group, a dichloromethoxy group, a trichloromethoxy group, a chloroethoxy group, a dichloroethoxy group, a trichloroethoxy group, a chloropropoxy group, a dichloropropoxy group, a trichloropropoxy group, a chlorobutoxy group, a dichlorobutoxy group, a trichlorobutoxy group, a chloropentyloxy group, a dichloropentyloxy group, a trichloropentyloxy group, a chlorohexyloxy group, a dichlorohexyloxy group, a trichlorohexyloxy group, a pentachloroethoxy group, a hexachloropropoxy group, or a nonachlorobutoxy group; and is preferably a fluoromethoxy group, a difluoromethoxy group, a trifluoromethoxy group, a fluoroethoxy group, a difluoroethoxy group, a trifluoroethoxy group, a fluoropropoxy group, a difluoropropoxy group, or a trifluoropropoxy group; and more preferably a fluoromethoxy group, a difluoromethoxy group, a trifluoromethoxy group, a fluoroethoxy group, a difluoroethoxy group, or a trifluoroethoxy group.

The $C_1$-$C_6$ alkoxy $C_1$-$C_6$ alkoxy group of the "$C_1$-$C_6$ alkoxy $C_1$-$C_6$ alkoxy group which may be substituted with one group or more than one group selected from substituent group β" in the definition of substituent group α is the above-mentioned $C_1$-$C_6$ alkoxy group substituted with one of the above-mentioned $C_1$-$C_6$ alkoxy groups and can be, for example, a methoxymethoxy group, a 2-methoxyethoxy group, a 3-methoxypropoxy group, a 4-methoxybutoxy group, a 5-methoxypentyloxy group, a 6-methoxyhexyloxy group, an ethoxymethoxy group, a 2-ethoxyethoxy group, a 3-ethoxypropoxy group, a 4-ethoxybutoxy group, a 5-ethoxypentyloxy group, or a 6-ethoxyhexyloxy group; and is preferably a 2-methoxyethoxy group, a 3-methoxypropoxy group, a 4-methoxybutoxy group, or a 5-methoxypentyloxy group.

The $C_1$-$C_6$ alkenyloxy group of the "$C_1$-$C_6$ alkenyloxy group which may be substituted with one group or more than one group selected from substituent group" in the definition of substituent group α can be, for example, a vinyloxy group, a 1-propenyloxy group, a 2-propenyloxy group, a 1-butenyloxy group, a 2-butenyloxy group, a 3-butenyloxy group, a 1-pentenyloxy group, a 2-pentenyloxy group, a 3-pentenyloxy group, a 4-pentenyloxy group, a 1-hexenyloxy group, a 2-hexenyloxy group, a 3-hexenyloxy group, a 4-hexenyloxy group, or a 5-hexenyloxy group; and is preferably a 1-propenyloxy group, a 2-propenyloxy group, a 1-butenyloxy group, a 2-butenyloxy group, or a 3-butenyloxy group.

The $C_1$-$C_6$ alkynyloxy group of the "$C_1$-$C_6$ alkynyloxy group which may be substituted with one group or more than one group selected from substituent group β" in the definition of substituent group α can be, for example, a 1-propynyloxy group, a 2-propynyloxy group, a 1-butynyloxy group, a 2-butynyloxy group, a 3-butynyloxy group, a 1-pentynyloxy group, a 2-pentynyloxy group, a 3-pentynyloxy group, a 4-pentynyloxy group, a 1-hexynyloxy group, a 2-hexynyloxy group, a 3-hexynyloxy group, a 4-hexynyloxy group, or a 5-hexynyloxy group; and is preferably a 1-propynyloxy group, a 2-propynyloxy group, a 1-butynyloxy group, a 2-butynyloxy group, or a 3-butynyloxy group.

The term "may be substituted" in the "$C_1$-$C_6$ alkoxy $C_1$-$C_6$ alkoxy group which may be substituted with one group or more than one group selected from substituent group β", the "$C_1$-$C_6$ alkenyloxy group which may be substituted with one group or more than one group selected from substituent group β", and the "$C_1$-$C_6$ alkynyloxy group which may be substituted with one group or more than one group selected from substituent group β" means unsubstituted or mono- to tri-substituted.

The "$C_3$-$C_{10}$ cycloalkyloxy group" in the definitions of substituent groups α and β is the above-mentioned $C_3$-$C_{10}$ cycloalkyl group to which an oxygen atom is bound and can be, for example, a cyclopropoxy group, a cyclobutoxy group, a cyclopentyloxy group, or a cyclohexyloxy group; and is preferably a cyclopropoxy group, a cyclobutoxy group, or a cyclopentyloxy group.

The "3- to 6-membered heterocyclyloxy group" in the definition of substituent group α is a cyclic group containing a nitrogen atom, an oxygen atom, and/or a sulfur atom and having 3 to 6 carbon atoms, to which an oxygen atom is bound; and can be, for example, an aziridinyloxy group, an azetidinyloxy group, a pyrrolidinyloxy group, a piperidinyloxy group, a thiranyloxy group, a thienyloxy group, a tetrahydrothienyloxy group, a tetrahydrothiopyranyloxy group, an oxiranyloxy group, an oxetanyloxy group, a tetrahydrofuryloxy group, or a tetrahydropyranyloxy group; and is preferably a tetrahydrofuryloxy group or a tetrahydropyranyloxy group.

The $C_6$-$C_{10}$ aryloxy group of the "$C_6$-$C_{10}$ aryloxy group which may be substituted with one group or more than one group selected from substituent group γ" in the definitions of substituent groups α and β is the above-mentioned $C_6$-$C_{10}$ aryl group to which an oxygen atom is bound and can be, for example, a phenoxy group, an indenyloxy group, or a naphthyloxy group, and is preferably a phenoxy group.

The term "may be substituted" in the above "$C_6$-$C_{10}$ aryloxy group which may be substituted with one group or more than one group selected from substituent group γ" means unsubstituted or mono- to tri-substituted.

The "$C_1$-$C_6$ alkyleneoxy group" in the definitions of substituent groups α and γ can be, for example, a methyleneoxy group, an ethyleneoxy group, a trimethyleneoxy group, a tetramethyleneoxy group, a pentamethyleneoxy group, or a hexamethyleneoxy group; and is preferably an ethyleneoxy group or a trimethyleneoxy group.

The "$C_1$-$C_6$ alkylenedioxy group" in the definitions of substituent groups α and γ can be, for example, a methylenedioxy group, an ethylenedioxy group, a trimethylenedioxy group, a tetramethylenedioxy group, a pentamethylenedioxy group, or a hexamethylenedioxy group; and is preferably a methylenedioxy group or an ethylenedioxy group.

The $C_1$-$C_6$ alkylthio group of the "$C_1$-$C_6$ alkylthio group which may be substituted with one group or more than one group selected from substituent group β" in the definition of substituent group α is the above-mentioned $C_1$-$C_6$ alkyl group to which a sulfur atom is bound, and is preferably a methylthio group, an ethylthio group, a propylthio group, an isopropylthio group, or a butylthio group, and more preferably a methylthio group or an ethylthio group.

The term "may be substituted" in the above "$C_1$-$C_6$ alkylthio group which may be substituted with one group or more than one group selected from substituent group β" means unsubstituted or mono- to tri-substituted.

The "$C_1$-$C_6$ haloalkylthio group" in the definition of substituent group α is the above-mentioned $C_1$-$C_6$ alkylthio group substituted with as many halogen atoms as possible and can be, for example, a fluoromethylthio group, a difluoromethylthio group, a trifluoromethylthio group, a fluoroethylthio group, a difluoroethylthio group, a trifluoroethylthio group, a fluoropropylthio group, a difluoropropylthio group, a trifluoropropylthio group, a fluorobutylthio group, a difluorobutylthio group, a trifluorobutylthio group, a fluoropentylthio group, a difluoropentylthio group, a trifluoropentylthio group, a fluorohexylthio group, a difluorohexylthio group, a trifluorohexylthio group, a pentafluoroethylthio group, a hexafluoropropylthio group, a nonafluorobutylthio group, a chloromethylthio group, a dichloromethylthio group, a trichloromethylthio group, a chloroethylthio group, a dichloroethylthio group, a trichloroethylthio group, a chloropropylthio group, a dichloropropylthio group, a trichloropropylthio group, a chlorobutylthio group, a dichlorobutylthio group, a trichlorobutylthio group, a chloropentylthio group, a dichloropentylthio group, a trichloropentylthio group, a chlorohexylthio group, a dichlorohexylthio group, a trichlorohexylthio group, a pentachloroethylthio group, a hexachloropropylthio group, or a nonachlorobutylthio group; and is preferably a fluoromethylthio group, a difluoromethylthio group, a trifluoromethylthio group, a fluoroethylthio group, a difluoroethylthio group, a trifluoroethylthio group, a fluoropropylthio group, a difluoropropylthio group, or a trifluoropropylthio group.

The $C_1$-$C_6$ alkylsulfonyl group of the "$C_1$-$C_6$ alkylsulfonyl group which may be substituted with one group or more than one group selected from substituent group β" in the definition of substituent group α is the above-mentioned $C_1$-$C_6$ alkyl group to which a sulfonyl group is bound and is preferably a methylsulfonyl group, an ethylsulfonyl group, a propylsulfonyl group, an isopropylsulfonyl group, or a butylsulfonyl group, and more preferably a methylsulfonyl group or an ethylsulfonyl group.

The term "may be substituted" in the "$C_1$-$C_6$ alkylsulfonyl group which may be substituted with one group or more than one group selected from substituent group β" means unsubstituted or mono- to tri-substituted.

The "$C_1$-$C_6$ haloalkylsulfonyl group" in the definition of substituent group α is the above-mentioned $C_1$-$C_6$ alkylsulfonyl group substituted with as many halogen atoms as possible and can be, for example, a fluoromethylsulfonyl group, a difluoromethylsulfonyl group, a trifluoromethylsulfonyl group, a fluoroethylsulfonyl group, a difluoroethylsulfonyl group, a trifluoroethylsulfonyl group, a fluoropropylsulfonyl group, a difluoropropylsulfonyl group, a trifluoropropylsulfonyl group, a fluorobutylsulfonyl group, a difluorobutylsulfonyl group, a trifluorobutylsulfonyl group, a fluoropentylsulfonyl group, a difluoropentylsulfonyl group, a trifluoropentylsulfonyl group, a fluorohexylsulfonyl group, a difluorohexylsulfonyl group, a trifluorohexylsulfonyl group, a pentafluoroethylsulfonyl group, a hexafluoropropylsulfonyl group, a nonafluorobutylsulfonyl group, a chloromethylsulfonyl group, a dichloromethylsulfonyl group, a trichloromethylsulfonyl group, a chloroethylsulfonyl group, a dichloroethylsulfonyl group, a trichloroethylsulfonyl group, a chloropropylsulfonyl group, a dichloropropylsulfonyl group, a trichloropropylsulfonyl group, a chlorobutylsulfonyl group, a dichlorobutylsulfonyl group, a trichlorobutylsulfonyl group, a chloropentylsulfonyl group, a dichloropentylsulfonyl group, a trichloropentylsulfonyl group, a chlorohexylsulfonyl group, a dichlorohexylsulfonyl group, a trichlorohexylsulfonyl group, a pentachloroethylsulfonyl group, a hexachloropropylsulfonyl group, or a nonachlorobutylsulfonyl group; and is preferably a fluoromethylsulfonyl group, a difluoromethylsulfonyl group, a trifluoromethylsulfonyl group, a fluoroethylsulfonyl group, a difluoroethylsulfonyl group, a trifluoroethylsulfonyl group, a fluoropropylsulfonyl group, a difluoropropylsulfonyl group, or a trifluoropropylsulfonyl group.

The $C_1$-$C_6$ alkylcarbonyl group of the "$C_1$-$C_6$ alkylcarbonyl group which may be substituted with one group or more than one group selected from substituent group β" in the definition of substituent group α is the above-mentioned $C_1$-$C_6$ alkyl group to which a carbonyl group is bound and can be, for example, an acetyl group, an ethylcarbonyl group, a propylcarbonyl group, a butylcarbonyl group, a pentylcarbonyl group, or a hexylcarbonyl group; and is preferably an acetyl group, an ethylcarbonyl group, or a propylcarbonyl group.

The term "may be substituted" in the above "$C_1$-$C_6$ alkylcarbonyl group which may be substituted with one group or more than one group selected from substituent group β" means unsubstituted or mono- to tri-substituted.

The "$C_1$-$C_6$ haloalkylcarbonyl group" in the definition of substituent group α is the above-mentioned $C_1$-$C_6$ haloalkyl group to which a carbonyl group is bound and can be, for example, a fluoromethylcarbonyl group, a difluoromethylcarbonyl group, a trifluoromethylcarbonyl group, a fluoroethylcarbonyl group, a difluoroethylcarbonyl group, a trifluoroethylcarbonyl group, a fluoropropylcarbonyl group, a difluoropropylcarbonyl group, a trifluoropropylcarbonyl group, a fluorobutylcarbonyl group, a difluorobutylcarbonyl group, a trifluorobutylcarbonyl group, a fluoropentylcarbonyl group, a difluoropentylcarbonyl group, a trifluoropentylcarbonyl group, a fluorohexylcarbonyl group, a difluorohexylcarbonyl group, a trifluorohexylcarbonyl group, a pentafluoroethylcarbonyl group, a hexafluoropropylcarbonyl group, a nonafluorobutylcarbonyl group, a chloromethylcarbonyl group, a dichloromethylcarbonyl group, a trichloromethylcarbonyl group, a chloroethylcarbonyl group, a dichloroethylcarbonyl group, a trichloroethylcarbonyl group, a chloropropylcarbonyl group, a dichloropropylcarbonyl group, a trichloropropylcarbonyl group, a chlorobutylcarbonyl group, a dichlorobutylcarbonyl group, a trichlorobutylcarbonyl group, a chloropentylcarbonyl group, a dichloropentylcarbonyl group, a trichloropentylcarbonyl group, a chlorohexylcarbonyl group, a dichlorohexylcarbonyl group, a trichlorohexylcarbonyl group, a pentachloroethylcarbonyl group, a hexachloropropylcarbonyl group, or a nonachlorobutylcarbonyl group; and is preferably a fluoromethylcarbonyl group, a difluoromethylcarbonyl group, a trifluoromethylcarbonyl group, a fluoroethylcarbonyl group, a difluoroethylcarbonyl group, a trifluoroethylcarbonyl group, a fluoropropylcarbonyl group, a difluoropropylcarbonyl group, or a trifluoropropylcarbonyl group.

The $C_6$-$C_{10}$ arylcarbonyl group of the "$C_6$-$C_{10}$ arylcarbonyl group which may be substituted with one group or more than one group selected from substituent group γ" in the definition of substituent group α is the above-mentioned $C_6$-$C_{10}$ aryl group to which a carbonyl group is bound and can be, for example, a benzoyl group, an indenylcarbonyl group, or a naphthylcarbonyl group and is preferably a benzoyl group.

The term "may be substituted" in the above "$C_6$-$C_{10}$ arylcarbonyl group which may be substituted with one group or more than one group selected from substituent group γ" means unsubstituted or mono- to tri-substituted.

The "$C_1$-$C_6$ alkoxycarbonyl group" in the definition of substituent group β is the above-mentioned $C_1$-$C_6$ alkoxy group to which a carbonyl group is bound and can be, for example, a linear or branched alkoxycarbonyl group having 1 to 6 carbon atoms; and is preferably a methoxycarbonyl group, an ethoxycarbonyl group, a propoxycarbonyl group, an isopropoxycarbonyl group, or a butoxycarbonyl group; and more preferably a methoxycarbonyl group or an ethoxycarbonyl group.

The "N—$C_6$-$C_{10}$ arylacetamido group" in the definition of substituent group β is an acetamido group having the above-mentioned $C_6$-$C_{10}$ aryl group on the nitrogen atom and can be, for example, an N-phenylacetamido group, an N-indenylacetamido group, or an N-naphthylacetamido group and is preferably an N-phenylacetamido group.

The "$C_1$-$C_6$ alkoxycarbonylamido group" in the definition of substituent group P is the above-mentioned $C_1$-$C_6$ alkoxycarbonyl group having a carbonyl group to which an amino group is bound and can be, for example, a linear or branched alkoxycarbonylamido group having 1 to 6 carbon atoms, and is preferably a methoxycarbonylamido group, an ethoxycarbonylamido group, a propoxycarbonylamido group, an isopropoxycarbonylamido group, or a butoxycarbonylamido group, and more preferably a methoxycarbonylamido group or an ethoxycarbonylamido group.

The "$C_2$-$C_6$ cyclic amino group" in the definition of substituent group γ can be, for example, an aziridine group, an azetidine group, a pyrrolidine group, or a piperidine group and is preferably a pyrrolidine group or a piperidine group.

In the compounds having Formula (I) according to the present invention, $R^1$ is preferably a phenyl group which may be substituted with one group or more than one group selected from substituent group α or a pyridyl group which may be substituted with one group or more than one group selected from substituent group α; more preferably a phenyl group which may be substituted with one group or more than one group selected from substituent group α; still more preferably a phenyl group substituted with any one group selected from the group consisting of $C_1$-$C_6$ alkoxy groups which may be substituted with one group or more than one group selected from substituent group β, $C_6$-$C_{10}$ aryloxy groups which may be substituted with one group or more than one group selected from substituent group γ, and $C_1$-$C_6$ haloalkoxy groups; and particularly still more preferably a 4-isobutyloxyphenyl group, a 4-(cyclopropylmethoxy)phenyl group, a 4-(2-cyclopropylethoxy)phenyl group, a 4-(1-methylcyclopropylmethoxy)phenyl group, a 4-(3,3,3-trifluoropropyloxy)phenyl group, a 4-(4,4,4-trifluorobutyloxy)phenyl group, a 4-(2-phenylethoxy)phenyl group, a 4-(2-(4-methoxyphenyl)ethoxy) phenyl group, a 4-(2-(3-methoxyphenyl)ethoxy)phenyl group, a 4-(2-(4-chlorophenyl)ethoxy)phenyl group, a 4-(2-(4-(N,N-dimethylamino)phenyl)ethoxy)phenyl group, a 4-(4-chlorophenoxy)phenyl group, or a 4-(4-trifluoromethylphenoxy)phenyl group.

$R^2$ is preferably a $C_6$-$C_{10}$ aryl group which may be substituted with one group or more than one group selected from substituent group α; more preferably a phenyl group which may be substituted with one group or more than one group selected from substituent group α; still more preferably a phenyl group substituted with any one group selected from the group consisting of halogen atoms, $C_1$-$C_6$ alkyl groups, $C_1$-$C_6$ haloalkyl groups, $C_3$-$C_6$ cycloalkyl groups, $C_1$-$C_6$ alkoxy groups, $C_3$-$C_6$ cycloalkyloxy groups, $C_1$-$C_6$ haloalkoxy groups, $C_1$-$C_6$ alkylthio groups, and 5- to 10-membered heteroaryl groups; and particularly still more preferably a 4-fluorophenyl group, a 4-chlorophenyl group, a 4-trifluoromethylphenyl group, a 4-isopropylphenyl group, a 4-cyclopropylphenyl group, a 4-isopropyloxyphenyl group, a 4-difluoromethoxyphenyl group, a 4-trifluoromethoxyphenyl group, a 4-(2,2,2-trifluoroethoxy)phenyl group, a 4-(2,2-difluoroethoxy)phenyl group, a 4-cyclopropyloxyphenyl group, a 4-ethoxyphenyl group, a 4-methylthiophenyl group, or a 4-(1H-pyrrol-1-yl)phenyl group.

X is preferably a group having the formula $N(R^3)R^4$ wherein $R^4$ is a hydrogen atom, and $R^3$ is a $C_1$-$C_6$ haloalkyl group, a $C_1$-$C_6$ alkyl group which may be substituted with one group or more than one group selected from substituent group β, or a $C_1$-$C_6$ hydroxyalkyl group which may be protected by a hydroxyl protecting group; more preferably a group having the formula $N(R^3)R^4$ wherein $R^4$ is a hydrogen atom, and $R^3$ is a $C_2$-$C_3$ haloalkyl group, a $C_2$-$C_3$ hydroxyalkyl group which may be protected by a hydroxyl protecting group, or a $C_1$-$C_3$ alkyl group substituted with a 1-hydroxycyclopropyl group; and still more preferably a 2-fluoroethylamino group, a 2,2-difluoroethylamino group, a 2-hydroxyethylamino group, a 1-(2-hydroxypropyl)amino group, a 1-hydroxycyclopropylmethylamino group, a 2-acetoxyethylamino group, a 2-(morpholin-4-ylacetoxy)ethylamino group, or a 2-(3-carboxypropionyloxy)ethylamino group.

In the compounds having Formula (I') according to the present invention, $R^5$ is preferably any one group selected from the group consisting of halogen atoms, $C_1$-$C_6$ alkyl groups which may be substituted with one group or more than one group selected from substituent group β, $C_1$-$C_6$ haloalkyl groups, $C_3$-$C_6$ cycloalkyl groups, $C_1$-$C_6$ alkoxy groups which may be substituted with one group or more than one group selected from substituent group β, $C_6$-$C_{10}$ aryloxy groups which may be substituted with one group or more than one group selected from substituent group γ, $C_1$-$C_6$ haloalkoxy groups, and $C_3$-$C_6$ cycloalkyloxy groups; more preferably any one group selected from the group consisting of $C_1$-$C_6$ alkoxy groups which may be substituted with one group or more than one group selected from substituent group β, $C_6$-$C_{10}$ aryloxy groups which may be substituted with one group or more than one group selected from substituent group γ, and $C_1$-$C_6$ haloalkoxy groups; and still more preferably an isobutyloxy group, a cyclopropylmethoxy group, a 2-cyclopropylethoxy group, a 1-methylcyclopropylmethoxy group, a 3,3,3-trifluoropropyloxy group, a 4,4,4-trifluorobutyloxy group, a 2-phenylethoxy group, a 2-(4-methoxyphenyl)ethoxy group, a 2-(3-methoxyphenyl)ethoxy group, a 2-(4-chlorophenyl)ethoxy group, a 2-(4-(N,N-dimethylamino)phenyl)ethoxy group, a 4-chlorophenoxy group, or a 4-trifluoromethylphenoxy group.

$R^6$ is preferably any one group selected from the group consisting of halogen atoms, $C_1$-$C_6$ alkyl groups, $C_1$-$C_6$ haloalkyl groups, $C_3$-$C_6$ cycloalkyl groups, $C_1$-$C_6$ alkoxy groups, $C_3$-$C_6$ cycloalkyloxy groups, $C_1$-$C_6$ haloalkoxy groups, $C_1$-$C_6$ alkylthio groups, and 5- to 10-membered heteroaryl groups; more preferably a fluorine atom, a chlorine atom, a trifluoromethyl group, an isopropyl group, a cyclopropyl group, an isopropyloxy group, a difluoromethoxy group, a trifluoromethoxy group, a 2,2,2-trifluoroethoxy group, a 2,2-difluoroethoxy group, a cyclopropyloxy group, an ethoxy group, a methylthio group, or a 1H-pyrrol-1-yl group; and still more preferably an ethoxy group, a trifluoromethyl group, a cyclopropyl group, a cyclopropyloxy group, a difluoromethoxy group, a trifluoromethoxy group, or a 2,2-difluoroethoxy group.

$R^7$ is preferably a $C_1$-$C_6$ haloalkyl group, a $C_1$-$C_6$ alkyl group which may be substituted with one group or more than one group selected from substituent group P, or a $C_1$-$C_6$ hydroxyalkyl group which may be protected by a hydroxyl protecting group; more preferably a $C_2$-$C_3$ haloalkyl group, a $C_2$-$C_3$ hydroxyalkyl group which may be protected by a hydroxyl protecting group, or a $C_1$-$C_3$ alkyl group substituted with 1-hydroxycyclopropyl; and still more preferably a 2-fluoroethyl group, a 2,2-difluoroethyl group, a 2-hydroxyethyl group, a 2-hydroxypropyl group, a 1-hydroxycyclopropylmethyl group, a 2-acetoxyethyl group, a 2-(morpholin-4-ylacetoxy)ethyl group, or a 2-(3-carboxypropionyloxy)ethyl group.

In preferred combinations of substituents of a compound having Formula (I') according to the present invention, $R^5$ is any one group selected from the group consisting of halogen atoms, $C_1$-$C_6$ alkyl groups which may be substituted with one group or more than one group selected from substituent group β, $C_1$-$C_6$ haloalkyl groups, $C_3$-$C_6$ cycloalkyl groups, $C_1$-$C_6$ alkoxy groups which may be substituted with one group or more than one group selected from substituent group β, $C_6$-$C_{10}$ aryloxy groups which may be substituted with one group or more than one group selected from substituent group γ, $C_1$-$C_6$ haloalkoxy groups, and $C_3$-$C_6$ cycloalkyloxy groups; $R^6$ is any one group selected from the group consisting of halogen atoms, $C_1$-$C_6$ alkyl groups, $C_1$-$C_6$ haloalkyl groups, $C_3$-$C_6$ cycloalkyl groups, $C_1$-$C_6$ alkoxy groups, $C_3$-$C_6$ cycloalkyloxy groups, $C_6$ haloalkoxy groups, $C_1$-$C_6$ alkylthio groups, and 5- to 10-membered heteroaryl groups; and $R^7$ is a $C_1$-$C_6$ haloalkyl group, a $C_1$-$C_6$ alkyl group which may be substituted with one group or more than one group selected from substituent group β, or a $C_1$-$C_6$ hydroxyalkyl group which may be protected by a hydroxyl protecting group. In more preferred combinations of substituents, $R^5$ is any one group selected from the group consisting of $C_1$-$C_6$ alkoxy groups which may be substituted with one group or more than one group selected from substituent group β, $C_6$-$C_{10}$ aryloxy groups which may be substituted with one group or more than one group selected from substituent group γ, and $C_1$-$C_6$ haloalkoxy groups; $R^6$ is a fluorine atom, a chlorine atom, a trifluoromethyl group, an isopropyl group, a cyclopropyl group, an isopropyloxy group, a difluoromethoxy group, a trifluoromethoxy group, a 2,2,2-trifluoroethoxy group, a 2,2-difluoroethoxy group, a cyclopropyloxy group, an ethoxy group, a methylthio group, or a 1H-pyrrol-1-yl group; and $R^7$ is a $C_2$-$C_3$ haloalkyl group, a $C_2$-$C_3$ hydroxyalkyl group which may be protected by a hydroxyl protecting group, or a $C_1$-$C_3$ alkyl group substituted with 1-hydroxycyclopropyl. In still more preferred combinations of substituents, $R^5$ is an isobutyloxy group, a cyclopropylmethoxy group, a 2-cyclopropylethoxy group, a 1-methylcyclopropylmethoxy group, a 3,3,3-trifluoropropyloxy group, a 4,4,4-trifluorobutyloxy group, a 2-phenylethoxy group, a 2-(4-methoxyphenyl)ethoxy group, a 2-(3-methoxyphenyl)ethoxy group, a 2-(4-chlorophenyl)ethoxy group, a 2-(4-(N,N-dimethylamino)phenyl)ethoxy group, a 4-chlorophenoxy group, or a 4-trifluoromethylphenoxy group; $R^6$ is an ethoxy group, a trifluoromethyl group, a cyclopropyl group, a cyclopropyloxy group, a difluoromethoxy group, a trifluoromethoxy group, or a 2,2-difluoroethoxy group; and $R^7$ is a 2-fluoroethyl group, a 2,2-difluoroethyl group, a 2-hydroxyethyl group, a 2-hydroxypropyl group, a 1-hydroxycyclopropylmethyl group, a 2-acetoxyethyl group, a 2-(morpholin-4-ylacetoxy)ethyl group, or a 2-(3-carboxypropionyloxy)ethyl group.

The compounds having Formula (I') according to the present invention are preferably:
4-(2-cyclopropylethoxy)-N-(2-(4-ethoxyphenyl)-1-{[(2-hydroxyethyl)amino]carbonyl}vinyl)benzamide,
4-(2-cyclopropylethoxy)-N-(2-[4-(cyclopropyloxy)phenyl]-1-{[(2-hydroxyethyl)amino]carbonyl}vinyl)benzamide,
4-(2-cyclopropylethoxy)-N-(2-[4-(difluoromethoxy)phenyl]-1-{[(2-hydroxyethyl)amino]carbonyl}vinyl)benzamide,
4-(2-cyclopropylethoxy)-N-{1-{[(2-hydroxyethyl)amino]carbonyl}-2-[4-(trifluoromethoxy)phenyl]vinyl}benzamide,
4-(2-cyclopropylethoxy)-N-(2-[4-(2,2-difluoroethoxy)phenyl]-1-{[(2-hydroxyethyl)amino]carbonyl}vinyl)benzamide,
4-(2-cyclopropylethoxy)-N-(2-(4-cyclopropylphenyl)-1-{[(2-hydroxyethyl)amino]carbonyl}vinyl)benzamide,
2-{[(2Z)-2-{[4-(2-cyclopropylethoxy)benzoyl]amino}-3-(4-cyclopropylphenyl)propen-2-oyl]amino}ethyl acetate,
2-{[(2Z)-2-{[4-(2-cyclopropylethoxy)benzoyl]amino}-3-(4-cyclopropylphenyl)propen-2-oyl]amino}ethyl succinate,
4-(2-cyclopropylethoxy)-N-{1-{[(2-hydroxyethyl)amino]carbonyl}-2-[4-(trifluoromethyl)phenyl]vinyl}benzamide,
4-(2-cyclopropylethoxy)-N-{1-{[(2-hydroxyethyl)amino]carbonyl}-2-[4-(1H-pyrrol-1-yl)phenyl]vinyl}benzamide, N-(2-(4-chlorophenyl)-1-{[(2-hydroxyethyl)amino]
  carbonyl}vinyl)-4-(2-cyclopropylethoxy)benzamide,
N-[1-{[(2-hydroxyethyl)amino]carbonyl}-2-(4-isopropoxyphenyl)vinyl]-4-[2-(4-methoxyphenyl)ethoxy]benzamide,
N-(2-[4-(cyclopropyloxy)phenyl]-1-{[(2-hydroxyethyl)amino]carbonyl}vinyl)-4-[2-(4-methoxyphenyl)ethoxy]benzamide,
N-{1-{[(2-hydroxyethyl)amino]carbonyl}-2-[4-(trifluoromethoxy)phenyl]vinyl}-4-[2-(4-methoxyphenyl)ethoxy]benzamide,
N-(2-(4-cyclopropylphenyl)-1-{[(2-hydroxyethyl)amino]carbonyl}vinyl)-4-[2-(4-methoxyphenyl)ethoxy]benzamide,
N-{1-{[(2-hydroxyethyl)amino]carbonyl}-2-[4-(methylthio)phenyl]vinyl}-4-[2-(4-methoxyphenyl)ethoxy]benzamide,
N-(2-(4-chlorophenyl)-1-{[(2-hydroxyethyl)amino]carbonyl}vinyl)-4-[2-(4-methoxyphenyl)ethoxy]benzamide,
4-{2-[4-(dimethylamino)phenyl]ethoxy}-N-[1-{[(2-hydroxyethyl)amino]carbonyl}-2-(4-isopropoxyphenyl)vinyl]benzamide,
4-{2-[4-(dimethylamino)phenyl]ethoxy}-N-{1-{[(2-hydroxyethyl)amino]carbonyl}-2-[4-(trifluoromethoxy)phenyl]vinyl}benzamide,
N-(2-(4-cyclopropylphenyl)-1-{[(2-hydroxyethyl)amino]carbonyl}vinyl)-4-{2-[4-(dimethylamino)phenyl]ethoxy}benzamide,
4-[2-(4-chlorophenyl)ethoxy]-N-(2-(4-ethoxyphenyl)-1-{[(2-hydroxyethyl)amino]carbonyl}vinyl)benzamide,
4-[2-(4-chlorophenyl)ethoxy]-N-(2-[4-(cyclopropyloxy)phenyl]-1-{[(2-hydroxyethyl)amino]carbonyl}vinyl)benzamide,
4-[2-(4-chlorophenyl)ethoxy]-N-(2-[4-(difluoromethoxy)phenyl]-1-{[(2-hydroxyethyl)amino]carbonyl}vinyl)benzamide,
4-[2-(4-chlorophenyl)ethoxy]-N-{1-{[(2-hydroxyethyl)amino]carbonyl}-2-[4-(trifluoromethoxy)phenyl]vinyl}benzamide,
4-[2-(4-chlorophenyl)ethoxy]-N-(2-(4-cyclopropylphenyl)-1-{[(2-hydroxyethyl)amino]carbonyl}vinyl)benzamide,
4-[2-(4-chlorophenyl)ethoxy]-N-(2-(4-chlorophenyl)-1-{[(2-hydroxyethyl)amino]carbonyl}vinyl)benzamide,
4-(cyclopropylmethoxy)-N-{1-{[(2-hydroxyethyl)amino]carbonyl}-2-[4-(trifluoromethoxy)phenyl]vinyl}benzamide,
4-(cyclopropylmethoxy)-N-{1-{[(2-hydroxyethyl)amino]carbonyl}-2-[4-(trifluoromethyl)phenyl]vinyl}benzamide,
N-{1-{[(2-hydroxyethyl)amino]carbonyl}-2-[4-(trifluoromethoxy)phenyl]vinyl}-4-(4,4,4-trifluorobutoxy)benzamide,
N-{1-{[(2-hydroxyethyl)amino]carbonyl}-2-[4-(trifluoromethyl)phenyl]vinyl}-4-(4,4,4-trifluorobutoxy)benzamide,
N-{1-{[(2-hydroxyethyl)amino]carbonyl}-2-[4-(trifluoromethoxy)phenyl]vinyl}-4-(3,3,3-trifluoropropoxy)benzamide,
N-{1-{[(2-hydroxyethyl)amino]carbonyl}-2-[4-(trifluoromethyl)phenyl]vinyl}-4-(3,3,3-trifluoropropoxy)benzamide,
N-{1-{[(2,2-difluoroethyl)amino]carbonyl}-2-[4-(trifluoromethoxy)phenyl]vinyl}-4-(3,3,3-trifluoropropoxy)benzamide,
N-{1-({[(2S)-2-hydroxypropyl]amino}carbonyl)-2-[4-(trifluoromethoxy)phenyl]vinyl}-4-(3,3,3-trifluoropropoxy)benzamide,
N-(2-[4-(difluoromethoxy)phenyl]-1-{[(2-hydroxyethyl)amino]carbonyl}vinyl)-4-[4-(trifluoromethyl)phenoxy]benzamide,
N-{1-{[(2-hydroxyethyl)amino]carbonyl}-2-[4-(trifluoromethoxy)phenyl]vinyl}-4-[4-(trifluoromethyl)phenoxy]benzamide,
N-{1-{[(2-hydroxyethyl)amino]carbonyl}-2-[4-(trifluoromethyl)phenyl]vinyl}-4-[4-(trifluoromethyl)phenoxy]benzamide,
4-(4-chlorophenoxy)-N-{1-{[(2-hydroxyethyl)amino]carbonyl}-2-[4-(trifluoromethoxy)phenyl]vinyl}benzamide, and
4-(4-chlorophenoxy)-N-{1-{[(2-hydroxyethyl)amino]carbonyl}-2-[4-(trifluoromethyl)phenyl]vinyl}benzamide;
more preferably:
4-(2-cyclopropylethoxy)-N-(2-(4-ethoxyphenyl)-1-{[(2-hydroxyethyl)amino]carbonyl}vinyl)benzamide,
4-(2-cyclopropylethoxy)-N-(2-[4-(cyclopropyloxy)phenyl]-1-{[(2-hydroxyethyl)amino]carbonyl}vinyl)benzamide,
4-(2-cyclopropylethoxy)-N-(2-[4-(difluoromethoxy)phenyl]-1-{[(2-hydroxyethyl)amino]carbonyl}vinyl)benzamide,
4-(2-cyclopropylethoxy)-N-{1-{[(2-hydroxyethyl)amino]carbonyl}-2-[4-(trifluoromethoxy)phenyl]vinyl}benzamide,
4-(2-cyclopropylethoxy)-N-(2-(4-cyclopropylphenyl)-1-{[(2-hydroxyethyl)amino]carbonyl}vinyl)benzamide,
2-{[(2Z)-2-{[4-(2-cyclopropylethoxy)benzoyl]amino}-3-(4-cyclopropylphenyl)propen-2-oyl]amino}ethyl acetate,
4-(2-cyclopropylethoxy)-N-{1-{[(2-hydroxyethyl)amino]carbonyl}-2-[4-(trifluoromethyl)phenyl]vinyl}benzamide,
N-(2-(4-chlorophenyl)-1-{[(2-hydroxyethyl)amino]carbonyl}vinyl)-4-(2-cyclopropylethoxy)benzamide,
N-{1-{[(2-hydroxyethyl)amino]carbonyl}-2-[4-(trifluoromethoxy)phenyl]vinyl}-4-[2-(4-methoxyphenyl)ethoxy]benzamide,
N-(2-(4-cyclopropylphenyl)-1-{[(2-hydroxyethyl)amino]carbonyl}vinyl)-4-[2-(4-methoxyphenyl)ethoxy]benzamide,
4-[2-(4-chlorophenyl)ethoxy]-N-{1-{[(2-hydroxyethyl)amino]carbonyl}-2-[4-(trifluoromethoxy)phenyl]vinyl}benzamide,
4-[2-(4-chlorophenyl)ethoxy]-N-(2-(4-cyclopropylphenyl)-1-{[(2-hydroxyethyl)amino]carbonyl}vinyl)benzamide,
4-(cyclopropylmethoxy)-N-{1-{[(2-hydroxyethyl)amino]carbonyl}-2-[4-(trifluoromethoxy)phenyl]vinyl}benzamide,
4-(cyclopropylmethoxy)-N-{1-{[(2-hydroxyethyl)amino]carbonyl}-2-[4-(trifluoromethyl)phenyl]vinyl}benzamide,
N-{1-{[(2-hydroxyethyl)amino]carbonyl}-2-[4-(trifluoromethoxy)phenyl]vinyl}-4-(4,4,4-trifluorobutoxy)benzamide,
N-{1-{[(2-hydroxyethyl)amino]carbonyl}-2-[4-(trifluoromethyl)phenyl]vinyl}-4-(4,4,4-trifluorobutoxy)benzamide,
N-{1-{[(2-hydroxyethyl)amino]carbonyl}-2-[4-(trifluoromethoxy)phenyl]vinyl}-4-(3,3,3-trifluoropropoxy)benzamide,
N-{1-{[(2-hydroxyethyl)amino]carbonyl}-2-[4-(trifluoromethyl)phenyl]vinyl}-4-(3,3,3-trifluoropropoxy)benzamide,
N-{1-{[(2,2-difluoroethyl)amino]carbonyl}-2-[4-(trifluoromethoxy)phenyl]vinyl}-4-(3,3,3-trifluoropropoxy)benzamide, N-{1-({[(2S)-2-hydroxypropyl]amino}carbonyl)-2-[4-(trifluoromethoxy)phenyl]vinyl}-4-(3,3,3-trifluoropropoxy)benzamide, N-(2-[4-(difluoromethoxy)phenyl]-1-{[(2-hydroxyethyl)amino]carbonyl}vinyl)-4-[4-(trifluoromethyl)phenoxy]benzamide, N-{1-{[(2-hydroxyethyl)amino]carbonyl}-2-[4-(trifluoromethoxy)phenyl]vinyl}-4-[4-(trifluoromethyl)phenoxy]benzamide, N-{1-{[(2-hydroxyethyl)amino]carbonyl}-2-[4-(trifluoromethyl)phenyl]vinyl}-4-[4-(trifluoromethyl)phenoxy]benzamide, 4-(4-chlorophenoxy)-N-{1-{[(2-hydroxyethyl)amino]carbonyl}-2-[4-(trifluoromethoxy)phenyl]vinyl}benzamide, and 4-(4-chlorophenoxy)-N-{1-{[(2-hydroxyethyl)amino]carbonyl}-2-[4-(trifluoromethyl)phenyl]vinyl}benzamide.

The term "bone metabolic disease" in the present invention means diseases characterized by a substantial decrease in bone mass or an increase in blood calcium concentration and diseases that require suppression of the bone resorption or the rate of bone resorption for their prophylaxis or treatment.

Examples of such bone metabolic disease include osteoporosis, hypercalcemia, bone metastasis of cancer, periodontal diseases, bone Paget's disease, and osteoarthrosis.

The above term "osteoporosis" means a systemic disease in which, due to a decrease in bone mass, the bone microarchitecture is disrupted and the mechanical strength of bone is reduced, resulting in an increased risk of fractures. Examples of osteoporosis include postmenopausal osteoporosis, senile osteoporosis, secondary osteoporosis caused by steroid or immunosuppressive agent use, osteoclasis or osteopenia due to rheumatoid arthritis, and osteopenia due to artificial joint replacement.

The above term "treatment" means to cure or improve a disease or a symptom or to suppress a symptom.

The above term "significantly decrease blood calcium concentration" generally means to decrease the blood calcium concentration that is strictly maintained at a constant value to a level lower than a general level. The decrease ratio is preferably 0.1% or more, more preferably 0.5% or more, still more preferably 1% or more, and particularly more preferably 5% or more.

The above term "its pharmacologically acceptable salt" means a basic salt or an acid salt produced by a reaction of a compound having Formula (I) of the present invention, when the compound has an acidic group or a basic group, with a base or an acid.

The pharmacologically acceptable "basic salt" of the compound having Formula (I) of the present invention is preferably an alkali metal salt such as a sodium salt, a potassium salt, or a lithium salt; an alkaline-earth metal salt such as a magnesium salt or a calcium salt; an organic basic salt such as an N-methylmorpholine salt, a triethylamine salt, a tributylamine salt, a diisopropylethylamine salt, a dicyclohexylamine salt, an N-methylpiperidine salt, a pyridine salt, a 4-pyrrolidinopyridine salt, or a picoline salt; or an amino acid salt such as a glycine salt, a lysine salt, an alginine salt, an ornithine salt, a glutamic acid salt, or an aspartic acid salt, and preferably an alkali metal salt.

The pharmacologically acceptable "acid salt" of the compound having Formula (I) of the present invention is preferably an inorganic acid salt, for example, a hydrohalide such as hydrofluoride, hydrochloride, hydrobromide, or hydroiodide, a nitrate, a perchlorate, a sulfate, or a phosphate; an organic acid salt, for example, a lower alkanesulfonate such as a methanesulfonate, a trifluoromethanesulfonate, or an ethanesulfonate, an arylsulfonate such as a benzenesulfonate or a p-toluenesulfonate, an acetate, a malate, a fumarate, a succinate, a citrate, an ascorbate, a tartrate, an oxalate, or a maleate; or an amino acid salt such as a glycine salt, a lysine salt, an alginine salt, an ornithine salt, a glutamic acid salt, or an aspartic acid salt, and most preferably a hydrohalide.

The compound having Formula (I) or a pharmacologically acceptable salt thereof of the present invention may become a hydrate by absorbing water or being attached with water when the salt is left in the air or recrystallized, and such a hydrate is included in the present invention.

The compound having Formula (I) or a pharmacologically acceptable salt thereof of the present invention has an acrylamide structure in its molecule and thereby can be present in two regioisomers, namely, (E)-isomer and (Z)-isomer, due to the double bond. In the compound according to the present invention, both these regioisomers and mixtures thereof are represented by a single Formula (I). Therefore, the present invention includes both these regioisomers and mixtures containing the regioisomers at any proportion and preferably includes mainly the (Z)-isomer. The isomers of the mixtures can be separated by a known separation method.

The compound having Formula (I) or a pharmacologically acceptable salt thereof of the present invention has optical isomers when it has an asymmetric carbon atom in its molecule. In the compound according to the present invention, all optical isomers and mixtures thereof are represented by a single Formula (I). Therefore, the present invention includes all these optical isomers and mixtures containing the optical isomers at any proportion.

The compounds having Formula (I) of the present invention which have been labeled with an isotope (for example, $^3$H, $^{14}$C, or $^{35}$S) are also included in the present invention.

Preferred examples of the compound having Formula (I) of the present invention are compounds having Formula (I-1), (I-2), or (I-3) described in the following Tables 1, 2, and 3, but the present invention is not limited to these compounds.

In the Tables, substituents are denoted by the following abbreviations. In a substituent represented by a plurality of abbreviations, the substituent consists of the substituents denoted by the abbreviations bound to each other. For example, 2-cPrEtO denotes a 2-cyclopropylethoxy group.

| | |
|---|---|
| di | di |
| Me | methyl group |
| Et | ethyl group |
| Pr | propyl group |
| cPr | cyclopropyl group |
| iPr | isopropyl group |
| cBu | cyclobutyl group |
| iBu | isobutyl group |
| tBu | tertiary butyl group |
| Pn | pentyl group |
| cPn | cyclopentyl group |
| cHx | cyclohexyl group |
| cHp | cycloheptyl group |
| Ph | phenyl group |
| diEtN | diethylamino group |
| diMeN | dimethylamino group |
| Thi | thiophen-2-yl group |
| Pyrr | pyrrol-1-yl group |
| Ind | inden-2-yl group |
| 1-cPen | cyclopenten-1-yl group |
| 2-cPen | cyclopenten-2-yl group |
| αNp | naphthalen-1-yl group |
| βNp | naphthalen-2-yl group |
| Ac | acetyl group |
| Ada | adamantyl group |
| Bn | benzyl group |

-continued

| | |
|---|---|
| Boc | t-butoxycarbonyl group |
| Bun | 3-buten-1-yl group |
| Bz | benzoyl group |
| BDO | 2-benzo[1,3]dioxol-5-yl group |
| $CF_3Pr$ | 4,4,4-trifluorobutyl group |
| $CF_3CF_2Pr$ | 4,4,[[4]]5,5,5-pentafluoropentanyl group |
| Chr | 2,2-dimethylchroman-6-yl group |
| DDQZ | 2,4-dioxo-1,4-dihydro-2h-quinazolin-3-yl group |
| 2-DHBD | 2,3-dihydrobenzo[1,4]dioxin-2-yl group |
| 6-DHBD | 2,3-dihydrobenzo[1,4]dioxin-6-yl group |
| MEDO | methylenedioxy group |
| Fur | furan-2-yl group |
| Mor | morpholin-4-yl group |
| Phtl | phthaloyl group |
| Pip | piperidin-4-yl group |
| Piz | piperazin-1-yl group |
| Pre | 2-propen-1-yl group |
| Pry | 2-propyn-1-yl group |
| Phthiz | benzothiazol-2-yl group |
| 2-Py | pyridin-2-yl group |
| 3-Py | pyridin-3-yl group |
| 4-Py | pyridin-4-yl group |
| Pyrd | pyrrolidin-1-yl group |
| DOPyrd | 2,5-dioxopyrrolidin-1-yl group |
| Pyrr | pyrrol-1-yl group |
| Quin | quinolin-3-yl group |
| THF | tetrahydrofuran-2-yl group |
| THP | tetrahydropyran-4-yl group |
| Triz | triazol-1-yl group |

TABLE 1

Exemplary compound table 1

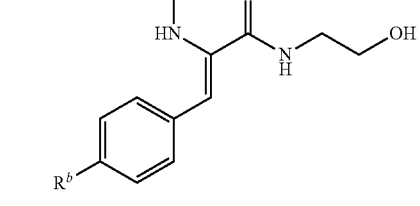

(I-1)

| Compound No. | $R^a$ | $R^b$ |
|---|---|---|
| 1-1 | iBuO | EtO |
| 1-2 | iBuO | iPrO |
| 1-3 | iBuO | cPrO |
| 1-4 | iBuO | $CHF_2O$ |
| 1-5 | iBuO | $CF_3O$ |
| 1-6 | iBuO | $CH_2FCH_2O$ |
| 1-7 | iBuO | $CHF_2CH_2O$ |
| 1-8 | iBuO | $CF_3CH_2O$ |
| 1-9 | iBuO | $CHF_2CF_2O$ |
| 1-10 | iBuO | Et |
| 1-11 | iBuO | iPr |
| 1-12 | iBuO | cPr |
| 1-13 | iBuO | $CF_3$ |
| 1-14 | iBuO | 1-cPen |
| 1-15 | iBuO | MeS |
| 1-16 | iBuO | EtS |
| 1-17 | iBuO | $CF_3S$ |
| 1-18 | iBuO | Pyrr |
| 1-19 | iBuO | Ph |
| 1-20 | iBuO | H |
| 1-21 | iBuO | F |
| 1-22 | iBuO | $NO_2$ |
| 1-23 | iBuO | CN |
| 1-24 | iBuO | iBu |
| 1-25 | iBuO | Ac |
| 1-26 | iBuO | cHx |
| 1-27 | iBuO | tBu |
| 1-28 | iBuO | 4-FPh |
| 1-29 | iBuO | 4-Py |
| 1-30 | iBuO | 3-Py |
| 1-31 | iBuO | 2-Py |
| 1-32 | iBuO | Triz |
| 1-33 | iBuO | AcNH |
| 1-34 | iBuO | diMeN |
| 1-35 | iBuO | diEtN |
| 1-36 | iBuO | Mor |
| 1-37 | iBuO | 2,5-diMePyrr |
| 1-38 | iBuO | $MeSO_2$ |
| 1-39 | iBuO | HO |
| 1-40 | iBuO | MeO |
| 1-41 | iBuO | PhO |
| 1-42 | iBuO | cBuO |
| 1-43 | iBuO | cPnO |
| 1-44 | iBuO | cHxO |
| 1-45 | iBuO | cHpO |
| 1-46 | iBuO | cHxMeO |
| 1-47 | iBuO | PrO |
| 1-48 | iBuO | tBuO |
| 1-49 | iBuO | iBuO |
| 1-50 | iBuO | cPrMeO |
| 1-51 | iBuO | 1-cPrEtO |
| 1-52 | iBuO | di($CH_2F$)CHO |
| 1-53 | iBuO | 1-$CF_3$EtO |
| 1-54 | iBuO | 2-$CF_3$EtO |
| 1-55 | iBuO | BnO |
| 1-56 | iBuO | Cl |
| 1-57 | iBuO | Br |
| 1-58 | 2-cPrEtO | EtO |
| 1-59 | 2-cPrEtO | iPrO |
| 1-60 | 2-cPrEtO | cPrO |
| 1-61 | 2-cPrEtO | $CHF_2O$ |
| 1-62 | 2-cPrEtO | $CF_3O$ |
| 1-63 | 2-cPrEtO | $CH_2FCH_2O$ |
| 1-64 | 2-cPrEtO | $CHF_2CH_2O$ |
| 1-65 | 2-cPrEtO | $CF_3CH_2O$ |
| 1-66 | 2-cPrEtO | Et |
| 1-67 | 2-cPrEtO | iPr |
| 1-68 | 2-cPrEtO | cPr |
| 1-69 | 2-cPrEtO | $CF_3$ |
| 1-70 | 2-cPrEtO | 1-cPen |
| 1-71 | 2-cPrEtO | MeS |
| 1-72 | 2-cPrEtO | Pyrr |
| 1-73 | 2-cPrEtO | Ph |
| 1-74 | 2-cPrEtO | H |
| 1-75 | 2-cPrEtO | F |
| 1-76 | 2-cPrEtO | $NO_2$ |
| 1-77 | 2-cPrEtO | CN |
| 1-78 | 2-cPrEtO | iBu |
| 1-79 | 2-cPrEtO | Ac |
| 1-80 | 2-cPrEtO | cHx |
| 1-81 | 2-cPrEtO | tBu |
| 1-82 | 2-cPrEtO | 4-FPh |
| 1-83 | 2-cPrEtO | 4-Py |

TABLE 1-continued

Exemplary compound table 1

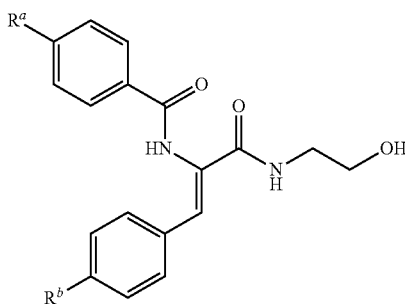

(I-1)

| Compound No. | $R^a$ | $R^b$ |
|---|---|---|
| 1-84 | 2-cPrEtO | 3-Py |
| 1-85 | 2-cPrEtO | 2-Py |
| 1-86 | 2-cPrEtO | Triz |
| 1-87 | 2-cPrEtO | AcNH |
| 1-88 | 2-cPrEtO | diMeN |
| 1-89 | 2-cPrEtO | diEtN |
| 1-90 | 2-cPrEtO | Mor |
| 1-91 | 2-cPrEtO | 2,5-diMePyrr |
| 1-92 | 2-cPrEtO | MeSO$_2$ |
| 1-93 | 2-cPrEtO | HO |
| 1-94 | 2-cPrEtO | MeO |
| 1-95 | 2-cPrEtO | PhO |
| 1-96 | 2-cPrEtO | cBuO |
| 1-97 | 2-cPrEtO | cPnO |
| 1-98 | 2-cPrEtO | cHxO |
| 1-99 | 2-cPrEtO | cHpO |
| 1-100 | 2-cPrEtO | cHxMeO |
| 1-101 | 2-cPrEtO | PrO |
| 1-102 | 2-cPrEtO | tBuO |
| 1-103 | 2-cPrEtO | iBuO |
| 1-104 | 2-cPrEtO | cPrMeO |
| 1-105 | 2-cPrEtO | 1-cPrEtO |
| 1-106 | 2-cPrEtO | di(CH$_2$F)CHO |
| 1-107 | 2-cPrEtO | 1-CF$_3$EtO |
| 1-108 | 2-cPrEtO | BnO |
| 1-109 | 2-cPrEtO | Cl |
| 1-110 | 2-cPrEtO | Br |
| 1-111 | 2-PhEtO | EtO |
| 1-112 | 2-PhEtO | iPrO |
| 1-113 | 2-PhEtO | cPrO |
| 1-114 | 2-PhEtO | CHF$_2$O |
| 1-115 | 2-PhEtO | CF$_3$O |
| 1-116 | 2-PhEtO | CH$_2$FCH$_2$O |
| 1-117 | 2-PhEtO | CHF$_2$CH$_2$O |
| 1-118 | 2-PhEtO | CF$_3$CH$_2$O |
| 1-119 | 2-PhEtO | Et |
| 1-120 | 2-PhEtO | iPr |
| 1-121 | 2-PhEtO | cPr |
| 1-122 | 2-PhEtO | CF$_3$ |
| 1-123 | 2-PhEtO | 1-cPen |
| 1-124 | 2-PhEtO | MeS |
| 1-125 | 2-PhEtO | Pyrr |
| 1-126 | 2-PhEtO | Ph |
| 1-127 | 2-PhEtO | Cl |
| 1-128 | 2-(4-MeOPh)EtO | EtO |
| 1-129 | 2-(4-MeOPh)EtO | iPrO |
| 1-130 | 2-(4-MeOPh)EtO | cPrO |
| 1-131 | 2-(4-MeOPh)EtO | CHF$_2$O |
| 1-132 | 2-(4-MeOPh)EtO | CF$_3$O |
| 1-133 | 2-(4-MeOPh)EtO | CH$_2$FCH$_2$O |
| 1-134 | 2-(4-MeOPh)EtO | CHF$_2$CH$_2$O |
| 1-135 | 2-(4-MeOPh)EtO | CF$_3$CH$_2$O |
| 1-136 | 2-(4-MeOPh)EtO | Et |
| 1-137 | 2-(4-MeOPh)EtO | iPr |
| 1-138 | 2-(4-MeOPh)EtO | cPr |
| 1-139 | 2-(4-MeOPh)EtO | CF$_3$ |
| 1-140 | 2-(4-MeOPh)EtO | 1-cPen |
| 1-141 | 2-(4-MeOPh)EtO | MeS |
| 1-142 | 2-(4-MeOPh)EtO | Pyrr |

TABLE 1-continued

Exemplary compound table 1

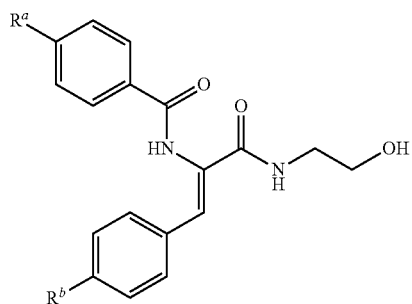

(I-1)

| Compound No. | $R^a$ | $R^b$ |
|---|---|---|
| 1-143 | 2-(4-MeOPh)EtO | Ph |
| 1-144 | 2-(4-MeOPh)EtO | Cl |
| 1-145 | 2-(3-MeOPh)EtO | EtO |
| 1-146 | 2-(3-MeOPh)EtO | iPrO |
| 1-147 | 2-(3-MeOPh)EtO | cPrO |
| 1-148 | 2-(3-MeOPh)EtO | CHF$_2$O |
| 1-149 | 2-(3-MeOPh)EtO | CF$_3$O |
| 1-150 | 2-(3-MeOPh)EtO | CH$_2$FCH$_2$O |
| 1-151 | 2-(3-MeOPh)EtO | CHF$_2$CH$_2$O |
| 1-152 | 2-(3-MeOPh)EtO | CF$_3$CH$_2$O |
| 1-153 | 2-(3-MeOPh)EtO | Et |
| 1-154 | 2-(3-MeOPh)EtO | iPr |
| 1-155 | 2-(3-MeOPh)EtO | cPr |
| 1-156 | 2-(3-MeOPh)EtO | CF$_3$ |
| 1-157 | 2-(3-MeOPh)EtO | 1-cPen |
| 1-158 | 2-(3-MeOPh)EtO | MeS |
| 1-159 | 2-(3-MeOPh)EtO | Pyrr |
| 1-160 | 2-(3-MeOPh)EtO | Ph |
| 1-161 | 2-(3-MeOPh)EtO | Cl |
| 1-162 | 2-(4-diMeNPh)EtO | EtO |
| 1-163 | 2-(4-diMeNPh)EtO | iPrO |
| 1-164 | 2-(4-diMeNPh)EtO | cPrO |
| 1-165 | 2-(4-diMeNPh)EtO | CHF$_2$O |
| 1-166 | 2-(4-diMeNPh)EtO | CF$_3$O |
| 1-167 | 2-(4-diMeNPh)EtO | CH$_2$FCH$_2$O |
| 1-168 | 2-(4-diMeNPh)EtO | CHF$_2$CH$_2$O |
| 1-169 | 2-(4-diMeNPh)EtO | CF$_3$CH$_2$O |
| 1-170 | 2-(4-diMeNPh)EtO | Et |
| 1-171 | 2-(4-diMeNPh)EtO | iPr |
| 1-172 | 2-(4-diMeNPh)EtO | cPr |
| 1-173 | 2-(4-diMeNPh)EtO | CF$_3$ |
| 1-174 | 2-(4-diMeNPh)EtO | 1-cPen |
| 1-175 | 2-(4-diMeNPh)EtO | MeS |
| 1-176 | 2-(4-diMeNPh)EtO | Pyrr |
| 1-177 | 2-(4-diMeNPh)EtO | Ph |
| 1-178 | 2-(4-diMeNPh)EtO | Cl |
| 1-179 | 2-(3-diMeNPh)EtO | EtO |
| 1-180 | 2-(3-diMeNPh)EtO | iPrO |
| 1-181 | 2-(3-diMeNPh)EtO | cPrO |
| 1-182 | 2-(3-diMeNPh)EtO | CHF$_2$O |
| 1-183 | 2-(3-diMeNPh)EtO | CF$_3$O |
| 1-184 | 2-(3-diMeNPh)EtO | CH$_2$FCH$_2$O |
| 1-185 | 2-(3-diMeNPh)EtO | CHF$_2$CH$_2$O |
| 1-186 | 2-(3-diMeNPh)EtO | CF$_3$CH$_2$O |
| 1-187 | 2-(3-diMeNPh)EtO | Et |
| 1-188 | 2-(3-diMeNPh)EtO | iPr |
| 1-189 | 2-(3-diMeNPh)EtO | cPr |
| 1-190 | 2-(3-diMeNPh)EtO | CF$_3$ |
| 1-191 | 2-(3-diMeNPh)EtO | 1-cPen |
| 1-192 | 2-(3-diMeNPh)EtO | MeS |
| 1-193 | 2-(3-diMeNPh)EtO | Pyrr |
| 1-194 | 2-(3-diMeNPh)EtO | Ph |
| 1-195 | 2-(3-diMeNPh)EtO | Cl |
| 1-196 | 2-(4-ClPh)EtO | EtO |
| 1-197 | 2-(4-ClPh)EtO | iPrO |
| 1-198 | 2-(4-ClPh)EtO | cPrO |
| 1-199 | 2-(4-ClPh)EtO | CHF$_2$O |
| 1-200 | 2-(4-ClPh)EtO | CF$_3$O |
| 1-201 | 2-(4-ClPh)EtO | CH$_2$FCH$_2$O |

TABLE 1-continued

Exemplary compound table 1

(I-1)

| Compound No. | $R^a$ | $R^b$ |
|---|---|---|
| 1-202 | 2-(4-ClPh)EtO | CHF$_2$CH$_2$O |
| 1-203 | 2-(4-ClPh)EtO | CF$_3$CH$_2$O |
| 1-204 | 2-(4-ClPh)EtO | Et |
| 1-205 | 2-(4-ClPh)EtO | iPr |
| 1-206 | 2-(4-ClPh)EtO | cPr |
| 1-207 | 2-(4-ClPh)EtO | CF$_3$ |
| 1-208 | 2-(4-ClPh)EtO | 1-cPen |
| 1-209 | 2-(4-ClPh)EtO | MeS |
| 1-210 | 2-(4-ClPh)EtO | Pyrr |
| 1-211 | 2-(4-ClPh)EtO | Ph |
| 1-212 | 2-(4-ClPh)EtO | Cl |
| 1-213 | 2-(4-FPh)EtO | EtO |
| 1-214 | 2-(4-FPh)EtO | iPrO |
| 1-215 | 2-(4-FPh)EtO | cPrO |
| 1-216 | 2-(4-FPh)EtO | CHF$_2$O |
| 1-217 | 2-(4-FPh)EtO | CF$_3$O |
| 1-218 | 2-(4-FPh)EtO | CH$_2$FCH$_2$O |
| 1-219 | 2-(4-FPh)EtO | CHF$_2$CH$_2$O |
| 1-220 | 2-(4-FPh)EtO | CF$_3$CH$_2$O |
| 1-221 | 2-(4-FPh)EtO | Et |
| 1-222 | 2-(4-FPh)EtO | iPr |
| 1-223 | 2-(4-FPh)EtO | cPr |
| 1-224 | 2-(4-FPh)EtO | CF$_3$ |
| 1-225 | 2-(4-FPh)EtO | 1-cPen |
| 1-226 | 2-(4-FPh)EtO | MeS |
| 1-227 | 2-(4-FPh)EtO | Pyrr |
| 1-228 | 2-(4-FPh)EtO | Ph |
| 1-229 | 2-(4-FPh)EtO | Cl |
| 1-230 | 2-(4-cPrPh)EtO | EtO |
| 1-231 | 2-(4-cPrPh)EtO | iPrO |
| 1-232 | 2-(4-cPrPh)EtO | cPrO |
| 1-233 | 2-(4-cPrPh)EtO | CHF$_2$O |
| 1-234 | 2-(4-cPrPh)EtO | CF$_3$O |
| 1-235 | 2-(4-cPrPh)EtO | CH$_2$FCH$_2$O |
| 1-236 | 2-(4-cPrPh)EtO | CHF$_2$CH$_2$O |
| 1-237 | 2-(4-cPrPh)EtO | CF$_3$CH$_2$O |
| 1-238 | 2-(4-cPrPh)EtO | Et |
| 1-239 | 2-(4-cPrPh)EtO | iPr |
| 1-240 | 2-(4-cPrPh)EtO | cPr |
| 1-241 | 2-(4-cPrPh)EtO | CF$_3$ |
| 1-242 | 2-(4-cPrPh)EtO | 1-cPen |
| 1-243 | 2-(4-cPrPh)EtO | MeS |
| 1-244 | 2-(4-cPrPh)EtO | Pyrr |
| 1-245 | 2-(4-cPrPh)EtO | Ph |
| 1-246 | 2-(4-cPrPh)EtO | Cl |
| 1-247 | cBuMeO | EtO |
| 1-248 | cBuMeO | iPrO |
| 1-249 | cBuMeO | cPrO |
| 1-250 | cBuMeO | CHF$_2$O |
| 1-251 | cBuMeO | CF$_3$O |
| 1-252 | cBuMeO | CH$_2$FCH$_2$O |
| 1-253 | cBuMeO | CHF$_2$CH$_2$O |
| 1-254 | cBuMeO | CF$_3$CH$_2$O |
| 1-255 | cBuMeO | Et |
| 1-256 | cBuMeO | iPr |
| 1-257 | cBuMeO | cPr |
| 1-258 | cBuMeO | CF$_3$ |
| 1-259 | cBuMeO | MeS |
| 1-260 | 3-cPrPrO | EtO |
| 1-261 | 3-cPrPrO | iPrO |
| 1-262 | 3-cPrPrO | cPrO |
| 1-263 | 3-cPrPrO | CHF$_2$O |
| 1-264 | 3-cPrPrO | CF$_3$O |
| 1-265 | 3-cPrPrO | CH$_2$FCH$_2$O |
| 1-266 | 3-cPrPrO | CHF$_2$CH$_2$O |
| 1-267 | 3-cPrPrO | CF$_3$CH$_2$O |
| 1-268 | 3-cPrPrO | Et |
| 1-269 | 3-cPrPrO | iPr |
| 1-270 | 3-cPrPrO | cPr |
| 1-271 | 3-cPrPrO | CF$_3$ |
| 1-272 | 3-cPrPrO | MeS |
| 1-273 | 3-cPrPrO | Cl |
| 1-274 | 2-CF$_3$EtO | iPrO |
| 1-275 | 2-CF$_3$EtO | cPrO |
| 1-276 | 2-CF$_3$EtO | CHF$_2$O |
| 1-277 | 2-CF$_3$EtO | CF$_3$O |
| 1-278 | 2-CF$_3$EtO | iPr |
| 1-279 | 2-CF$_3$EtO | cPr |
| 1-280 | 2-CF$_3$EtO | CF$_3$ |
| 1-281 | 2-CF$_3$EtO | MeS |
| 1-282 | 2-CF$_3$EtO | Cl |
| 1-283 | 2-ThiEtO | iPrO |
| 1-284 | 2-ThiEtO | cPrO |
| 1-285 | 2-ThiEtO | CHF$_2$O |
| 1-286 | 2-ThiEtO | CF$_3$O |
| 1-287 | 2-ThiEtO | iPr |
| 1-288 | 2-ThiEtO | cPr |
| 1-289 | 2-ThiEtO | CF$_3$ |
| 1-290 | 2-ThiEtO | MeS |
| 1-291 | 2-ThiEtO | Cl |
| 1-292 | 2-PyrrEtO | iPrO |
| 1-293 | 2-PyrrEtO | cPrO |
| 1-294 | 2-PyrrEtO | CHF$_2$O |
| 1-295 | 2-PyrrEtO | CF$_3$O |
| 1-296 | 2-PyrrEtO | iPr |
| 1-297 | 2-PyrrEtO | cPr |
| 1-298 | 2-PyrrEtO | CF$_3$ |
| 1-299 | 2-PyrrEtO | MeS |
| 1-300 | 2-PyrrEtO | Cl |
| 1-301 | 3-PhPrO | iPrO |
| 1-302 | 3-PhPrO | iPr |
| 1-303 | 3-PhPrO | cPrO |
| 1-304 | 3-PhPrO | cPr |
| 1-305 | 3-PhPrO | CF$_3$O |
| 1-306 | 3-PhPrO | CF$_3$ |
| 1-307 | 4-PhBuO | iPrO |
| 1-308 | 4-PhBuO | iPr |
| 1-309 | 4-PhBuO | cPrO |
| 1-310 | 4-PhBuO | cPr |
| 1-311 | 4-PhBuO | CF$_3$O |
| 1-312 | 4-PhBuO | CF$_3$ |
| 1-313 | 2-PhOEtO | iPrO |
| 1-314 | 2-PhOEtO | iPr |
| 1-315 | 2-PhOEtO | cPrO |
| 1-316 | 2-PhOEtO | cPr |
| 1-317 | 2-PhOEtO | CF$_3$O |
| 1-318 | 2-PhOEtO | CF$_3$ |
| 1-319 | 2-PhOEtO | CHF$_2$O |

TABLE 1-continued

Exemplary compound table 1

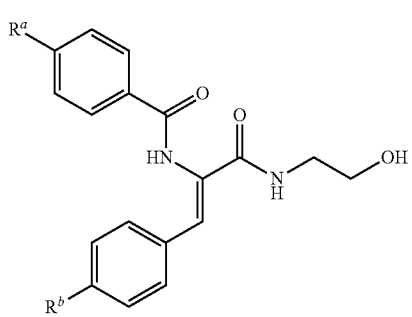

(I-1)

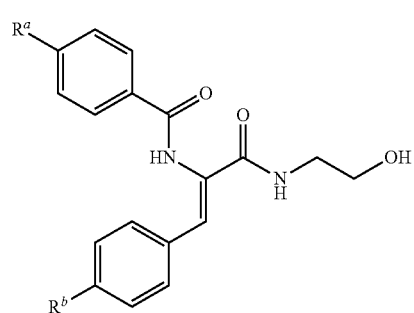

(I-1)

| Compound No. | $R^a$ | $R^b$ |
|---|---|---|
| 1-320 | 2-PhOEtO | CHF$_2$CH$_2$O |
| 1-321 | 2-PhOEtO | MeS |
| 1-322 | 2-PhOEtO | Cl |
| 1-323 | 3-cPrPrO | iPrO |
| 1-324 | 3-cPrPrO | iPr |
| 1-325 | 3-cPrPrO | cPrO |
| 1-326 | 3-cPrPrO | cPr |
| 1-327 | 3-cPrPrO | CF$_3$O |
| 1-328 | 3-cPrPrO | CF$_3$ |
| 1-329 | 3-cPrPrO | CHF$_2$O |
| 1-330 | 3-cPrPrO | CHF$_2$CH$_2$O |
| 1-331 | BDOEtO | iPrO |
| 1-332 | BDOEtO | iPr |
| 1-333 | BDOEtO | cPrO |
| 1-334 | BDOEtO | cPr |
| 1-335 | 4-EtPhO | iPrO |
| 1-336 | 4-EtPhO | iPr |
| 1-337 | 4-EtPhO | cPrO |
| 1-338 | 4-EtPhO | cPr |
| 1-339 | 4-EtPhO | CF$_3$O |
| 1-340 | 4-EtPhO | CF$_3$ |
| 1-341 | IndMeO | iPrO |
| 1-342 | IndMeO | cPrO |
| 1-343 | IndMeO | CF$_3$O |
| 1-344 | 2-(2-cPen)EtO | iPrO |
| 1-345 | 2-(2-cPen)EtO | cPrO |
| 1-346 | 2-(2-cPen)EtO | CF$_3$O |
| 1-347 | 2-PhPrO | iPrO |
| 1-348 | 2-PhPrO | cPrO |
| 1-349 | 2-PhPrO | CF$_3$O |
| 1-350 | 4-cPrBuO | iPrO |
| 1-351 | 4-cPrBuO | cPrO |
| 1-352 | 4-cPrBuO | CF$_3$O |
| 1-353 | 2-(βNp)EtO | iPrO |
| 1-354 | 2-(βNp)EtO | cPrO |
| 1-355 | 2-(βNp)EtO | CF$_3$O |
| 1-356 | 2-(3-CF$_3$Ph)EtO | iPrO |
| 1-357 | 2-(3-CF$_3$Ph)EtO | cPrO |
| 1-358 | 2-(3-CF$_3$Ph)EtO | CF$_3$O |
| 1-359 | 2-(2-FPh)EtO | iPrO |
| 1-360 | 2-(2-FPh)EtO | cPrO |
| 1-361 | 2-(2-FPh)EtO | CF$_3$O |
| 1-362 | 2-(4-CNPh)EtO | iPrO |
| 1-363 | 2-(4-CNPh)EtO | cPrO |
| 1-364 | 2-(4-CNPh)EtO | CF$_3$O |
| 1-365 | 2-(4-CF$_3$Ph)EtO | iPrO |
| 1-366 | 2-(4-CF$_3$Ph)EtO | cPrO |
| 1-367 | 2-(4-CF$_3$Ph)EtO | CF$_3$O |
| 1-368 | 2-(4-MePh)EtO | iPrO |
| 1-369 | 2-(4-MePh)EtO | cPrO |
| 1-370 | 2-(4-MePh)EtO | CF$_3$O |
| 1-371 | 2-(4-iPrOPh)EtO | iPrO |
| 1-372 | 2-(4-iPrOPh)EtO | cPrO |
| 1-373 | 2-(4-iPrOPh)EtO | CF$_3$O |
| 1-374 | H | iPrO |
| 1-375 | H | cPrO |
| 1-376 | H | CF$_3$O |
| 1-377 | NO$_2$ | iPrO |
| 1-378 | NO$_2$ | cPrO |
| 1-379 | NO$_2$ | CF$_3$O |
| 1-380 | CN | iPrO |
| 1-381 | CN | cPrO |
| 1-382 | CN | CF$_3$O |
| 1-383 | diMeN | iPrO |
| 1-384 | diMeN | cPrO |
| 1-385 | diMeN | CF$_3$O |
| 1-386 | F | iPrO |
| 1-387 | F | cPrO |
| 1-388 | F | CF$_3$O |
| 1-389 | CF$_3$ | iPrO |
| 1-390 | CF$_3$ | cPrO |
| 1-391 | CF$_3$ | CF$_3$O |
| 1-392 | Bn | iPrO |
| 1-393 | Bn | cPrO |
| 1-394 | Bn | CF$_3$O |
| 1-395 | Ph | iPrO |
| 1-396 | Ph | cPrO |
| 1-397 | Ph | CF$_3$O |
| 1-398 | iBu | iPrO |
| 1-399 | iBu | cPrO |
| 1-400 | iBu | CF$_3$O |
| 1-401 | Bu | iPrO |
| 1-402 | Bu | cPrO |
| 1-403 | Bu | CF$_3$O |
| 1-404 | 1-cPen | iPrO |
| 1-405 | 1-cPen | cPrO |
| 1-406 | 1-cPen | CF$_3$O |
| 1-407 | cHx | iPrO |
| 1-408 | cHx | cPrO |
| 1-409 | cHx | CF$_3$O |
| 1-410 | Bz | iPrO |
| 1-411 | Bz | cPrO |
| 1-412 | Bz | CF$_3$O |
| 1-413 | iPrO | iPrO |
| 1-414 | iPrO | cPrO |
| 1-415 | iPrO | CF$_3$O |
| 1-416 | tBuO | iPrO |
| 1-417 | tBuO | cPrO |
| 1-418 | tBuO | CF$_3$O |
| 1-419 | 1-cPrEtO | iPrO |
| 1-420 | 1-cPrEtO | cPrO |
| 1-421 | 1-cPrEtO | CF$_3$O |
| 1-422 | 1-cPnEtO | iPrO |
| 1-423 | 1-cPnEtO | cPrO |
| 1-424 | 1-cPnEtO | CF$_3$O |
| 1-425 | 1-PhEtO | iPrO |
| 1-426 | 1-PhEtO | cPrO |
| 1-427 | 1-PhEtO | CF$_3$O |
| 1-428 | THPO | iPrO |
| 1-429 | THPO | cPrO |
| 1-430 | THPO | CF$_3$O |
| 1-431 | cHxO | iPrO |
| 1-432 | cHxO | cPrO |
| 1-433 | cHxO | CF$_3$O |
| 1-434 | cHxO | cPr |
| 1-435 | cPnO | iPrO |
| 1-436 | cPnO | cPrO |
| 1-437 | cPnO | CF$_3$O |

TABLE 1-continued

Exemplary compound table 1

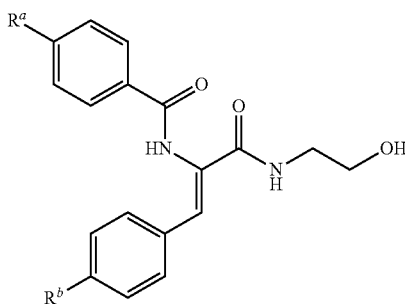

(I-1)

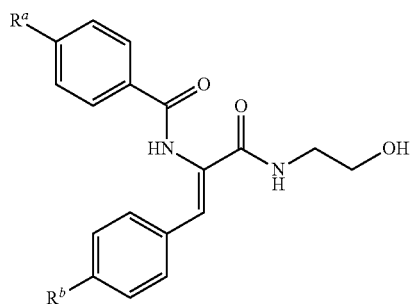

(I-1)

| Compound No. | $R^a$ | $R^b$ |
|---|---|---|
| 1-438 | cPrMeO | iPrO |
| 1-439 | cPrMeO | cPrO |
| 1-440 | cPrMeO | CF$_3$O |
| 1-441 | (1-Me-cPr)MeO | iPrO |
| 1-442 | (1-Me-cPr)MeO | cPrO |
| 1-443 | (1-Me-cPr)MeO | CF$_3$O |
| 1-444 | (1-Ph-cPr)MeO | iPrO |
| 1-445 | (1-Ph-cPr)MeO | cPrO |
| 1-446 | (1-Ph-cPr)MeO | CF$_3$O |
| 1-447 | cBuMeO | iPrO |
| 1-448 | cBuMeO | cPrO |
| 1-449 | cBuMeO | CF$_3$O |
| 1-450 | cPnMeO | iPrO |
| 1-451 | cPnMeO | cPrO |
| 1-452 | cPnMeO | CF$_3$O |
| 1-453 | cPnMeO | cPr |
| 1-454 | cHxMeO | iPrO |
| 1-455 | cHxMeO | cPrO |
| 1-456 | cHxMeO | CF$_3$O |
| 1-457 | (1-Me-cHx)MeO | iPrO |
| 1-458 | (1-Me-cHx)MeO | cPrO |
| 1-459 | (1-Me-cHx)MeO | CF$_3$O |
| 1-460 | AdaMeO | iPrO |
| 1-461 | AdaMeO | cPrO |
| 1-462 | AdaMeO | CF$_3$O |
| 1-463 | cHpMeO | iPrO |
| 1-464 | cHpMeO | cPrO |
| 1-465 | cHpMeO | CF$_3$O |
| 1-466 | 2-cPnEtO | iPrO |
| 1-467 | 2-cPnEtO | cPrO |
| 1-468 | 2-cPnEtO | CHF$_2$O |
| 1-469 | 2-cPnEtO | CHF$_2$CH$_2$O |
| 1-470 | 2-cPnEtO | CF$_3$ |
| 1-471 | 2-cPnEtO | cPr |
| 1-472 | 2-cPnEtO | Mes |
| 1-473 | 2-(1-cPen)EtO | iPrO |
| 1-474 | 2-(1-cPen)EtO | cPrO |
| 1-475 | 2-(1-cPen)EtO | CF$_3$O |
| 1-476 | 2-(1-cPen)EtO | cPr |
| 1-477 | 2-cHxEtO | iPrO |
| 1-478 | 2-cHxEtO | cPrO |
| 1-479 | 2-cHxEtO | CF$_3$O |
| 1-480 | 2-cHxPrO | iPrO |
| 1-481 | 2-cHxPrO | cPrO |
| 1-482 | 2-cHxPrO | CF$_3$O |
| 1-483 | CHF$_2$O | iPrO |
| 1-484 | CHF$_2$O | cPrO |
| 1-485 | CHF$_2$O | CF$_3$O |
| 1-486 | CF$_3$O | iPrO |
| 1-487 | CF$_3$O | cPrO |
| 1-488 | CF$_3$O | CF$_3$O |
| 1-489 | CF$_3$CH$_2$O | iPrO |
| 1-490 | CF$_3$CH$_2$O | cPrO |
| 1-491 | CF$_3$CH$_2$O | CF$_3$O |
| 1-492 | CH$_2$FCH$_2$O | iPrO |
| 1-493 | CH$_2$FCH$_2$O | cPrO |
| 1-494 | CH$_2$FCH$_2$O | CF$_3$O |
| 1-495 | CHF$_2$CF$_2$O | iPrO |
| 1-496 | CHF$_2$CF$_2$O | cPrO |
| 1-497 | CHF$_2$CF$_2$O | CF$_3$O |
| 1-498 | 3-FPrO | iPrO |
| 1-499 | 3-FPrO | cPrO |
| 1-500 | 3-FPrO | CF$_3$O |
| 1-501 | CHF$_2$CF$_2$CH$_2$O | iPrO |
| 1-502 | CHF$_2$CF$_2$CH$_2$O | cPrO |
| 1-503 | CHF$_2$CF$_2$CH$_2$O | CF$_3$O |
| 1-504 | 3-CF$_3$PrO | iPrO |
| 1-505 | 3-CF$_3$PrO | cPrO |
| 1-506 | 3-CF$_3$PrO | CF$_3$O |
| 1-507 | 3-CF$_3$CF$_2$PrO | iPrO |
| 1-508 | 3-CF$_3$CF$_2$PrO | cPrO |
| 1-509 | 3-CF$_3$CF$_2$PrO | CF$_3$O |
| 1-510 | MeO | iPrO |
| 1-511 | MeO | cPrO |
| 1-512 | MeO | CF$_3$O |
| 1-513 | PhO | iPrO |
| 1-514 | PhO | cPrO |
| 1-515 | PhO | CHF$_2$O |
| 1-516 | PhO | CF$_3$O |
| 1-517 | 4-CF$_3$PhO | iPrO |
| 1-518 | 4-CF$_3$PhO | cPrO |
| 1-519 | 4-CF$_3$PhO | CF$_3$O |
| 1-520 | BnO | iPrO |
| 1-521 | BnO | cPrO |
| 1-522 | BnO | CF$_3$O |
| 1-523 | 3-PhPreO | iPrO |
| 1-524 | 3-PhPreO | cPrO |
| 1-525 | 3-PhPreO | CF$_3$O |
| 1-526 | 3-PhPryO | iPrO |
| 1-527 | 3-PhPryO | cPrO |
| 1-528 | 3-PhPryO | CF$_3$O |
| 1-529 | 5-PhPnO | iPrO |
| 1-530 | 5-PhPnO | cPrO |
| 1-531 | 5-PhPnO | CF$_3$O |
| 1-532 | βNpMeO | iPrO |
| 1-533 | βNpMeO | cPrO |
| 1-534 | βNpMeO | CF$_3$O |
| 1-535 | αNpMeO | iPrO |
| 1-536 | αNpMeO | cPrO |
| 1-537 | αNpMeO | CF$_3$O |
| 1-538 | PhthizMeO | iPrO |
| 1-539 | PhthizMeO | cPrO |
| 1-540 | PhthizMeO | CF$_3$O |
| 1-541 | 2-(αNp)EtO | iPrO |
| 1-542 | 2-(αNp)EtO | cPrO |
| 1-543 | 2-(αNp)EtO | CF$_3$O |
| 1-544 | 2-(3,4-DiMeOPh)EtO | iPrO |
| 1-545 | 2-(3,4-DiMeOPh)EtO | cPrO |
| 1-546 | 2-(3,4-DiMeOPh)EtO | CF$_3$O |
| 1-547 | 2-(2-CF$_3$Ph)EtO | iPrO |
| 1-548 | 2-(2-CF$_3$Ph)EtO | cPrO |
| 1-549 | 2-(2-CF$_3$Ph)EtO | CF$_3$O |
| 1-550 | 2-(2-Cl-4-FPh)EtO | iPrO |
| 1-551 | 2-(2-Cl-4-FPh)EtO | cPrO |
| 1-552 | 2-(2-Cl-4-FPh)EtO | CF$_3$O |
| 1-553 | 2-(4-iPrOPh)EtO | iPrO |
| 1-554 | 2-(4-iPrOPh)EtO | cPrO |
| 1-555 | 2-(4-iPrOPh)EtO | CF$_3$O |

TABLE 1-continued

Exemplary compound table 1

(I-1)

Structure: 4-R$^a$-benzoyl-NH-C(=CH-C$_6$H$_4$-R$^b$)-C(=O)-NH-CH$_2$CH$_2$OH

| Compound No. | R$^a$ | R$^b$ |
|---|---|---|
| 1-556 | 2-(4-tBuPh)EtO | iPrO |
| 1-557 | 2-(4-tBuPh)EtO | cPrO |
| 1-558 | 2-(4-tBuPh)EtO | CF$_3$O |
| 1-559 | 3-(4-CF$_3$Ph)PrO | iPrO |
| 1-560 | 3-(4-CF$_3$Ph)PrO | cPrO |
| 1-561 | 3-(4-CF$_3$Ph)PrO | CF$_3$O |
| 1-562 | 3-(3,4-diMeOPh)PrO | iPrO |
| 1-563 | 3-(3,4-diMeOPh)PrO | cPrO |
| 1-564 | 3-(3,4-diMeOPh)PrO | CF$_3$O |
| 1-565 | 3-(3-Py)PrO | iPrO |
| 1-566 | 3-(3-Py)PrO | cPrO |
| 1-567 | 3-(3-Py)PrO | CF$_3$O |
| 1-568 | 3-(4-Py)PrO | iPrO |
| 1-569 | 3-(4-Py)PrO | cPrO |
| 1-570 | 3-(4-Py)PrO | CF$_3$O |
| 1-571 | 2-PyrrEtO | iPrO |
| 1-572 | 2-PyrrEtO | cPrO |
| 1-573 | 2-PyrrEtO | CF$_3$O |
| 1-574 | 3-PyrrEtO | iPrO |
| 1-575 | 3-PyrrEtO | cPrO |
| 1-576 | 3-PyrrEtO | CF$_3$O |
| 1-577 | 2-DOPyrdEtO | iPrO |
| 1-578 | 2-DOPyrdEtO | cPrO |
| 1-579 | 2-DOPyrdEtO | CF$_3$O |
| 1-580 | 2-PyrdEtO | iPrO |
| 1-581 | 2-PyrdEtO | cPrO |
| 1-582 | 2-PyrdEtO | CF$_3$O |
| 1-583 | 2-(N-Ac-N-PhN)EtO | iPrO |
| 1-584 | 2-(N-Ac-N-PhN)EtO | cPrO |
| 1-585 | 2-(N-Ac-N-PhN)EtO | CF$_3$O |
| 1-586 | 2-iBuOEtO | iPrO |
| 1-587 | 2-iBuOEtO | cPrO |
| 1-588 | 2-iBuOEtO | CF$_3$O |
| 1-589 | 2-cPrMeOEtO | iPrO |
| 1-590 | 2-cPrMeOEtO | cPrO |
| 1-591 | 2-cPrMeOEtO | CF$_3$O |
| 1-592 | 2-cPrMeOEtO | cPr |
| 1-593 | 2-iPrOEtO | iPrO |
| 1-594 | 2-iPrOEtO | cPrO |
| 1-595 | 2-iPrOEtO | CF$_3$O |
| 1-596 | 2-cPnOEtO | iPrO |
| 1-597 | 2-cPnOEtO | cPrO |
| 1-598 | 2-cPnOEtO | CF$_3$O |
| 1-599 | 2-cPnOEtO | cPr |
| 1-600 | 2-(4-FPhO)EtO | iPrO |
| 1-601 | 2-(4-FPhO)EtO | cPrO |
| 1-602 | 2-(4-FPhO)EtO | CF$_3$O |
| 1-603 | 2-BnOEtO | iPrO |
| 1-604 | 2-BnOEtO | cPrO |
| 1-605 | 2-BnOEtO | CF$_3$O |
| 1-606 | 2-DHBDMeO | iPrO |
| 1-607 | 2-DHBDMeO | cPrO |
| 1-608 | 2-DHBDMeO | CF$_3$O |
| 1-609 | 4,4-diMeBunO | iPrO |
| 1-610 | 4,4-diMeBunO | cPrO |
| 1-611 | 4,4-diMeBunO | CF$_3$O |
| 1-612 | iBuS | iPrO |
| 1-613 | iBuS | cPrO |
| 1-614 | iBuS | CF$_3$O |
| 1-615 | 2-(4-iBuOPh)EtO | iPrO |
| 1-616 | 2-(4-iBuOPh)EtO | cPrO |
| 1-617 | 2-(4-iBuOPh)EtO | CF$_3$O |
| 1-618 | 2-(4-iBuOPh)EtO | cPr |
| 1-619 | 2-(3,4-diMeOPh)EtO | iPrO |
| 1-620 | 2-(3,4-diMeOPh)EtO | cPrO |
| 1-621 | 2-(3,4-diMeOPh)EtO | CHF$_2$O |
| 1-622 | 2-(3,4-diMeOPh)EtO | CF$_3$O |
| 1-623 | 2-(3,4-diMeOPh)EtO | CHF$_2$CH$_2$O |
| 1-624 | 2-(3,4-diMeOPh)EtO | cPr |
| 1-625 | 2-(3,4-diMeOPh)EtO | MeS |
| 1-626 | 2-(3,4-diMeOPh)EtO | CF$_3$ |
| 1-627 | 2-(3,4-diMeOPh)EtO | Cl |
| 1-628 | 2-(4-PyrdPh)EtO | iPrO |
| 1-629 | 2-(4-PyrdPh)EtO | cPrO |
| 1-630 | 2-(4-PyrdPh)EtO | CF$_3$O |
| 1-631 | 2-(4-PyrdPh)EtO | cPr |
| 1-632 | 2-(4-PyrdPh)EtO | Cl |

In the above Table 1, preferred examples of the compound having Formula (I-1) according to the present invention are those denoted by Exemplary Compound Nos. 1-58 to 1-110, 1-128 to 1-144, 1-162 to 1-178, 1-196 to 1-212, 1-274 to 1-282, 1-438 to 1-443, 1-504 to 1-506, and 1-517 to 1-519; and more preferred examples are Exemplary Compound No. 1-58: (Example 15) 4-(2-cyclopropylethoxy)-N-((Z)-2-(4-ethoxyphenyl)-1-{[(2-hydroxyethyl)amino]carbonyl}vinyl)benzamide, Exemplary Compound No. 1-60: (Example 16) 4-(2-cyclopropylethoxy)-N-((Z)-2-[4-(cyclopropyloxy)phenyl]-1-{[(2-hydroxyethyl)amino]carbonyl}vinyl)benzamide, Exemplary Compound No. 1-61: (Example 10) 4-(2-cyclopropylethoxy)-N-((Z)-2-[4-(difluoromethoxy)phenyl]-1-{[(2-hydroxyethyl)amino]carbonyl}vinyl)benzamide, Exemplary Compound No. 1-62: (Example 11) 4-(2-cyclopropylethoxy)-N-{(Z)-1-{[(2-hydroxyethyl)amino]carbonyl}-2-[4-(trifluoromethoxy)phenyl]vinyl}benzamide, Exemplary Compound No. 1-64: (Example 12) 4-(2-cyclopropylethoxy)-N-((Z)-2-[4-(2,2-difluoroethoxy)phenyl]-1-{[(2-hydroxyethyl)amino]carbonyl}vinyl)benzamide, Exemplary Compound No. 1-68: (Example 9) 4-(2-cyclopropylethoxy)-N-((Z)-2-(4-cyclopropylphenyl)-1-{[(2-hydroxyethyl)amino]carbonyl}vinyl)benzamide, Exemplary Compound No. 1-69: (Example 19) 4-(2-cyclopropylethoxy)-N-{(Z)-1-{[(2-hydroxyethyl)amino]carbonyl}-2-[4-(trifluoromethyl)phenyl]vinyl}benzamide, Exemplary Compound No. 1-72: (Example 18) 4-(2-cyclopropylethoxy)-N-{(Z)-1-{[(2-hydroxyethyl)amino]carbonyl}-2-[4-(1H-pyrrol-1-yl)phenyl]vinyl}benzamide, Exemplary Compound No. 1-109: (Example 14) N-((Z)-2-(4-chlorophenyl)-1-{[(2-hydroxyethyl)amino]carbonyl}vinyl)-4-(2-cyclopropylethoxy)benzamide, Exemplary Compound No. 1-129: (Example 7) N-[(Z)-1-{[(2-hydroxyethyl)amino]carbonyl}-2-(4-isopropoxyphenyl)vinyl]-4-[2-(4-methoxyphenyl)ethoxy]benzamide, Exemplary Compound No. 1-130: (Example 6) N-((Z)-2-[4-(cyclopropyloxy)phenyl]-1-{[(2-hydroxyethyl)amino]carbonyl}vinyl)-4-[2-(4-methoxyphenyl)ethoxy]benzamide, Exemplary Compound No. 1-132: (Example 3) N-{(Z)-1-{[(2-hydroxyethyl)amino]carbonyl}-2-[4-(trifluoromethoxy)phenyl]vinyl}-4-[2-(4-methoxyphenyl)ethoxy]benzamide, Exemplary Compound No. 1-138: (Example 5) N-((Z)-2-(4-cyclopropylphenyl)-1-{[(2-hydroxyethyl)amino]carbonyl}vinyl)-4-[2-(4-methoxyphenyl)ethoxy]benzamide, Exemplary Compound No. 1-141: (Example 8) N-{(Z)-1-{[(2-hydroxyethyl)amino]carbonyl}-2-[4-(methylthio)phenyl]vinyl}-4-[2-(4-methoxyphenyl)ethoxy]benzamide, Exemplary Compound No. 1-144: (Example 1) N-((Z)-2-(4-chlorophenyl)-1-{[(2-hydroxyethyl)amino]carbonyl}vinyl)-4-[2-(4-methoxyphenyl)ethoxy]benzamide, Exemplary Compound No. 1-163: (Example 27) 4-{2-[4-(dimethylamino)phenyl]ethoxy}-N-[(Z)-1-{[(2-hydroxyethyl)amino]carbonyl}-2-(4-isopropoxyphenyl)vinyl]benzamide, Exemplary Compound No. 1-166: (Example 23) 4-{2-[4-(dimethylamino)phenyl]ethoxy}-N-{(Z)-1-{[(2-hydroxyethyl)amino]carbonyl}-2-[4-(trifluoromethoxy)phenyl]vinyl}benzamide, Exemplary Compound No. 1-172: (Example 25) N-((Z)-2-(4-cyclopropylphenyl)-1-{[(2-hydroxyethyl)amino]carbonyl}vinyl)-4-{2-[4-(dimethylamino)phenyl]ethoxy}benzamide, Exemplary Compound No. 1-196: (Example 83) 4-[2-(4-chlorophenyl)ethoxy]-N-((Z)-2-(4-ethoxyphenyl)-1-{[(2-hydroxyethyl)amino]carbonyl}vinyl)benzamide, Exemplary Compound No. 1-198: (Example 81) 4-[2-(4-chlorophenyl)ethoxy]-N-((Z)-2-[4-(cyclopropyloxy)phenyl]-1-{[(2-hydroxyethyl)amino]carbonyl}vinyl)benzamide, Exemplary Compound No. 1-199: (Example 78) 4-[2-(4-chlorophenyl)ethoxy]-N-((Z)-2-[4-(difluoromethoxy)phenyl]-1-{[(2-hydroxyethyl)amino]carbonyl}vinyl)benzamide, Exemplary Compound No. 1-200: (Example 79) 4-[2-(4-chlorophenyl)ethoxy]-N-{(Z)-1-{[(2-hydroxyethyl)amino]carbonyl}-2-[4-(trifluoromethoxy)phenyl]vinyl}benzamide, Exemplary Compound No. 1-206: (Example 80) 4-[2-(4-chlorophenyl)ethoxy]-N-((Z)-2-(4-cyclopropylphenyl)-1-{[(2-hydroxyethyl)amino]carbonyl}vinyl)benzamide, Exemplary Compound No. 1-212: (Example 82) 4-[2-(4-chlorophenyl)ethoxy]-N-((Z)-2-(4-chlorophenyl)-1-{[(2-hydroxyethyl)amino]carbonyl}vinyl)benzamide, Exemplary Compound No. 1-277: (Example 108) N-{(Z)-1-{[(2-hydroxyethyl)amino]carbonyl}-2-[4-(trifluoromethoxy)phenyl]vinyl}-4-(3,3,3-trifluoropropoxy)benzamide, Exemplary Compound No. 1-440: (Example 104) 4-(cyclopropylmethoxy)-N-{(Z)-1-{[(2-hydroxyethyl)amino]carbonyl}-2-[4-(trifluoromethoxy)phenyl]vinyl}benzamide, Exemplary Compound No. 1-506: (Example 107) N-{(Z)-1-{[(2-hydroxyethyl)amino]carbonyl}-2-[4-(trifluoromethoxy)phenyl]vinyl}-4-(4,4,4-trifluorobutoxy)benzamide, and Exemplary Compound No. 1-519: (Example 112) N-{(Z)-1-{[(2-hydroxyethyl)amino]carbonyl}-2-[4-(trifluoromethoxy)phenyl]vinyl}-4-[4-(trifluoromethyl)phenoxy]benzamide.

TABLE 2

Exemplary compound table 2

(I-2)

| Compound No. | $R^c$ | $R^d$ |
|---|---|---|
| 2-1 | βNp | 4-iPrOPh |
| 2-2 | 3-MeO-4-cPnOPh | 4-iPrOPh |
| 2-3 | 3,4-MEDOPh | 4-iPrOPh |
| 2-4 | 2-i-BuOPh | 4-iPrOPh |
| 2-5 | 3-i-BuOPh | 4-iPrOPh |
| 2-6 | 4-i-BuOPh | βNp |
| 2-7 | 4-i-BuOPh | 6-MeO(βNp) |
| 2-8 | 4-i-BuOPh | Chr |
| 2-9 | 4-i-BuOPh | 6-DHBD |
| 2-10 | 4-i-BuOPh | 2-iPrOPh |
| 2-11 | 4-i-BuOPh | 3-iPrOPh |
| 2-12 | 4-i-BuOPh | 3,5-diBnOPh |
| 2-13 | 4-i-BuOPh | 3,5-diMeOPh |
| 2-14 | 4-i-BuOPh | 3,4,5-triMeOPh |
| 2-15 | 4-i-BuOPh | 6-MeO(3-Py) |
| 2-16 | 4-i-BuOPh | 6-CF$_3$(3-Py) |
| 2-17 | 4-i-BuOPh | Quin |
| 2-18 | 4-i-BuOPh | 1-iBuPip |
| 2-19 | 4-i-BuO(3-Py) | 4-iPrOPh |
| 2-20 | 4-i-BuO(3-F)Ph | 4-iPrOPh |
| 2-21 | 4-i-BuO(2-F)Ph | 4-iPrOPh |

In the above Table 2, preferred examples of the compound having Formula (I-2) according to the present invention are Exemplary Compound No. 2-6: N-[(Z)-1-{[(2-hydroxyethyl)amino]carbonyl}-2-(2-naphthyl)vinyl]-4-isobutoxybenzamide, Exemplary Compound No. 2-16: N-(Z)-1-{[(2-hydroxyethyl)amino]carbonyl-2-[6-(trifluoromethyl)pyridin-3-yl]vinyl}-4-isobutoxybenzamide, Exemplary Compound No. 2-19: N-[(Z)-1-{[(2-hydroxyethyl)amino]carbonyl}-2-(4-isopropoxyphenyl)vinyl]-6-isobutoxynicotinamide, and Exemplary Compound No. 2-21: 2-fluoro-N-[(Z)-1-{[(2-hydroxyethyl)amino]carbonyl}-2-(4-isopropoxyphenyl)vinyl]-4-isobutoxybenzamide.

TABLE 3

Exemplary compound table 3

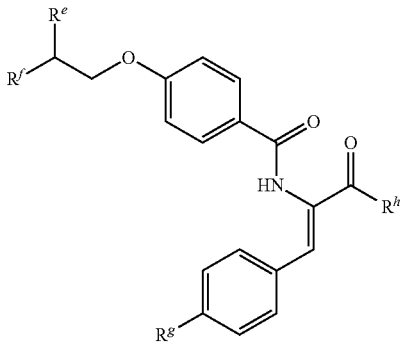

(I-3)

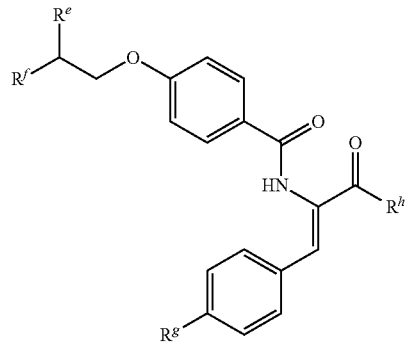

(I-3)

| Compound No. | $R^e$ | $R^f$ | $R^g$ | $R^h$ |
|---|---|---|---|---|
| 3-1 | Me | Me | iPrO | 2-HOPrNH |
| 3-2 | Me | Me | iPrO | 2-HOBuNH |
| 3-3 | Me | Me | iPrO | (1-HO-cPr)MeNH |
| 3-4 | Me | Me | iPrO | 2-HO-2-MePreNH |
| 3-5 | Me | Me | iPrO | 2,3-diHOPrNH |
| 3-6 | Me | Me | iPrO | 1-HO-2-MeEtNH |
| 3-7 | Me | Me | iPrO | 2-HO-1,1-diMeEtNH |
| 3-8 | Me | Me | iPrO | 2-HOEt(Me)N |
| 3-9 | Me | Me | iPrO | 2-AcOEtNH |
| 3-10 | Me | Me | iPrO | 3-HOPrNH |
| 3-11 | Me | Me | iPrO | 4-HOBuNH |
| 3-12 | Me | Me | iPrO | 2-MeOEtNH |
| 3-13 | Me | Me | iPrO | THFMeNH |
| 3-14 | Me | Me | iPrO | MeOCOMeNH |
| 3-15 | Me | Me | iPrO | HOOCMeNH |
| 3-16 | Me | Me | iPrO | PhNHCOOEtNH |
| 3-17 | Me | Me | iPrO | 2-HOPhNH |
| 3-18 | Me | Me | iPrO | 3-HOPhNH |
| 3-19 | Me | Me | iPrO | PhNH |
| 3-20 | Me | Me | iPrO | FurMeNH |
| 3-21 | Me | Me | iPrO | 2-PyMeNH |
| 3-22 | Me | Me | iPrO | 4-HOPhNH |
| 3-23 | Me | Me | iPrO | ThiMeNH |
| 3-24 | Me | Me | iPrO | 2-PhEtNH |
| 3-25 | Me | Me | iPrO | 2-(2-Py)EtNH |
| 3-26 | Me | Me | iPrO | $H_2$NCOMeNH |
| 3-27 | Me | Me | iPrO | 2-HO-cPnNH |
| 3-28 | Me | Me | iPrO | CNMeNH |
| 3-29 | Me | Me | iPrO | PrNH |
| 3-30 | Me | Me | iPrO | 2-FEtNH |
| 3-31 | Me | Me | iPrO | $H_2$N |
| 3-32 | Me | Me | iPrO | $H_2$NEtNH |
| 3-33 | Me | Me | iPrO | AcNHEtNH |
| 3-34 | Me | Me | iPrO | $H_2$NCONHEtNH |
| 3-35 | Me | Me | iPrO | BocNHEtNH |
| 3-36 | Me | Me | iPrO | PhtlNEtNH |
| 3-37 | Me | Me | iPrO | 2-DDQZEtNH |
| 3-38 | Me | Me | iPrO | Pyrd |
| 3-39 | Me | Me | iPrO | Mor |
| 3-40 | Me | Me | iPrO | 4-BocPiz |
| 3-41 | Me | Me | iPrO | HO |
| 3-42 | Me | Me | iPrO | EtO |
| 3-43 | Me | Me | iPrO | 2-HOEtO |
| 3-44 | Me | Me | iPrO | EtONH |
| 3-45 | Me | Me | iPrO | 2-HOEtONH |
| 3-46 | Me | Me | iPrO | 2-(MorAcO)EtNH |
| 3-47 | Me | Me | iPrO | 2-(2-(HHOC)EtCOO)EtNH |
| 3-48 | Me | Me | cPrO | 2-HOPrNH |
| 3-49 | Me | Me | cPrO | 2-HOBuNH |
| 3-50 | Me | Me | cPrO | (1-HO-cPr)MeNH |
| 3-51 | Me | Me | cPrO | 1-HO-2-MeEtNH |
| 3-52 | Me | Me | cPrO | 2-AcOEtNH |
| 3-53 | Me | Me | cPrO | 2-HOPhNH |
| 3-54 | Me | Me | cPrO | PrNH |
| 3-55 | Me | Me | cPrO | $H_2$NCOMeNH |
| 3-56 | Me | Me | cPrO | 2-(MorAcO)EtNH |
| 3-57 | Me | Me | cPrO | 2-(2-(HHOC)EtCOO)EtNH |
| 3-58 | Me | Me | $CF_3$O | 2-HOPrNH |
| 3-59 | Me | Me | $CF_3$O | 2-HOBuNH |
| 3-60 | Me | Me | $CF_3$O | (1-HO-cPr)MeNH |
| 3-61 | Me | Me | $CF_3$O | 1-HO-2-MeEtNH |
| 3-62 | Me | Me | $CF_3$O | 2-AcOEtNH |
| 3-63 | Me | Me | $CF_3$O | 2-HOPhNH |
| 3-64 | Me | Me | $CF_3$O | PrNH |
| 3-65 | Me | Me | $CF_3$O | $H_2$NCOMeNH |
| 3-66 | Me | Me | $CF_3$O | 2-(MorAcO)EtNH |
| 3-67 | Me | Me | $CF_3$O | 2-(2-(HOOC)EtCOO)EtNH |
| 3-68 | Me | Me | cPr | 2-HOPrNH |
| 3-69 | Me | Me | cPr | 2-HOBuNH |
| 3-70 | Me | Me | cPr | (1-HO-cPr)MeNH |
| 3-71 | Me | Me | cPr | 1-HO-2-MeEtNH |
| 3-72 | Me | Me | cPr | 2-AcOEtNH |
| 3-73 | Me | Me | cPr | 2-HOPhNH |
| 3-74 | Me | Me | cPr | PrNH |
| 3-75 | Me | Me | cPr | $H_2$NCOMeNH |
| 3-76 | Me | Me | cPr | 2-(MorAcO)EtNH |
| 3-77 | Me | Me | cPr | 2-(2-(HOOC)EtCOO)EtNH |
| 3-78 | H | cPr | iPrO | 2-HOPrNH |
| 3-79 | H | cPr | iPrO | 2-HOBuNH |
| 3-80 | H | cPr | iPrO | (1-HO-cPr)MeNH |
| 3-81 | H | cPr | iPrO | 1-HO-2-MeEtNH |
| 3-82 | H | cPr | iPrO | 2-AcOEtNH |
| 3-83 | H | cPr | iPrO | 2-HOPhNH |
| 3-84 | H | cPr | iPrO | PrNH |
| 3-85 | H | cPr | iPrO | $H_2$NCOMeNH |
| 3-86 | H | cPr | iPrO | 2-(MorAcO)EtNH |
| 3-87 | H | cPr | iPrO | 2-(2-(HOOC)EtCOO)EtNH |
| 3-88 | H | cPr | cPrO | 2-HOPrNH |
| 3-89 | H | cPr | cPrO | 2-HOBuNH |
| 3-90 | H | cPr | cPrO | (1-HO-cPr)MeNH |
| 3-91 | H | cPr | cPrO | 1-HO-2-MeEtNH |
| 3-92 | H | cPr | cPrO | 2-AcOEtNH |
| 3-93 | H | cPr | cPrO | 2-HOPhNH |
| 3-94 | H | cPr | cPrO | PrNH |
| 3-95 | H | cPr | cPrO | $H_2$NCOMeNH |
| 3-96 | H | cPr | cPrO | 2-(MorAcO)EtNH |
| 3-97 | H | cPr | cPrO | 2-(2-(HOOC)EtCOO)EtNH |
| 3-98 | H | cPr | $CF_3$O | 2-HOPrNH |
| 3-99 | H | cPr | $CF_3$O | 2-HOBuNH |
| 3-100 | H | cPr | $CF_3$O | (1-HO-cPr)MeNH |
| 3-101 | H | cPr | $CF_3$O | 1-HO-2-MeEtNH |
| 3-102 | H | cPr | $CF_3$O | 2-AcOEtNH |
| 3-103 | H | cPr | $CF_3$O | 2-HOPhNH |
| 3-104 | H | cPr | $CF_3$O | PrNH |
| 3-105 | H | cPr | $CF_3$O | $H_2$NCOMeNH |
| 3-106 | H | cPr | $CF_3$O | 2-(MorAcO)EtNH |
| 3-107 | H | cPr | $CF_3$O | 2-(2-(HOOC)EtCOO)EtNH |
| 3-108 | H | cPr | cPr | 2-HOPrNH |
| 3-109 | H | cPr | cPr | 2-HOBuNH |
| 3-110 | H | cPr | cPr | (1-HO-cPr)MeNH |
| 3-111 | H | cPr | cPr | 1-HO-2-MeEtNH |
| 3-112 | H | cPr | cPr | 2-AcOEtNH |
| 3-113 | H | cPr | cPr | 2-HOPhNH |
| 3-114 | H | cPr | cPr | PrNH |

TABLE 3-continued

Exemplary compound table 3

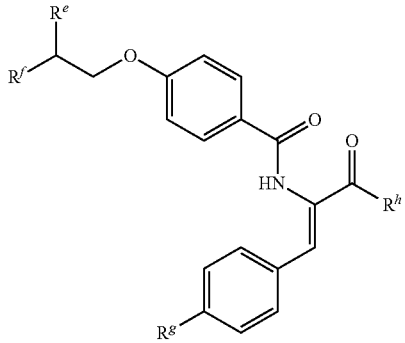

(I-3)

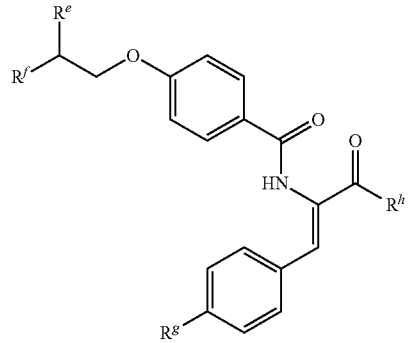

(I-3)

| Compound No. | $R^e$ | $R^f$ | $R^g$ | $R^h$ |
|---|---|---|---|---|
| 3-115 | H | cPr | cPr | H$_2$NCOMeNH |
| 3-116 | H | cPr | cPr | 2-(MorAcO)EtNH |
| 3-117 | H | cPr | cPr | 2-(2-(HOOC)EtCOO)EtNH |
| 3-118 | H | Ph | iPrO | 2-HOPrNH |
| 3-119 | H | Ph | iPrO | 2-HOBuNH |
| 3-120 | H | Ph | iPrO | (1-HO-cPr)MeNH |
| 3-121 | H | Ph | iPrO | 1-HO-2-MeEtNH |
| 3-122 | H | Ph | iPrO | 2-AcOEtNH |
| 3-123 | H | Ph | iPrO | 2-HOPhNH |
| 3-124 | H | Ph | iPrO | PrNH |
| 3-125 | H | Ph | iPrO | H$_2$NCOMeNH |
| 3-126 | H | Ph | iPrO | 2-(MorAcO)EtNH |
| 3-127 | H | Ph | iPrO | 2-(2-(HOOC)EtCOO)EtNH |
| 3-128 | H | Ph | cPrO | 2-HOPrNH |
| 3-129 | H | Ph | cPrO | 2-HOBuNH |
| 3-130 | H | Ph | cPrO | (1-HO-cPr)MeNH |
| 3-131 | H | Ph | cPrO | 1-HO-2-MeEtNH |
| 3-132 | H | Ph | cPrO | 2-AcOEtNH |
| 3-133 | H | Ph | cPrO | 2-HOPhNH |
| 3-134 | H | Ph | cPrO | PrNH |
| 3-135 | H | Ph | cPrO | H$_2$NCOMeNH |
| 3-136 | H | Ph | cPrO | 2-(MorAcO)EtNH |
| 3-137 | H | Ph | cPrO | 2-(2-(HOOC)EtCOO)EtNH |
| 3-138 | H | Ph | CF$_3$O | 2-HOPrNH |
| 3-139 | H | Ph | CF$_3$O | 2-HOBuNH |
| 3-140 | H | Ph | CF$_3$O | (1-HO-cPr)MeNH |
| 3-141 | H | Ph | CF$_3$O | 1-HO-2-MeEtNH |
| 3-142 | H | Ph | CF$_3$O | 2-AcOEtNH |
| 3-143 | H | Ph | CF$_3$O | 2-HOPhNH |
| 3-144 | H | Ph | CF$_3$O | PrNH |
| 3-145 | H | Ph | CF$_3$O | H$_2$NCOMeNH |
| 3-146 | H | Ph | CF$_3$O | 2-(MorAcO)EtNH |
| 3-147 | H | Ph | CF$_3$O | 2-(2-(HOOC)EtCOO)EtNH |
| 3-148 | H | Ph | cPr | 2-HOPrNH |
| 3-149 | H | Ph | cPr | 2-HOBuNH |
| 3-150 | H | Ph | cPr | (1-HO-cPr)MeNH |
| 3-151 | H | Ph | cPr | 1-HO-2-MeEtNH |
| 3-152 | H | Ph | cPr | 2-AcOEtNH |
| 3-153 | H | Ph | cPr | 2-HOPhNH |
| 3-154 | H | Ph | cPr | PrNH |
| 3-155 | H | Ph | cPr | H$_2$NCOMeNH |
| 3-156 | H | Ph | cPr | 2-(MorAcO)EtNH |
| 3-157 | H | Ph | cPr | 2-(2-(HOOC)EtCOO)EtNH |
| 3-158 | H | 4-MeOPh | iPrO | 2-HOPrNH |
| 3-159 | H | 4-MeOPh | iPrO | 2-HOBuNH |
| 3-160 | H | 4-MeOPh | iPrO | (1-HO-cPr)MeNH |
| 3-161 | H | 4-MeOPh | iPrO | 1-HO-2-MeEtNH |
| 3-162 | H | 4-MeOPh | iPrO | 2-AcOEtNH |
| 3-163 | H | 4-MeOPh | iPrO | 2-HOPhNH |
| 3-164 | H | 4-MeOPh | iPrO | PrNH |
| 3-165 | H | 4-MeOPh | iPrO | H$_2$NCOMeNH |
| 3-166 | H | 4-MeOPh | iPrO | 2-(MorAcO)EtNH |
| 3-167 | H | 4-MeOPh | iPrO | 2-(2-(HOOC)EtCOO)EtNH |
| 3-168 | H | 4-MeOPh | cPrO | 2-HOPrNH |
| 3-169 | H | 4-MeOPh | cPrO | 2-HOBuNH |
| 3-170 | H | 4-MeOPh | cPrO | (1-HO-cPr)MeNH |
| 3-171 | H | 4-MeOPh | cPrO | 1-HO-2-MeEtNH |
| 3-172 | H | 4-MeOPh | cPrO | 2-AcOEtNH |
| 3-173 | H | 4-MeOPh | cPrO | 2-HOPhNH |
| 3-174 | H | 4-MeOPh | cPrO | PrNH |
| 3-175 | H | 4-MeOPh | cPrO | H$_2$NCOMeNH |
| 3-176 | H | 4-MeOPh | cPrO | 2-(MorAcO)EtNH |
| 3-177 | H | 4-MeOPh | cPrO | 2-(2-(HOOC)EtCOO)EtNH |
| 3-178 | H | 4-MeOPh | CF$_3$O | 2-HOPrNH |
| 3-179 | H | 4-MeOPh | CF$_3$O | 2-HOBuNH |
| 3-180 | H | 4-MeOPh | CF$_3$O | (1-HO-cPr)MeNH |
| 3-181 | H | 4-MeOPh | CF$_3$O | 1-HO-2-MeEtNH |
| 3-182 | H | 4-MeOPh | CF$_3$O | 2-AcOEtNH |
| 3-183 | H | 4-MeOPh | CF$_3$O | 2-HOPhNH |
| 3-184 | H | 4-MeOPh | CF$_3$O | PrNH |
| 3-185 | H | 4-MeOPh | CF$_3$O | H$_2$NCOMeNH |
| 3-186 | H | 4-MeOPh | CF$_3$O | 2-(MorAcO)EtNH |
| 3-187 | H | 4-MeOPh | CF$_3$O | 2-(2-(HOOC)EtCOO)EtNH |
| 3-188 | H | 4-MeOPh | cPr | 2-HOPrNH |
| 3-189 | H | 4-MeOPh | cPr | 2-HOBuNH |
| 3-190 | H | 4-MeOPh | cPr | (1-HO-cPr)MeNH |
| 3-191 | H | 4-MeOPh | cPr | 1-HO-2-MeEtNH |
| 3-192 | H | 4-MeOPh | cPr | 2-AcOEtNH |
| 3-193 | H | 4-MeOPh | cPr | 2-HOPhNH |
| 3-194 | H | 4-MeOPh | cPr | PrNH |
| 3-195 | H | 4-MeOPh | cPr | H$_2$NCOMeNH |
| 3-196 | H | 4-MeOPh | cPr | 2-(MorAcO)EtNH |
| 3-197 | H | 4-MeOPh | cPr | 2-(2-(HOOC)EtCOO)EtNH |
| 3-198 | H | 4-diMeNPh | iPrO | 2-HOPrNH |
| 3-199 | H | 4-diMeNPh | iPrO | 2-HOBuNH |
| 3-200 | H | 4-diMeNPh | iPrO | (1-HO-cPr)MeNH |
| 3-201 | H | 4-diMeNPh | iPrO | 1-HO-2-MeEtNH |
| 3-202 | H | 4-diMeNPh | iPrO | 2-AcOEtNH |
| 3-203 | H | 4-diMeNPh | iPrO | 2-HOPhNH |
| 3-204 | H | 4-diMeNPh | iPrO | PrNH |
| 3-205 | H | 4-diMeNPh | iPrO | H$_2$NCOMeNH |
| 3-206 | H | 4-diMeNPh | iPrO | 2-(MorAcO)EtNH |
| 3-207 | H | 4-diMeNPh | iPrO | 2-(2-(HOOC)EtCOO)EtNH |
| 3-208 | H | 4-diMeNPh | cPrO | 2-HOPrNH |
| 3-209 | H | 4-diMeNPh | cPrO | 2-HOBuNH |
| 3-210 | H | 4-diMeNPh | cPrO | (1-HO-cPr)MeNH |
| 3-211 | H | 4-diMeNPh | cPrO | 1-HO-2-MeEtNH |
| 3-212 | H | 4-diMeNPh | cPrO | 2-AcOEtNH |
| 3-213 | H | 4-diMeNPh | cPrO | 2-HOPhNH |
| 3-214 | H | 4-diMeNPh | cPrO | PrNH |
| 3-215 | H | 4-diMeNPh | cPrO | H$_2$NCOMeNH |
| 3-216 | H | 4-diMeNPh | cPrO | 2-(MorAcO)EtNH |
| 3-217 | H | 4-diMeNPh | cPrO | 2-(2-(HOOC)EtCOO)EtNH |
| 3-218 | H | 4-diMeNPh | CF$_3$O | 2-HOPrNH |
| 3-219 | H | 4-diMeNPh | CF$_3$O | 2-HOBuNH |
| 3-220 | H | 4-diMeNPh | CF$_3$O | (1-HO-cPr)MeNH |
| 3-221 | H | 4-diMeNPh | CF$_3$O | 1-HO-2-MeEtNH |
| 3-222 | H | 4-diMeNPh | CF$_3$O | 2-AcOEtNH |
| 3-223 | H | 4-diMeNPh | CF$_3$O | 2-HOPhNH |
| 3-224 | H | 4-diMeNPh | CF$_3$O | PrNH |
| 3-225 | H | 4-diMeNPh | CF$_3$O | H$_2$NCOMeNH |
| 3-226 | H | 4-diMeNPh | CF$_3$O | 2-(MorAcO)EtNH |
| 3-227 | H | 4-diMeNPh | CF$_3$O | 2-(2-(HOOC)EtCOO)EtNH |
| 3-228 | H | 4-diMeNPh | cPr | 2-HOPrNH |

TABLE 3-continued

Exemplary compound table 3

(I-3)

Structure with $R^e$, $R^f$, $R^g$, $R^h$ substituents on the core formula.

| Compound No. | $R^e$ | $R^f$ | $R^g$ | $R^h$ |
|---|---|---|---|---|
| 3-229 | H | 4-diMeNPh | cPr | 2-HOBuNH |
| 3-230 | H | 4-diMeNPh | cPr | (1-HO-cPr)MeNH |
| 3-231 | H | 4-diMeNPh | cPr | 1-HO-2-MeEtNH |
| 3-232 | H | 4-diMeNPh | cPr | 2-AcOEtNH |
| 3-233 | H | 4-diMeNPh | cPr | 2-HOPhNH |
| 3-234 | H | 4-diMeNPh | cPr | PrNH |
| 3-235 | H | 4-diMeNPh | cPr | H$_2$NCOMeNH |
| 3-236 | H | 4-diMeNPh | cPr | 2-(MorAcO)EtNH |
| 3-237 | H | 4-diMeNPh | cPr | 2-(2-(HOOC)EtCOO)EtNH |
| 3-238 | H | 4-ClPh | iPrO | 2-HOPrNH |
| 3-239 | H | 4-ClPh | iPrO | 2-HOBuNH |
| 3-240 | H | 4-ClPh | iPrO | (1-HO-cPr)MeNH |
| 3-241 | H | 4-ClPh | iPrO | 1-HO-2-MeEtNH |
| 3-242 | H | 4-ClPh | iPrO | 2-AcOEtNH |
| 3-243 | H | 4-ClPh | iPrO | 2-HOPhNH |
| 3-244 | H | 4-ClPh | iPrO | PrNH |
| 3-245 | H | 4-ClPh | iPrO | H$_2$NCOMeNH |
| 3-246 | H | 4-ClPh | iPrO | 2-(MorAcO)EtNH |
| 3-247 | H | 4-ClPh | iPrO | 2-(2-(HOOC)EtCOO)EtNH |
| 3-248 | H | 4-ClPh | cPrO | 2-HOPrNH |
| 3-249 | H | 4-ClPh | cPrO | 2-HOBuNH |
| 3-250 | H | 4-ClPh | cPrO | (1-HO-cPr)MeNH |
| 3-251 | H | 4-ClPh | cPrO | 1-HO-2-MeEtNH |
| 3-252 | H | 4-ClPh | cPrO | 2-AcOEtNH |
| 3-253 | H | 4-ClPh | cPrO | 2-HOPhNH |
| 3-254 | H | 4-ClPh | cPrO | PrNH |
| 3-255 | H | 4-ClPh | cPrO | H$_2$NCOMeNH |
| 3-256 | H | 4-ClPh | cPrO | 2-(MorAcO)EtNH |
| 3-257 | H | 4-ClPh | cPrO | 2-(2-(HOOC)EtCOO)EtNH |
| 3-258 | H | 4-ClPh | CF$_3$O | 2-HOPrNH |
| 3-259 | H | 4-ClPh | CF$_3$O | 2-HOBuNH |
| 3-260 | H | 4-ClPh | CF$_3$O | (1-HO-cPr)MeNH |
| 3-261 | H | 4-ClPh | CF$_3$O | 1-HO-2-MeEtNH |
| 3-262 | H | 4-ClPh | CF$_3$O | 2-AcOEtNH |
| 3-263 | H | 4-ClPh | CF$_3$O | 2-HOPhNH |
| 3-264 | H | 4-ClPh | CF$_3$O | PrNH |
| 3-265 | H | 4-ClPh | CF$_3$O | H$_2$NCOMeNH |
| 3-266 | H | 4-ClPh | CF$_3$O | 2-(MorAcO)EtNH |
| 3-267 | H | 4-ClPh | CF$_3$O | 2-(2-(HOOC)EtCOO)EtNH |
| 3-268 | H | 4-ClPh | cPr | 2-HOPrNH |
| 3-269 | H | 4-ClPh | cPr | 2-HOBuNH |
| 3-270 | H | 4-ClPh | cPr | (1-HO-cPr)MeNH |
| 3-271 | H | 4-ClPh | cPr | 1-HO-2-MeEtNH |
| 3-272 | H | 4-ClPh | cPr | 2-AcOEtNH |
| 3-273 | H | 4-ClPh | cPr | 2-HOPhNH |
| 3-274 | H | 4-ClPh | cPr | PrNH |
| 3-275 | H | 4-ClPh | cPr | H$_2$NCOMeNH |
| 3-276 | H | 4-ClPh | cPr | 2-(MorAcO)EtNH |
| 3-277 | H | 4-ClPh | cPr | 2-(2-(HOOC)EtCOO)EtNH |

In the above Table 3, preferred examples of the compound having Formula (I-3) according to the present invention are those denoted by Exemplary Compound Nos. 3-48 to 3-77, 3-88 to 3-117, 3-128 to 3-157, 3-168 to 3-197, 3-208 to 3-237, and 3-248 to 3-277; and more preferable examples are Exemplary Compound No. 3-92: 2-({(2Z)-2-{[4-(2-cyclopropylethoxy)benzoyl]amino}-3-[4-(cyclopropyloxy)phenyl]propen-2-oyl}amino)ethyl acetate, Exemplary Compound No. 3-102: 2-{[(2Z)-2-{[4-(2-cyclopropylethoxy)benzoyl]amino}-3-[4-(trifluoromethoxy)phenyl]propen-2-oyl]amino}ethyl acetate, Exemplary Compound No. 3-112: (Example 20) 2-{[(2Z)-2-{[4-(2-cyclopropylethoxy)benzoyl]amino}-3-(4-cyclopropylphenyl)propen-2-oyl]amino}ethyl acetate, Exemplary Compound No. 3-172: 2-{[(2Z)-3-[4-(cyclopropyloxy)phenyl]-2-({-4-[2-(4-methoxyphenyl)ethoxy]benzoyl}amino)propen-2-oyl]amino}ethyl acetate, Exemplary Compound No. 3-182: 2-({(2Z)-2-({4-[2-(4-methoxyphenyl)ethoxy]benzoyl}amino)-3-[4-(trifluoromethoxy)phenyl]propen-2-oyl}amino)ethyl acetate, Exemplary Compound No. 3-192: 2-{[(2Z)-3-(4-cyclopropylphenyl)-2-({4-[2-(4-methoxyphenyl)ethoxy]benzoyl}amino)propen-2-oyl]amino}ethyl acetate, Exemplary Compound No. 3-212: 2-({(2Z)-3-[4-(cyclopropyloxy)phenyl]-2-[(4-{2-[4-(dimethylamino)phenyl]ethoxy}benzoyl)amino]propen-2-oyl}amino)ethyl acetate, Exemplary Compound No. 3-222: 2-({(2Z)-2-[(4-{2-[4-(dimethylamino)phenyl]ethoxy}benzoyl)amino]-3-[4-(trifluoromethoxy)phenyl]propen-2-oyl}amino)ethyl acetate, Exemplary Compound No. 3-232: 2-({(2Z)-3-(4-cyclopropylphenyl)-2-[(4-{2-[4-(dimethylamino)phenyl]ethoxy}benzoyl)amino]propen-2-oyl}amino)ethyl acetate, Exemplary Compound No. 3-252: 2-({(2Z)-2-({4-[2-(4-chlorophenyl)ethoxy]benzoyl}amino)-3-[4-(cyclopropoxy)phenyl]propen-2-oyl}amino)ethyl acetate, Exemplary Compound No. 3-262: 2-({(2Z)-2-({4-[2-(4-chlorophenyl)ethoxy]benzoyl}amino)-3-[4-(trifluoromethoxy)phenyl]propen-2-oyl}amino)ethyl acetate, and Exemplary Compound No. 3-272: 2-{[(2Z)-2-({4-[2-(4-chlorophenyl)ethoxy]benzoyl}amino)-3-(4-cyclopropylphenyl)propen-2-oyl]amino}ethyl acetate.

(General Manufacturing Process)

The compound having Formula (I) according to the present invention can be manufactured according to the following processes.

The following manufacturing processes are generally conducted according to known methods described in, for example, "ORGANIC FUNCTIONAL GROUP PREPARATIONS", 2nd edition, ACADEMIC PRESS, INC., (1989) or "Comprehensive Organic Transformations", VCH Publishers Inc., (1989).

Some functional groups, in the stage of raw materials to intermediates for manufacturing, require to be protected by suitable protecting groups which can be readily converted to the functional groups. In such a case, desired compounds can be obtained by removing the protecting groups according to need.

Examples of such functional groups include a hydroxyl group, a carboxyl group, a carbonyl group, and an amino group. Protecting groups for these functional groups are described in, for example, Greene and Wuts, "Protective Groups in Organic Synthesis", 3rd edition, John Wiley & Sons, Inc., (1999) and can be optionally used according to reaction conditions.

Carboxyl protecting groups, for example, $C_1$-$C_6$ alkyl (for example, methyl, ethyl, propyl, isopropyl, butyl, and tert-butyl), $C_7$-$C_{11}$ aralkyl (for example, benzyl), phenyl, trityl, silyl (for example, trimethylsilyl, triethylsilyl, dimethylphenylsilyl, tert-butyldimethylsilyl, and tert-butyldiethylsilyl), and $C_2$-$C_6$ alkenyl (for example, 1-allyl) are used. These groups may be substituted with, for example, one to three halogen atoms (for example, fluorine, chlorine, bromine, and iodine), $C_1$-$C_6$ alkoxy (for example, methoxy, ethoxy, and propoxy), or nitro.

Hydroxyl protecting groups, for example, $C_1$-$C_6$ alkyl (for example, methyl, ethyl, propyl, isopropyl, butyl, and tert-butyl), phenyl, trityl, $C_7$-$C_{11}$ aralkyl (for example, benzyl), formyl, $C_1$-$C_6$ alkylcarbonyl (for example, acetyl and propionyl), benzoyl, $C_7$-$C_{11}$ aralkylcarbonyl (for example, benzylcarbonyl), 2-tetrahydropyranyl, 2-tetrahydrofuranyl, silyl (for example, trimethylsilyl, triethylsilyl, dimethylphenylsilyl, tert-butyldimethylsilyl, and tert-butyldiethylsilyl), and $C_2$-$C_6$ alkenyl (for example, 1-allyl) are used. These groups may be substituted with, for example, one to three halogen atoms (for example, fluorine, chlorine, bromine, and iodine), $C_1$-$C_6$ alkyl (for example, methyl, ethyl, and n-propyl), $C_1$-$C_6$ alkoxy (for example, methoxy, ethoxy, and propoxy), or nitro.

Carbonyl protecting groups, for example, cyclic acetal (for example, 1,3-dioxane) and noncyclic acetal (for example, di-$C_1$-$C_6$ alkylacetal) are used.

Amino protecting groups, for example, formyl, $C_1$-$C_6$ alkylcarbonyl (for example, acetyl and propionyl), $C_1$-$C_6$ alkoxycarbonyl (for example, methoxycarbonyl, ethoxycarbonyl, and tert-butoxycarbonyl), benzoyl, $C_7$-$C_{11}$ aralkylcarbonyl (for example, benzylcarbonyl), $C_7$-$C_{14}$ aralkyloxycarbonyl (for example, benzyloxycarbonyl and 9-fluorenylmethoxycarbonyl), trityl, phthaloyl, N,N-dimethylaminomethylene, silyl (for example, trimethylsilyl, triethylsilyl, dimethylphenylsilyl, tert-butyldimethylsilyl, and tert-butyldiethylsilyl), and $C_2$-$C_6$ alkenyl (for example, 1-allyl) are used. These groups may be substituted with, for example, one to three halogen atoms (for example, fluorine, chlorine, bromine, and iodine), $C_1$-$C_6$ alkoxy (for example, methoxy, ethoxy, and propoxy), or nitro.

The above-mentioned protecting groups are removed by known methods, such as, a method using acid, base, ultraviolet light, hydrazine, phenylhydrazine, sodium N-methyldithiocarbamate, tetrabutylammonium fluoride, palladium acetate, or a trialkylsilyl halide (for example, trimethylsilyl iodide or trimethylsilyl bromide), or a reducing method.

The following process A is for manufacturing a compound having Formula (I).

Process A

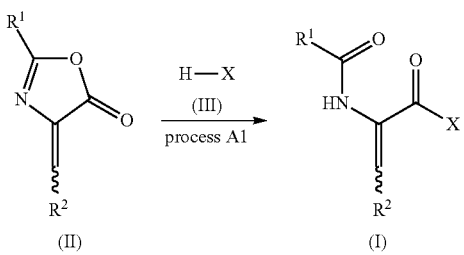

In the above formula, $R^1$, $R^2$, and X represent the same meanings as those described above.

Process A1 is a process for manufacturing a compound having Formula (I) and is conducted by a reaction between a compound having formula (II) and a compound having formula (III) in the presence of a solvent.

The compound having formula (III) used in the above reaction is preferably a primary or secondary aliphatic amine such as methylamine, ethylamine, propylamine, isopropylamine, butylamine, isobutylamine, 2-fluoroethylamine, 2-methoxyethylamine, ethanolamine, ethoxyamine, aminoacetonitrile, 1-amino-2-propanol, 2-amino-2-methyl-1-propanol, 2-amino-1-propanol, 3-amino-1-propanol, N-acetylethylenediamine, benzylamine, furfurylamine, thiophene-2-methylamine, 2-(aminomethyl)pyridine, 1-phenylethylamine, 2-phenylethylamine, dimethylamine, diethylamine, pyrrolidine, piperidine, morpholine, piperazine, or 2-(methylamino)ethanol; or an aromatic amine such as aniline, 2-aminophenol, 3-aminophenol, 4-aminophenol, 4-fluoroaniline, 4-chloroaniline, or 4-methoxyaniline; more preferably a primary aliphatic amine; and particularly preferably ethanolamine.

Examples of the solvent used in the above reaction include aliphatic hydrocarbons such as hexane, heptane, ligroin, and petroleum ether; aromatic hydrocarbons such as toluene, benzene, and xylene; ethers such as diethyl ether, diisopropyl ether, tetrahydrofuran, dioxane, dimethoxyethane, and diethylene glycol dimethyl ether; amides such as N,N-dimethylacetamide and hexamethylphosphoric acid triamide; and lower alkyl alcohols such as methanol, ethanol, propanol, and butanol. In order to obtain a (Z)-isomer as a position isomer, alcohols and ethers are preferred, alcohols are more preferred, and ethanol is particularly more preferred. In order to obtain an (E)-isomer as a position isomer, aromatic hydrocarbons are preferred, and toluene is more preferred.

The reaction temperature varies depending on, for example, the raw compounds, the solvent, and the kind of the base and is usually 0° C. to 200° C. and preferably 25° C. to 80° C.

The reaction time varies depending on, for example, the raw materials, the solvent, the base, and the reaction temperature and is usually 1 minute to 24 hours and preferably 10 minutes to 6 hours.

After the completion of the reaction, the target compound in this process is collected from the reaction mixture according to a conventional method. For example, the reaction mixture is optionally neutralized or filtered for removal of insoluble substances, if present. The reaction solution is extracted with an organic solvent which is not miscible with water, such as toluene, and is washed with water. The organic layer containing the target compound is concentrated under reduced pressure to remove the solvent to give the target compound.

The obtained target compound can be separated and purified, according to need, by a usual method such as recrystallization, reprecipitation, or a method which is widely used for separation and purification of organic compounds (for example, adsorption column chromatography using a carrier such as silica gel, alumina, or Florisil composed of magnesium-silica gel; partition column chromatography using a carrier such as Sephadex LH-20 (Pharmacia), Amberlite XAD-11 (Rohm and Haas), or Diaion HP-20 (Mitsubishi Chemical Company); ion-exchange chromatography; or normal-phase and reversed-phase column chromatography using silica gel or alkylated silica gel, and preferably silica-gel column chromatography).

The isomers can be separated, if necessary, by any of the above-mentioned separation/purification means at a suitable stage after the completion of the reaction of the above each process or after the completion of a desired process.

When a compound having a structure of Formula (I) is present as isomers, such as regioisomers, rotational isomers, or diastereomers, the isomers can be separated, if desired, into their respective isometric forms by the above-mentioned separation/purification means. In this process, (E)-isomer and (Z)-isomer are produced as regioisomers and can be separated from each other by the above-mentioned separation/purification means.

When a compound having a structure of Formula (I) exists as a racemic mixture, the mixture can be separated into (S)-isomer and (R)-isomer by a conventional optical resolution method.

The following Process B is for manufacturing a compound having Formula (II).

Process B

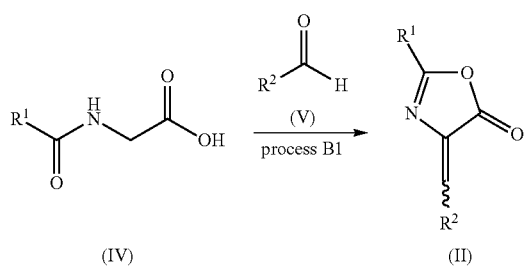

In the above formula, $R^1$ and $R^2$ represent the same meanings as those described above.

Process B1 is a process for manufacturing a compound having Formula (II) and is conducted by a reaction between a compound having a formula (IV) and a compound having a formula (V) in the presence or absence of a solvent.

Examples of the solvent used in the above reaction include aliphatic hydrocarbons such as hexane, heptane, ligroin, and petroleum ether; aromatic hydrocarbons such as toluene, benzene, and xylene; ethers such as diethyl ether, diisopropyl ether, tetrahydrofuran, dioxane, dimethoxyethane, and diethylene glycol dimethyl ether; amides such as N,N-dimethylacetamide and hexamethylphosphoric acid triamide; and acid anhydrides such as acetic anhydride. In particular, acid anhydrides are preferred, and acetic anhydride is more preferred.

The reaction temperature varies depending on, for example, the raw materials, the solvent, and the kind of the base and is usually 25° C. to 200° C. and preferably 80° C. to 120° C.

The reaction time varies depending on, for example, the raw materials, the solvent, the base, and the reaction temperature and is usually 1 minute to 1 hour and preferably 10 minutes to 6 hours.

The compound having formula (II) prepared in this process is obtained as a mixture of regioisomers, (E)-isomer and (Z)-isomer, in which the (Z)-isomer is preferred in general. In order to manufacture the (E)-isomer, the ratio of the (E)-isomer can be increased by further treating the compound having formula (II) prepared in this process with an acid.

Examples of the acid used in the above acid treatment include Bronsted acids, for example, inorganic acids, such as hydrochloric acid, hydrobromic acid, sulfuric acid, perchloric acid, and phosphoric acid, and organic acids, such as acetic acid, formic acid, oxalic acid, methanesulfonic acid, p-toluenesulfonic acid, camphorsulfonic acid, trifluoroacetic acid, and trifluoromethanesulfonic acid; Lewis acids such as zinc chloride, tin tetrachloride, boron trichloride, boron trifluoride, and boron tribromide; and acidic ion-exchange resins. Inorganic acids are preferred, and hydrobromic acid is more preferred.

The solvent used in the above acid treatment is preferably acetic acid.

The reaction temperature varies depending on, for example, the raw materials and the kinds of the acid and solvent used and is usually −20° C. to 100° C. and preferably 0° C. to 25° C.

The reaction time varies depending on the reaction temperature, the raw materials, and the kinds of the reaction reagent or solvent used and is usually 10 minutes to 10 hours and preferably 30 minutes to 2 hours.

After the completion of the reaction, the target compound of this process is collected from the reaction mixture according to the same method as in Process A.

The following Process C is for manufacturing a compound having formula (IV).

Process C

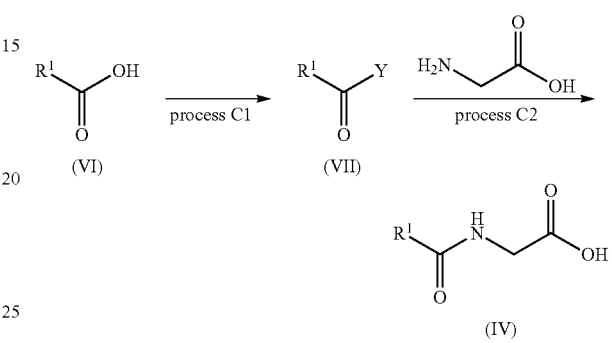

In the above formula, $R^1$ represents the same meaning as that described above. Y represents a halogen atom or a group represented by a formula $-O-S(O)_2R^C$ (where $R^C$ represents a methoxy group or a phenyl group which may be substituted with one to three groups selected from the group consisting of $C_1$-$C_6$ alkyl groups which may be substituted with one to three halogen atoms and halogen atoms).

Process C1 is for manufacturing a compound having formula (VII).

The process is conducted by a reaction between a compound having formula (VI) and a halogenating agent or a sulfonylating agent in a solvent in the presence or absence of a base.

In the above reaction, any halogenating agent which is generally used for halogenating primary alcohols can be used without any limitation, and examples thereof include oxalyl chloride; thionylhalides such as thionylchloride and thionylbromide; phosphorus trihalides such as phosphorus trichloride and phosphorus tribromide; phosphorus pentahalides such as phosphorus pentachloride and phosphorus pentabromide; phosphorus oxyhalides such as phosphorus oxychloride and phosphorus oxybromide; Vilsmeier reagents such as N,N-dimethylchloroforminium chloride and N,N-dimethylbromoforminium bromide; combinations of phosphines such as triphenylphosphine and halogens or methane tetrahalides; and combinations of phosphines, azodicarboxylic acid esters, and metal halides such as a combination of triphenylphosphine, diethyl azodicarboxylate, and lithium bromide. Oxalyl chloride is preferred, and a combination of oxalyl chloride and a catalytic amount of dimethylformamide is more preferred. The addition of dimethylformamide enhances the reaction rate.

In the above reaction, any sulfonylating agent which is generally used for sulfonylation can be used without any limitation, and examples thereof include sulfonyl halides such as methanesulfonyl chloride and p-toluenesulfonyl chloride, and sulfonic anhydride. Methanesulfonyl chloride and p-toluenesulfonyl chloride are preferred.

The base used in the above reaction varies depending on, for example, the reagent used, but is not specifically limited. For example, organic bases such as imidazole, pyridine, triethylamine, and N-methylimidazole can be used, and imidazole, pyridine, and triethylamine are preferred.

Examples of the solvent used in the above reaction include aliphatic hydrocarbons such as hexane and heptane; aromatic hydrocarbons such as toluene and xylene; halogenated hydrocarbons such as dichloromethane and 1,2-dichloroethane; esters such as ethyl acetate and butyl acetate; ethers such as tetrahydrofuran, diethyl ether, and t-butylmethyl ether; and amides such as 1-methyl-2-pyrrolidinone, N,N-dimethylformamide, and N,N-dimethylacetamide. Halogenated hydrocarbons are preferred, and dichloromethane is more preferred.

The reaction temperature varies depending on, for example, the raw materials, the reagent used, and the kind of the solvent and is usually −20° C. to 100° C. and preferably 0° C. to 25° C.

The reaction time varies depending on the reaction temperature, the raw materials, the reaction reagent, and the solvent used and is usually 10 minutes to 12 hours and preferably 2 hours to 3 hours.

Process C2 is for manufacturing a compound having formula (IV).

The process is conducted by a reaction between a compound having formula (VII) and glycine in a solvent in the presence of a base.

The base used in the above reaction varies depending on, for example, the reagent used, but is not specifically limited. For example, organic bases such as imidazole, pyridine, triethylamine, N-methylimidazole, and diisopropylethylamine are used, and triethylamine is preferred.

Examples of the solvent used in the above reaction include alcohols such as methanol, ethanol, n-propanol, isopropanol, n-butanol, isobutanol, t-butanol, isoamyl alcohol, diethylene glycol, glycerine, octanol, cyclohexanol, and methyl cellosolve; ethers such as diethyl ether, diisopropyl ether, tetrahydrofuran, dioxane, dimethoxyethane, and diethylene glycol dimethyl ether; water; and solvent mixtures such as mixtures of water and the above-mentioned organic solvents. Solvent mixtures of ethers and water are preferred, and a solvent mixture of tetrahydrofuran and water is more preferred.

The reaction temperature varies depending on, for example, the raw materials, the reagent used, and the kind of the solvent used and is usually −20° C. to 100° C. and preferably 0° C. to 25° C.

The reaction time varies depending on the reaction temperature, the raw materials, the reaction reagent, and the kind of the solvent used and is usually 10 minutes to 24 hours and preferably 1 hour to 12 hours.

After the completion of the reaction, the target compound of this process is collected from the reaction mixture according to the same method as in Process A.

The following Process D is an alternative process to Process C for manufacturing a compound having formula (IV).

Process D

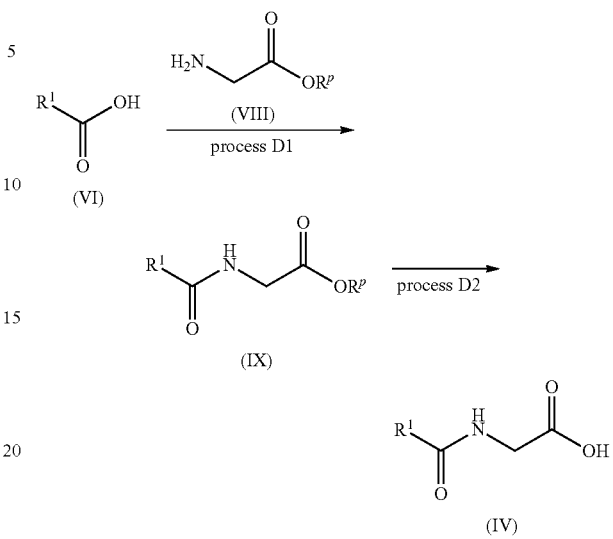

In the above formula, $R^1$ represents the same meaning as that described above. $R^P$ represents a carboxyl protecting group and is the same as those described above.

Process D1 is for manufacturing a compound having a formula (IX) and is conducted by a reaction between a compound having a formula (VI) and a compound having a formula (VIII) in the presence of a condensing agent in a solvent in the presence or absence of a base.

Any condensing agent can be used in the above reaction without any limitation, and examples thereof include azodicarboxylic acid di-lower alkyl ester-triphenylphosphines such as azodicarboxylic acid diethyl ester-triphenylphosphine; carbodiimide derivatives such as N,N'-dicyclohexylcarbodiimide (DCC) and 1-ethyl-3-(3-dimethylaminopropyl)carbodiimide (EDCI); 2-halo-1-lower alkyl pyridinium halides such as 2-chloro-1-methylpyridinium iodide; diarylphosphorylazides such as diphenylphosphorylazide (DPPA); chloroformic acid esters such as ethyl chloroformate and isobutyl chloroformate; phosphoryl chlorides such as diethyl phosphoryl chloride; imidazole derivatives such as N,N'-carbodiimidazole (CDI); benzotriazole derivatives such as O-(7-azabenzotriazol-1-yl)-N,N,N',N'-tetramethyluronium hexafluorophosphate (HATU) and (1H-benzotriazol-1-yloxy)tripyrrolidinophosphonium hexafluorophosphate (PyBOP); and 4-(4,6-dimethoxy-1,3,5-triazin-2-yl)-4-methylmorphorinium chloride (DMT-MM). DMT-MM is preferred.

The base used in the above reaction varies depending on, for example, the reagent used, but is not specifically limited. Examples of the base include organic bases such as imidazole, pyridine, triethylamine, N-methylimidazole, and diisopropylethylamine. Triethylamine is preferred.

Examples of the solvent used in the above reaction include halogenated hydrocarbons such as dichloromethane and 1,2-dichloroethane; alcohols such as methanol, ethanol, n-propanol, isopropanol, n-butanol, isobutanol, t-butanol, isoamyl alcohol, diethylene glycol, glycerine, octanol, cyclohexanol, and methyl cellosolve; ethers such as diethyl ether, diisopropyl ether, tetrahydrofuran, dioxane, dimethoxyethane, and diethylene glycol dimethyl ether; and water. Alcohols and water are preferred, and ethanol is more preferred.

The reaction temperature varies depending on, for example, the raw materials, the reagent used, and the kind of the solvent and is usually −20° C. to 100° C. and preferably 0° C. to 50° C.

The reaction time varies depending on the reaction temperature, the raw materials, the reaction reagent, and the kind of the solvent used and is usually 10 minutes to 24 hours and preferably 1 hour to 12 hours.

After the completion of the reaction, the target compound of this process is collected from the reaction mixture according to the same method as in Process A.

Process D2 is for manufacturing a compound having a formula (IV) and is conducted by hydrolysis of a compound having formula (IX) in a solvent in the presence of a base.

Examples of the base used in the above reaction include alkali metal carbonates such as lithium carbonate, sodium carbonate, and potassium carbonate; alkali metal bicarbonates such as lithium hydrogen carbonate, sodium hydrogen carbonate, and potassium hydrogen carbonate; alkali metal hydrides such as lithium hydride, sodium hydride, and potassium hydride; alkali metal hydroxides such as lithium hydroxide, sodium hydroxide, and potassium hydroxide; and alkali metal alkoxides such as lithium methoxide, sodium methoxide, sodium ethoxide, and potassium t-butoxide. Alkali metal hydroxides are preferred, and lithium hydroxide and sodium hydroxide are more preferred.

Examples of the solvent used in the above reaction include ethers such as diethyl ether, diisopropyl ether, tetrahydrofuran, dioxane, dimethoxyethane, and diethylene glycol dimethyl ether; lower alkyl nitriles such as acetonitrile and propionitrile; amides such as formamide, N,N-dimethylformamide, N,N-dimethylacetamide, and hexamethylphosphoric acid triamide; lower alkyl alcohols such as methanol, ethanol, propanol, and butanol; and water. Alcohols, ethers, and water are preferred, and ethanol is more preferred.

The reaction temperature varies depending on, for example, the raw materials, the reagent used, and the kind of the solvent and is usually 0° C. to 100° C. and preferably 25° C. to 80° C.

The reaction time varies depending on the reaction temperature, the raw materials, the reaction reagent, and the kind of the solvent used and is usually 10 minutes to 12 hours and preferably 2 to 3 hours.

After the completion of the reaction, the target compound of this process is collected from the reaction mixture according to the same method as in Process A.

The following Process E is an alternative process to process D2 of Process D for manufacturing a compound having formula (IV) from a compound having formula (IX).

Process E

In the above formula, $R^1$ is the same meaning as that described above. RP represents protecting groups which can be deprotected with an acid, among the above-mentioned carboxyl protecting groups.

The "protecting groups which can be deprotected with an acid" are preferably a THP (tetrahydropyranyl) group, a tetrahydrofuranyl group, an MEM (methoxyethoxymethyl) group, a BOM (benzyloxymethyl) group, a tertiary butyl (t-butyl) group, a diphenylmethyl group, a 9-anthrylmethyl group, and a 5-dibenzoylsuberyl group.

Process E1 is for manufacturing a compound having formula (IV) and is conducted by hydrolysis of a compound having formula (IX) in a solvent in the presence of an acid.

Examples of the acid used in the above reaction include Bronsted acids, for example, inorganic acids, such as hydrochloric acid, hydrobromic acid, sulfuric acid, perchloric acid, and phosphoric acid, and organic acids, such as acetic acid, formic acid, oxalic acid, methanesulfonic acid, p-toluenesulfonic acid, camphorsulfonic acid, trifluoroacetic acid, and trifluoromethanesulfonic acid; Lewis acids such as zinc chloride, tin tetrachloride, boron trichloride, boron trifluoride, and boron tribromide; and acidic ion-exchange resins. Inorganic acids and organic acids are preferred, and trifluoroacetic acid is more preferred.

Examples of the solvent used in the above reaction include aliphatic hydrocarbons such as hexane, heptane, ligroin, and petroleum ether; aromatic hydrocarbons such as toluene, benzene, and xylene; halogenated hydrocarbons such as dichloromethane and 1,2-dichloroethane; ethers such as diethyl ether, diisopropyl ether, tetrahydrofuran, dioxane, dimethoxyethane, and diethylene glycol dimethyl ether; lower alkyl nitriles such as acetonitrile and propionitrile; and amides such as formamide, N,N-dimethylformamide, N,N-dimethylacetamide, and hexamethylphosphoric acid triamide. Halogenated hydrocarbons are preferred, and dichloromethane is more preferred.

The reaction temperature varies depending on, for example, the raw materials, the reagent used, and the kind of the solvent and is usually 0 to 100° C. and preferably 0 to 50° C.

The reaction time varies depending on the reaction temperature, the raw materials, the reaction reagent, and the kind of the solvent used and is usually 10 minutes to 6 hours and preferably 1 to 3 hours.

After the completion of the reaction, the target compound of this process is collected from the reaction mixture according to the same method as in Process A.

The following Process F is for manufacturing a compound having formula (VI') which can be used as a compound having formula (VI) in Process C or D.

Process F

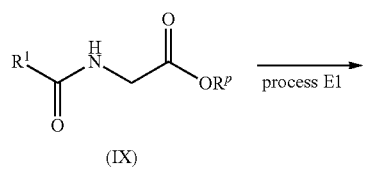

(IX)

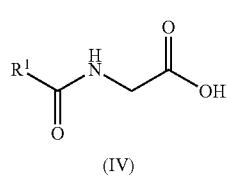

(IV)

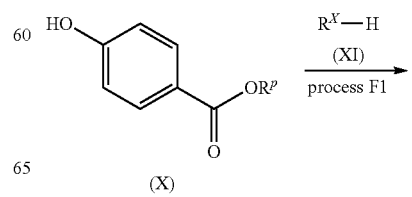

(X)

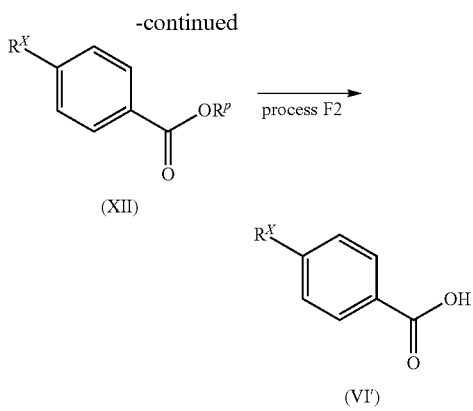

In the above formula, $R^P$ represents the same meaning as that in the above-mentioned Process D or E, and $R^x$ represents a group selected from the group consisting of $C_1$-$C_6$ alkoxy groups which may be substituted with one group or more than one group selected from substituent group β, $C_1$-$C_6$ haloalkoxy groups, $C_1$-$C_6$ alkoxy $C_1$-$C_6$ alkoxy groups which may be substituted with one group or more than one group selected from substituent group β, $C_1$-$C_6$ alkenyloxy groups which may be substituted with one group or more than one group selected from substituent group β, $C_1$-$C_6$ alkynyloxy groups which may be substituted with one group or more than one group selected from substituent group β, $C_3$-$C_6$ cycloalkyloxy groups, 3- to 6-membered heterocyclyloxy groups, $C_6$-$C_{10}$ aryloxy groups which may be substituted with one group or more than one group selected from substituent group γ, $C_1$-$C_6$ alkylthio groups which may be substituted with one group or more than one group selected from substituent group β, and $C_1$-$C_6$ haloalkylthio groups, among groups selected from substituent group α.

Process F1 is for manufacturing a compound having formula (XII) and is conducted by a reaction between a compound having formula (X) and a compound having formula (XI) in a solvent using a Mitsunobu reagent or the like.

The Mitsunobu reagent or the like used in the above reaction is preferably a combination of an azo compound, for example, a diazodicarboxylic acid lower alkyl ester such as diethyl azodicarboxylate or diisopropyl azodicarboxylate or an azodicarbonyl such as 1,1'-(azodicarbony)dipiperidine and a phosphine, for example, a triarylphosphine such as triphenylphosphine or a tri-lower alkyl phosphine such as tributylphosphine; or a tributyl phosphoranylidene acetonitrile, more preferably a combination of a diazodicarboxylic acid lower alkyl ester and a triarylphosphine, or tributyl phosphoranylidene acetonitrile, and particularly more preferably a combination of diethyl azodicarboxylate and triphenylphosphine, or tributyl phosphoranylidene acetonitrile.

The case that the Mitsunobu reagent or the like is tributyl phosphoranylidene acetonitrile Examples of the solvent used include aliphatic hydrocarbons such as hexane, heptane, ligroin, and petroleum ether; aromatic hydrocarbons such as toluene, benzene, and xylene; halogenated hydrocarbons such as dichloromethane and 1,2-dichloroethane; and ethers such as diethyl ether, diisopropyl ether, tetrahydrofuran, dioxane, dimethoxyethane, and diethylene glycol dimethyl ether. Aromatic hydrocarbons are preferred, and toluene is more preferred.

The reaction temperature varies depending on, for example, the raw materials, the reagent used, and the kind of the solvent used and is usually 0 to 150° C. and preferably 50 to 120° C.

The reaction time varies depending on the reaction temperature, the raw materials, the reaction reagent, and the kind of the solvent used and is usually 30 minutes to 12 hours and preferably 2 to 5 hours.

(2) The case that the Mitsunobu reagent or the like is a combination of an azo compound and a phosphine Examples of the solvent used include aliphatic hydrocarbons such as hexane, heptane, ligroin, and petroleum ether; aromatic hydrocarbons such as toluene, benzene, and xylene; halogenated hydrocarbons such as dichloromethane and 1,2-dichloroethane; and ethers such as diethyl ether, diisopropyl ether, tetrahydrofuran, dioxane, dimethoxyethane, and diethylene glycol dimethyl ether. Ethers are preferred, and tetrahydrofuran is more preferred.

The reaction temperature varies depending on, for example, the raw materials, the reagent used, and the kind of the solvent and is usually −20 to 80° C. and preferably 0 to 50° C.

The reaction time varies depending on the reaction temperature, the raw materials, the reaction reagent, and the kind of the solvent used and is usually 30 minutes to 24 hours and preferably 1 to 3 hours.

After the completion of the reaction, the target compound of this process is collected from the reaction mixture according to the same method as in Process A.

Process F2 is for manufacturing a compound having a formula (VI') and is conducted by hydrolysis of a compound having formula (XII) in a solvent in the presence of a base or an acid by the same process of process D2 of Process D or process E1 of Process E.

(Description of Usefulness)

The amido derivative which is an active ingredient of the drug of the present invention or its pharmacologically acceptable salt is low in toxicity and is excellent in bone resorption-suppressing activity. Therefore, the drug of the present invention is particularly valuable as a prophylactic or therapeutic agent (in particular, therapeutic agent) for osteoporosis.

When the compound having Formula (I), which is an active ingredient of the drug of the present invention, or its pharmacologically acceptable salt is used as the above-mentioned prophylactic or therapeutic agent (in particular, therapeutic agent), the compound or the salt itself or a mixture with an optional pharmacologically acceptable filler, diluent, or the like can be administered, for example, orally as a tablet, a capsule, granules, powder, or syrup; or parenterally as an injection or a suppository.

These formulations are prepared by widely known methods using additives such as fillers (for example, organic fillers: sugar derivatives such as lactose, white sugar, glucose, mannitol, and sorbitol; starch derivatives such as corn starch, potato starch, α-starch, and dextrin; cellulose derivatives such as crystal cellulose; gum arabic; dextran; and pullulan, and inorganic fillers: silicate derivatives such as light anhydrous silicic acid, synthetic aluminum silicate, calcium silicate, and magnesium aluminometasilicate; phosphates such as calcium hydrogen phosphate; carbonates such as calcium carbonate; and sulfates such as calcium sulfate), lubricants (for example, stearic acid, stearic acid metal salts such as calcium stearate, and magnesium stearate; talc; colloidal silica; waxes such as bee gum and spermaceti; boric acid; adipic acid; sulfuric acid salts such as sodium sulfate; glycol; fumaric acid; sodium benzoate; D,L-leucine; fatty acid sodium salts; laurylsulfuric acid salts such as sodium laurylsulfate and magnesium laurylsulfate; silic acids such as silicic anhydride and silicate hydrate; and the above-mentioned starch derivatives), binders (for example, hydroxypropylcellulose, hydroxypropylmethylcellulose, polyvinylpyrrolidone, macrogol, and the same compounds as the above-mentioned fillers), disintegrating agents (for example, cellulose derivatives such as low-substituted hydroxypropylcellulose, carboxylmethylcellulose, carboxylmethylcellulose calcium, and internally-crosslinked carboxylmethylcellulose sodium; and chemically modified starch/cellulose such as carboxylmethyl starch, carboxylmethyl starch sodium, and crosslinked polyvinylpyrrolidone), stabilizers (for example, paraoxybenzoic acid esters such as methylparaben and propylparaben; alcohols such as chlorobutanol, benzylalcohol, and phenylethylalcohol; benzalkonium chloride; phenols such as phenol and cresol; thimerosal; dehydroacetic acid; and sorbic acid), flavoring agents (for example, sweeteners, acidifiers, and flavors which are usually used), and diluents.

The dosage and administration regimen vary depending on, for example, the symptom and the age. Usually, the formulation is administered as follows:

For oral administration, the dose per administration is 0.001 to 100 mg/kg and preferably 0.01 to 10 mg/kg.

In intravenous administration, the dose per administration is 0.0001 to 10 mg/kg and preferably 0.001 to 1 mg/kg.

The administration frequency and the administration interval vary depending on the disease to be treated and its severity or the purpose, i.e., therapeutic use or prophylactic use, and are usually one to three times a day or one to six times weekly to monthly. The pharmaceutical composition according to the present invention has satisfactory physical stability, bioabsorption, and pharmacokinetics and thereby has an excellent advantage as the administration frequency may be low.

ADVANTAGES OF THE INVENTION

The present inventors have conducted intensive studies on drugs having excellent blood calcium concentration-decreasing activity and bone mass decrease-suppressing activity and have found drugs comprising the compounds having Formula (I) of the present invention.

The compounds having Formula (I) of the present invention are low in toxicity and have excellent bone resorption-suppressing activity and thereby blood calcium concentration-decreasing activity and bone mass decrease-suppressing activity. Therefore, the compound is valuable as a prophylactic or therapeutic agent (in particular, therapeutic agent) for the above-mentioned bone metabolic diseases.

BEST MODE FOR CARRYING OUT THE INVENTION

Examples

The present invention will now be further described in detail with reference to Examples and Test Examples, but is not limited to them.

Example 1

N-((Z)-2-(4-Chlorophenyl)-1-{[(2-hydroxyethyl)amino]carbonyl}vinyl)-4-[2-(4-methoxyphenyl)ethoxy]benzamide (Exemplary Compound No. 1-144)

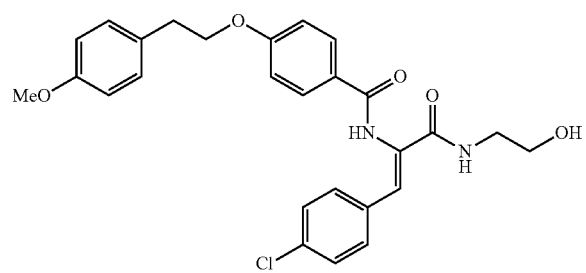 [SMILES: COc1ccc(CCOc2ccc(C(=O)N/C(=C\c3ccc(Cl)cc3)C(=O)NCCO)cc2)cc1]

(1a) N-(4-Hydroxybenzoyl)glycine tert-butyl ester

Oxalyl chloride (8.7 mL, 99.7 mmol) and several drops of N,N-dimethylformaldehyde (hereinafter DMF) were added to a solution of dichloromethane (40 mL) containing 4-benzyloxybenzoic acid (11.1 g, 48.6 mmol) under ice-cooling. The mixture was stirred at room temperature for 2 hours, and then the solvent was evaporated. The resulting residue was dissolved in dichloromethane (100 mL), and then glycine tert-butyl ester hydrochloride (8.20 g, 48.9 mmol) and N-ethyl-N,N-diisopropylamine (21 mL, 120 mmol) were added thereto under ice-cooling. The mixture was stirred at room temperature for 19 hours, and then water was added thereto to terminate the reaction. The mixture was extracted with dichloromethane twice, and the organic layers were combined and concentrated. The resulting residue was purified by silica gel column chromatography (hexane:ethyl acetate, 9:1 to 2:1, v/v) to give N-[4-(benzyloxy)benzoyl]glycine tert-butyl ester. All the given ester was dissolved in methanol (165 mL), and 20% palladium hydroxide-carbon (926 mg) was added thereto. The mixture was vigorously stirred under a hydrogen atmosphere at room temperature for 3.5 hours. The reaction mixture was filtered through Celite and then concentrated to give 12.2 g of the title compound (colorless crystalline solid, yield: quantitative).

$^1$H-nuclear magnetic resonance spectrum (400 MHz, DMSO-$d_6$) δ ppm:

9.97 (1H, s), 8.54 (1H, brt, J=6 Hz), 7.70 (2H, d, J=9 Hz), 6.78 (2H, d, J=9 Hz), 3.83 (2H, d, J=6 Hz), 1.41 (9H, s).

(1b) N-{4-[2-(4-Methoxyphenyl)ethoxy]benzoyl}glycine (Tributyl phosphoranylidene)acetonitrile (428 μL, 1.50 mmol) was added to a solution of toluene (7 mL) containing N-(4-hydroxybenzoyl)glycine tert-butyl ester (264 mg, 1.05 mmol) prepared in Example 1 (1a) and 2-(4-methoxyphenyl)ethanol (176 mg, 1.16 mmol). The mixture was stirred at 100° C. for 3.5 hours, and then water was added thereto. The mixture was extracted with ethyl acetate. The organic layers were combined, washed with water and saturated brine, and dried over anhydrous magnesium sulfate. Then, the solvent was evaporated. The resulting residue was purified by silica gel column chromatography (hexane to hexane:ethyl acetate, 6:1, 4:1, and 3:1, v/v) to give an oily substance (358 mg). To a solution of dichloromethane (1 mL) containing this oily substance (358 mg, 0.929 mmol), trifluoroacetic acid (0.5 mL) was added. The mixture was stirred at room temperature for 1 hour, and then the solvent was evaporated. Diisopropyl ether was added to the resulting residue to suspend it. The produced precipitate was collected by filtration and was washed with diisopropyl ether to give 248 mg of the title compound (colorless crystalline solid, yield: 72%).

$^1$H-nuclear magnetic resonance spectrum (400 MHz, DMSO-$d_6$) δ ppm:

12.50 (1H, brs), 8.67 (1H, t, J=5 Hz), 7.83 (2H, d, J=8 Hz), 7.24 (2H, d, J=8 Hz), 7.00 (2H, d, J=8 Hz), 6.87 (2H, d, J=8 Hz), 4.20 (2H, t, J=6 Hz), 3.89 (2H, d, J=5 Hz), 3.72 (3H, s), 2.98 (2H, t, J=6 Hz).

(1c) (4Z)-4-(4-Chlorobenzylidene)-2-{4-[2-(4-methoxyphenyl)ethoxy]phenyl}-1,3-oxazol-5(4H)-one A mixture of N-{4-[2-(4-methoxyphenyl)ethoxy]benzoyl}glycine (329 mg, 1.00 mmol) prepared in Example 1 (1b), 4-chlorobenzaldehyde (148 mg, 1.05 mmol), sodium acetate (111 mg, 1.35 mmol), and acetic anhydride (467 μL, 5.00 mmol) was stirred at 120° C. for 20 minutes, and then water was added thereto to terminate the reaction. Then, continuously, the mixture was vigorously stirred until the mixture was cooled to room temperature. The deposited precipitate was collected by filtration, washed with water and hexane, and dried by heating under reduced pressure to give 376 mg of the title compound (yellow powder, yield: 87%).

Hereinafter, the compound obtained in this cyclizing reaction is called an oxazolone.

$^1$H-nuclear magnetic resonance spectrum (400 MHz, CDCl$_3$) δ ppm:

8.11 (2H, d, J=9 Hz), 8.09 (2H, d, J=9 Hz), 7.42 (2H, d, J=9 Hz), 7.20 (2H, d, J=8 Hz), 7.09 (1H, s), 6.99 (2H, d, J=9 Hz), 6.86 (2H, d, J=8 Hz), 4.22 (2H, t, J=7 Hz), 3.80 (3H, s), 3.08 (2H, t, J=7 Hz).

(1d) N-((Z)-2-(4-Chlorophenyl)-1-{[(2-hydroxyethyl)amino]carbonyl}vinyl)-4-[2-(4-methoxyphenyl)ethoxy]benzamide 2-Aminoethanol (18 μL, 0.30 mmol) was added to a solution of ethanol (0.7 mL) containing (4Z)-4-(4-chlorobenzylidene)-2-{-4-[2-(4-methoxyphenyl)ethoxy]phenyl}-1,3-oxazol-5(4H)-one prepared in Example 1 (1c) (108 mg, 0.25 mmol). The mixture was stirred at 60° C. for 3 hours. The solvent was evaporated, and the residue was purified by thin layer chromatography for separation (ethyl acetate:methanol, 30:1, v/v, developed three times) to give 88 mg of the title compound (white amorphous solid, yield: 71%).

MS (FAB) m/z: 495 [M+H]$^+$;

$^1$H-nuclear magnetic resonance spectrum (400 MHz, DMSO-d$_6$) δ ppm:

9.75 (1H, brs), 8.06 (1H, t, J=5 Hz), 7.94 (2H, d, J=8 Hz), 7.53 (2H, d, J=8 Hz), 7.39 (2H, d, J=7 Hz), 7.25 (2H, d, J=7 Hz), 7.14 (1H, s), 7.04 (2H, d, J=8 Hz), 6.88 (2H, d, J=7 Hz), 4.63 (1H, t, J=6 Hz), 4.23 (2H, t, J=7 Hz), 3.73 (3H, s), 3.44 (2H, q, J=6 Hz), 3.23 (2H, q, J=6 Hz), 2.99 (2H, t, J=6 Hz).

Example 2

N-((Z)-2-[4-(Difluoromethoxy)phenyl]-1-{[(2-hydroxyethyl)amino]carbonyl}vinyl)-4-[2-(4-methoxyphenyl)ethoxy]benzamide (Exemplary Compound No. 1-131)

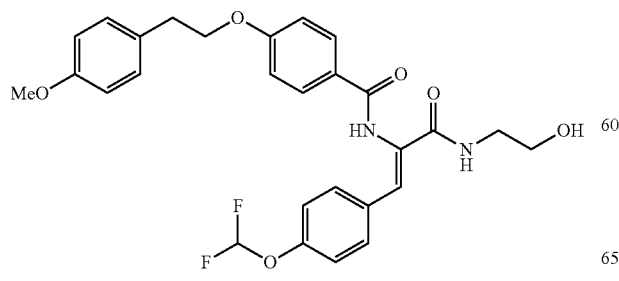

The same reaction as in Example 1 (1c) was conducted using N-{4-[2-(4-methoxyphenyl)ethoxy]benzoyl}glycine (329 mg) prepared in Example 1 (1b) and 4-(difluoromethoxy)benzaldehyde (139 μL) to give the corresponding oxazolone (334 mg). Then, the same reaction as in Example 1 (1d) was conducted using 121 mg of this oxazolone to give 114 mg of the title compound (white amorphous solid).

MS (FAB) m/z: 527 [M+14]$^+$;

$^1$H-nuclear magnetic resonance spectrum (400 MHz, CDCl$_3$) δ ppm:

7.89 (1H, brs), 7.77 (2H, d, J=9 Hz), 7.37 (2H, d, J=9 Hz), 7.20 (2H, d, J=9 Hz), 7.05 (2H, d, J=9 Hz), 7.00 (1H, s), 6.91 (2H, d, J=9 Hz), 6.87 (2H, d, J=9 Hz), 6.77 (1H, t, J=6 Hz), 6.49 (1H, t, J=74 Hz), 4.17 (2H, t, J=7 Hz), 3.80 (3H, s), 3.77 (2H, t, J=5 Hz), 3.49 (2H, q, J=5 Hz), 3.06 (2H, t, J=7 Hz).

Example 3

N-{(Z)-1-{[(2-Hydroxyethyl)amino]carbonyl}-2-[4-(trifluoromethoxy)phenyl]vinyl}-4-[2-(4-methoxyphenyl)ethoxy]benzamide (Exemplary Compound No. 1-132)

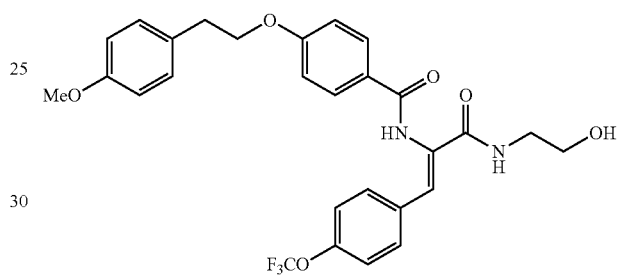

The same reaction as in Example 1 (1c) was conducted using N-{4-[2-(4-methoxyphenyl)ethoxy]benzoyl}glycine (329 mg) prepared in Example 1 (1b) and 4-(trifluoromethoxy)benzaldehyde (150 μl) to give the corresponding oxazolone (366 mg). Then, the same reaction as in Example 1 (1d) was conducted using 160 mg of this oxazolone to give 126 mg of the title compound (white powder).

mp: 139 to 141° C.;

$^1$H-nuclear magnetic resonance spectrum (400 MHz, DMSO-d$_6$) δ ppm:

9.80 (1H, brs), 8.08 (1H, t, J=5 Hz), 7.95 (2H, d, J=8 Hz), 7.64 (2H, d, J=7 Hz), 7.33 (2H, d, J=8 Hz), 7.25 (2H, d, J=7 Hz), 7.17 (1H, s), 7.04 (2H, d, J=8 Hz), 6.88 (2H, d, J=8 Hz), 4.64 (1H, t, J=5 Hz), 4.23 (2H, t, J=6 Hz), 3.73 (3H, s), 3.46 (2H, q, J=6 Hz), 3.24 (2H, q, J=6 Hz), 3.00 (2H, t, J=6 Hz).

Example 4

N-((Z)-2-[4-(2,2-Difluoroethoxy)phenyl]-1-{[(2-hydroxyethyl)amino]carbonyl}vinyl)-4-[2-(4-methoxyphenyl)ethoxy]benzamide (Exemplary Compound No. 1-134)

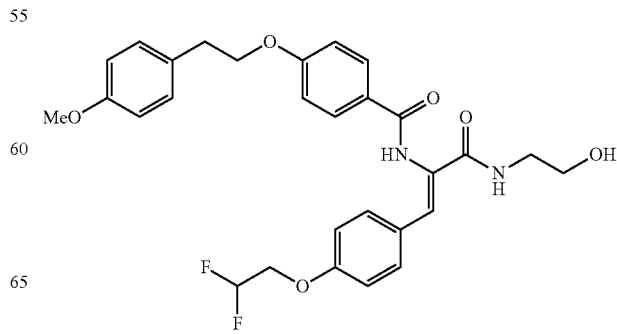

(4a) 4-(2,2-Difluoroethoxy)benzaldehyde

With reference to the document (J. Med. Chem., (1994), 37, 3977-3985), sodium hydride (3.36 g, 55%, 77.1 mmol) was added to a solution of DMF (100 mL) containing 2,2-difluoroethanol (5.75 g, 70.1 mmol) over 5 minutes under nitrogen gas flow under ice-cooling. The mixture was stirred at the same temperature for 10 minutes, and then a solution of DMF (40 mL) containing 4-fluorobenzaldehyde (9.56 g, 77.0 mmol) was added dropwise thereto over 5 minutes. The mixture was stirred at room temperature for 4 hours and was then poured into ice water (500 mL). The resulting mixture was extracted with ether:hexane (300 mL, 1:1, v/v) three times. The extracted organic layer was washed with water (300 mL) three times and then with saturated brine, and was dried over anhydrous magnesium sulfate. Then, the solvent was evaporated to give a crude product. An ether/hexane mixture solution (20 mL, 1:10, v/v) was added to the crude product, and the supernatant fluid was removed. This procedure was repeated four times in total to wash the crystals to give 10.1 g of the title compound (colorless crystalline solid, yield: 77%).

$^1$H-nuclear magnetic resonance spectrum (500 MHz, CDCl$_3$) δ ppm:

9.92 (1H, s), 7.87 (2H, d, J=8 Hz), 7.04 (2H, d, J=8 Hz), 6.13 (1H, tt, J=55 Hz, 4 Hz), 4.27 (2H, td, J=13 Hz, 4 Hz).

(4b) N-((Z)-2-[4-(2,2-Difluoroethoxy)phenyl]-1-{[(2-hydroxyethyl)amino]carbonyl}vinyl)-4-[2-(4-methoxyphenyl)ethoxy]benzamide The same reaction as in Example 1 (1c) was conducted using N-{4-[2-(4-methoxyphenyl)ethoxy]benzoyl}glycine (329 mg) prepared in Example 1 (1b) and 4-(2,2-difluoroethoxy)benzaldehyde (196 mg) prepared in Example 4 (4a) to give the corresponding oxazolone (306 mg). Then, the same reaction as in Example 1 (1d) was conducted using 158 mg of this oxazolone to give 144 mg of the title compound (white powder).

mp: 172 to 174° C.;

$^1$H-nuclear magnetic resonance spectrum (400 MHz, DMSO-d$_6$) δ ppm:

9.69 (1H, brs), 7.96 (2H, d, J=8 Hz), 7.93 (1H, t, J=5 Hz), 7.51 (2H, d, J=8 Hz), 7.25 (2H, d, J=7 Hz), 7.20 (1H, s), 7.04 (2H, d, J=8 Hz), 6.97 (2H, d, J=8 Hz), 6.88 (2H, d, J=7 Hz), 6.36 (1H, tt, J=55 Hz, 3 Hz), 4.63 (1H, t, J=7 Hz), 4.30 (2H, td, J=14 Hz, 3 Hz), 4.23 (2H, t, J=7 Hz), 3.73 (3H, s), 3.43 (2H, q, J=6 Hz), 3.22 (2H, q, J=6 Hz), 3.00 (2H, t, J=7 Hz).

Example 5

N-((Z)-2-(4-Cyclopropylphenyl)-1-{[(2-hydroxyethyl)amino]carbonyl}vinyl)-4-[2-(4-methoxyphenyl)ethoxy]benzamide (Exemplary Compound No. 1-138)

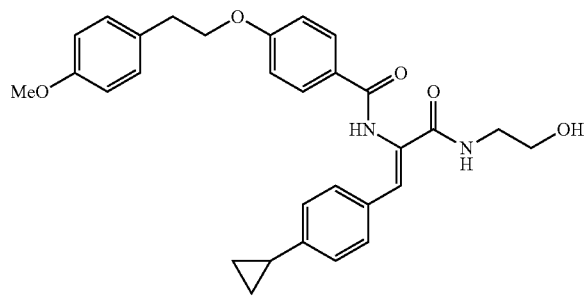 [SMILES: COc1ccc(CCOc2ccc(C(=O)N/C(=C\c3ccc(C4CC4)cc3)C(=O)NCCO)cc2)cc1]

The same reaction as in Example 1 (1c) was conducted using N-{4-[2-(4-methoxyphenyl)ethoxy]benzoyl}glycine (329 mg) prepared in Example 1 (1b) and 4-cyclopropylbenzaldehyde (which is the compound disclosed in Tetrahedron Lett., (2002), 43, 6987-6990, 154 mg) to give the corresponding oxazolone (300 mg). Then, the same reaction as in Example 1 (1d) was conducted using 154 mg of this oxazolone to give 155 mg of the title compound (white amorphous solid).

MS (FAB) m/z: 501 [M+H]$^+$;

$^1$H-nuclear magnetic resonance spectrum (400 MHz, CDCl$_3$) δ ppm:

7.79 (2H, d, J=9 Hz), 7.71 (1H, brs), 7.28 (2H, d, J=8 Hz), 7.20 (2H, d, J=8 Hz), 7.05 (1H, s), 7.02 (2H, d, J=8 Hz), 6.93 (2H, d, J=9 Hz), 6.87 (2H, d, J=9 Hz), 6.65 (1H, t, J=5 Hz), 4.18 (2H, t, J=7 Hz), 3.80 (3H, s), 3.78 (2H, t, J=5 Hz), 3.50 (2H, q, J=5 Hz), 3.06 (2H, t, J=7 Hz), 1.89-1.83 (1H, m), 1.01-0.96 (2H, m), 0.71-0.67 (2H, m).

Example 6

N-((Z)-2-[4-(Cyclopropyloxy)phenyl]-1-{[(2-hydroxyethyl)amino]carbonyl}vinyl)-4-[2-(4-methoxyphenyl)ethoxy]benzamide (Exemplary Compound No. 1-130)

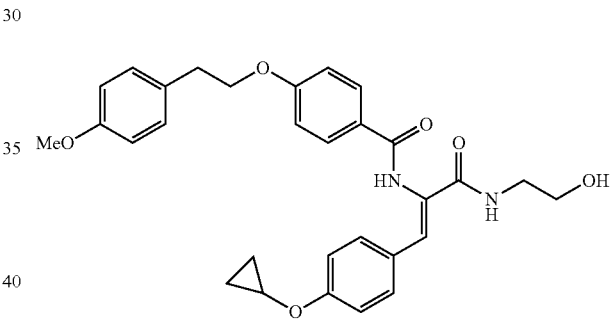

(6a) 1-Bromo-4-(2-chloroethoxy)benzene

With reference to the document (J. Org. Chem., (2002), 67, 1093-1101), potassium carbonate (83.0 g, 600 mmol) was added to a solution of DMF (500 mL) containing 4-bromophenol (50.4 g, 291 mmol) at room temperature. The mixture was stirred at the same temperature for 30 minutes, and then 2-chloroethyl 4-methylbenzenesulfonate (70.2 g, 299 mmol) was added thereto. The mixture was stirred at 50° C. for 24 hours. The reaction solution was cooled to 10° C., and water (500 mL) was added thereto to precipitate a white solid. This white solid was collected by filtration, washed with water (500 mL), and dried at 50° C. under reduced pressure to give 58.6 g of the title compound (yield: 86%).

mp: 54 to 56° C.;

$^1$H-nuclear magnetic resonance spectrum (400 MHz, CDCl$_3$) δ ppm:

7.39 (2H, d, J=9 Hz), 6.81 (2H, d, J=9 Hz), 4.20 (2H, t, J=6 Hz), 3.80 (2H, t, J=6 Hz).

(6b) 1-Bromo-4-(vinyloxy)benzene

Tert-Butoxypotassium (33.7 g, 300 mmol) was added to a solution of tetrahydrofuran (hereinafter THF) (250 mL) containing 1-bromo-4-(2-chloroethoxy)benzene (58.6 g, 249 mmol) prepared in Example 6 (6a) over 10 minutes at −10° C. The mixture was stirred at room temperature for 21 hours, and water (500 mL) was added thereto. The resulting mixture was extracted with methyl tert-butyl ether (200 mL, 150 mL) twice. The organic layers were combined, washed with saturated brine (100 mL) twice, and dried over anhydrous magnesium sulfate. Then, the solvent was evaporated. The resulting residue was dissolved in hexane (100 mL), and the precipitated insoluble substance was removed by filtration. The insoluble substance was further washed with hexane (5 mL) five times. The filtrates were combined, concentrated, and purified by silica gel column chromatography (hexane) to give 39.0 g of the title compound (colorless oil, yield: 79%).

$^1$H-nuclear magnetic resonance spectrum (400 MHz, CDCl$_3$) δ ppm:
7.43 (2H, d, J=9 Hz), 6.89 (2H, d, J=9 Hz), 6.59 (1H, dd, J=14 Hz, 6 Hz), 4.78 (1H, dd, J=14 Hz, 2 Hz), 4.47 (1H, dd, J=6 Hz, 2 Hz).

(6c) 4-(Cyclopropyloxy)benzaldehyde

With reference to the document (Tetrahedron Lett., (1998), 39, 8621-8624), the following cyclopropanization was conducted. Diethyl zinc (1.0 M hexane solution, 250 mL, 250 mmol) was added to dichloromethane (250 mL), and a solution of dichloromethane (120 mL) containing trifluoroacetic acid (19.2 mL, 249 mmol) was added thereto under ice-cooling over 100 minutes. The mixture was further stirred for 1 hour. Then, a solution of dichloromethane (100 mL) containing chloroiodomethane (20.1 mL, 250 mmol) was added thereto under ice-cooling over 40 minutes, and a solution of dichloromethane (120 mL) containing 1-bromo-4-(vinyloxy)benzene (32.8 g, 165 mmol) prepared in Example 6 (6b) was further added thereto at the same temperature over 20 minutes. The mixture was stirred at room temperature for 1.5 hours. Then, 0.1 N hydrochloric acid (400 mL) was added to the reaction solution. The mixture was stirred for 30 minutes, filtered through Celite, and washed with hexane (200 mL). The filtrate and the hexane washing solution were combined. The organic layer was washed with 0.1 N hydrochloric acid (100 mL) and then with saturated brine (100 mL) containing about 1 g of sodium sulfite twice. The organic layer was dried over anhydrous magnesium sulfate, and the solvent was evaporated to give 36.0 g of 1-bromo-4-(cyclopropyloxy)benzene (yellow oil).

$^1$H-nuclear magnetic resonance spectrum (400 MHz, CDCl$_3$) δ ppm:
7.37 (2H, d, J=9 Hz), 6.93 (2H, d, J=9 Hz), 3.72-3.68 (1H, m), 0.79-0.73 (4H, m).

To a solution of THF (350 mL) containing this crude product (36.0 g, 165 mmol), n-butyllithium (116 mL, 1.56 M hexane solution, 181 mmol) was added at −66° C. over 40 minutes under a nitrogen atmosphere. The mixture was stirred at the same temperature for 1 hour. Then, DMF (23.6 g, 323 mmol) was added dropwise to the reaction solution over 12 minutes. The mixture was stirred at the same temperature for 30 minutes and left standing at room temperature overnight, and then a saturated ammonium chloride aqueous solution (150 mL) was added dropwise thereto over 5 minutes. The organic layer was separated and was washed with a saturated ammonium chloride aqueous solution (100 mL) and saturated brine (100 mL). The washing solution was combined and was extracted with hexane (200 mL). All organic layers were combined and dried over anhydrous magnesium sulfate. The solvent was evaporated, and the resulting residue was purified by silica gel column chromatography (hexane: ethyl acetate, 9:1, v/v) to give 23.3 g of the title compound (light yellow oil, yield: 87%).

$^1$H-nuclear magnetic resonance spectrum (400 MHz, CDCl$_3$) δ ppm:
9.87 (1H, s), 7.82 (2H, d, J=9 Hz), 7.14 (2H, d, J=9 Hz), 3.83-3.79 (1H, m), 0.87-0.81 (4H, m).

(6d) N-((Z)-2-[4-(Cyclopropyloxy)phenyl]-1-{[(2-hydroxyethyl)amino]carbonyl}vinyl)-4-[2-(4-methoxyphenyl)ethoxy]benzamide The same reaction as in Example 1 (1c) was conducted using N-{4-[2-(4-methoxyphenyl)ethoxy]benzoyl}glycine (329 mg) prepared in Example 1 (1b) and 4-(cyclopropyloxy)benzaldehyde (170 mg) prepared in Example 6 (6c) to give the corresponding oxazolone (304 mg). Then, the same reaction as in Example 1 (1d) was conducted using 159 mg of this oxazolone to give 159 mg of the title compound (white amorphous solid).

MS (FAB) m/z: 517 [M+H]$^+$;
$^1$H-nuclear magnetic resonance spectrum (400 MHz, CDCl$_3$) δ ppm:
7.81 (2H, d, J=9 Hz), 7.68 (1H, brs), 7.35 (2H, d, J=9 Hz), 7.21 (2H, d, J=8 Hz), 7.10 (1H, s), 7.00 (2H, d, J=9 Hz), 6.94 (2H, d, J=9 Hz), 6.87 (2H, d, J=8 Hz), 6.64 (1H, t, J=6 Hz), 4.19 (2H, t, J=7 Hz), 3.80 (3H, s), 3.78 (2H, t, J=5 Hz), 3.71 (1H, sept, J=3 Hz), 3.51 (2H, q, J=5 Hz), 3.06 (2H, t, J=7 Hz), 0.78-0.75 (4H, m).

Example 7

N-[(Z)-1-{[(2-Hydroxyethyl)amino]carbonyl}-2-(4-isopropoxyphenyl)vinyl]-4-[2-(4-methoxyphenyl)ethoxy]benzamide (Exemplary Compound No. 1-129)

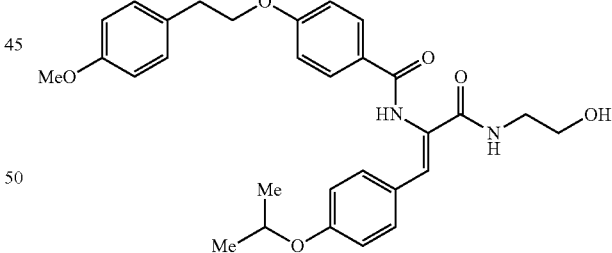

The same reaction as in Example 1 (1c) was conducted using N-{4-[2-(4-methoxyphenyl)ethoxy]benzoyl}glycine (248 mg) prepared in Example 1 (1b) and 4-isopropoxybenzaldehyde (131 μL) to give the corresponding oxazolone (227 mg). Then, the same reaction as in Example 1 (1d) was conducted using all this oxazolone to give 122 mg of the title compound (white amorphous solid).

MS (FAB) m/z: 519 [M+H]$^+$;
$^1$H-nuclear magnetic resonance spectrum (400 MHz, DMSO-d$_6$) δ ppm:
9.67 (1H, brs), 7.97 (2H, d, J=8 Hz), 7.89 (1H, brt, J=5 Hz), 7.47 (2H, d, J=8 Hz), 7.26 (2H, d, J=8 Hz), 7.18 (1H, s), 7.05 (2H, d, J=8 Hz), 6.89 (2H, d, J=8 Hz), 6.86 (2H, d, J=8 Hz), 4.64-4.58 (2H, m), 4.23 (2H, t, J=7 Hz), 3.73 (3H, s), 3.43 (2H, q, J=6 Hz), 3.22 (2H, q, J=6 Hz), 3.00 (2H, t, J=7 Hz), 1.23 (6H, d, J=6 Hz).

Example 8

N-{(Z)-1-{[(2-Hydroxyethyl)amino]carbonyl}-2-[4-(methylthio)phenyl]vinyl}-4-[2-(4-methoxyphenyl)ethoxy]benzamide (Exemplary Compound No. 1-141)

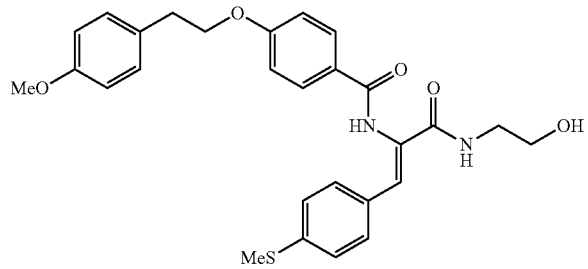 [SMILES: COc1ccc(CCOc2ccc(C(=O)N/C(=C\c3ccc(SC)cc3)C(=O)NCCO)cc2)cc1]

The same reaction as in Example 1 (1c) was conducted using N-{4-[2-(4-methoxyphenyl)ethoxy]benzoyl}glycine (329 mg) prepared in Example 1 (1b) and 4-(methylthio)benzaldehyde (140 µL) to give the corresponding oxazolone (342 mg). Then, the same reaction as in Example 1 (1d) was conducted using 156 mg of this oxazolone to give 134 mg of the title compound (white powder).

mp: 61 to 63° C.;
$^1$H-nuclear magnetic resonance spectrum (500 MHz, CDCl$_3$) δ ppm:
7.79-7.78 (3H, m), 7.30 (2H, d, J=9 Hz), 7.21 (2H, d, J=9 Hz), 7.16 (2H, d, J=9 Hz), 7.02 (1H, s), 6.92 (2H, d, J=9 Hz), 6.87 (2H, d, J=9 Hz), 6.70 (1H, t, J=6 Hz), 4.18 (2H, t, J=7 Hz), 3.80 (3H, s), 3.77 (2H, t, J=5 Hz), 3.50 (2H, q, J=5 Hz), 3.06 (2H, t, J=7 Hz), 2.45 (3H, s).

Example 9

4-(2-Cyclopropylethoxy)-N-((Z)-2-(4-cyclopropylphenyl)-1-{[(2-hydroxyethyl)amino]carbonyl}vinyl)benzamide (Exemplary Compound No. 1-68)

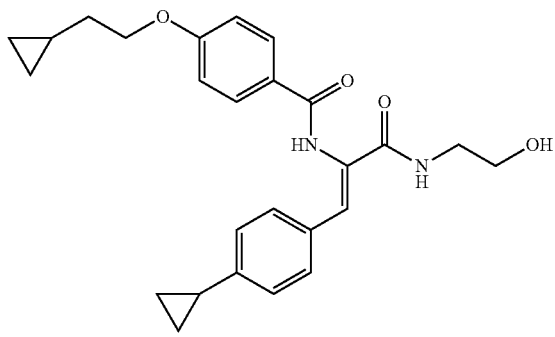 [SMILES: O=C(NCCO)/C(=C/c1ccc(C2CC2)cc1)NC(=O)c1ccc(OCCC2CC2)cc1]

(9a) 4-(2-Cyclopropylethoxy)benzoic acid

Methyl 4-hydroxybenzoate (8.83 g, 58.0 mmol), 2-cyclopropylethanol (5.13 g, 59.6 mmol), and triphenylphosphine (15.7 g, 59.9 mmol) were dissolved in THF (250 mL). Then, diethyl azodicarboxylate (29.8 mL, 40% toluene solution, 59.6 mmol) was added thereto under ice-cooling while stirring. The mixture was stirred at room temperature for 2 days, and then water (200 mL) was added to the reaction solution. The resulting mixture was extracted with ethyl acetate twice. The organic layers were combined, washed with saturated brine, and dried over anhydrous magnesium sulfate, and then the solvent was evaporated. The resulting residue was dissolved in diethyl ether. The produced precipitate was removed by filtration, and diethyl ether was evaporated. This filtration procedure was repeated twice, and the residue was purified by silica gel column chromatography (hexane:ethyl acetate, 20:1, v/v) to give an oily substance (13.2 g). All this oily substance was dissolved in ethanol (200 mL), and a 2 M lithium hydroxide aqueous solution (60 mL, 120 mmol) was added thereto. The mixture was stirred at 60° C. for 50 minutes, and then 10% hydrochloric acid (40 mL) was added thereto under ice-cooling. The resulting mixture was extracted with ethyl acetate twice. The organic layers were combined, washed with saturated brine, and dried over anhydrous magnesium sulfate. Then, the solvent was evaporated. The resulting residue was suspended in diisopropyl ether, and the precipitate was collected by filtration and dried under reduced pressure to give 9.28 g of the title compound (powder, yield: 78%).

$^1$H-nuclear magnetic resonance spectrum (400 MHz, DMSO-d$_6$) δ ppm:
12.6 (1H, s), 7.88 (2H, d, J=9 Hz), 7.02 (2H, d, J=9 Hz), 4.10 (2H, t, J=7 Hz), 1.64 (2H, q, J=7 Hz), 0.88-0.79 (1H, m), 0.46-0.42 (2H, m), 0.15-0.11 (2H, m).

(9b) N-[4-(2-Cyclopropylethoxy)benzoyl]glycine

Oxalyl chloride (8.64 mL, 99.0 mmol) and one drop of DMF were added to a solution of dichloromethane (30 mL) containing 4-(2-cyclopropylethoxy)benzoic acid (9.28 g, 45.0 mmol) prepared in Example 9 (9a) under ice-cooling. The mixture was stirred at room temperature for 1.75 hours, and the solvent was evaporated. Then, the resulting residue was suspended in THF (3 mL). This suspension added dropwise to a 50% THF aqueous solution (120 mL) containing glycine (4.41 g, 58.7 mmol) and triethylamine (15.7 mL, 112 mmol) under ice-cooling. The mixture was stirred at room temperature for 1.5 hours, and then 10% hydrochloric acid (40 mL) was added thereto under ice-cooling. The produced precipitate was collected by filtration, washed with water, and dried by heating under reduced pressure to give 11.4 g of the title compound (powder, yield: 97%).

$^1$H-nuclear magnetic resonance spectrum (400 MHz, DMSO-d$_6$) δ ppm:
12.5 (1H, brs), 8.64 (1H, brt, J=6 Hz), 7.81 (2H, d, J=9 Hz), 6.98 (2H, d, J=9 Hz), 4.07 (2H, t, J=7 Hz), 3.88 (2H, d, J=6 Hz), 1.63 (2H, q, J=7 Hz), 0.88-0.78 (1H, m), 0.46-0.42 (2H, m), 0.15-0.11 (2H, m).

(9c) (4Z)-4-(4-Cyclopropylbenzylidene)-2-[4-(2-cyclopropylethoxy)phenyl]-1,3-oxazol-5(4H)-one A mixture of N-[4-(2-cyclopropylethoxy)benzoyl]glycine (184 mg, 0.699 mmol) prepared in Example 9 (9b), 4-cyclopropylbenzaldehyde (113 mg, 0.769 mmol) prepared in Example 5, sodium acetate (75 mg, 0.909 mmol), and acetic anhydride (660 µL, 6.99 mmol) was stirred at 120° C. for 30 minutes and was then allowed to cool to room temperature. Hexane (2 mL) and water (4 mL) were added to the resulting solidified product which was washed by ultrasonic vibration.

The precipitate was collected by filtration, washed with water and hexane, and dried by heating under reduced pressure to give 196 mg of the title compound (white powder, yield: 74%).

¹H-nuclear magnetic resonance spectrum (400 MHz, CDCl₃) δ ppm:

8.12 (2H, d, J=9 Hz), 8.10 (2H, d, J=8 Hz), 7.16 (1H, s), 7.15 (2H, d, J=8 Hz), 7.03 (2H, d, J=9 Hz), 4.14 (2H, t, J=7 Hz), 1.99-1.93 (1H, m), 1.73 (2H, q, J=6 Hz), 1.10-1.05 (2H, m), 0.93-0.83 (1H, m), 0.83-0.79 (2H, m), 0.55-0.50 (2H, m), 0.17-0.14 (2H, m).

(9d) 4-(2-Cyclopropylethoxy)-N-((Z)-2-(4-cyclopropylphenyl)-1-{[(2-hydroxyethyl)amino]carbonyl}vinyl)benzamide 2-Aminoethanol (20 μL, 0.33 mmol) was added to a solution of ethanol (1.6 mL) containing (4Z)-4-(4-cyclopropylbenzylidene)-2-[4-(2-cyclopropylethoxy)phenyl]-1,3-oxazol-5(4H)-one (95 mg, 0.25 mmol) prepared in Example 9 (9c). The mixture was stirred at 60° C. for 1 hour, and then the solvent was removed. The residue was washed with hexane:ethyl acetate (3:1, v/v). The precipitate was collected by filtration and dried under reduced pressure to give 95 mg of the title compound (white powder, yield: 86%).

mp: 195 to 200° C. (dec.)

¹H-nuclear magnetic resonance spectrum (400 MHz, DMSO-d₆) δ ppm:

9.67 (1H, brs), 7.95-7.91 (3H, m), 7.39 (2H, d, J=8 Hz), 7.15 (1H, brs), 7.02 (2H, d, J=9 Hz), 7.00 (2H, d, J=9 Hz), 4.62 (1H, t, J=5 Hz), 4.10 (2H, t, J=7 Hz), 3.43 (2H, q, J=6 Hz), 3.22 (2H, q, J=6 Hz), 1.90-1.83 (1H, m), 1.65 (2H, q, J=7 Hz), 0.95-0.91 (2H, m), 0.89-0.80 (1H, m), 0.68-0.64 (2H, m), 0.47-0.43 (2H, m), 0.16-0.12 (2H, m).

Example 10

4-(2-Cyclopropylethoxy)-N-((Z)-2-[4-(difluoromethoxy)phenyl]-1-{[(2-hydroxyethyl)amino]carbonyl}vinyl)benzamide (Exemplary Compound No. 1-61)

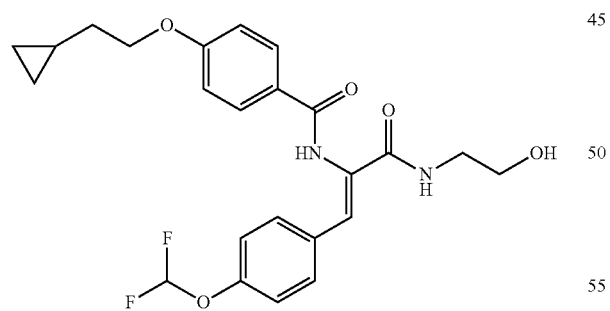

The same reaction as in Example 9 (9c) was conducted using N-[4-(2-cyclopropylethoxy)benzoyl]glycine (150 mg) prepared in Example 9 (9b) and 4-(difluoromethoxy)benzaldehyde (83 μL) to give the corresponding oxazolone (188 mg). Then, the same reaction as in Example 9 (9d) was conducted using 90 mg of this oxazolone to give 76 mg of the title compound (white powder).

mp: 153 to 155° C.;

¹H-nuclear magnetic resonance spectrum (400 MHz, DMSO-d₆) δ ppm:

9.72 (1H, brs), 8.00 (1H, brt, J=6 Hz), 7.93 (2H, d, J=9 Hz), 7.56 (2H, d, J=9 Hz), 7.23 (1H, t, J=74 Hz), 7.16 (1H, s), 7.12 (2H, d, J=9 Hz), 7.02 (2H, d, J=9 Hz), 4.62 (1H, t, J=5 Hz), 4.10 (2H, t, J=7 Hz), 3.43 (2H, q, J=6 Hz), 3.22 (2H, q, J=6 Hz), 1.64 (2H, q, J=7 Hz), 0.88-0.81 (1H, m), 0.47-0.43 (2H, m), 0.16-0.12 (2H, m).

(Example 11

4-(2-Cyclopropylethoxy)-N-{(Z)-1-{[(2-hydroxyethyl)amino]carbonyl}-2-[4-(trifluoromethoxy)phenyl]vinyl}benzamide (Exemplary Compound No. 1-62)

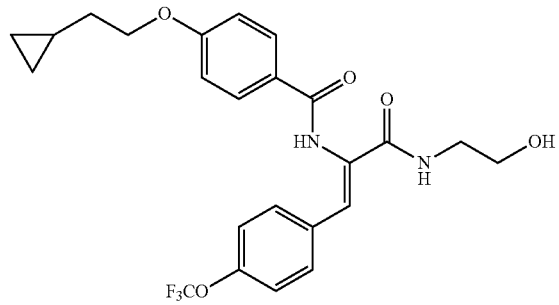 [SMILES: O=C(NCCO)/C(=C/c1ccc(OC(F)(F)F)cc1)NC(=O)c1ccc(OCCC2CC2)cc1]

The same reaction as in Example 9 (9c) was conducted using N-[4-(2-cyclopropylethoxy)benzoyl]glycine (150 mg) prepared in Example 9 (9b) and 4-(trifluoromethoxy)benzaldehyde (90 pit) to give the corresponding oxazolone (176 mg). Then, the same reaction as in Example 9 (9d) was conducted using 80 mg of this oxazolone to give 74 mg of the title compound (white powder).

mp: 142 to 144° C.;

¹H-nuclear magnetic resonance spectrum (400 MHz, DMSO-d₆) δ ppm:

9.75 (1H, brs), 8.04 (1H, t, J=6 Hz), 7.93 (2H, d, J=9 Hz), 7.62 (2H, d, J=9 Hz), 7.32 (2H, d, J=8 Hz), 7.14 (1H, brs), 7.02 (2H, d, J=9 Hz), 4.62 (1H, t, J=5 Hz), 4.10 (2H, t, J=7 Hz), 3.43 (2H, q, J=6 Hz), 3.22 (2H, q, J=6 Hz), 1.64 (2H, q, J=7 Hz), 0.89-0.79 (1H, m), 0.47-0.42 (2H, m), 0.16-0.12 (2H, m).

Example 12

4-(2-Cyclopropylethoxy)-N-((Z)-2-[4-(2,2-difluoroethoxy)phenyl]-1-{[(2-hydroxyethyl)amino]carbonyl}vinyl)benzamide (Exemplary Compound No. 1-64)

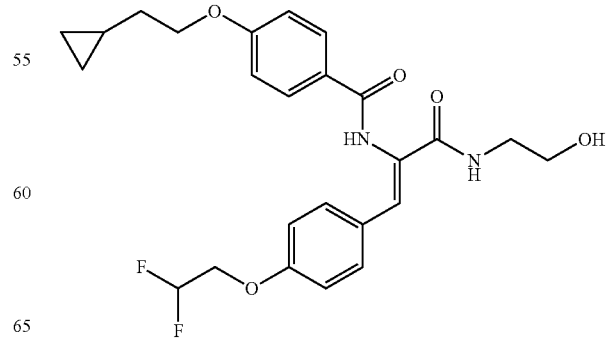

The same reaction as in Example 9 (9c) was conducted using N-[4-(2-cyclopropylethoxy)benzoyl]glycine (212 mg) prepared in Example 9 (9b) and 4-(2,2-difluoroethoxy)benzaldehyde (170 mg) prepared in Example 4 (4a) to give the corresponding oxazolone (281 mg). Then, the same reaction as in Example 9 (9d) was conducted using all this oxazolone to give 164 mg of the title compound (light yellow amorphous solid).

MS (FAB) m/z: 475 [M+H]$^+$;

$^1$H-nuclear magnetic resonance spectrum (400 MHz, DMSO-d$_6$) δ ppm:

9.69 (1H, s), 7.98 (2H, d, J=9 Hz), 7.94 (1H, brt, J=5 Hz), 7.52 (2H, d, J=9 Hz), 7.20 (1H, s), 7.05 (2H, d, J=9 Hz), 6.98 (2H, d, J=9 Hz), 6.36 (1H, tt, J=54 Hz, 3 Hz), 4.63 (1H, t, J=5 Hz), 4.31 (2H, td, J=14 Hz, 3 Hz), 4.11 (2H, t, J=7 Hz), 3.44 (2H, q, J=6 Hz), 3.23 (2H, q, J=6 Hz), 1.65 (2H, q, J=7 Hz), 0.89-0.81 (1H, m), 0.47-0.43 (2H, m), 0.16-0.12 (2H, m).

Example 13

4-(2-Cyclopropylethoxy)-N-{(Z)-1-{[(2-hydroxyethyl)amino]carbonyl}-2-[4-(2,2,2-trifluoroethoxy)phenyl]vinyl}benzamide (Exemplary Compound No. 1-65)

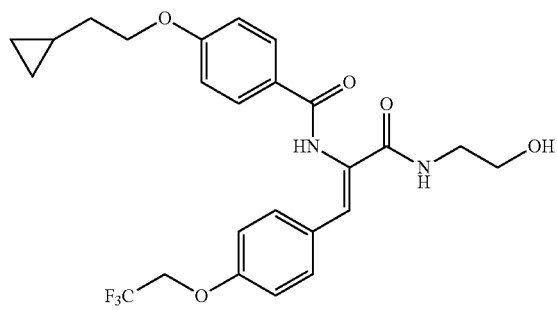 [SMILES: O=C(NCCO)/C(=C/c1ccc(OCC(F)(F)F)cc1)NC(=O)c1ccc(OCCC2CC2)cc1]

(13a) 4-(2,2,2-Trifluoroethoxy)benzaldehyde

Sodium hydride (787 mg, 55%, 18.0 mmol) was suspended in DMF (10 mL) under a nitrogen atmosphere, and a solution of DMF (5 mL) containing 4-hydroxybenzaldehyde (2.00 g, 16.4 mmol) was dropwise added thereto over 5 minutes at room temperature. A light yellow insoluble substance was precipitated immediately after the addition. After 5 minutes, a solution of DMF (5 mL) containing 2,2,2-trifluoroethyl 4-methylbenzenesulfonate (4.00 g, 17.2 mmol) was added dropwise thereto to give a brown solution. This brown solution was stirred at room temperature for 1 hour, and then water (100 mL) and ethyl acetate (150 mL) were added thereto. The organic layer was separated, further washed with water (50 mL) five times, with a 10% sodium hydroxide aqueous solution (50 mL) three times, and with saturated brine, and dried over anhydrous magnesium sulfate. The solvent was evaporated to give a crude product. This crude product was purified by silica gel column chromatography (hexane:ethyl acetate, 5:1, v/v) to give 1.40 g of the title compound (light yellow oil, yield: 42%).

$^1$H-nuclear magnetic resonance spectrum (400 MHz, CDCl$_3$) δ ppm:

9.94 (1H, s), 7.89 (2H, d, J=9 Hz), 7.07 (2H, d, J=9 Hz), 4.44 (2H, q, J=8 Hz).

(13b) 4-(2-Cyclopropylethoxy)-N-{(Z)-1-{[(2-hydroxyethyl)amino]carbonyl}-2-[4-(2,2,2-trifluoroethoxy)phenyl]vinyl}benzamide The same reaction as in Example 9 (9c) was conducted using N-[4-(2-cyclopropylethoxy)benzoyl]glycine (150 mg) prepared in Example 9 (9b) and 4-(2,2,2-trifluoroethoxy)benzaldehyde (128 mg) prepared in Example 13 (13a) to give the corresponding oxazolone (215 mg). Then, the same reaction as in Example 9 (9d) was conducted using 96 mg of this oxazolone to give 65 mg of the title compound (white powder).

mp: 173 to 175° C.;

$^1$H-nuclear magnetic resonance spectrum (400 MHz, DMSO-d$_6$) δ ppm:

9.66 (1H, brs), 7.96-7.92 (3H, m), 7.51 (2H, d, J=9 Hz), 7.18 (1H, s), 7.02 (2H, d, J=9 Hz), 7.00 (2H, d, J=9 Hz), 4.74 (2H, q, J=9 Hz), 4.62 (1H, brt, J=5 Hz), 4.10 (2H, t, J=7 Hz), 3.42 (2H, q, J=6 Hz), 3.22 (2H, q, J=6 Hz), 1.64 (2H, q, J=7 Hz), 0.88-0.81 (1H, m), 0.47-0.43 (2H, m), 0.16-0.12 (2H, m).

Example 14

N-((Z)-2-(4-Chlorophenyl)-1-{[(2-hydroxyethyl)amino]carbonyl}vinyl)-4-(2-cyclopropylethoxy)benzamide (Exemplary Compound No. 1-109)

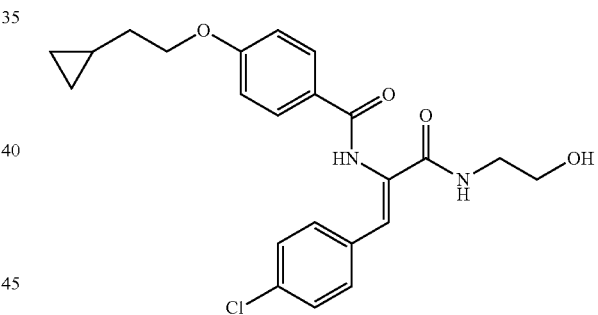

The same reaction as in Example 9 (9c) was conducted using N-[4-(2-cyclopropylethoxy)benzoyl]glycine (213 mg) prepared in Example 9 (9b) and 4-chlorobenzaldehyde (131 mg) to give the corresponding oxazolone (288 mg). Then, the same reaction as in Example 9 (9d) was conducted using all this oxazolone to give 56 mg of the title compound (white powder).

mp: 143 to 145° C.;

$^1$H-nuclear magnetic resonance spectrum (400 MHz, DMSO-d$_6$) δ ppm:

9.75 (1H, s), 8.06 (1H, brt, J=5 Hz), 7.95 (2H, d, J=9 Hz), 7.54 (2H, d, J=9 Hz), 7.40 (2H, d, J=8 Hz), 7.14 (1H, s), 7.04 (2H, d, J=8 Hz), 4.64 (1H, t, J=5 Hz), 4.11 (2H, t, J=6 Hz), 3.44 (2H, q, J=6 Hz), 3.23 (2H, q, J=6 Hz), 1.65 (2H, q, J=6 Hz), 0.88-0.81 (1H, m), 0.47-0.43 (2H, m), 0.16-0.12 (2H, m).

Example 15

4-(2-Cyclopropylethoxy)-N-((Z)-2-(4-ethoxyphenyl)-1-{[(2-hydroxyethyl)amino]carbonyl}vinyl)benzamide (Exemplary Compound No. 1-58)

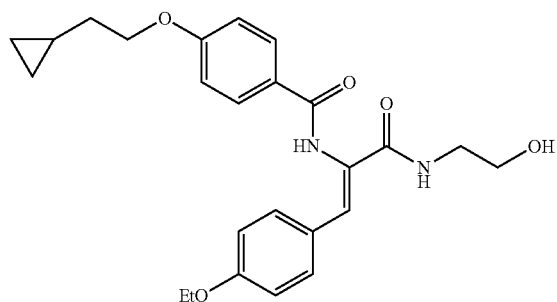 [SMILES: O=C(NCCO)/C(=C/c1ccc(Cl)cc1)NC(=O)c1ccc(OCCC2CC2)cc1]

The same reaction as in Example 9 (9c) was conducted using N-[4-(2-cyclopropylethoxy)benzoyl]glycine (210 mg) prepared in Example 9 (9b) and 4-ethoxybenzaldehyde (122 µL) to give the corresponding oxazolone (180 mg). Then, the same reaction as in Example 9 (9d) was conducted using all this oxazolone to give 154 mg of the title compound (white amorphous).

MS (FAB) m/z: 439 [M+H]$^+$;
$^1$H-nuclear magnetic resonance spectrum (400 MHz, DMSO-d$_6$) δ ppm:
9.64 (1H, s), 7.95 (2H, d, J=9 Hz), 7.87 (1H, brt, J=5 Hz), 7.46 (2H, d, J=9 Hz), 7.17 (1H, s), 7.02 (2H, d, J=9 Hz), 6.85 (2H, d, J=9 Hz), 4.61 (1H, t, J=6 Hz), 4.10 (2H, t, J=7 Hz), 3.99 (2H, q, J=7 Hz), 3.42 (2H, q, J=6 Hz), 3.21 (2H, q, J=6 Hz), 1.65 (2H, q, J=7 Hz), 1.29 (3H, t, J=7 Hz), 0.88-0.81 (1H, m), 0.47-0.43 (2H, m), 0.16-0.12 (2H, m).

Example 16

4-(2-Cyclopropylethoxy)-N-((Z)-2-[4-(cyclopropyloxy)phenyl]-1-{[(2-hydroxyethyl)amino]carbonyl}vinyl)benzamide (Exemplary Compound No. 1-60)

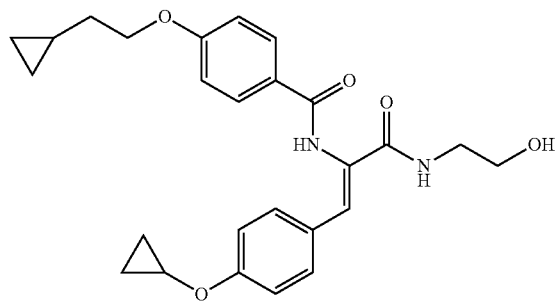 [SMILES: O=C(NCCO)/C(=C/c1ccc(OC2CC2)cc1)NC(=O)c1ccc(OCCC2CC2)cc1]

The same reaction as in Example 9 (9c) was conducted using N-[4-(2-cyclopropylethoxy)benzoyl]glycine (263 mg) prepared in Example 9 (9b) and 4-(cyclopropyloxy)benzaldehyde (170 mg) prepared in Example 6 (6c) to give the corresponding oxazolone (235 mg). Then, the same reaction as in Example 9 (9d) was conducted using 156 mg of this oxazolone to give 157 mg of the title compound (white powder).

mp: 132 to 134° C.;
$^1$H-nuclear magnetic resonance spectrum (500 MHz, CDCl$_3$) δ ppm:
7.88 (1H, brs), 7.82 (2H, d, J=9 Hz), 7.34 (2H, d, J=8 Hz), 7.06 (1H, s), 6.98 (2H, d, J=9 Hz), 6.93 (2H, d, J=8 Hz), 6.79 (1H, brt, J=6 Hz), 4.08 (2H, t, J=6 Hz), 3.75 (2H, t, J=5 Hz), 3.70 (1H, sept, J=3 Hz), 3.47 (2H, q, J=5 Hz), 1.71 (2H, q, J=6 Hz), 0.89-0.82 (1H, m), 0.78-0.73 (4H, m), 0.52-0.49 (2H, m), 0.15-0.12 (2H, m).

(Example 17)

4-(2-Cyclopropylethoxy)-N-[(Z)-1-{[(2-hydroxyethyl)amino]carbonyl}-2-(4-isopropoxyphenyl)vinyl]benzamide (Exemplary Compound No. 1-59)

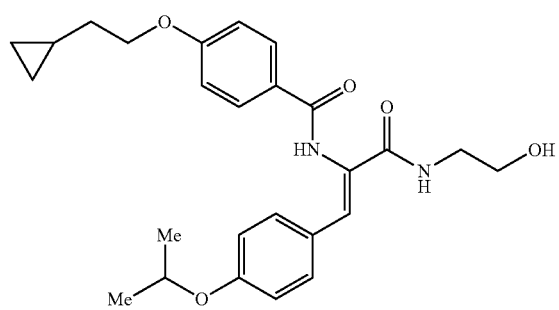 [SMILES: CC(C)Oc1ccc(/C=C(\NC(=O)c2ccc(OCCC3CC3)cc2)C(=O)NCCO)cc1]

The same reaction as in Example 9 (9c) was conducted using N-[4-(2-cyclopropylethoxy)benzoyl]glycine (211 mg) prepared in Example 9 (9b) and 4-isopropoxybenzaldehyde (139 µL) to give the corresponding oxazolone (188 mg). Then, the same reaction as in Example 9 (9d) was conducted using all this oxazolone to give 90.0 mg of the title compound (white amorphous).

MS (FAB) m/z: 453 [M+H]$^+$;
$^1$H-nuclear magnetic resonance spectrum (400 MHz, DMSO-d$_6$) δ ppm:
9.67 (1H, s), 7.98 (2H, d, J=9 Hz), 7.89 (1H, brt, J=5 Hz), 7.47 (2H, d, J=9 Hz), 7.18 (1H, s), 7.05 (2H d, J=9 Hz), 6.85 (2H, d, J=9 Hz), 4.65-4.59 (2H, m), 4.11 (2H, t, J=7 Hz), 3.41 (2H, q, J=6 Hz), 3.22 (2H, q, J=6 Hz), 1.65 (2H, q, J=7 Hz), 1.23 (6H, d, J=6 Hz), 0.88-0.82 (1H, m), 0.47-0.43 (2H, m), 0.16-0.12 (2H, m).

Example 18

4-(2-Cyclopropylethoxy)-N-{(Z)-1-{[(2-hydroxyethyl)amino]carbonyl}-2-[4-(1H-pyrrol-1-yl)phenyl]vinyl}benzamide (Exemplary Compound No. 1-72)

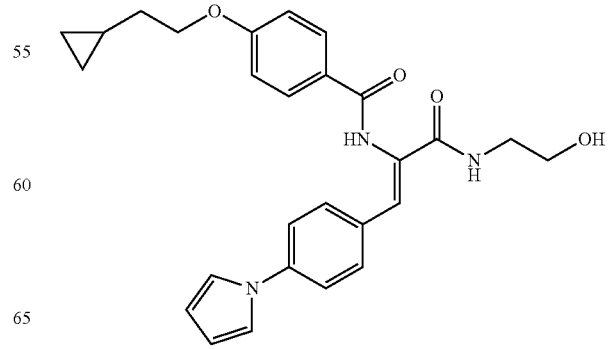

The same reaction as in Example 9 (9c) was conducted using N-[4-(2-cyclopropylethoxy)benzoyl]glycine (212 mg) prepared in Example 9 (9b) and 4-(1H-pyrrol-1-yl)benzaldehyde (153 mg) to give the corresponding oxazolone (328 mg). Then, the same reaction as in Example 9 (9d) was conducted using all this oxazolone to give 113 mg of the title compound (white amorphous).

MS (FAB) m/z: 460 [M+H]$^+$;

$^1$H-nuclear magnetic resonance spectrum (400 MHz, DMSO-d$_6$) δ ppm:

9.78 (1H, s), 8.03-7.98 (3H, m), 7.62 (2H, d, J=8 Hz), 7.58 (2H, d, J=9 Hz), 7.42-7.41 (2H, m), 7.23 (1H, s), 7.06 (2H, d, J=8 Hz), 6.26-6.25 (2H, m), 4.65 (1H, t, J=6 Hz), 4.12 (2H, t, J=6 Hz), 3.45 (2H, q, J=6 Hz), 3.24 (2H, q, J=6 Hz), 1.65 (2H, q, J=6 Hz), 0.88-0.82 (1H, m), 0.48-0.43 (2H, m), 0.16-0.14 (2H, m).

Example 19

4-(2-Cyclopropylethoxy)-N-{(Z)-1-{[(2-hydroxyethyl)amino]carbonyl}-2-[4-(trifluoromethyl)phenyl]vinyl}benzamide (Exemplary Compound No. 1-69)

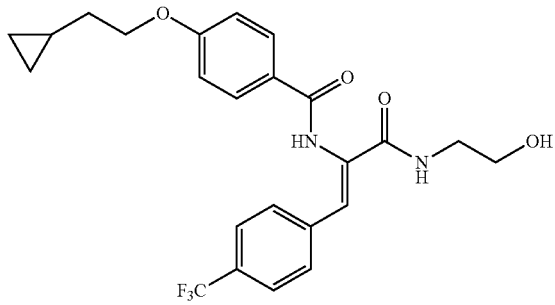 [SMILES: O=C(NCCO)/C(=C/c1ccc(C(F)(F)F)cc1)NC(=O)c1ccc(OCCC2CC2)cc1]

The same reaction as in Example 9 (9c) was conducted using N-[4-(2-cyclopropylethoxy)benzoyl]glycine (212 mg) prepared in Example 9 (9b) and 4-(trifluoromethyl)benzaldehyde (122 pt) to give the corresponding oxazolone (235 mg). Then, the same reaction as in Example 9 (9d) was conducted using all this oxazolone to give 163 mg of the title compound (white powder).

mp: 174 to 176° C.;

$^1$H-nuclear magnetic resonance spectrum (400 MHz, DMSO-d$_6$) δ ppm:

9.80 (1H, s), 8.13 (1H, brt, J=6 Hz), 7.92 (2H, d, J=9 Hz), 7.69 (2H, d, J=9 Hz), 7.64 (2H, d, J=9 Hz), 7.14 (1H, s), 7.02 (2H, d, J=9 Hz), 4.63 (1H, t, J=5 Hz), 4.10 (2H, t, J=7 Hz), 3.45 (2H, q, J=6 Hz), 3.23 (2H, q, J=6 Hz), 1.64 (2H, q, J=7 Hz), 0.87-0.81 (1H, m), 0.47-0.42 (2H, m), 0.16-0.12 (2H, m).

Example 20

2-{[(2Z)-2-{[4-(2-Cyclopropylethoxy)benzoyl]amino}-3-(4-cyclopropylphenyepropen-2-oyl]amino}ethyl acetate (Exemplary Compound No. 3-112)

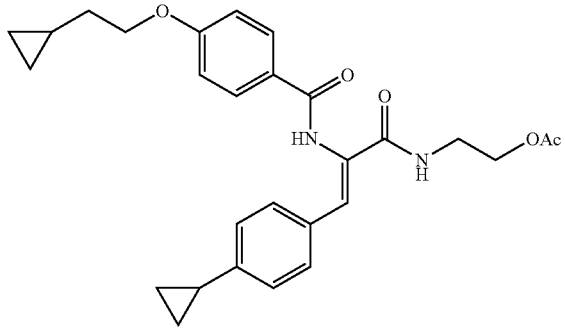 [SMILES: CC(=O)OCCNC(=O)/C(=C/c1ccc(C2CC2)cc1)NC(=O)c1ccc(OCCC2CC2)cc1]

Acetyl chloride (97.0 μL, 1.36 mmol) and 1,4-diazabicyclo[2.2.2]octane (287 mg, 2.56 mmol) were added to a solution of dichloromethane (2 mL) containing 4-(2-cyclopropylethoxy)-N-((Z)-2-(4-cyclopropylphenyl)-1-{[(2-hydroxyethyl)amino]carbonyl}vinyl)benzamide (197 mg, 0.453 mmol) prepared in Example 9 (9d). The mixture was stirred at room temperature for 14 hours, and then water was added thereto to terminate the reaction. The mixture was extracted with dichloromethane, and the organic layer was concentrated. The resulting residue was purified by silica gel column chromatography (hexane:ethyl acetate, 1:3, v/v) to give 146 mg of the title compound (white powder, yield: 68%).

mp: 80 to 82° C.;

$^1$H-nuclear magnetic resonance spectrum (400 MHz, CDCl$_3$) δ ppm:

7.80 (2H, d, J=9 Hz), 7.65 (1H, bis), 7.28 (2H, d, J=8 Hz), 7.04 (1H, s), 6.99 (2H, d, J=8 Hz), 6.93 (2H, d, J=9 Hz), 6.73 (1H, brt, J=5 Hz), 4.20 (2H, t, J=5 Hz), 4.08 (2H, t, J=7 Hz), 3.60 (2H, q, J=5 Hz), 2.03 (3H, s), 1.89-1.82 (1H, m), 1.70 (2H, q, J=7 Hz), 1.00-0.96 (2H, m), 0.90-0.84 (1H, m), 0.71-0.67 (2H, m), 0.53-0.48 (2H, m), 0.16-0.12 (2H, m).

Example 21

2-{[(2Z)-2-{[4-(2-Cyclopropylethoxy)benzoyl]amino}-3-(4-cyclopropylphenyl)propen-2-oyl]amino}ethyl morpholin-4-yl acetate (Exemplary Compound No. 3-116)

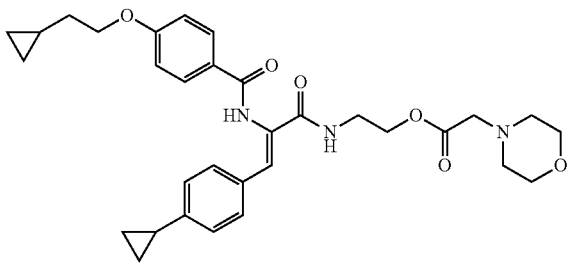 [SMILES: O=C(CN1CCOCC1)OCCNC(=O)/C(=C/c1ccc(C2CC2)cc1)NC(=O)c1ccc(OCCC2CC2)cc1]

According to the method disclosed in the document (J. Med. Chem., (1994), 37, 4538-4554), 73 mg of the title compound (white amorphous, yield: 16%) was synthesized using 4-(2-cyclopropylethoxy)-N-((Z)-2-(4-cyclopropylphenyl)-1-{[(2-hydroxyethyl)amino]carbonyl}vinyl)benzamide (355 mg, 0.817 mmol) prepared in Example 9 (9d).

MS (ESI) m/z: 562 [M+H]$^+$;

$^1$H-nuclear magnetic resonance spectrum (500 MHz, DMSO-d$_6$) δ ppm:

9.71 (1H, s), 8.13 (1H, brt, J=6 Hz), 7.97 (2H, d, J=9 Hz), 7.42 (2H, d, J=8H), 7.13 (1H, s), 7.05 (2H, d, J=8 Hz), 7.03 (2H, d, J=8 Hz), 4.13-4.09 (4H, m), 3.56-3.54 (4H, m), 3.41-3.38 (2H, m), 3.19 (2H, s), 2.48-2.47 (4H, m), 1.90-1.85 (1H, m), 1.65 (2H, q, J=6 Hz), 0.94-0.93 (2H, m), 0.87-0.82 (1H, m), 0.68-0.65 (2H, m), 0.47-0.43 (2H, m), 0.15-0.14 (2H, m).

Example 22

2-{[(2Z)-2-{[4-(2-Cyclopropylethoxy)benzoyl]amino}-3-(4-cyclopropylphenyl)propen-2-oyl]amino}ethyl succinate (Exemplary Compound No. 3-117)

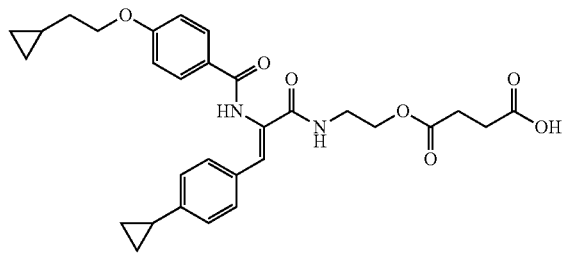 [SMILES: O=C(O)CCC(=O)OCCNC(=O)/C(=C/c1ccc(C2CC2)cc1)NC(=O)c1ccc(OCCC2CC2)cc1]

According to the method disclosed in the document (Tetrahedron Lett., (1989), 30, 5045-5048), 198 mg of the title compound (white powder, yield: 88%) was synthesized using 4-(2-cyclopropylethoxy)-N-((Z)-2-(4-cyclopropylphenyl)-1-{[(2-hydroxyethyeamino]carbonyl}vinyl)benzamide (182 mg, 0.817 mmol) prepared in Example 9 (9d).

mp: 118° C. (dec.)

$^1$H-nuclear magnetic resonance spectrum (500 MHz, DMSO-$d_6$) δ ppm:

12.22 (1H, s), 9.71 (1H, s), 8.15 (1H, brt, J=6 Hz), 7.98 (2H, d, J=8 Hz), 7.43 (2H, d, J=8 Hz), 7.14 (1H, s), 7.04 (2H, d, J=8 Hz), 7.02 (2H, d, J=8 Hz), 4.11 (2H, t, J=7 Hz), 4.06 (2H, t, J=6 Hz), 3.38 (2H, q, J=6 Hz), 2.52-2.46 (4H, m), 1.90-1.85 (1H, m), 1.65 (2H, q, J=7 Hz), 0.95-0.92 (2H, m), 0.89-0.81 (1H, m), 0.68-0.64 (2H, m), 0.47-0.43 (2H, m), 0.16-0.13 (2H, m).

Example 23

4-{2-[4-(Dimethylamino)phenyl]ethoxy}-N-{(Z)-1-{[(2-hydroxyethyl)amino]carbonyl}-2-[4-(trifluoromethoxy)phenyl]vinyl}benzamide (Exemplary Compound No. 1-166)

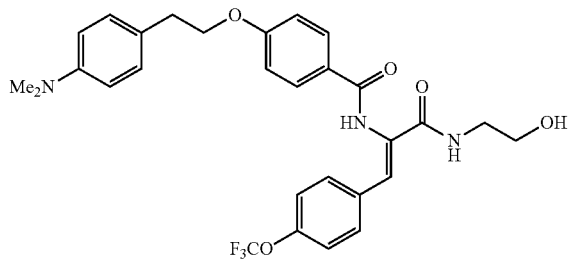

(23a) 4-{2-[4-(Dimethylamino)phenyl]ethoxy}benzoic acid

The same reaction as in Example 9 (9a) was conducted using 2-[4-(dimethylamino)phenyl]ethanol (567 mg, 3.43 mmol) to give 567 mg of the title compound (powder, yield: 63%).

$^1$H-nuclear magnetic resonance spectrum (400 MHz, DMSO-$d_6$) δ ppm:

12.56 (1H, brs), 7.84 (2H, d, J=9 Hz), 7.11 (2H, d, J=9 Hz), 6.98 (2H, d, J=9 Hz), 6.66 (2H, d, J=9 Hz), 4.16 (2H, t, J=7 Hz), 2.92 (2H, t, J=7 Hz), 2.84 (6H, s).

(23b) N-(4-{2-[4-(Dimethylamino)phenyl]ethoxy}benzoyl)glycine

N-Ethyl-N,N-diisopropylamine (388 μL, 2.23 mmol) and 4-(4,6-dimethoxy-1,3,5-triazin-2-yl)-4-methylmorpholinium chloride (615 mg, 2.22 mmol) were added to a solution of ethanol (10 mL) containing 4-{2-[4-(dimethylamino)phenyl]ethoxy}benzoic acid (567 mg, 1.99 mmol) prepared in Example 23 (23a) and glycine methyl ester hydrochloride (280 mg, 2.23 mmol). The mixture was stirred at room temperature for 18 hours, and a saturated sodium hydrogen carbonate aqueous solution was added thereto to terminate the reaction. The mixture was extracted with ethyl acetate twice, and the organic layers were dried over anhydrous magnesium sulfate. Then, the solvent was evaporated. The resulting residue was purified by silica gel column chromatography (hexane:ethyl acetate, 1:1 to 2:5, v/v) to give an oily compound. To a solution of ethanol (6 mL) containing the resulting compound, a 2 M lithium hydroxide aqueous solution (1.60 mL, 3.20 mmol) was added. The mixture was stirred at 60° C. for 40 minutes, and then 10% hydrochloric acid (3.5 mL) was added thereto under ice-cooling. The mixture was extracted with ethyl acetate, and the organic layers were combined, washed with saturated brine, and dried over anhydrous magnesium sulfate. The solvent was evaporated to give 395 mg of the title compound (white powder, yield: 58%)

$^1$H-nuclear magnetic resonance spectrum (400 MHz, DMSO-$d_6$) δ ppm:

12.50 (1H, brs), 8.65 (1H, brt, J=6 Hz), 7.80 (2H, d, J=9 Hz), 7.11 (2H, d, J=9 Hz), 6.98 (2H, d, J=9 Hz), 6.66 (2H, d, J=9 Hz), 4.15 (2H, t, J=7 Hz), 3.87 (2H, d, J=6 Hz), 2.92 (2H, t, J=7 Hz), 2.84 (6H, s).

(23c) (4Z)-2-(4-{2-[4-(Dimethylamino)phenyl]ethoxy}phenyl)-4-[4-(trifluoromethoxy)benzylidene]-1,3-oxazol-5(4H)-one A mixture of N-(4-{2-[4-(dimethylamino)phenyl]ethoxy}benzoyl)glycine (241 mg, 0.676 mmol) prepared in Example 23 (23b), 4-(trifluoromethoxy)benzaldehyde (106 pt, 0.742 mmol), sodium acetate (83.9 mg, 1.02 mmol), and acetic anhydride (319 μL, 3.38 mmol) was stirred at 120° C. for 15 minutes and then allowed to cool to room temperature. A saturated sodium hydrogen carbonate aqueous solution, hexane, and ethanol were added to the resulting solidified product which was washed by ultrasonic vibration. The precipitate was collected by filtration and dried by heating under reduced pressure to give 234 mg of the title compound (orange solid, yield: 70%).

$^1$H-nuclear magnetic resonance spectrum (400 MHz, CDCl$_3$) δ ppm:

8.25 (2H, d, J=9 Hz), 8.11 (2H, d, J=9 Hz), 7.31 (2H, d, J=9 Hz), 7.18 (2H, d, J=8 Hz), 7.13 (1H, s), 7.02 (2H, d, J=9 Hz), 6.73 (2H, d, J=8 Hz), 4.22 (2H, t, J=7 Hz), 3.05 (2H, t, J=7 Hz), 2.94 (6H, s).

(23d) 4-{2-[4-(Dimethylamino)phenyl]ethoxy}-N-{(Z)-1-{[(2-hydroxyethyl)amino]carbonyl}-2-[4-(trifluoromethoxy)phenyl]vinyl}benzamide 2-Aminoethanol (57 μL, 0.944 mmol) was added to a solution of ethanol (0.5 mL) containing (4Z)-2-(4-{2-[4-(dimethylamino)phenyl]ethoxy}phenyl)-4-[4-(trifluoromethoxy)

benzylidene]-1,3-oxazol-5(4H)-one (234 mg, 0.471 mmol) prepared in Example 23 (23c). The mixture was stirred at 60° C. for 2.5 hours, and then the solvent was evaporated. The resulting residue was purified by silica gel column chromatography (ethyl acetate:methanol, 50:1, v/v) to give 167 mg of the title compound (white amorphous solid, yield: 64%).

MS (FAB) m/z: 558 [M+14]$^+$;
$^1$H-nuclear magnetic resonance spectrum (400 MHz, DMSO-$d_6$) δ ppm:
9.79 (1H, s), 8.07 (1H, brt, J=5 Hz), 7.95 (2H, d, J=9 Hz), 7.64 (2H, d, J=9 Hz), 7.34 (2H, d, J=8 Hz), 7.16 (1H, s), 7.14 (2H, d, J=8 Hz), 7.04 (2H, d, J=9 Hz), 6.69 (2H, d, J=9 Hz), 4.64 (1H, t, J=5 Hz), 4.19 (2H, q, J=7 Hz), 3.45 (2H, q, J=6 Hz), 3.23 (2H, q, J=6 Hz), 2.94 (2H, t, J=7 Hz), 2.85 (6H, s).

Example 24

N-((Z)-2-[4-(Difluoromethoxy)phenyl]-1-{[(2-hydroxyethyl)amino]carbonyl}vinyl)-4-{2-[4-(dimethylamino)phenyl]ethoxy}benzamide (Exemplary Compound No. 1-165)

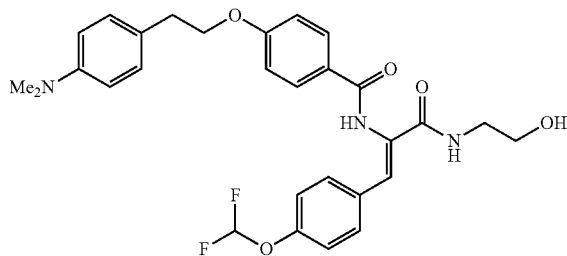 [SMILES: CN(C)c1ccc(CCOc2ccc(C(=O)N/C(=C\c3ccc(OC(F)F)cc3)C(=O)NCCO)cc2)cc1]

The same reaction as in Example 23 (23c) was conducted using N-(4-{2-[4-(dimethylamino)phenyl]ethoxy}benzoyl) glycine (230 mg) prepared in Example 23 (23b) and 4-(difluoromethoxy)benzaldehyde (93.8 μL) to give the corresponding oxazolone (387 mg). Then, the same reaction as in Example 23 (23d) was conducted using all this oxazolone to give 247 mg of the title compound (white amorphous solid).

MS (FAB) m/z: 540 [M+H]$^+$;
$^1$H-nuclear magnetic resonance spectrum (500 MHz, DMSO-$d_6$) δ ppm:
9.73 (1H, s), 8.02 (1H, brt, J=5 Hz), 7.95 (2H, d, J=9 Hz), 7.58 (2H, d, J=9 Hz), 7.25 (1H, t, J=74 Hz), 7.18 (1H, s), 7.14 (2H, d, J=8 Hz), 7.13 (2H, d, J=9 Hz), 7.04 (2H, d, J=9 Hz), 6.69 (2H, d, J=9 Hz), 4.63 (1H, t, J=5 Hz), 4.19 (2H, t, J=7 Hz), 3.44 (2H, q, J=6 Hz), 3.23 (2H, q, J=6 Hz), 2.94 (2H, t, J=7 Hz), 2.85 (6H, s).

Example 25

N-((Z)-2-(4-Cyclopropylphenyl)-1-{[(2-hydroxyethyl)amino]carbonyl}vinyl)-4-{2-[4-(dimethylamino)phenyl]ethoxy}benzamide (Exemplary Compound No. 1-172)

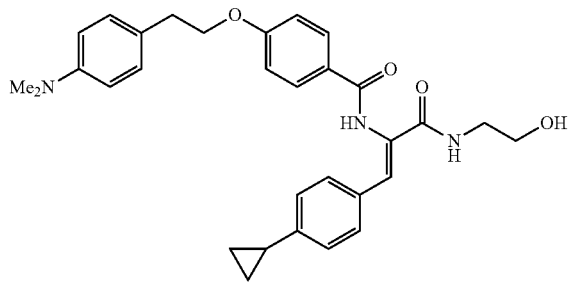 [SMILES: CN(C)c1ccc(CCOc2ccc(C(=O)N/C(=C\c3ccc(C4CC4)cc3)C(=O)NCCO)cc2)cc1]

The same reaction as in Example 23 (23c) was conducted using N-(4-{2-[4-(dimethylamino)phenyl]ethoxy}benzoyl) glycine (324 mg) prepared in Example 23 (23b) and 4-cyclopropylbenzaldehyde (170 mg) prepared in Example 5 to give the corresponding oxazolone (360 mg). Then, the same reaction as in Example 23 (23d) was conducted using all this oxazolone to give 293 mg of the title compound (white amorphous solid).

MS (FAB) m/z: 514 [M+H]$^+$;
$^1$H-nuclear magnetic resonance spectrum (400 MHz, DMSO-$d_6$) δ ppm:
9.69 (1H, s), 7.97-7.93 (3H, m), 7.41 (2H, d, J=7 Hz), 7.17 (1H, s), 7.15 (2H, d, J=8 Hz), 7.04 (2H, d, J=8 Hz), 7.02 (2H, d, J=8 Hz), 6.69 (2H, d, J=7 Hz), 4.63 (1H, t, J=5 Hz), 4.20 (2H, t, J=7 Hz), 3.43 (2H, q, J=6 Hz), 3.22 (2H, q, J=6 Hz), 2.94 (2H, t, J=7 Hz), 2.86 (6H, s), 1.90-1.84 (1H, m), 0.95-0.91 (2H, m), 0.67-0.64 (2H, m).

Example 26

N-((Z)-2-(4-Cyclopropylphenyl)-1-{[(2-hydroxyethyl)amino]carbonyl}vinyl)-4-{2-[4-(dimethylamino)phenyl]ethoxy}benzamide hydrochloride (Exemplary Compound No. 1-172)

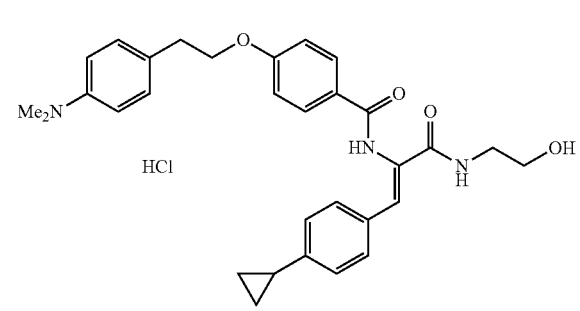 [SMILES: CN(C)c1ccc(CCOc2ccc(C(=O)N/C(=C\c3ccc(C4CC4)cc3)C(=O)NCCO)cc2)cc1 ; Cl]

A mixture solution of a 4 N hydrochloric acid ethyl acetate solution (97 pt, 0.388 mmol) and methanol (680 pt) was added to a solution of methanol (3 mL) containing N-((Z)-2-(4-cyclopropylphenyl)-1-{[(2-hydroxyethyl)amino] carbonyl}vinyl)-4-{2-[4-(dimethylamino)phenyl] ethoxy}benzamide (133 mg, 0.259 mmol) prepared in Example 25. The resulting mixture was stirred at room temperature for 45 minutes. The reaction mixture was concentrated and dried to give 150 mg of the title compound (white amorphous solid).

Elemental analysis (%), as $C_{31}H_{35}N_3O_4 \cdot HCl \cdot 3/2H_2O$:
Theoretical value: C, 64.52; H, 6.81; N, 7.28; Cl, 6.14,
Measured value: C, 64.47; H, 6.86; N, 6.82; Cl, 5.75.

Example 27

4-{2-[4-(Dimethylamino)phenyl]ethoxy}-N-[(Z)-1-{[(2-hydroxyethyl)amino]carbonyl}-2-(4-isopropoxyphenyl)vinyl]benzamide (Exemplary Compound No. 1-163)

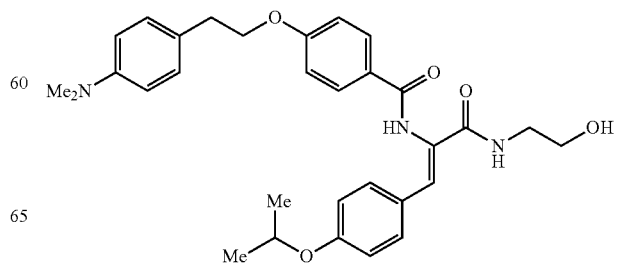

The same reaction as in Example 23 (23c) was conducted using N-(4-{2-[4-(dimethylamino)phenyl]ethoxy}benzoyl)glycine (255 mg) prepared in Example 23 (23b) and 4-(isopropoxy)benzaldehyde (174 mg) to give the corresponding oxazolone (189 mg). Then, the same reaction as in Example 23 (23d) was conducted using 185 mg of this oxazolone to give 89 mg of the title compound (white amorphous solid).

MS (FAB) m/z: 532 [M+H]$^+$;

$^1$H-nuclear magnetic resonance spectrum (400 MHz, DMSO-$d_6$) δ ppm:

9.63 (1H, brs), 7.94 (2H, d, J=9 Hz), 7.86 (1H, brt, J=5 Hz), 7.44 (2H, d, J=9 Hz), 7.16 (1H, s), 7.12 (2H, d, J=9 Hz), 7.02 (2H, d, J=9 Hz), 6.84 (2H, d, J=9 Hz), 6.67 (2H, d, J=9 Hz), 4.63-4.57 (2H, m), 4.18 (2H, t, J=7 Hz), 3.42 (2H, q, J=6 Hz), 3.21 (2H, q, J=6 Hz), 2.93 (2H, t, J=7 Hz), 2.85 (6H, s), 1.22 (6H, d, J=6 Hz).

Example 28

4-{2-[4-(Dimethylamino)phenyl]ethoxy}-N-[(Z)-1-{[(2-hydroxyethyl)amino]carbonyl}-2-(4-isopropoxyphenyl)vinyl]benzamide hydrochloride (Exemplary Compound No. 1-163)

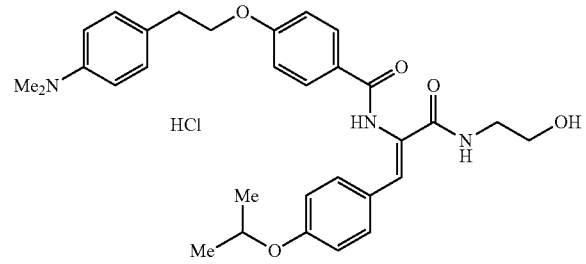 [SMILES: CC(C)Oc1ccc(/C=C(\NC(=O)c2ccc(OCCc3ccc(N(C)C)cc3)cc2)C(=O)NCCO)cc1 ; Cl]

A mixture solution of a 4 N hydrochloric acid ethyl acetate solution (27 μL, 0.108 mmol) and methanol (186 pt) was added to a solution of methanol (1 mL) containing 4-{2-[4-(dimethylamino)phenyl]ethoxy}-N-[(Z)-1-{[(2-hydroxyethyl)amino]carbonyl}-2-(4-isopropoxyphenyl)vinyl]benzamide (37.7 mg, 0.071 mmol) prepared in Example 27. The resulting mixture was stirred at room temperature for 40 minutes. The reaction mixture was concentrated and dried to give 42.3 mg of the title compound (white powder, yield: 99%).

mp: 103 to 105° C.;

Elemental analysis (%), as $C_{31}H_{37}N_3O_5 \cdot HCl \cdot 2H_2O$:
Theoretical value: C, 61.63; H, 7.01; N, 6.96; Cl, 5.87,
Measured value: C, 61.62; H, 6.74; N, 6.93; Cl, 5.67.

Example 29

4-{2-[4-(Dimethylamino)phenyl]ethoxy}-N-{(Z)-1-{[(2-hydroxyethyl)amino]carbonyl}-2-[4-(trifluoromethyl)phenyl]vinyl}benzamide (Exemplary Compound No. 1-173)

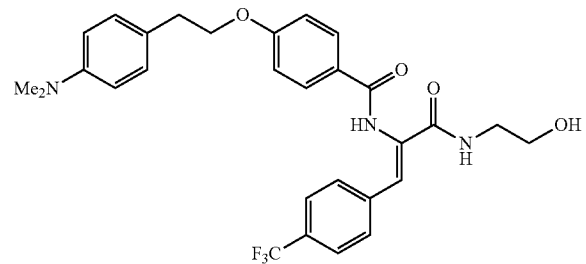 [SMILES: CN(C)c1ccc(CCOc2ccc(C(=O)N/C(=C\c3ccc(C(F)(F)F)cc3)C(=O)NCCO)cc2)cc1]

The same reaction as in Example 23 (23c) was conducted using N-(4-{2-[4-(dimethylamino)phenyl]ethoxy}benzoyl)glycine (202 mg) prepared in Example 23 (23b) and 4-(trifluoromethyl)benzaldehyde (90.6 μL) to give the corresponding oxazolone (241 mg). Then, the same reaction as in Example 23 (23d) was conducted using all this oxazolone to give 165 mg of the title compound (white amorphous solid).

MS (FAB) m/z: 542 [M+H]$^+$;

$^1$H-nuclear magnetic resonance spectrum (400 MHz, DMSO-$d_6$) δ ppm:

9.84 (1H, s), 8.16 (1H, brt, J=6 Hz), 7.93 (2H, d, J=8 Hz), 7.70 (4H, s), 7.16 (1H, s), 7.14 (2H, d, J=8 Hz), 7.04 (2H, d, J=8 Hz), 6.69 (2H, d, J=8 Hz), 4.65 (1H, t, J=5 Hz), 4.19 (2H, t, J=7 Hz), 3.45 (2H, q, J=6 Hz), 3.23 (2H, q, J=6 Hz), 2.94 (2H, t, J=7 Hz), 2.85 (6H, s).

(Example 30) N-((Z)-2-[4-(Difluoromethoxy)phenyl]-1-{[(2-hydroxyethyeamino]carbonyl}vinyl)-4-isobutoxybenzamide (Exemplary Compound No. 1-4)

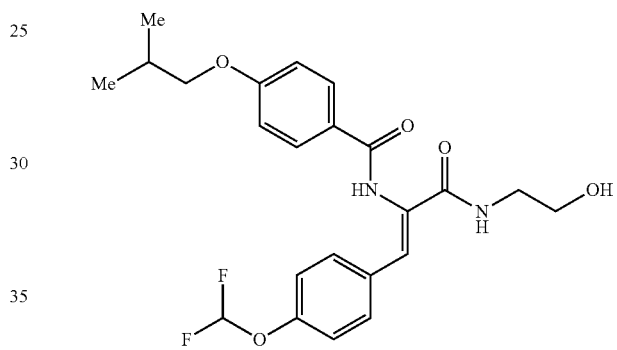

(30a) N-(4-Isobutoxybenzoyl)glycine

The same reaction as in Example 9 (9b) was conducted using 4-isobutoxybenzoic acid (55.0 g, 283 mmol) prepared according to the method disclosed in the document (J. Am. Chem. Soc., 61, 3050 (1939)) to give 50.2 g of the title compound (colorless crystalline solid, yield: 71%).

mp: 140 to 142° C.

(30b) N-((Z)-2-[4-(Difluoromethoxy)phenyl]-1-{[(2-hydroxyethyl)amino]carbonyl}vinyl)-4-isobutoxybenzamide The same reaction as in Example 9 (9c) was conducted using N-(4-isobutoxybenzoyl)glycine (184 mg) prepared in Example 30 (30a) and 4-(difluoromethoxy)benzaldehyde (165 mg) to give 195 mg of the corresponding oxazolone. Then, the same reaction as in Example 9 (9d) was conducted using all this oxazolone to give 99 mg of the title compound (white powder).

mp: 75 to 78° C.;

$^1$H-nuclear magnetic resonance spectrum (400 MHz, CDCl$_3$) δ ppm:

8.17 (1H, brs), 7.78 (2H, d, J=9 Hz), 7.35 (2H, d, J=9 Hz), 7.02 (2H, d, J=9 Hz), 6.97 (1H, brt, J=5 Hz), 6.94 (1H, s), 6.89 (2H, d, J=9 Hz), 6.47 (1H, t, J=74 Hz), 3.75 (2H, d, J=7 Hz), 3.73-3.72 (2H, m), 3.44 (2H, q, J=5 Hz), 3.26 (1H, brs), 2.10 (1H, sept, J=7 Hz), 1.04 (6H, d, J=7 Hz).

Example 31

N-{(Z)-1-{[(2-Hydroxyethyl)amino]carbonyl}-2-[4-(trifluoromethoxy)phenyl]vinyl}-4-isobutoxybenzamide (Exemplary Compound No. 1-5)

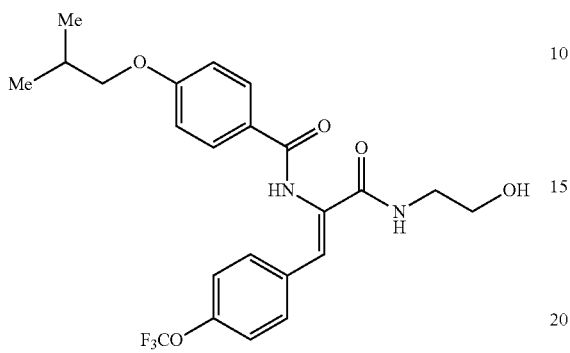

The same reaction as in Example 9 (9c) was conducted using N-(4-isobutoxybenzoyl)glycine (539 mg) prepared in Example 30 (30a) and 4-(trifluoromethoxy)benzaldehyde (351 μL) to give the corresponding oxazolone (659 mg). Then, the same reaction as in Example 9 (9d) was conducted using 106 mg of this oxazolone to give 58 mg of the title compound (white powder).

mp: 170 to 171° C.;
$^1$H-nuclear magnetic resonance spectrum (400 MHz, CDCl$_3$) δ ppm:
7.76 (3H, brd, J=9 Hz), 7.39 (2H, d, J=9 Hz), 7.15 (2H, d, J=8 Hz), 7.01 (1H, s), 6.91 (2H, d, J=9 Hz), 6.68 (1H, brt, J=6 Hz), 3.78 (2H, brs), 3.76 (2H, d, J=7 Hz), 3.51 (2H, q, J=5 Hz), 2.97 (1H, brs), 2.11 (1H, sept, J=7 Hz), 1.04 (6H, d, J=7 Hz).

Example 32

N-((Z)-2-[4-(2,2-Difluoroethoxy)phenyl]-1-{[(2-hydroxyethyl)amino]carbonyl}vinyl)-4-isobutoxybenzamide (Exemplary Compound No. 1-7)

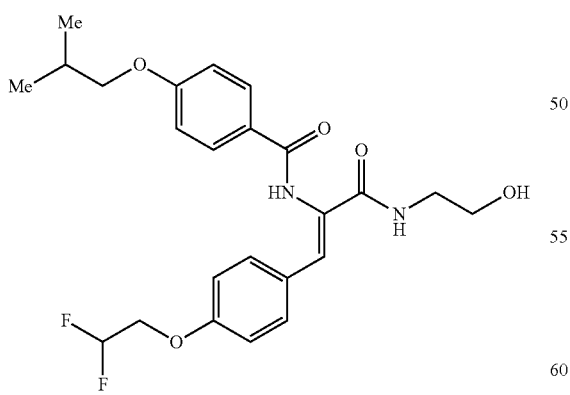

The same reaction as in Example 9 (9c) was conducted using N-(4-isobutoxybenzoyl)glycine (184 mg) prepared in Example 30 (30a) and 4-(2,2-difluoroethoxy)benzaldehyde (150 mg) prepared in Example 4 (4a) to give the corresponding oxazolone (256 mg). Then, the same reaction as in Example 9 (9d) was conducted using 122 mg of this oxazolone to give 63 mg of the title compound (white powder).

mp: 150 to 151° C.;
$^1$H-nuclear magnetic resonance spectrum (400 MHz, DMSO-d$_6$) δ ppm:
9.66 (1H, brs), 7.97-7.90 (3H, m), 7.49 (2H, d, J=9 Hz), 7.18 (1H, s), 7.02 (2H, d, J=9 Hz), 6.95 (2H, d, J=9 Hz), 6.34 (1H, tt, J=54 Hz, 4 Hz), 4.62 (1H, brt, J=5 Hz), 4.29 (2H, td, J=15 Hz, 3 Hz), 3.83 (2H, d, J=6 Hz), 3.43 (2H, q, J=6 Hz), 3.21 (2H, q, J=6 Hz), 2.04 (1H, sept, J=7 Hz), 1.00 (6H, d, J=–7 Hz).

Example 33

N-{(Z)-1-{[(2-Hydroxyethyl)amino]carbonyl}-2-[4-(2,2,2-trifluoroethoxy)phenyl]vinyl}-4-isobutoxybenzamide (Exemplary Compound No. 1-8)

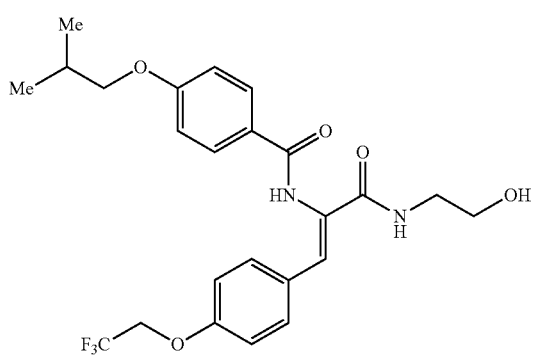 [SMILES: CC(C)COc1ccc(C(=O)N/C(=C\c2ccc(OCC(F)(F)F)cc2)C(=O)NCCO)cc1]

The same reaction as in Example 9 (9c) was conducted using N-(4-isobutoxybenzoyl)glycine (500 mg) prepared in Example 30 (30a) and 4-(2,2,2-trifluoroethoxy)benzaldehyde (447 mg) prepared in Example 13 (13a) to give the corresponding oxazolone (592 mg). Then, the same reaction as in Example 9 (9d) was conducted using 100 mg of this oxazolone to give 85 mg of the title compound (white solid).

mp: 176 to 178° C.;
$^1$H-nuclear magnetic resonance spectrum (400 MHz, CDCl$_3$) δ ppm:
7.80 (2H, d, J=9 Hz), 7.70 (1H, brs), 7.38 (2H, d, J=9 Hz), 7.08 (1H, s), 6.94 (2H, d, J=9 Hz), 6.90 (2H, d, J=9 Hz), 6.66 (1H, brs), 4.33 (2H, q, J=8 Hz), 3.80-3.76 (4H, m), 3.52 (2H, q, J=5 Hz), 2.10 (1H, sept, J=7 Hz), 1.05 (6H, d J=7 Hz).

Example 34

N-((Z)-2-(4-Ethylphenyl)-1-{[(2-hydroxyethyl)amino]carbonyl}vinyl)-4-isobutoxybenzamide (Exemplary Compound No. 1-10)

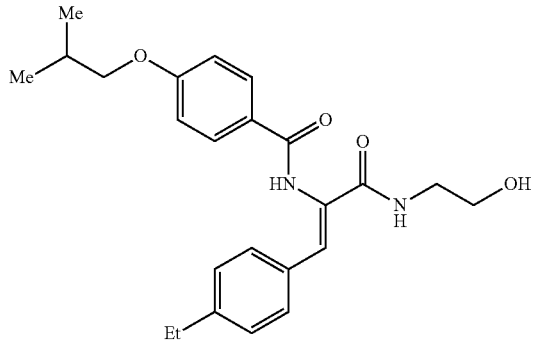 [SMILES: CCc1ccc(/C=C(\NC(=O)c2ccc(OCC(C)C)cc2)C(=O)NCCO)cc1]

The same reaction as in Example 9 (9c) was conducted using N-(4-isobutoxybenzoyl)glycine (520 mg) prepared in Example 30 (30a) and 4-ethylbenzaldehyde (312 μL) to give the corresponding oxazolone (442 mg). The same reaction as in Example 9 (9d) was conducted using 122 mg of this oxazolone to give 110 mg of the title compound (white powder).

mp: 174 to 176° C.;
¹H-nuclear magnetic resonance spectrum (400 MHz, CDCl₃) δ ppm:
7.81 (2H, d, J=9 Hz), 7.61 (1H, brs), 7.33 (2H, d, J=8 Hz), 7.19 (2H, d, J=8 Hz), 7.10 (1H, s), 6.95 (2H, d, J=9 Hz), 6.56 (1H, t, J=6 Hz), 3.83-3.80 (2H, m), 3.78 (2H, d, J=7 Hz), 3.53 (2H, q, J=5 Hz), 2.64 (2H, q, J=7 Hz), 2.11 (1H, quint, J=7 Hz), 1.23 (3H, t, J=7 Hz), 1.04 (6H, d, J=7 Hz).

Example 35
N-[(Z)-1-{[(2-Hydroxyethyl)amino]carbonyl}-2-(4-isopropylphenyl)vinyl]-4-isobutoxybenzamide (Exemplary Compound No. 1-11)

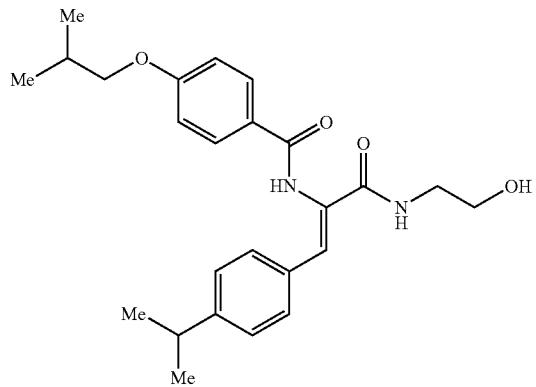 [SMILES: CC(C)COc1ccc(C(=O)N/C(=C\c2ccc(C(C)C)cc2)C(=O)NCCO)cc1]

The same reaction as in Example 9 (9c) was conducted using N-(4-isobutoxybenzoyl)glycine (183 mg) prepared in Example 30 (30a) and 4-isopropylbenzaldehyde (118 mg) to give the corresponding oxazolone (188 mg). Then, the same reaction as in Example 9 (9d) was conducted using all this oxazolone to give 127 mg of the title compound (white powder).

mp: 178 to 180° C.;
¹H-nuclear magnetic resonance spectrum (400 MHz, CDCl₃) δ ppm:
8.06 (1H, brs), 7.80 (2H, d, J=9 Hz), 7.31 (2H, d, J=8 Hz), 7.16 (2H, d, J=8 Hz), 7.00 (1H, s), 6.90-6.88 (3H, m), 3.75 (2H, d, J=6 Hz), 3.71 (2H, q, J=5 Hz), 3.43-3.40 (3H, m), 2.86 (1H, sept, J=7 Hz), 2.10 (1H, sept, J=7 Hz), 1.22 (6H, d, J=7 Hz), 1.04 (6H, d, J=7 Hz).

Example 36
N-((Z)-2-(4-Cyclopropylphenyl)-1-{[(2-hydroxyethyl)amino]carbonyl}vinyl)-4-isobutoxybenzamide (Exemplary Compound No. 1-12)

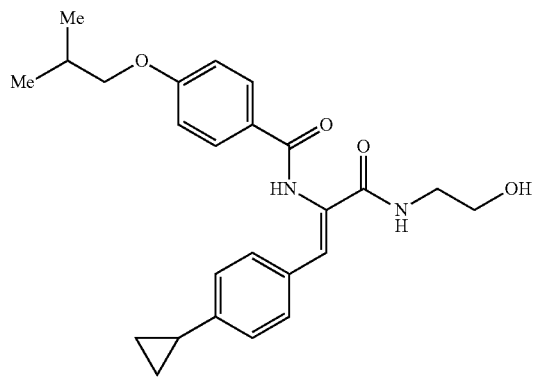 [SMILES: CC(C)COc1ccc(C(=O)N/C(=C\c2ccc(C3CC3)cc2)C(=O)NCCO)cc1]

The same reaction as in Example 9 (9c) was conducted using N-(4-isobutoxybenzoyl)glycine (215 mg) prepared in Example 30 (30a) and 4-cyclopropylbenzaldehyde (135 mg) prepared in Example 5 to give the corresponding oxazolone (215 mg). Then, the same reaction as in Example 9 (9d) was conducted using all this oxazolone to give 126 mg of the title compound (white powder).

mp: 180 to 181° C.;
¹H-nuclear magnetic resonance spectrum (400 MHz, DMSO-d₆) δ ppm:
9.69 (1H, brs), 7.96 (2H, d, J=9 Hz), 7.94 (1H, brt, J=6 Hz), 7.42 (2H, d, J=8 Hz), 7.17 (1H, s), 7.04 (2H, d, J=9 Hz), 7.02 (2H, d, J=8 Hz), 4.62 (1H, t, J=5 Hz), 3.84 (2H, d, J=6 Hz), 3.43 (2H, q, J=6 Hz), 3.22 (2H, q, J=6 Hz), 2.05 (1H, sept, J=7 Hz), 1.90-1.85 (1H, m), 1.00 (6H, d, J=7 Hz), 0.95-0.91 (2H, m), 0.67-0.64 (2H, m).

Example 37
N-((Z)-2-(4-Cyclopent-1-en-1-ylphenyl)-1-{[(2-hydroxyethyl)amino]carbonyl}vinyl)-4-isobutoxybenzamide (Exemplary Compound No. 1-14)

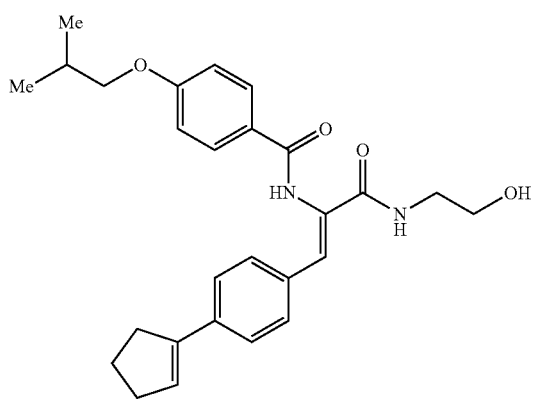 [SMILES: CC(C)COc1ccc(C(=O)N/C(=C\c2ccc(C3=CCCC3)cc2)C(=O)NCCO)cc1]

(37a) 4-Cyclopent-1-en-1-ylbenzaldehyde n-Butyllithium (7.2 mL, 1.56 M hexane solution, 11.2 mmol) was added to a solution in THF (25 mL) of 1-bromo-4-(dimethoxymethyl)benzene (2.29 g, 9.91 mmol) at −78° C. The mixture was stirred at the same temperature for 2 hours, and then cyclopentanone (1.34 mL, 15.1 mmol) was added thereto. The resulting mixture was heated to room temperature and then stirred for 1 hour. The reaction was terminated by adding a saturated ammonium chloride aqueous solution, and an extraction with ethyl acetate was conducted three times. The resulting organic layers were washed with water and saturated brine and then dried over anhydrous magnesium sulfate. The solvent was evaporated, and the resulting residue was purified by silica gel column chromatography (hexane:ethyl acetate, 5:1, v/v) to give an oily compound. Trifluoroacetic acid (9 mL) was added to a dichloromethane-water (9.1 mL, 100:1, v/v) mixture solution containing the resulting oily compound at room temperature, and the mixture was continuously stirred for 20 minutes. The solvent was evaporated, and the resulting residue was purified by silica gel column chromatography (hexane:ethyl acetate, 10:1, v/v) to give 1.18 g of the title compound (light brown crystalline solid, yield: 90%).

¹H-nuclear magnetic resonance spectrum (400 MHz, CDCl₃) δ ppm:

9.97 (1H, s), 7.83 (2H, d, J=8 Hz), 7.58 (2H, d, J=8 Hz), 6.41-6.40 (1H, m), 2.77-2.73 (2H, m), 2.60-2.56 (2H, m), 2.06 (2H, quint, J=7 Hz).

(37b) N-((Z)-2-(4-Cyclopent-1-en-1-ylphenyl)-1-{[(2-hydroxyethyl)amino]carbonyl}vinyl)-4-isobutoxybenzamide The same reaction as in Example 9 (9c) was conducted using N-(4-isobutoxybenzoyl)glycine (216 mg) prepared in Example 30 (30a) and 4-cyclopent-1-en-1-ylbenzaldehyde (157 mg) prepared in Example 37 (37a) to give the corresponding oxazolone (194 mg). Then, the same reaction as in Example 9 (9d) was conducted using all this oxazolone to give 128 mg of the title compound (white amorphous solid).

MS (FAB) m/z: 449 [M+H]⁺;

¹H-nuclear magnetic resonance spectrum (400 MHz, DMSO-d₆) δ ppm:

9.72 (1H, s), 7.98-7.94 (3H, m), 7.48 (2H, d, J=8 Hz), 7.39 (2H, d, J=8 Hz), 7.16 (1H, s), 7.02 (2H, d, J=8 Hz), 6.31 (1H, brs), 4.62 (1H, brt, J=5 Hz), 3.82 (2H, d, J=6 Hz), 3.43 (2H, q, J=6 Hz), 3.22 (2H, q, J=6 Hz), 2.63-2.59 (2H, m), 2.47-2.44 (2H, m), 2.04 (1H, sept, J=6 Hz), 1.92 (2H, quint, J=7 Hz), 0.99 (6H, d, J=6 Hz).

Example 38

N-((Z)-2-(4-Ethoxyphenyl)-1-{[(2-hydroxyethyl)amino]carbonyl}vinyl)-4-isobutoxybenzamide (Exemplary Compound No. 1-1)

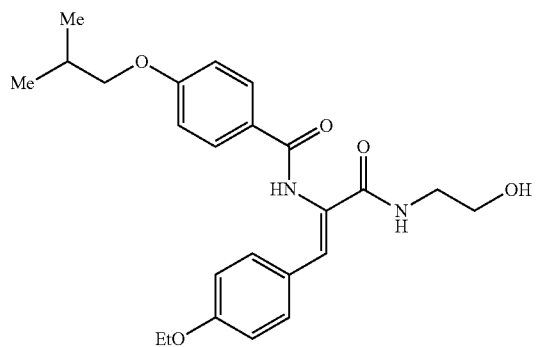 [SMILES: CCOc1ccc(/C=C(\NC(=O)c2ccc(OCC(C)C)cc2)C(=O)NCCO)cc1]

The same reaction as in Example 9 (9c) was conducted using N-(4-isobutoxybenzoyl)glycine (514 mg) prepared in Example 30 (30a) and 4-ethoxybenzaldehyde (338 mg) to give the corresponding oxazolone (422 mg). Then, the same reaction as in Example 9 (9d) was conducted using 102 mg of this oxazolone to give 54 mg of the title compound (white powder).

mp: 124 to 125° C.;

¹H-nuclear magnetic resonance spectrum (400 MHz, DMSO-d₆) δ ppm:

9.64 (1H, brs), 7.95 (2H, d, J=9 Hz), 7.86 (1H, brt, J=5 Hz), 7.46 (2H, d, J=9 Hz), 7.17 (1H, s), 7.02 (2H, d, J=9 Hz), 6.85 (2H, d, J=9 Hz), 4.61 (1H, brt, J=6 Hz), 4.00 (2H, q, J=7 Hz), 3.83 (2H, q, J=7 Hz), 3.42 (2H, q, J=6 Hz), 3.21 (2H, q, J=6 Hz), 2.04 (1H, sept, J=6 Hz), 1.29 (3H, t, J=7 Hz), 1.00 (6H, d, J=7 Hz).

Example 39

N-((Z)-2-[4-(Cyclopropyloxy)phenyl]-1-{[(2-hydroxyethyl)amino]carbonyl}vinyl)-4-isobutoxybenzamide (Exemplary Compound No. 1-3)

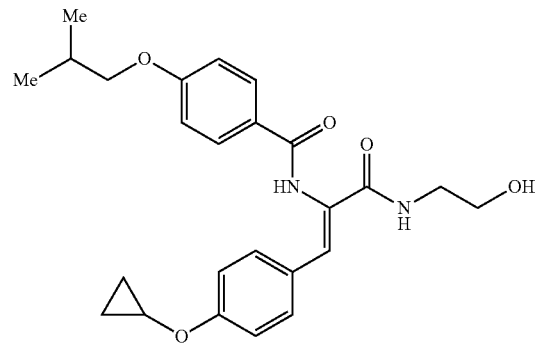 [SMILES: CC(C)COc1ccc(C(=O)N/C(=C\c2ccc(OC3CC3)cc2)C(=O)NCCO)cc1]

The same reaction as in Example 9 (9c) was conducted using N-(4-isobutoxybenzoyl)glycine (155 mg) prepared in Example 30 (30a) and 4-(cyclopropyloxy)benzaldehyde (200 mg) prepared in Example 6 (6c) to give the corresponding oxazolone (141 mg). Then, the same reaction as in Example 9 (9d) was conducted using 126 mg of this oxazolone to give 126 mg of the title compound (white amorphous solid).

MS (FAB) m/z: 439 [M+H]⁺;

¹H-nuclear magnetic resonance spectrum (400 MHz, CDCl₃) δ ppm:

8.03 (1H, brs), 7.79 (2H, d, J=9 Hz), 7.29 (2H, d, J=9 Hz), 6.99 (1H, s), 6.93 (2H, d, J=9 Hz), 6.89 (1H, t, J=6 Hz), 6.87 (2H, t, J=9 Hz), 3.74 (2H, d, J=6 Hz), 3.71-3.67 (3H, m), 3.42 (2H, q, J=5 Hz), 3.38 (1H, brs), 2.09 (1H, sept, J=7 Hz), 1.04 (6H, d, J=7 Hz), 0.80-0.71 (4H, m).

Example 40

N-{(Z)-1-{[(2-Hydroxyethyl)amino]carbonyl}-2-[4-(1,1,2,2-tetrafluoroethoxy)phenyl]vinyl}-4-isobutoxybenzamide (Exemplary Compound No. 1-9)

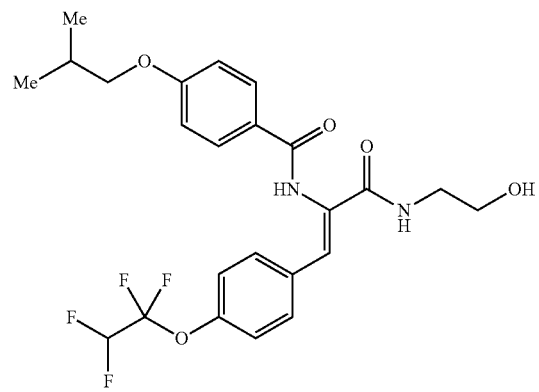 [SMILES: CC(C)COc1ccc(C(=O)N/C(=C\c2ccc(OC(F)(F)C(F)F)cc2)C(=O)NCCO)cc1]

The same reaction as in Example 9 (9c) was conducted using N-(4-isobutoxybenzoyl)glycine (518 mg) prepared in Example 30 (30a) and 4-(1,1,2,2-tetrafluoroethoxy)benzaldehyde (375 μL) to give the corresponding oxazolone (715 mg). Then, the same reaction as in Example 9 (9d) was conducted using 101 mg of this oxazolone to give 89 mg of the title compound (white solid).

mp: 174 to 177° C.;

¹H-nuclear magnetic resonance spectrum (400 MHz, CDCl₃) δ ppm:

7.79 (2H, d, J=9 Hz), 7.66 (1H, brs), 7.42 (2H, d, J=9 Hz), 7.19 (2H, d, J=8 Hz), 7.07 (1H, s), 6.95 (2H, d, J=9 Hz), 6.62 (1H, brt, J=6 Hz), 5.90 (1H, tt, J=53 Hz, 3 Hz), 3.83-3.79 (2H, m), 3.78 (2H, d, J=6 Hz), 3.53 (2H, q, J=5 Hz), 2.91 (1H, brs), 2.11 (1H, quint, J=7 Hz), 1.04 (6H, d, J=7 Hz).

Example 41

N-{(Z)-1-{[(2-Hydroxyethyl)amino]carbonyl}-2-[4-(methylthio)phenyl]vinyl}-4-isobutoxybenzamide (Exemplary Compound No. 1-15)

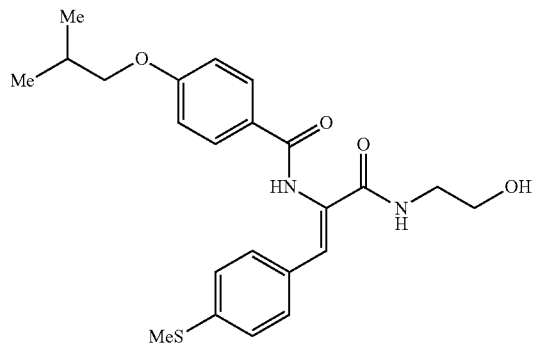

The same reaction as in Example 9 (9c) was conducted using N-(4-isobutoxybenzoyl)glycine (520 mg) prepared in Example 30 (30a) and 4-(methylthio)benzaldehyde (303 pt) to give the corresponding oxazolone (594 mg). Then, the same reaction as in Example 9 (9d) was conducted using 129 mg of this oxazolone to give 134 mg of the title compound (white powder).

mp: 161 to 163° C.;

¹H-nuclear magnetic resonance spectrum (400 MHz, CDCl₃) δ ppm:

8.30 (1H, brs), 7.78 (2H, d, J=9 Hz), 7.24 (2H, d, J=9 Hz), 7.09 (2H, d, J=9 Hz), 7.08 (1H, brt, J=5 Hz), 6.88 (1H, s), 6.87 (2H, d, J=9 Hz), 3.74 (2H, d, J=7 Hz), 3.67 (2H, brs), 3.46 (1H, brs), 3.39 (2H, q, J=5 Hz), 2.43 (3H, s), 2.10 (1H, sept, J=7 Hz), 1.04 (6H, d, J=7 Hz).

Example 42

N-((Z)-2-[4-(Ethylthio)phenyl]-1-{[(2-hydroxyethyl)amino]carbonyl}vinyl)-4-isobutoxybenzamide (Exemplary Compound No. 1-16)

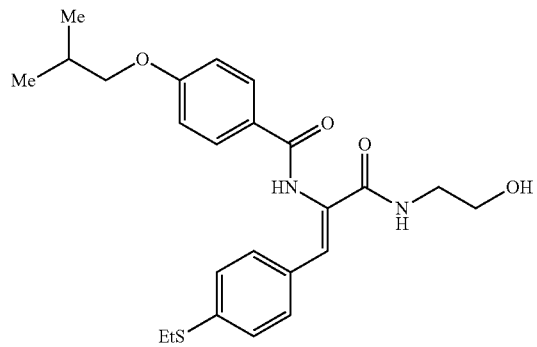

The same reaction as in Example 9 (9c) was conducted using N-(4-isobutoxybenzoyl)glycine (520 mg) prepared in Example 30 (30a) and 4-(ethylthio)benzaldehyde (387 mg) to give the corresponding oxazolone (574 mg). Then, the same reaction as in Example 9 (9d) was conducted using 100 mg of this oxazolone to give 82 mg of the title compound (white powder).

mp: 153 to 155° C.;

¹H-nuclear magnetic resonance spectrum (400 MHz, CDCl₃) δ ppm:

7.80 (2H, d, J=9 Hz), 7.70 (1H, brs), 7.31 (2H, d, J=8 Hz), 7.23 (2H, d, J=9 Hz), 7.05 (1H, brs), 6.94 (2H, d, J=9 Hz), 6.65 (1H, brs), 3.81-3.76 (4H, m), 3.51 (2H, q, J=5 Hz), 3.05 (1H, brs), 2.95 (2H, q, J=7 Hz), 2.16-2.04 (1H, m), 1.33 (3H, t, J=7 Hz), 1.04 (6H, d, J=7 Hz).

Example 43

N-((Z)-1-{[(2-Hydroxyethyl)amino]carbonyl}-2-{4-[(trifluoromethyl)thio]phenyl}vinyl)-4-isobutoxybenzamide (Exemplary Compound No. 1-17)

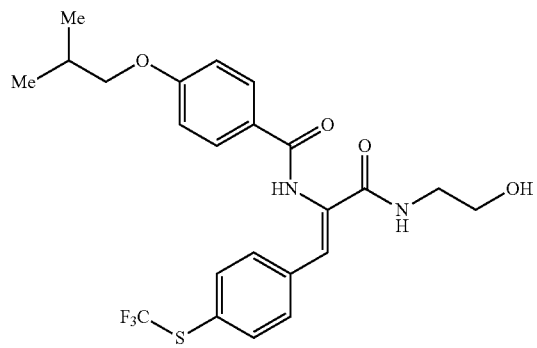 [SMILES: CC(C)COc1ccc(C(=O)N/C(=C\c2ccc(SC(F)(F)F)cc2)C(=O)NCCO)cc1]

The same reaction as in Example 9 (9c) was conducted using N-(4-isobutoxybenzoyl)glycine (512 mg) prepared in Example 30 (30a) and 4-[(trifluoromethyl)thio]benzaldehyde (462 mg) to give the corresponding oxazolone (719 mg).

Then, the same reaction as in Example 9 (9d) was conducted using 101 mg of this oxazolone to give 101 mg of the title compound (light yellow amorphous solid).

MS (FAB) m/z: 483 [M+H]+;
$^1$H-nuclear magnetic resonance spectrum (400 MHz, CDCl$_3$) δ ppm:
8.39 (1H, brs), 7.76 (2H, d, J=9 Hz), 7.53 (2H, d, J=8 Hz), 7.35 (2H, d, J=8 Hz), 7.07 (1H, brt, J=5 Hz), 6.87 (2H, d, J=9 Hz), 6.85 (1H, s), 3.75 (2H, d, J=7 Hz), 3.70 (2H, q, J=4 Hz), 3.40 (2H, q, J=5 Hz), 3.28 (1H, brt, J=5 Hz), 2.10 (1H, sept, J=7 Hz), 1.04 (6H, d, J=7 Hz).

Example 44

N-{(Z)-1-{[(2-Hydroxyethyl)amino]carbonyl}-2-[4-(1H-pyrrol-1-yl)phenyl]vinyl}-4-isobutoxybenzamide (Exemplary Compound No. 1-18)

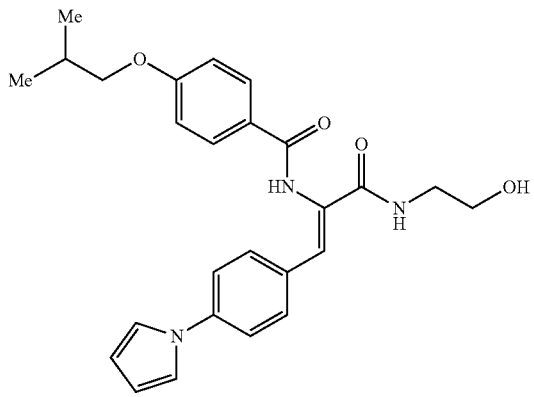 [SMILES: CC(C)COc1ccc(C(=O)N/C(=C\c2ccc(-n3cccc3)cc2)C(=O)NCCO)cc1]

The same reaction as in Example 9 (9c) was conducted using N-(4-isobutoxybenzoyl)glycine (520 mg) prepared in Example 30 (30a) and 4-(1H-pyrrol-1-yl)benzaldehyde (390 mg) to give the corresponding oxazolone (723 mg). Then, the same reaction as in Example 9 (9d) was conducted using 200 mg of this oxazolone to give 163 mg of the title compound (white powder).

mp: 174 to 176° C.;
$^1$H-nuclear magnetic resonance spectrum (400 MHz, CDCl$_3$) δ ppm:
8.18 (1H, brs), 7.76 (2H, d, J=9 Hz), 7.38 (2H, d, J=9 Hz), 7.26 (2H, d, J=9 Hz), 7.02 (2H, t, J=2 Hz), 6.99 (1H, brt, J=6 Hz), 6.96 (1H, brs), 6.84 (2H, d, J=9 Hz), 6.31 (2H, t, J=2 Hz), 3.74-3.69 (4H, m), 3.44 (2H, q, J=4 Hz), 2.08 (1H, sept, J=7 Hz), 1.03 (6H, d, J=7 Hz).

Example 45

N-{(Z)-1-{[(2-Hydroxyethyl)amino]carbonyl}-2-[4-(trifluoromethyl)phenyl]vinyl}-4-isobutoxybenzamide (Exemplary Compound No. 1-13)

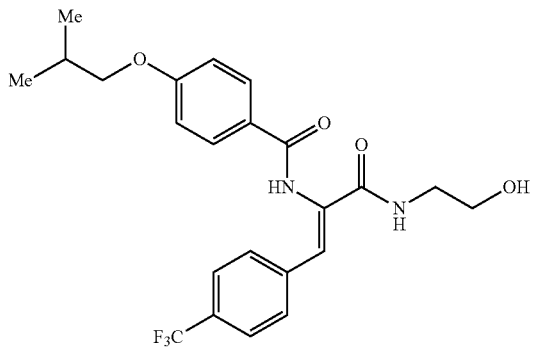 [SMILES: CC(C)COc1ccc(C(=O)N/C(=C\c2ccc(C(F)(F)F)cc2)C(=O)NCCO)cc1]

The same reaction as in Example 9 (9c) was conducted using N-(4-isobutoxybenzoyl)glycine (524 mg) prepared in Example 30 (30a) and 4-(trifluoromethyl)benzaldehyde (314 μL) to give the corresponding oxazolone (663 mg). Then, the same reaction as in Example 9 (9d) was conducted using 95 mg of this oxazolone to give 43 mg of the title compound (colorless crystalline solid).

mp: 207 to 210° C.;
$^1$H-nuclear magnetic resonance spectrum (400 MHz, CDCl$_3$) δ ppm:
7.82 (1H, brs), 7.74 (2H, d, J=9 Hz), 7.56 (2H, d, J=8 Hz), 7.46 (2H, d, J=8 Hz), 7.00 (1H, s), 6.91 (2H, d, J=9 Hz), 6.68 (1H, brt, J=6 Hz), 3.80 (2H, brs), 3.76 (2H, d, J=7 Hz), 3.52 (2H, q, J=5 Hz), 2.92 (1H, brs), 2.10 (1H, sept, J=7 Hz), 1.04 (6H, d, J=7 Hz).

Example 46

4-(Cyclobutylmethoxy)-N-{(Z)-1-{[(2-hydroxyethyl)amino]carbonyl}-2-[4-(trifluoromethoxy)phenyl]vinyl}benzamide (Exemplary Compound No. 1-251)

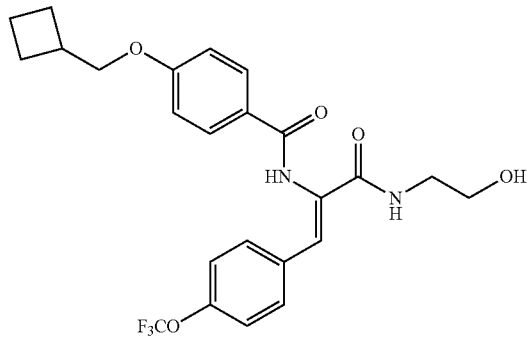 [SMILES: O=C(NCCO)/C(=C/c1ccc(OC(F)(F)F)cc1)NC(=O)c1ccc(OCC2CCC2)cc1]

(46a) N-[4-(Cyclobutylmethoxy)benzoyl]glycine

The same reactions as in Example 9 (9a) and (9b) were conducted using methyl 4-hydroxybenzoate (3.81 g, 25.0 mmol) and cyclobutylmethanol (2.36 mL, 25.0 mmol) to give 6.41 g of the title compound (colorless oil, yield: 97%).

(46b) 4-(Cyclobutylmethoxy)-N-{(Z)-1-{[(2-hydroxyethyl)amino]carbonyl}-2-[4-(trifluoromethoxy)phenyl]vinyl}benzamide The same reaction as in Example 9 (9c) was conducted using N-[4-(cyclobutylmethoxy)benzoyl]glycine (150 mg) prepared in Example 46 (46a) and 4-(trifluoromethoxy)benzaldehyde (90 μL) to give the corresponding oxazolone (161 mg). Then, the same reaction as in Example 9 (9d) was conducted using 81 mg of this oxazolone to give 73 mg of the title compound (white powder).

mp: 168 to 170° C.;
$^1$H-nuclear magnetic resonance spectrum (400 MHz, DMSO-d$_6$) δ ppm:
9.75 (1H, brs), 8.04 (1H, t, J=6 Hz), 7.92 (2H, d, J=9 Hz), 7.62 (2H, d, J=9H), 7.32 (2H, d, J=8 Hz), 7.14 (1H, brs), 7.02 (2H, d, J=9 Hz), 4.62 (1H, brt, J=6 Hz), 4.02 (2H, d, J=7 Hz), 3.43 (2H, q, J=6 Hz), 3.22 (2H, q, J=6 Hz), 2.73 (1H, sept, J=7 Hz), 2.12-2.04 (2H, m), 1.96-1.79 (4H, m).

Example 47

N-[(Z)-1-{[(2-Hydroxyethyl)amino]carbonyl}-2-(4-isopropoxyphenyl)vinyl]-4-(2-phenylethoxy)benzamide (Exemplary Compound No. 1-112)

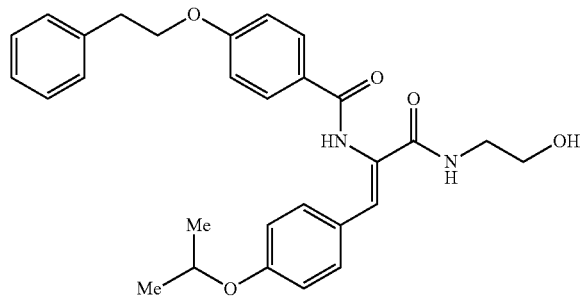 [SMILES: CC(C)Oc1ccc(/C=C(\NC(=O)c2ccc(OCCc3ccccc3)cc2)C(=O)NCCO)cc1]

(47a) N-[4-(2-Phenylethoxy)benzoyl]glycine

The same reactions as in Example 9 (9a) and (9b) were conducted using methyl 4-hydroxybenzoate (2.23 g, 14.7 mmol) and 2-phenylethanol (1.80 mL, 15.1 mmol) to give 3.23 g of the title compound (light yellow powder, yield: 74%).

[In this case, a 2 N sodium hydroxide aqueous solution was used instead of a 2 M lithium hydroxide aqueous solution.]

(47b) N-[(Z)-1-{[(2-Hydroxyethyl)amino]carbonyl}-2-(4-isopropoxyphenyl)vinyl]-4-(2-phenylethoxy)benzamide The same reaction as in Example 9 (9c) was conducted using N-[4-(2-phenylethoxy)benzoyl]glycine (174 mg) prepared in Example 47 (47a) and 4-isopropoxybenzaldehyde (101 μL) to give the corresponding oxazolone (205 mg). Then, the same reaction as in Example 9 (9d) was conducted using all this oxazolone to give 111 mg of the title compound (white amorphous solid).

MS (FAB) m/z: 488 [M+H]$^+$;
$^1$H-nuclear magnetic resonance spectrum (400 MHz, DMSO-$d_6$) δ ppm:
9.64 (1H, brs), 7.95 (2H, d, J=9 Hz), 7.86 (1H, brt, J=6 Hz), 7.45 (2H, d, J=9 Hz), 7.34-7.28 (4H, m), 7.23-7.20 (1H, m), 7.16 (1H, s), 7.03 (2H, d, J=9 Hz), 6.84 (2H, d, J=9 Hz), 4.63-4.57 (2H, m), 4.28 (2H, t, J=7 Hz), 3.42 (2H, q, J=6 Hz), 3.21 (2H, q, J=6 Hz), 3.06 (2H, t, J=7 Hz), 1.22 (6H, d, J=7 Hz).

Example 48

N-((Z)-2-[4-(Difluoromethoxy)phenyl]-1-{[(2-hydroxyethyl)amino]carbonyl}vinyl)-4-(2-phenylethoxy)benzamide (exemplary compound no. 1-114)

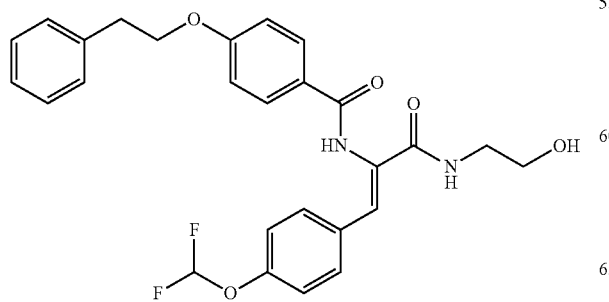

The same reaction as in Example 9 (9c) was conducted using N-[4-(2-phenylethoxy)benzoyl]glycine (150 mg) prepared in Example 47 (47a) and 4-(difluoromethoxy)benzaldehyde (73 μL) to give the corresponding oxazolone (181 mg). Then, the same reaction as in Example 9 (9d) was conducted using 88 mg of this oxazolone to give 74 mg of the title compound (white powder).

mp: 155 to 157° C.;
$^1$H-nuclear magnetic resonance spectrum (400 MHz, DMSO-$d_6$) δ ppm:
9.71 (1H, brs), 8.00 (1H, brt, J=6 Hz), 7.93 (2H, d, J=9 Hz), 7.56 (2H, d, J=9 Hz), 7.33-7.28 (4H, m), 7.23 (1H, t, J=74 Hz), 7.22-7.19 (1H, m), 7.16 (1H, s), 7.11 (2H, d, J=9 Hz), 7.03 (2H, d, J=9 Hz), 4.62 (1H, brt, J=5 Hz), 4.27 (2H, t, J=7 Hz), 3.42 (2H, q, J=6 Hz), 3.22 (2H, q, J=6 Hz), 3.06 (2H, t, J=7 Hz).

Example 49

N-{(Z)-1-{[(2-Hydroxyethyl)amino]carbonyl}-2-[4-(trifluoromethoxy)phenyl]vinyl}-4-(2-phenylethoxy)benzamide (Exemplary Compound No. 1-115)

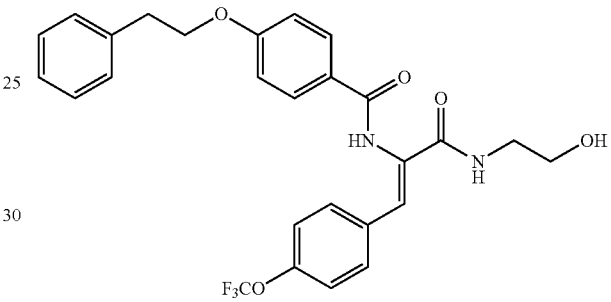

The same reaction as in Example 9 (9c) was conducted using N-[4-(2-phenylethoxy)benzoyl]glycine (150 mg) prepared in Example 47 (47a) and 4-(trifluoromethoxy)benzaldehyde (79 μL) to give the corresponding oxazolone (172 mg). Then, the same reaction as in Example 9 (9d) was conducted using 80 mg of this oxazolone to give 64 mg of the title compound (white amorphous solid).

MS (FAB) m/z: 515 [M+H]$^+$;
$^1$H-nuclear magnetic resonance spectrum (400 MHz, DMSO-$d_6$) δ ppm:
9.76 (1H, brs), 8.04 (1H, brt, J=6 Hz), 7.92 (2H, d, J=9 Hz), 7.61 (2H, d, J=9 Hz), 7.34-7.28 (6H, m), 7.23-7.20 (1H, m), 7.14 (1H, s), 7.03 (2H, d, J=9 Hz), 4.62 (1H, brt, J=5 Hz), 4.27 (2H, t, J=7 Hz), 3.43 (2H, q, J=6 Hz), 3.22 (2H, q, J=6 Hz), 3.06 (2H, t, J=7 Hz).

Example 50

N-{(Z)-1-{[(2-Hydroxyethyl)amino]carbonyl}-2-[4-(2,2,2-trifluoroethoxy)phenyl]vinyl}-4-(2-phenylethoxy)benzamide (Exemplary Compound No. 1-118)

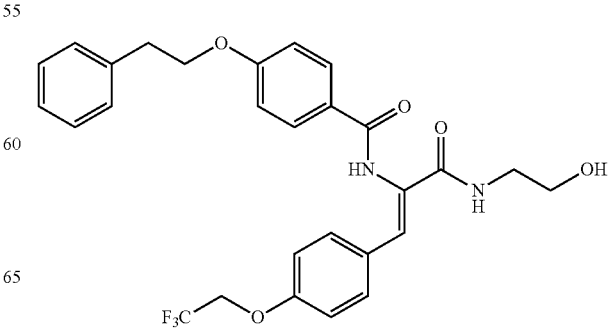

The same reaction as in Example 9 (9c) was conducted using N-[4-(2-phenylethoxy)benzoyl]glycine (150 mg) prepared in Example 47 (47a) and 4-(2,2,2-trifluoroethoxy)benzaldehyde (113 mg) prepared in Example 13 (13a) to give the corresponding oxazolone (186 mg). Then, the same reaction as in Example 9 (9d) was conducted using 88 mg of this oxazolone to give 64 mg of the title compound (white solid).

mp: 194 to 196° C.;

$^1$H-nuclear magnetic resonance spectrum (400 MHz, DMSO-$d_6$) δ ppm:

9.68 (1H, brs), 7.95-7.92 (3H, m), 7.50 (2H, d, J=9 Hz), 7.34-7.28 (4H, m), 7.24-7.19 (2H, m), 7.03 (2H, d, J=9 Hz), 6.99 (2H, d, J=9 Hz), 4.74 (2H, q, J=9 Hz), 4.62 (1H, brt, J=5 Hz), 4.27 (2H, t, J=7 Hz), 3.42 (2H, q, J=6 Hz), 3.21 (2H, q, J=6 Hz), 3.06 (2H, t, J=7 Hz).

Example 51

N-((Z)-2-(4-Cyclopropylphenyl)-1-{[(2-hydroxyethyl)amino]carbonyl}vinyl)-4-(2-phenylethoxy)benzamide (Exemplary Compound No. 1-121)

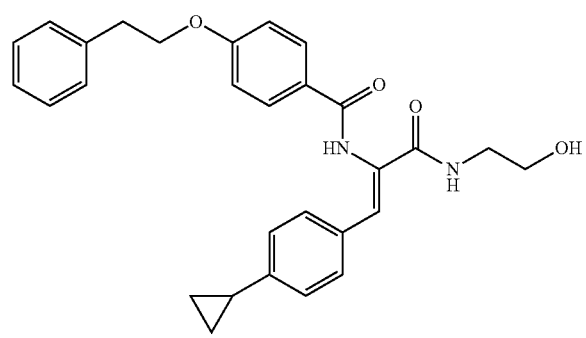 [SMILES: O=C(NCCO)/C(=C/c1ccc(C2CC2)cc1)NC(=O)c1ccc(OCCc2ccccc2)cc1]

The same reaction as in Example 9 (9c) was conducted using N-[4-(2-phenylethoxy)benzoyl]glycine (180 mg) prepared in Example 47 (47a) and 4-cyclopropylbenzaldehyde (97 mg) prepared in Example 5 to give the corresponding oxazolone (196 mg). Then, the same reaction as in Example 9 (9d) was conducted using 95 mg of this oxazolone to give 67 mg of the title compound (light yellow powder).

mp: 113 to 115° C.;

$^1$H-nuclear magnetic resonance spectrum (400 MHz, DMSO-$d_6$) δ ppm:

9.66 (1H, brs), 7.94 (2H, d, J=9 Hz), 7.92 (1H, t, J=6 Hz), 7.39 (2H, d, J=8 Hz), 7.34-7.28 (4H, m), 7.24-7.20 (1H, m), 7.14 (1H, brs), 7.03 (2H, d, J=9 Hz), 7.00 (2H, d, J=9 Hz), 4.61 (1H, t, J=6 Hz), 4.28 (2H, t, J=7 Hz), 3.42 (2H, q, J=6 Hz), 3.21 (2H, q, J=6 Hz), 3.06 (2H, t, J=7 Hz), 1.90-1.83 (1H, m), 0.95-0.90 (2H, m), 0.67-0.63 (2H, m).

Example 52

N-((Z)-2-[4-(Cyclopropyloxy)phenyl]-1-{[(2-hydroxyethyl)amino]carbonyl}vinyl)-4-(2-phenylethoxy)benzamide (Exemplary Compound No. 1-113)

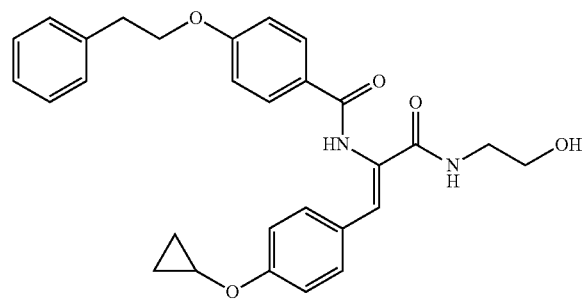 [SMILES: O=C(NCCO)/C(=C/c1ccc(OC2CC2)cc1)NC(=O)c1ccc(OCCc2ccccc2)cc1]

The same reaction as in Example 9 (9c) was conducted using N-[4-(2-phenylethoxy)benzoyl]glycine (185 mg) prepared in Example 47 (47a) and 4-(cyclopropyloxy)benzaldehyde (180 mg) prepared in Example 6 (6c) to give the corresponding oxazolone (220 mg). Then, the same reaction as in Example 9 (9d) was conducted using 101 mg of this oxazolone to give 58 mg of the title compound (light yellow amorphous solid).

MS (FAB) m/z: 487 [M+H]$^+$;

$^1$H-nuclear magnetic resonance spectrum (400 MHz, DMSO-$d_6$) δ ppm:

9.65 (1H, brs), 7.95 (2H, d, J=9 Hz), 7.89 (1H, brt, J=6 Hz), 7.47 (2H, d, J=9 Hz), 7.34-7.28 (4H, m), 7.23-7.20 (1H, m), 7.17 (1H, s), 7.03 (2H, d, J=9 Hz), 6.98 (2H, d, J=9 Hz), 4.61 (1H, brt, J=5 Hz), 4.27 (2H, t, J=7 Hz), 3.81 (1H, quint, J=3 Hz), 3.42 (2H, q, J=6 Hz), 3.21 (2H, q, J=6 Hz), 3.06 (2H, t, J=7 Hz), 0.78-0.73 (2H, m), 0.63-0.59 (2H, m).

Example 53

N-[(Z)-1-{[(2-Hydroxyethyl)amino]carbonyl}-2-(4-isopropylphenyl)vinyl]-4-(2-phenylethoxy)benzamide (Exemplary Compound No. 1-120)

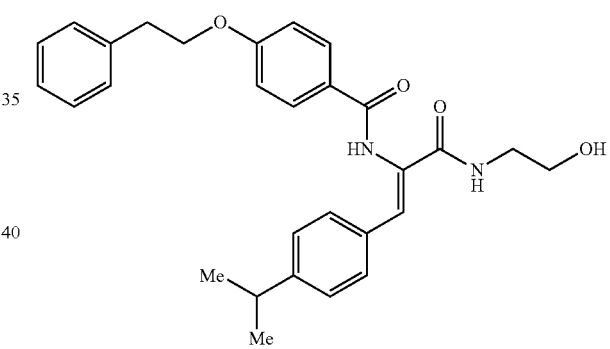

The same reaction as in Example 9 (9c) was conducted using N-[4-(2-phenylethoxy)benzoyl]glycine (187 mg) prepared in Example 47 (47a) and 4-isopropylbenzaldehyde (104 μL) to give the corresponding oxazolone (147 mg). Then, the same reaction as in Example 9 (9d) was conducted using all this oxazolone to give 114 mg of the title compound (white amorphous solid).

MS (FAB) m/z: 473 [M+H]$^+$;

$^1$H-nuclear magnetic resonance spectrum (400 MHz, DMSO-$d_6$) δ ppm:

9.69 (1H, s), 7.95-7.90 (3H, m), 7.44 (2H, d, J=8 Hz), 7.34-7.28 (4H, m), 7.24-7.22 (1H, m), 7.18 (2H, d, J=9 Hz), 7.16 (1H, s), 7.04 (2H, d, J=9 Hz), 4.61 (1H, t, J=5 Hz), 4.28 (2H, t, J=7 Hz), 3.42 (2H, q, J=6 Hz), 3.21 (2H, q, J=6 Hz), 3.06 (2H, t, J=7 Hz), 2.83 (1H, sept, J=7 Hz), 1.16 (6H, d, J=7 Hz).

Example 54

N-[(Z)-1-{[(2-Hydroxyethyl)amino]carbonyl}-2-(4-isopropoxyphenyl)vinyl]-4-(3,3,3-trifluoropropoxy)benzamide (Exemplary Compound No. 1-274)

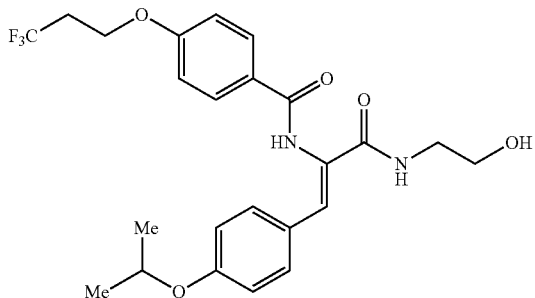 [SMILES: CC(C)Oc1ccc(/C=C(\NC(=O)c2ccc(OCCC(F)(F)F)cc2)C(=O)NCCO)cc1]

(54a) N-[4-(3,3,3-Trifluoropropoxy)benzoyl]glycine

The same reactions as in Example 9 (9a) and (9b) were conducted using methyl 4-hydroxybenzoate (1.52 g, 9.99 mmol) and 3,3,3-trifluoropropan-1-ol (1.14 g, 9.99 mmol) to give 385 mg of the title compound (white powder, yield: 14%).

(54b) N-[(Z)-1-[(2-Hydroxyethyl)amino]carbonyl-2-(4-isopropoxyphenyl)vinyl]-4-(3,3,3-trifluoropropoxy)benzamide The same reaction as in Example 9 (9c) was conducted using N-[4-(3,3,3-trifluoropropoxy)benzoyl]glycine (291 mg) prepared in Example 54 (54a) and 4-isopropoxybenzaldehyde (173 mg) to give the corresponding oxazolone (240 mg). Then, the same reaction as in Example 9 (9d) was conducted using 76 mg of this oxazolone to give 69 mg of the title compound (white powder).

mp: 84 to 86° C.;
$^1$H-nuclear magnetic resonance spectrum (400 MHz, CDCl$_3$) δ ppm:
8.76 (1H, brs), 7.79 (2H, d, J=9 Hz), 7.32 (1H, brt, J=6 Hz), 7.20 (2H, d, J=9 Hz), 6.78 (2H, d, J=9 Hz), 6.77 (1H, s), 6.68 (2H, d, J=9 Hz), 4.45 (1H, sept, J=6 Hz), 4.15 (2H, t, J=6 Hz), 3.74 (1H, brs), 3.54 (2H, brs), 3.24 (2H, q, J=4 Hz), 2.66-2.55 (2H, m), 1.28 (6H, d, J=6 Hz).

Example 55

N-((Z)-2-(4-Cyclopropylphenyl)-1-{[(2-hydroxyethyl)amino]carbonyl}vinyl)-4-(3,3,3-trifluoropropoxy)benzamide (Exemplary Compound No. 1-279)

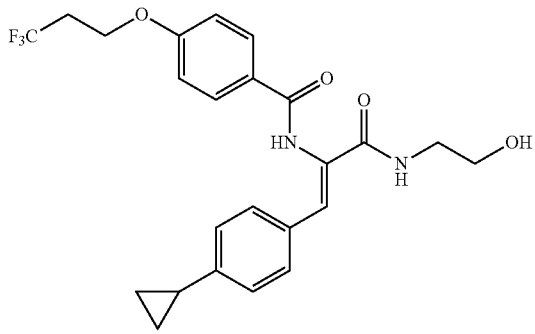 [SMILES: O=C(NCCO)/C(=C/c1ccc(C2CC2)cc1)NC(=O)c1ccc(OCCC(F)(F)F)cc1]

The same reaction as in Example 9 (9c) was conducted using N-[4-(3,3,3-trifluoropropoxy)benzoyl]glycine (1.46 g) prepared in Example 54 (54a) and 4-cyclopropylbenzaldehyde (768 mg) prepared in Example 5 to give the corresponding oxazolone (1.72 g). Then, the same reaction as in Example 9 (9d) was conducted using all this oxazolone 1.22 g of the title compound (white powder).

mp: 185 to 187° C.;
$^1$H-nuclear magnetic resonance spectrum (400 MHz, DMSO-d$_6$) δ ppm:
9.69 (1H, brs), 7.96 (2H, d, J=9 Hz), 7.93 (1H, brt, J=5 Hz), 7.39 (2H, d, J=8 Hz), 7.15 (1H, s), 7.06 (2H, d, J=9 Hz), 7.00 (2H, d, J=8 Hz), 4.61 (1H, t, J=5 Hz), 4.29 (2H, t, J=6 Hz), 3.43 (2H, q, J=6 Hz), 3.22 (2H, q, J=6 Hz), 2.88-2.77 (2H, m), 1.90-1.83 (1H, m), 0.95-0.91 (2H, m), 0.67-0.64 (2H, m).

Example 56

N-[(Z)-1-{[(2-Hydroxyethyl)amino]carbonyl}-2-(4-isopropoxyphenyl)vinyl]-4-(2-phenoxyethoxy)benzamide (Exemplary Compound No. 1-313)

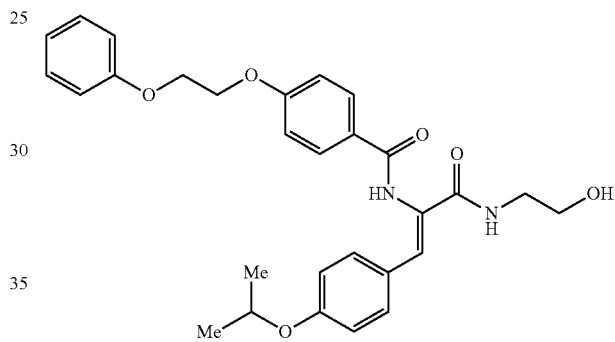

(56a) N-[4-(2-Phenoxyethoxy)benzoyl]glycine

The same reaction as in Example 1 (1b) was conducted using N-(4-hydroxybenzoyl)glycine tert-butyl ester (249 mg, 0.991 mmol) prepared in Example 1 (1a) and 2-phenoxyethanol (163 μL, 1.19 mmol) to give 241 mg of the title compound (white powder, yield: 78%).

(56b) N-[(Z)-1-{[(2-Hydroxyethyl)amino]carbonyl}-2-(4-isopropoxyphenyl)vinyl]-4-(2-phenoxyethoxy)benzamide The same reaction as in Example 1 (1c) was conducted using N-[4-(2-phenoxyethoxy)benzoyl]glycine (241 mg) prepared in Example 56 (56a) and 4-isopropoxybenzaldehyde (133 μL) to give the corresponding oxazolone (250 mg). Then, the same reaction as in Example 1 (1d) was conducted using all this oxazolone to give 129 mg of the title compound (white amorphous solid).

MS (FAB) m/z: 505 [M+H]$^+$;
$^1$H-nuclear magnetic resonance spectrum (400 MHz, DMSO-d$_6$) δ ppm:
9.66 (1H, brs), 7.97 (2H, d, J=9 Hz), 7.88 (1H, brt, J=6 Hz), 7.45 (2H, d, J=9 Hz), 7.29 (2H, dd, J=9 Hz, 7 Hz), 7.16 (1H, s), 7.09 (2H, d, J=9 Hz), 6.98 (2H, d, J=9 Hz), 6.94 (1H, t, J=7 Hz), 6.84 (2H, d, J=7 Hz), 4.64-4.58 (2H, m), 4.42-4.40 (2H, m), 4.35-4.32 (2H, m), 3.43 (2H, q, J=6 Hz), 3.22 (2H, q, J=6 Hz), 1.23 (6H, d, J=6 Hz).

Example 57

N-{(Z)-1-{[(2-Hydroxyethyl)amino]carbonyl}-2-[4-(trifluoromethoxy)phenyl]vinyl}-4-(2-phenoxyethoxy)benzamide (Exemplary Compound No. 1-317)

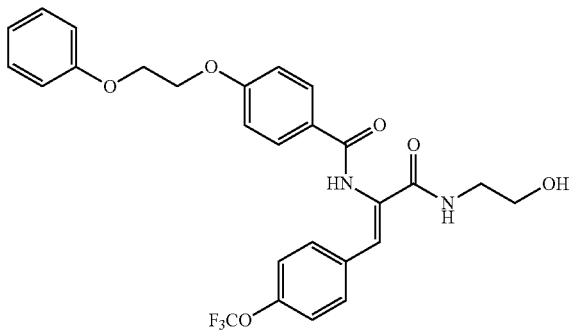 [SMILES: O=C(NCCO)/C(=C/c1ccc(OC(F)(F)F)cc1)NC(=O)c1ccc(OCCOc2ccccc2)cc1]

The same reaction as in Example 1 (1c) was conducted using N-[4-(2-phenoxyethoxy)benzoyl]glycine (157 mg) prepared in Example 56 (56a) and 4-(trifluoromethoxy)benzaldehyde (69 µL) to give the corresponding oxazolone (176 mg). The same reaction as in Example 1 (1d) was conducted using 175 mg of this oxazolone to give 58 mg of the title compound (white amorphous solid).

MS (ESI) m/z: 531 [M+H]$^+$;

$^1$H-nuclear magnetic resonance spectrum (400 MHz, DMSO-d$_6$) δ ppm:

9.81 (1H, brs), 8.08 (1H, brt, J=6 Hz), 7.97 (2H, d, J=9 Hz), 7.65 (2H, d, J=9 Hz), 7.34 (2H, d, J=9 Hz), 7.31 (2H, d, J=8 Hz), 7.17 (1H, s), 7.11 (2H, d, J=8 Hz), 7.00 (2H, d, J=9 Hz), 6.96 (1H, t, J=7 Hz), 4.64 (1H, brt, J=5 Hz), 4.43-4.41 (2H, m), 4.35-4.33 (2H, m), 3.45 (2H, q J=6 Hz), 3.24 (2H, q, J=6 Hz).

Example 58

N-((Z)-2-(4-Cyclopropylphenyl)-1-{[(2-hydroxyethyl)amino]carbonyl}vinyl)-4-(2-phenoxyethoxy)benzamide (Exemplary Compound No. 1-316)

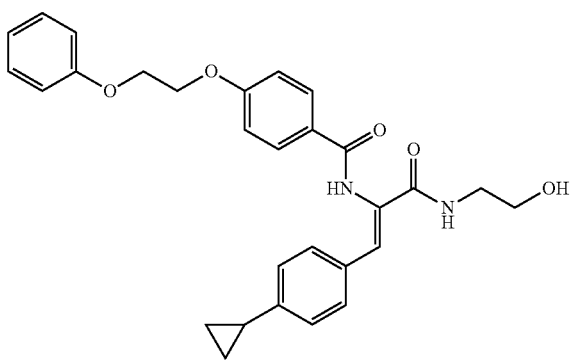 [SMILES: O=C(NCCO)/C(=C/c1ccc(C2CC2)cc1)NC(=O)c1ccc(OCCOc2ccccc2)cc1]

The same reaction as in Example 1 (1c) was conducted using N-[4-(2-phenoxyethoxy)benzoyl]glycine (157 mg) prepared in Example 56 (56a) and 4-cyclopropylbenzaldehyde (71 mg) prepared in Example 5 to give the corresponding oxazolone (166 mg). The same reaction as in Example 1 (1d) was conducted using 165 mg of this oxazolone to give 62 mg of the title compound (light yellow amorphous solid).

MS (ESI) m/z: 487 [M+H]$^+$;

$^1$H-nuclear magnetic resonance spectrum (400 MHz, DMSO-d$_6$) δ ppm:

9.72 (1H, brs), 8.00-7.94 (3H, m), 7.42 (2H, d, J=8 Hz), 7.32 (2H, t, J=8 Hz), 7.18 (1H, s), 7.11 (2H, d, J=8 Hz), 7.05-6.95 (5H, m), 4.63 (1H, brt, J=5 Hz), 4.43-4.40 (2H, m), 4.36-4.33 (2H, m), 3.44 (2H, q, J=6 Hz), 3.23 (2H, q, J=6 Hz), 1.91-1.84 (1H, m), 0.96-0.91 (2H, m), 0.68-0.64 (2H, m).

Example 59

4-(3-Cyclopropylpropoxy)-N-[(Z)-1-{[(2-hydroxyethyl)amino]carbonyl}-2-(4-isopropoxyphenyl)vinyl]benzamide (Exemplary Compound No 1-323)

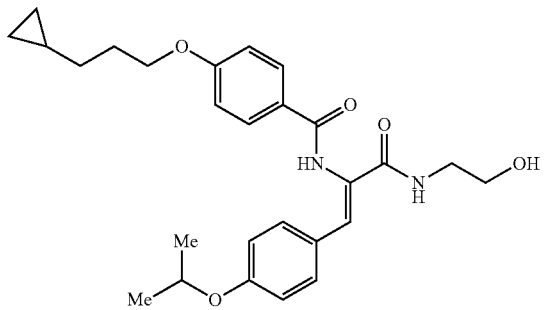 [SMILES: CC(C)Oc1ccc(/C=C(\NC(=O)c2ccc(OCCCC3CC3)cc2)C(=O)NCCO)cc1]

(59a) N-[4-(3-Cyclopropylpropoxy)benzoyl]glycine

The same reactions as in Example 9 (9a) and (9b) were conducted using methyl 4-hydroxybenzoate (6.09 g, 40.0 mmol) and 3-cyclopropylpropan-1-ol (which is the compound disclosed in Helv. Chim. Acta, (2003), 86, 865-893, 4.41 g, 44.0 mmol) to give 5.74 g of the title compound (white powder, yield: 51%).

(59b) 4-(3-Cyclopropylpropoxy)-N-[(Z)-1-{[(2-hydroxyethyl)amino]carbonyl}-2-(4-isopropoxyphenyl)vinyl]benzamide The same reaction as in Example 9 (9c) was conducted using N-[4-(3-cyclopropylpropoxy)benzoyl]glycine (139 mg) prepared in Example 59 (59a) and 4-isopropoxybenzaldehyde (86 mg) to give the corresponding oxazolone (124 mg). Then, the same reaction as in Example 9 (9d) was conducted using 91 mg of this oxazolone to give 63 mg of the title compound (white powder).

mp: 64 to 66° C.;

$^1$H-nuclear magnetic resonance spectrum (400 MHz, CDCl$_3$) δ ppm: 8.29 (1H, brs), 7.81 (2H, d, J=9 Hz), 7.28 (2H, d, J=9 Hz), 7.07 (1H, brt, J=6 Hz), 6.95 (1H, s), 6.86 (2H, d, J=9 Hz), 6.75 (2H, d, J=9 Hz), 4.50 (1H, sept, J=6 Hz), 4.01 (2H, t, J=6 Hz), 3.64 (2H, t, J=5 Hz), 3.36 (2H, q, J=5 Hz), 1.90 (2H, quint, J=7 Hz), 1.38 (2H, q, J=7 Hz), 1.31 (6H, d, J=6 Hz), 0.75-0.67 (1H, m), 0.47-0.43 (2H, m), 0.07-0.04 (2H, m).

Example 60

4-(3-Cyclopropylpropoxy)-N-{(Z)-1-{[(2-hydroxy-ethyl)amino]carbonyl}-2-[4-(trifluoromethoxy)phenyl]vinyl}benzamide (Exemplary Compound No. 1-327)

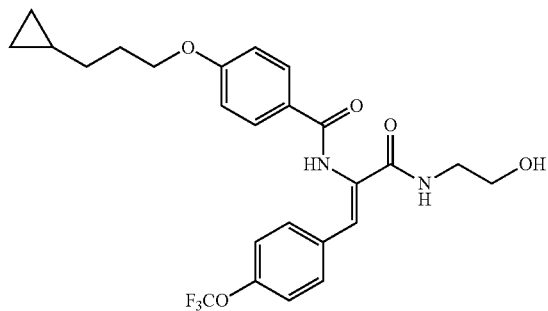 [SMILES: O=C(NCCO)/C(=C/c1ccc(OC(F)(F)F)cc1)NC(=O)c1ccc(OCCCC2CC2)cc1]

The same reaction as in Example 9 (9c) was conducted using N-[4-(3-cyclopropylpropoxy)benzoyl]glycine (277 mg) prepared in Example 59 (59a) and 4-(trifluoromethoxy)benzaldehyde (150 μL) to give the corresponding oxazolone (224 mg). Then, the same reaction as in Example 9 (9d) was conducted using 151 mg of this oxazolone to give 123 mg of the title compound (colorless amorphous solid).

MS (FAB) m/z: 493 [M+H]$^+$;

$^1$H-nuclear magnetic resonance spectrum (500 MHz, CDCl$_3$) δ ppm:
7.91 (1H, brs), 7.78 (2H, d, J=9 Hz), 7.40 (2H, d, J=9 Hz), 7.16 (2H, d, J=8 Hz), 7.01 (1H, s), 6.92 (2H, d, J=9 Hz), 6.78 (1H, t, J=5 Hz), 4.05 (2H, t, J=6 Hz), 3.78 (2H, brq, J=4 Hz), 3.49 (2H, q, J=4 Hz), 3.05 (1H, brt, J=6 Hz), 1.92 (2H, quint, J=7 Hz), 1.39 (2H, q, J=7 Hz), 0.74-0.67 (1H, m), 0.47-0.43 (2H, m), 0.07-0.04 (2H, m).

Example 61

4-(3-Cyclopropylpropoxy)-N-((Z)-2-[4-(2,2-difluoroethoxy)phenyl]-1-{[(2-hydroxyethyl)amino]carbonyl}vinyl)benzamide (Exemplary Compound No. 1-330)

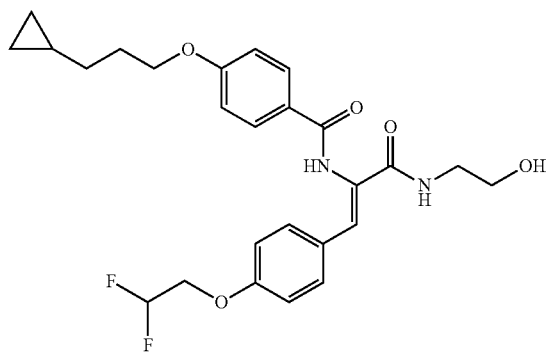 [SMILES: O=C(NCCO)/C(=C/c1ccc(OCC(F)F)cc1)NC(=O)c1ccc(OCCCC2CC2)cc1]

The same reaction as in Example 9 (9c) was conducted using N-[4-(3-cyclopropylpropoxy)benzoyl]glycine (277 mg) prepared in Example 59 (59a) and 4-(2,2-difluoroethoxy)benzaldehyde (196 mg) prepared in Example 4 (4a) to give the corresponding oxazolone (244 mg). Then, the same reaction as in Example 9 (9d) was conducted using 150 mg of this oxazolone to give 84 mg of the title compound (white powder).

mp: 149 to 151° C.;

$^1$H-nuclear magnetic resonance spectrum (500 MHz, CDCl$_3$) δ ppm:
7.81-7.79 (3H, m), 7.36 (2H, d, J=9 Hz), 7.06 (1H, s), 6.93 (2H, d, J=9 Hz), 6.86 (2H, d, J=8 Hz), 6.74 (1H, t, J=6 Hz), 6.07 (1H, tt, J=55 Hz, 4 Hz), 4.16 (2H, td, J=13 Hz, 4 Hz), 4.05 (2H, t, J=7 Hz), 3.77 (2H, t, J=5 Hz), 3.50 (2H, q, J=5 Hz), 1.92 (2H, quint, J=7 Hz), 1.39 (2H, q, J=7 Hz), 0.76-0.68 (1H, m), 0.47-0.44 (2H, m), 0.07-0.04 (2H, m).

Example 62

N-((Z)-2-(4-Cyclopropylphenyl)-1-{[(2-hydroxyethyl)amino]carbonyl}vinyl)-4-(3-cyclopropylpropoxy)benzamide (Exemplary Compound No. 1-326)

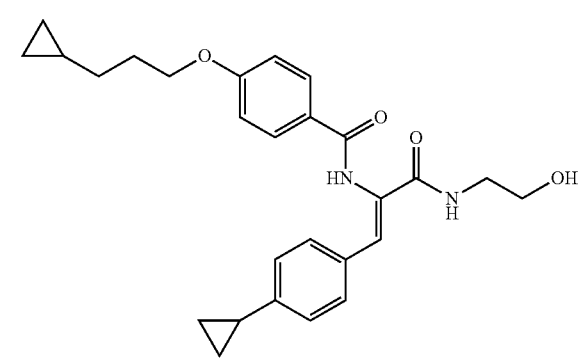 [SMILES: O=C(NCCO)/C(=C/c1ccc(C2CC2)cc1)NC(=O)c1ccc(OCCCC2CC2)cc1]

The same reaction as in Example 9 (9c) was conducted using N-[4-(3-cyclopropylpropoxy)benzoyl]glycine (277 mg) prepared in Example 59 (59a) and 4-cyclopropylbenzaldehyde (154 mg) prepared in Example 5 to give the corresponding oxazolone (260 mg). Then, the same reaction as in Example 9 (9d) was conducted using 151 mg of this oxazolone to give 148 mg of the title compound (white powder).

mp: 170 to 171° C.;

$^1$H-nuclear magnetic resonance spectrum (400 MHz, CDCl$_3$) δ ppm:
7.80 (2H, d, J=9 Hz), 7.67 (1H, brs), 7.29 (2H, d, J=8 Hz), 7.06 (1H, s), 7.03 (2H, d, J=9 Hz), 6.94 (2H, d, J=8 Hz), 6.61 (1H, brt, J=5 Hz), 4.06 (2H, t, J=7 Hz), 3.79 (2H, brs), 3.51 (2H, q, J=5 Hz), 3.09 (1H, brs), 1.96-1.84 (3H, m), 1.39 (2H, q, J=7 Hz), 1.02-0.97 (2H, m), 0.73-0.68 (3H, m), 0.47-0.43 (2H, m), 0.07-0.04 (2H, m).

Example 63

N-[(Z)-1-{[(2-Hydroxyethyl)amino]carbonyl}-2-(4-isopropoxyphenyl)vinyl]-4-[2-(2-thienylethoxy)]benzamide (Exemplary Compound No. 1-283)

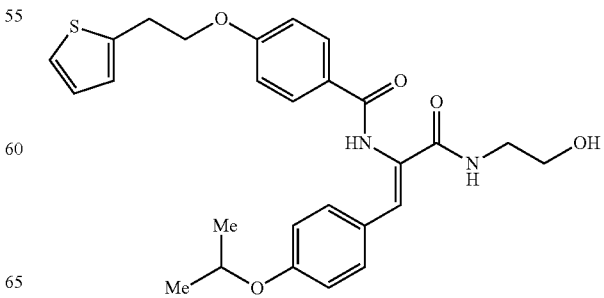

(63a) N-{4-[2-(2-Thienyl)ethoxy]benzoyl}glycine

The same reactions as in Example 9 (9a) and (9b) were conducted using methyl 4-hydroxybenzoate (1.55 g, 10.2 mmol) and 2-(2-thienyl)ethanol (1.20 mL, 10.8 mmol) to give 2.02 g of the title compound (white powder, yield: 65%).

[In this case, a 2 N sodium hydroxide aqueous solution was used instead of a 2 M lithium hydroxide aqueous solution.]

(63b) N-[(Z)-1-{[(2-Hydroxyethyl)amino]carbonyl}-2-(4-isopropoxyphenyl)vinyl]-4-[2-(2-thienylethoxy)]benzamide The same reaction as in Example 9 (9c) was conducted using N-{4-[2-(2-thienyl)ethoxy]benzoyl}glycine (251 mg) prepared in Example 63 (63a) and 4-isopropoxybenzaldehyde (139 μL) to give the corresponding oxazolone (191 mg). Then, the same reaction as in Example 9 (9d) was conducted using all this oxazolone to give 134 mg of the title compound (white amorphous solid).

MS (FAB) m/z: 495 [M+H]$^+$;

$^1$H-nuclear magnetic resonance spectrum (400 MHz, DMSO-d$_6$) δ ppm:

9.65 (1H, brs), 7.96 (2H, d, J=9 Hz), 7.87 (1H, brt, J=6 Hz), 7.45 (2H, d, J=9 Hz), 7.35 (1H, dd, J=5 Hz, 2 Hz), 7.16 (1H, s), 7.05 (2H, d, J=9 Hz), 6.99-6.95 (2H, m), 6.84 (2H, d, J=9 Hz), 4.63-4.57 (2H, m), 4.27 (2H, t, J=6H), 3.42 (2H, q, J=6 Hz), 3.28 (2H, t, J=6 Hz), 3.21 (2H, q, J=6 Hz), 1.22 (6H, d, J=6 Hz).

Example 64

N-((Z)-2-(4-Cyclopropylphenyl)-1-{[(2-hydroxyethyl)amino]carbonyl}vinyl)-4-[2-(2-thienyl)ethoxy]benzamide (Exemplary Compound No. 1-288)

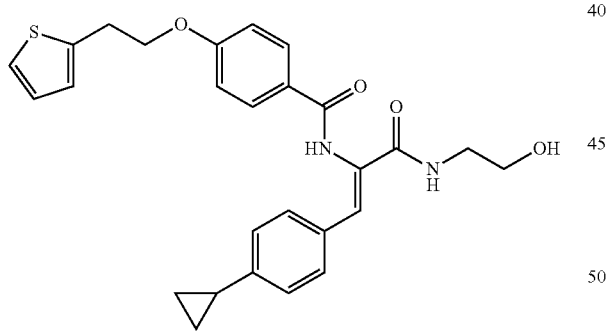

The same reaction as in Example 9 (9c) was conducted using N-{4-[2-(2-thienyl)ethoxy]benzoyl}glycine (279 mg) prepared in Example 63 (63a) and 4-cyclopropylbenzaldehyde (171 mg) prepared in Example 5 to give the corresponding oxazolone (268 mg). Then, the same reaction as in Example 9 (9d) was conducted using all this oxazolone to give 124 mg of the title compound (white amorphous solid).

MS (FAB) m/z: 477 [M+H]$^+$;

$^1$H-nuclear magnetic resonance spectrum (500 MHz, DMSO-d$_6$) δ ppm:

9.71 (1H, s), 7.98-7.94 (3H, m), 7.41 (2H, d, J=8 Hz), 7.37 (1H, dd, J=5 Hz, 1 Hz), 7.17 (1H, s), 7.07 (2H, d, J=9 Hz), 7.02 (2H, d, J=8 Hz), 7.00-6.97 (2H, m), 4.63 (1H, t, J=5 Hz), 4.29 (2H, t, J=6 Hz), 3.43 (2H, q, J=6 Hz), 3.29 (2H, t, J=6 Hz), 3.22 (2H, q, J=6 Hz), 1.90-1.84 (1H, m), 0.95-0.91 (2H, m), 0.67-0.64 (2H, m).

Example 65

N-{(Z)-1-{[(2-Hydroxyethyl)amino]carbonyl}-2-[4-(trifluoromethoxy)phenyl]vinyl}-4-[2-(1H-pyrrol-1-yl)ethoxy]benzamide (Exemplary Compound No. 1-295)

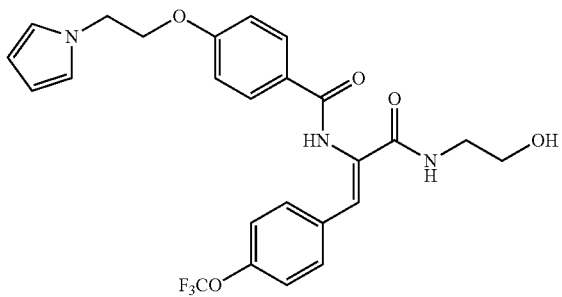 [SMILES: O=C(NCCO)/C(=C/c1ccc(OC(F)(F)F)cc1)NC(=O)c1ccc(OCCn2cccc2)cc1]

(65a) N-{4-[2-(1H-Pyrrol-1-yl)ethoxy]benzoyl}glycine

The same reaction as in Example 23 (23a) was conducted using methyl 4-hydroxybenzoate (913 mg, 6.00 mmol) and 2-(1H-pyrrol-1-yl)ethanol (692 μL, 6.60 mmol) to give the corresponding benzoic acid derivative (1.23 g, yield: 89%). Then, the same reaction as in Example 23 (23b) was conducted using 578 mg (2.50 mmol) of this derivative to give 568 mg of the title compound (colorless crystalline solid, yield: 79%).

(65b) N-{(Z)-1-[(2-Hydroxyethyl)amino]carbonyl-2-[4-(trifluoromethoxy)phenyl]vinyl}-4-[2-(1H-pyrrol-1-yl)ethoxy]benzamide The same reaction as in Example 23 (23c) was conducted using N-{4-[2-(1H-pyrrol-1-yl)ethoxy]benzoyl}glycine (120 mg) prepared in Example 65 (65a) and 4-(trifluoromethoxy)benzaldehyde (63 μL) to give the corresponding oxazolone (128 mg). Then, the same reaction as in Example 23 (23d) was conducted using all this oxazolone to give 91 mg of the title compound (white amorphous solid).

MS (FAB) m/z: 504 [M+H]$^+$;

$^1$H-nuclear magnetic resonance spectrum (400 MHz, CDCl$_3$) δ ppm:

8.36 (1H, brs), 7.75 (2H, d, J=8 Hz), 7.35 (2H, d, J=9 Hz), 7.10 (2H, d, J=8 Hz), 7.01 (1H, t, J=6 Hz), 6.87 (1H, s), 6.82 (2H, d, J=9 Hz), 6.75 (2H, t, J=2 Hz), 6.18 (2H, t, J=2 Hz), 4.28 (2H, t, J=5 Hz), 4.20 (2H, t, J=5 Hz), 3.70 (2H, t, J=5 Hz), 3.39 (2H, q, J=5 Hz), 3.26 (1H, brs).

Example 66

N-((Z)-2-(4-Cyclopropylphenyl)-1-{[(2-hydroxyethyl)amino]carbonyl}vinyl)-4-[2-(1H-pyrrol-1-yl)ethoxy]benzamide (Exemplary Compound No. 1-297)

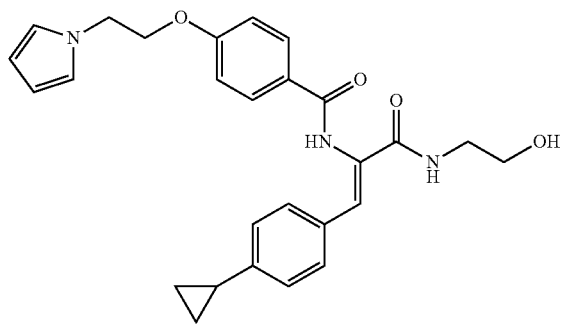 [SMILES: O=C(NCCO)/C(=C/c1ccc(C2CC2)cc1)NC(=O)c1ccc(OCCn2cccc2)cc1]

The same reaction as in Example 23 (23c) was conducted using N-{4-[2-(1H-pyrrol-1-yl)ethoxy]benzoyl}glycine (173 mg) prepared in Example 65 (65a) and 4-cyclopropylbenzaldehyde (92 mg) prepared in Example 5 to give the corresponding oxazolone (178 mg). Then, the same reaction as in Example 23 (23d) was conducted using all this oxazolone to give 118 mg of the title compound (light yellow amorphous solid).

MS (FAB) m/z: 460 [M+H]$^+$;

$^1$H-nuclear magnetic resonance spectrum (400 MHz, DMSO-d$_6$) δ ppm:

9.67 (1H, brs), 7.93 (2H, d, J=9 Hz), 7.92 (1H, t, J=6 Hz), 7.38 (2H, d, J=9 Hz), 7.14 (1H, s), 7.01 (2H, d, J=9 Hz), 6.99 (2H, d, J=9 Hz), 6.82 (2H, t, J=2 Hz), 5.98 (2H, t, J=2 Hz), 4.61 (1H, t, J=5 Hz), 4.32-4.26 (4H, m), 3.42 (2H, q, J=6 Hz), 3.21 (2H, q, J=6 Hz), 1.89-1.83 (1H, m), 0.95-0.90 (2H, m), 0.67-0.63 (2H, m).

Example 67

N-[(Z)-1-{[(2-Hydroxyethyl)amino]carbonyl}-2-(4-isopropoxyphenyl)vinyl]-4-[2-(3-methoxyphenyl)ethoxy]benzamide (Exemplary Compound No. 1-146)

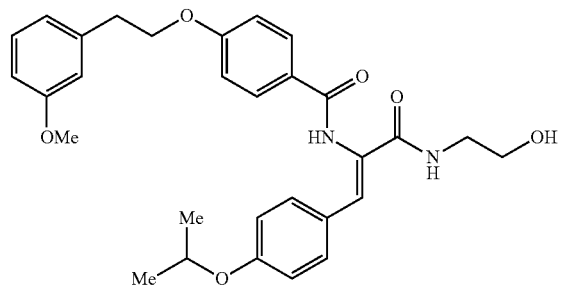 [SMILES: COc1cccc(CCOc2ccc(C(=O)N/C(=C\c3ccc(OC(C)C)cc3)C(=O)NCCO)cc2)c1]

(67a) N-{4-[2-(3-Methoxyphenyl)ethoxy]benzoyl}glycine

The same reactions as in Example 9 (9a) and (9b) were conducted using methyl 4-hydroxybenzoate (4.26 g, 28.0 mmol) and 2-(3-methoxyphenyl)ethanol (4.32 mL, 31.0 mmol) to give 8.54 g of the title compound (colorless crystal, yield: 92%).

(67b) N-[(Z)-1-{[(2-Hydroxyethyl)amino]carbonyl}-2-(4-isopropoxyphenyl)vinyl]-4-[2-(3-methoxyphenyl)ethoxy]benzamide The same reaction as in Example 9 (9c) was conducted using N-{4-[2-(3-methoxyphenyl)ethoxy]benzoyl}glycine (264 mg) prepared in Example 67 (67a) and 4-isopropoxybenzaldehyde (138 mg) to give the corresponding oxazolone (236 mg). Then, the same reaction as in Example 9 (9d) was conducted using 151 mg of this oxazolone to give 138 mg of the title compound (white amorphous solid).

MS (FAB) m/z: 519 [M+H]$^+$;

$^1$H-nuclear magnetic resonance spectrum (400 MHz, CDCl$_3$) δ ppm:

8.31 (1H, brs), 7.70 (2H, d, J=9 Hz), 7.17-7.12 (3H, m), 7.05 (1H, brt, J=6 Hz), 6.81 (1H, s), 6.78-6.69 (5H, m), 6.63 (2H, d, J=9 Hz), 4.39 (1H, sept, J=6 Hz), 4.08 (2H, t, J=7 Hz), 3.72 (3H, s), 3.57 (1H, brd, J=5 Hz), 3.53 (2H, brd, J=4 Hz), 3.24 (2H, q, J=4 Hz), 2.98 (2H, t, J=7 Hz), 1.21 (6H, d, J=6 Hz).

Example 68

N-{(Z)-1-{[(2-Hydroxyethyl)amino]carbonyl}-2-[4-(trifluoromethoxy)phenyl]vinyl}-4-[2-(3-methoxyphenyl)ethoxy]benzamide (Exemplary Compound No. 1-149)

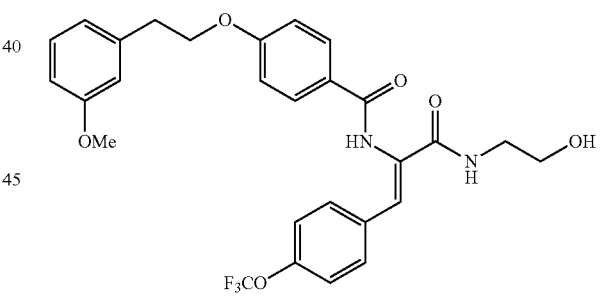

The same reaction as in Example 9 (9c) was conducted using N-{4-[2-(3-methoxyphenyl)ethoxy]benzoyl}glycine (329 mg) prepared in Example 67 (67a) and 4-(trifluoromethoxy)benzaldehyde (200 mg) to give the corresponding oxazolone (416 mg). Then, the same reaction as in Example 9 (9d) was conducted using 121 mg of this oxazolone to give 96 mg of the title compound (colorless amorphous solid).

MS (FAB) m/z: 545 [M+H]$^+$;

$^1$H-nuclear magnetic resonance spectrum (500 MHz, DMSO-d$_6$) δ ppm:

9.80 (1H, brs), 8.08 (1H, t, J=6 Hz), 7.97 (2H, d, J=9 Hz), 7.65 (2H, d, J=9 Hz), 7.34 (2H, d, J=8 Hz), 7.23 (1H, t, J=8 Hz), 7.18 (1H, s), 7.06 (2H, d, J=9 Hz), 6.93 (1H, s), 6.91 (1H, d, J=9 Hz), 6.81 (1H, dd, J=8 Hz, 2 Hz), 4.65 (1H, t, J=6 Hz), 4.29 (2H, t, J=7 Hz), 3.75 (3H, s), 3.47 (2H, q, J=6 Hz), 3.25 (2H, q, J=6 Hz), 3.04 (2H, t, J=7 Hz).

Example 69

N-((Z)-2-(4-Cyclopropylphenyl)-1-{[(2-hydroxyethyl)amino]carbonyl}vinyl)-4-[2-(3-methoxyphenyl)ethoxy]benzamide (Exemplary Compound No. 1-155)

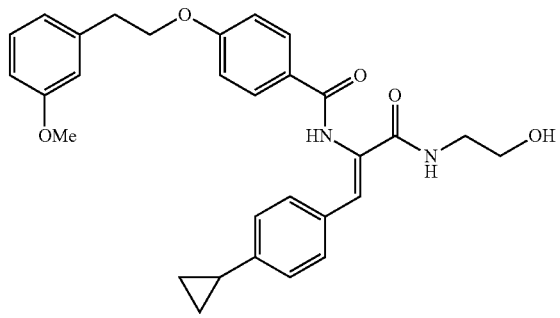 [SMILES: COc1cccc(CCOc2ccc(C(=O)N/C(=C\c3ccc(C4CC4)cc3)C(=O)NCCO)cc2)c1]

The same reaction as in Example 9 (9c) was conducted using N-{4-[2-(3-methoxyphenyl)ethoxy]benzoyl}glycine (231 mg) prepared in Example 67 (67a) and 4-cyclopropylbenzaldehyde (108 mg) prepared in Example 5 to give the corresponding oxazolone (249 mg). Then, the same reaction as in Example 9 (9d) was conducted using 101 mg of this oxazolone to give 97 mg of the title compound (white amorphous solid).

MS (FAB) m/z: 501 [M+H]$^+$;

$^1$H-nuclear magnetic resonance spectrum (500 MHz, DMSO-$d_6$) δ ppm:

9.69 (1H, brs), 7.96 (2H, d, J=9 Hz), 7.94 (1H, t, J=5 Hz), 7.41 (2H, d, J=8 Hz), 7.23 (1H, t, J=8 Hz), 7.17 (1H, s), 7.05 (2H, d, J=8 Hz), 7.02 (2H, d, J=8 Hz), 6.92-6.90 (2H, m), 6.81 (1H, dd, J=8 Hz, 2 Hz), 4.62 (1H, t, J=6 Hz), 4.28 (2H, t, J=7 Hz), 3.75 (3H, s), 3.44 (2H, q, J=6 Hz), 3.23 (2H, q, J=6 Hz), 3.04 (2H, t, J=7 Hz), 1.87 (1H, sept, J=5 Hz), 0.95-0.91 (2H, m), 0.67-0.64 (2H, m).

Example 70

N-((Z)-2-(4-Chlorophenyl)-1-{[(2-hydroxyethyl)amino]carbonyl}vinyl)-4-[2-(3-methoxyphenyl)ethoxy]benzamide (Exemplary Compound No. 1-161)

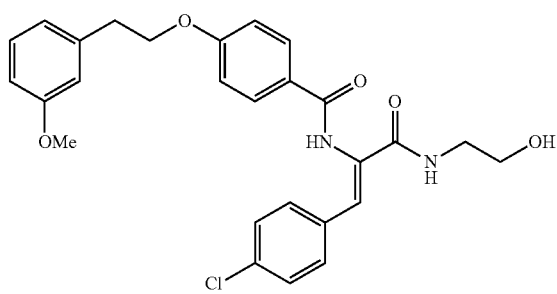 [SMILES: COc1cccc(CCOc2ccc(C(=O)N/C(=C\c3ccc(Cl)cc3)C(=O)NCCO)cc2)c1]

The same reaction as in Example 9 (9c) was conducted using N-{4-[2-(3-methoxyphenyl)ethoxy]benzoyl}glycine (329 mg) prepared in Example 67 (67a) and 4-chlorobenzaldehyde (148 mg) to give the corresponding oxazolone (396 mg). Then, the same reaction as in Example 9 (9d) was conducted using 108 mg of this oxazolone to give 90 mg of the title compound (white powder).

mp: 54 to 56° C.;

$^1$H-nuclear magnetic resonance spectrum (500 MHz, DMSO-$d_6$) δ ppm:

9.76 (1H, brs), 8.06 (1H, t, J=6 Hz), 7.95 (2H, d, J=9 Hz), 7.53 (2H, d, J=9 Hz), 7.39 (2H, d, J=8 Hz), 7.23 (1H, t, J=8 Hz), 7.15 (1H, s), 7.05 (2H, d, J=9 Hz), 6.92 (1H, s), 6.91 d, J=9 Hz), 6.81 (1H, dd, J=8 Hz, 2 Hz), 4.64 (1H, t, J=6 Hz), 4.28 (2H, t, J=7 Hz), 3.75 (3H, s), 3.45 (2H, q, J=6 Hz), 3.24 (2H, q, J=6 Hz), 3.04 (2H, t, J=7 Hz).

Example 71

4-[2-(1,3-Benzodioxol-5-yl)ethoxy]-N-[(Z)-1-{[(2-hydroxyethyl)amino]carbonyl}-2-(4-isopropoxyphenyl)vinyl]benzamide (Exemplary Compound No. 1-331)

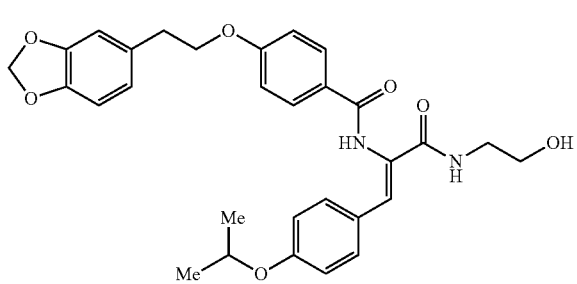 [SMILES: CC(C)Oc1ccc(/C=C(\NC(=O)c2ccc(OCCc3ccc4c(c3)OCO4)cc2)C(=O)NCCO)cc1]

(71a) N-{4-[2-(1,3-Benzodioxol-5-yl)ethoxy]benzoyl}glycine

The same reaction as in Example 1 (1b) was conducted using N-(4-hydroxybenzoyl)glycine tert-butyl ester (300 mg, 1.19 mmol) prepared in Example 1 (1a) and 2-(1,3-benzodioxol-5-yl)ethanol (which is the compound disclosed in Tetrahedron, (2003), 59, 3369-3378, 239 mg, 1.44 mmol) to give 356 mg of the title compound (pale red powder, yield: 87%).

(71b) 4-[2-(1,3-Benzodioxol-5-yl)ethoxy]-N-[(Z)-1-{[(2-hydroxyethyl)amino]carbonyl}-2-(4-isopropoxyphenyl)vinyl]benzamide The same reaction as in Example 1 (1c) was conducted using N-{4-[2-(1,3-benzodioxol-5-yl)ethoxy]benzoyl}glycine (179 mg) prepared in Example 71 (71a) and 4-isopropoxybenzaldehyde (95 µL) to give the corresponding oxazolone (212 mg). Then, the same reaction as in Example 1 (1d) was conducted using all this oxazolone to give 94 mg of the title compound (light yellow amorphous solid).

MS (FAB) m/z: 533 [M+H]$^+$;

$^1$H-nuclear magnetic resonance spectrum (400 MHz, DMSO-$d_6$) δ ppm:

9.64 (1H, brs), 7.95 (2H, d, J=9 Hz), 7.86 (1H, t, J=6 Hz), 7.45 (2H, d, J=9 Hz), 7.16 (1H, s), 7.03 (2H, d, J=9 Hz), 6.93 (1H, d, J=2 Hz), 6.85 (1H, d, J=2 Hz), 6.83 (2H, s), 6.77 (1H, dd, J=8 Hz, 2 Hz), 5.96 (2H, s), 4.63-4.57 (2H, m), 4.22 (2H, t, J=7 Hz), 3.42 (2H, t, J=6 Hz), 3.21 (2H, q, J=6 Hz), 2.98 (2H, t, J=7 Hz), 1.23 (6H, d, J=6 Hz).

Example 72

4-[2-(1,3-Benzodioxol-5-yl)ethoxy]-N-((Z)-2-(4-cyclopropylphenyl)-1-{[(2-hydroxyethyl)amino]carbonyl}vinyl)benzamide (Exemplary Compound No. 1-334)

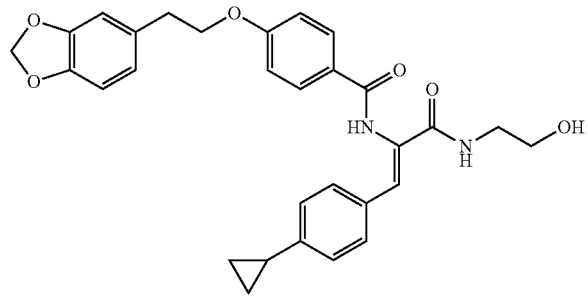 [SMILES: O=C(NCCO)/C(=C/c1ccc(C2CC2)cc1)NC(=O)c1ccc(OCCc2ccc3c(c2)OCO3)cc1]

The same reaction as in Example 1 (1c) was conducted using N-{4-[2-(1,3-benzodioxol-5-yl)ethoxy]benzoyl}glycine (180 mg) prepared in Example 71 (71a) and 4-cyclopropylbenzaldehyde (95 mg) prepared in Example 5 to give the corresponding oxazolone (192 mg). Then, the same reaction as in Example 1 (1d) was conducted using all this oxazolone to give 123 mg of the title compound (white powder).

mp: 113 to 115° C.;

$^1$H-nuclear magnetic resonance spectrum (500 MHz, DMSO-d$_6$) δ ppm:

9.69 (1H, brs), 7.95 (2H, d, J=8 Hz), 7.94 (1H, t, J=6 Hz), 7.41 (2H, d, J=8 Hz), 7.17 (1H, s), 7.04 (2H, d, J=9 Hz), 7.02 (2H, d, J=8 Hz), 6.95 (1H, d, J=1 Hz), 6.85 (1H, d, J=8 Hz), 6.79 (1H, dd, J=8 Hz, 1 Hz), 5.98 (2H, s), 4.62 (1H, brt, J=5 Hz), 4.23 (2H, t, J=7 Hz), 3.43 (2H, q, J=6 Hz), 3.22 (2H, q, J=6 Hz), 2.98 (2H, t, J=7 Hz), 1.87 (1H, quint, J=3 Hz), 0.95-0.91 (2H, m), 0.67-0.64 (2H, m).

Example 73

4-[2-(4-Fluorophenyl)ethoxy]-N-[(Z)-1-{[(2-hydroxyethyl)amino]carbonyl}-2-(4-isopropoxyphenyl)vinyl]benzamide (Exemplary Compound No. 1-214)

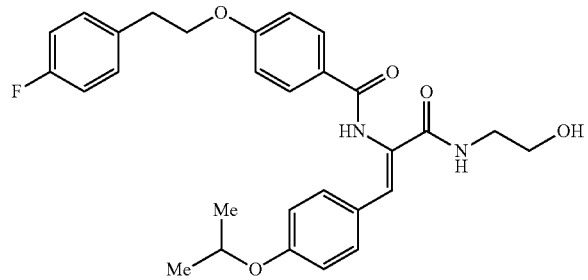 [SMILES: CC(C)Oc1ccc(/C=C(\NC(=O)c2ccc(OCCc3ccc(F)cc3)cc2)C(=O)NCCO)cc1]

(73a) N-{4-[2-(4-Fluorophenyl)ethoxy]benzoyl}glycine

The same reaction as in Example 1 (1b) was conducted using N-(4-hydroxybenzoyl)glycine tert-butyl ester (249 mg, 0.991 mmol) prepared in Example 1 (1a) and 2-(4-fluorophenyl)ethanol (150 µL, 1.20 mmol) to give 241 mg of the title compound (yield: 91%).

(73b) 4-[2-(4-Fluorophenyl)ethoxy]-N-[(Z)-1-{[(2-hydroxyethyl)amino]carbonyl}-2-(4-isopropoxyphenyl)vinyl]benzamide The same reaction as in Example 1 (1c) was conducted using N-{4-[2-(4-fluorophenyl)ethoxy]benzoyl}glycine (250 mg) prepared in Example 73 (73a) and 4-isopropoxybenzaldehyde (137 µL) to give the corresponding oxazolone (215 mg). Then, the same reaction as in Example 1 (1d) was conducted using all this oxazolone to give 122 mg of the title compound (white amorphous solid).

MS (FAB) m/z: 507 [M+H]$^+$;

$^1$H-nuclear magnetic resonance spectrum (400 MHz, DMSO-d$_6$) δ ppm:

9.64 (1H, brs), 7.95 (2H, d, J=9 Hz), 7.86 (1H, brt, J=6 Hz), 7.45 (2H, d, J=9 Hz), 7.36 (2H, dd, J=9 Hz, 6 Hz), 7.16 (1H, s), 7.12 (2H, t, J=9 Hz), 7.03 (2H, d, J=9 Hz), 6.84 (2H, d, J=9 Hz), 4.63-4.57 (2H, m), 4.26 (2H, t, J=7 Hz), 3.42 (2H, q, J=6 Hz), 3.21 (2H, q, J=6 Hz), 3.05 (2H, t, J=7 Hz), 1.22 (6H, d, J=6 Hz).

Example 74

4-[2-(4-Fluorophenyl)ethoxy]-N-{(Z)-1-{[(2-hydroxyethyl)amino]carbonyl}-2-[4-(trifluoromethoxy)phenyl]vinyl}benzamide (Exemplary Compound No. 1-217)

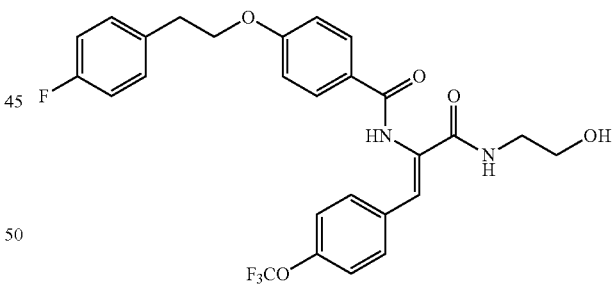

The same reaction as in Example 1 (1c) was conducted using N-{4-[2-(4-fluorophenyl)ethoxy]benzoyl}glycine (317 mg) prepared in Example 73 (73a) and 4-(trifluoromethoxy)benzaldehyde (200 mg) to give the corresponding oxazolone (360 mg). Then, the same reaction as in Example 1 (1d) was conducted using 109 mg of this oxazolone to give 92 mg of the title compound (colorless amorphous solid).

MS (FAB) m/z: 533 [M+H]$^+$;

$^1$H-nuclear magnetic resonance spectrum (500 MHz, DMSO-d$_6$) δ ppm:

9.79 (1H, brs), 8.07 (1H, t, J=5 Hz), 7.95 (2H, d, J=8 Hz), 7.64 (2H, d, J=9 Hz), 7.38 (2H, dd, J=8 Hz, 6 Hz), 7.34 (2H, d, J=8 Hz), 7.16 (1H, s), 7.14 (2H, t, J=9 Hz), 7.05 (2H, d, J=9

Hz), 4.64 (1H, t, J=5 Hz), 4.27 (2H, t, J=7 Hz), 3.45 (2H, q, J=6 Hz), 3.24 (2H, q, J=6 Hz), 3.06 (2H, t, J=7 Hz).

Example 75

N-((Z)-2-(4-Cyclopropylphenyl)-1-{[(2-hydroxyethyl)amino]carbonyl}vinyl)-4-[2-(4-fluorophenyl)ethoxy]benzamide (Exemplary Compound No. 1-223)

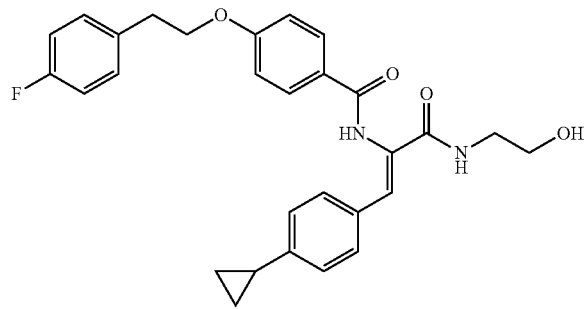 [SMILES: O=C(NCCO)/C(=C/c1ccc(C2CC2)cc1)NC(=O)c1ccc(OCCc2ccc(F)cc2)cc1]

The same reaction as in Example 1 (1c) was conducted using N-{4-[2-(4-fluorophenyl)ethoxy]benzoyl}glycine (254 mg) prepared in Example 73 (73a) and 4-cyclopropylbenzaldehyde (130 mg) prepared in Example 5 to give the corresponding oxazolone (226 mg). Then, the same reaction as in Example 1 (1d) was conducted using all this oxazolone to give 166 mg of the title compound (white amorphous solid).

MS (FAB) m/z: 489 [M+H]⁺;
¹H-nuclear magnetic resonance spectrum (400 MHz, DMSO-d₆) δ ppm:
9.67 (1H, s), 7.95-7.91 (3H, m), 7.40-7.34 (4H, m), 7.15 (1H, s), 7.13 (2H, t, J=9 Hz), 7.03 (2H, d, J=9 Hz), 6.99 (2H, d, J=9 Hz), 4.61 (1H, t, J=5 Hz), 4.26 (2H, t, J=7 Hz), 3.42 (2H, q, J=6 Hz), 3.21 (2H, q, J=6 Hz), 3.05 (2H, t, J=7 Hz), 1.90-1.83 (1H, m), 0.95-0.90 (2H, m), 0.67-0.63 (2H, m).

Example 76

N-((Z)-2-[4-(Cyclopropyloxy)phenyl]-1-{[(2-hydroxyethyl)amino]carbonyl}vinyl)-4-[2-(4-fluorophenyl)ethoxy]benzamide (Exemplary Compound No. 1-215)

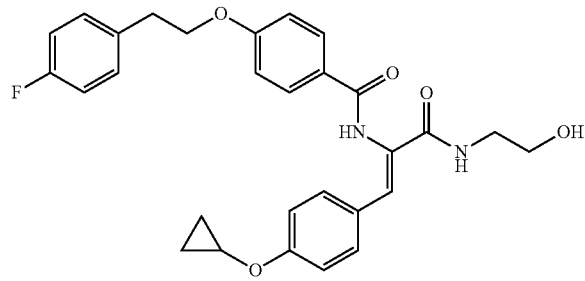 [SMILES: O=C(NCCO)/C(=C/c1ccc(OC2CC2)cc1)NC(=O)c1ccc(OCCc2ccc(F)cc2)cc1]

The same reaction as in Example 1 (1c) was conducted using N-{4-[2-(4-fluorophenyl)ethoxy]benzoyl}glycine (203 mg) prepared in Example 73 (73a) and 4-(cyclopropyloxy)benzaldehyde (116 mg) prepared in Example 6 (6c) to give the corresponding oxazolone (179 mg). Then, the same reaction as in Example 1 (1d) was conducted using all this oxazolone to give 132 mg of the title compound (white amorphous solid).

MS (FAB) ink: 505 [M+H]⁺;
¹H-nuclear magnetic resonance spectrum (400 MHz, DMSO-d₆) δ ppm:
9.65 (1H, s), 7.95 (2H, d, J=9 Hz), 7.89 (1H, brt, J=6 Hz), 7.47 (2H, d, J=9 Hz), 7.36 (2H, dd, J=9 Hz, 6 Hz), 7.17 (1H, s), 7.12 (2H, t, J=9 Hz), 7.03 (2H, d, J=9 Hz), 6.98 (2H, d, J=9 Hz), 4.62 (1H, t, J=5 Hz), 4.26 (2H, t, J=7 Hz), 3.81 (1H, sept, J=3 Hz), 3.42 (2H, q, J=6 Hz), 3.21 (2H, q, J=6 Hz), 3.05 (2H, t, J=7 Hz), 0.78-0.73 (2H, m), 0.63-0.59 (2H, m).

Example 77

N-((Z)-2-(4-Chlorophenyl)-1-{[(2-hydroxyethyl)amino]carbonyl}vinyl)-4-[2-(4-fluorophenyl)ethoxy]benzamide (Exemplary Compound No. 1-229)

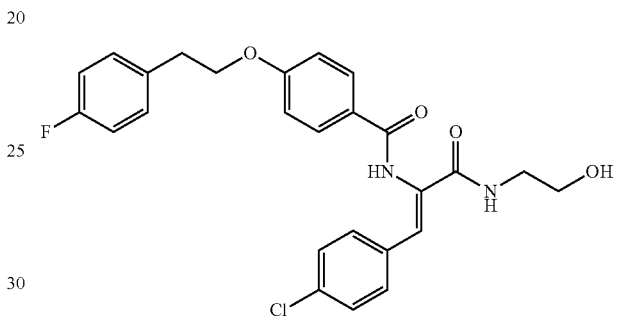

The same reaction as in Example 1 (1c) was conducted using N-{4-[2-(4-fluorophenyl)ethoxy]benzoyl}glycine (317 mg) prepared in Example 73 (73a) and 4-chlorobenzaldehyde (148 mg) to give the corresponding oxazolone (342 mg). Then, the same reaction as in Example 1 (1d) was conducted using 110 mg of this oxazolone to give 98 mg of the title compound (white powder).

mp: 60 to 63° C.;
¹H-nuclear magnetic resonance spectrum (500 MHz, DMSO-d₆) δ ppm:
9.76 (1H, brs), 8.06 (1H, t, J=5 Hz), 7.95 (2H, d, J=9 Hz), 7.54 (2H, d, J=8 Hz), 7.40-7.37 (4H, m), 7.15 (1H, s), 7.15 (2H, t, J=9 Hz), 7.05 (2H, d, J=9 Hz), 4.64 (1H, t, J=5 Hz), 4.27 (2H, t, J=7 Hz), 3.45 (2H, q, J=6 Hz), 3.24 (2H, q, J=6 Hz), 3.06 (2H, t, J=7 Hz).

Example 78

4-[2-(4-Chlorophenyl)ethoxy]-N-((Z)-2-[4-(difluoromethoxy)phenyl]-1-{[(2-hydroxyethyl)amino]carbonyl}vinyl)benzamide (Exemplary Compound No. 1-199)

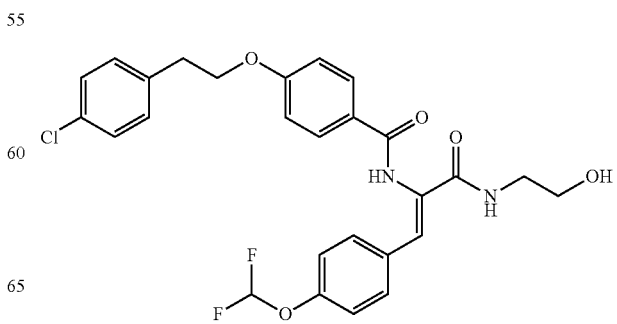

(78a) N-{4-[2-(4-Chlorophenyl)ethoxy]benzoyl}glycine (Tributylphosphoranylidene)acetonitrile (1.31 g, 4.89 mmol) was added to a solution of toluene (12 mL) containing N-(4-hydroxybenzoyl)glycine ethyl ester (which is the compound disclosed in J. Med. Chem., (1999), 42, 1041-1052, 663 mg, 2.97 mmol) and 2-(4-chlorophenyl)ethanol (447 µL, 3.30 mmol). The mixture was stirred at 100° C. for 4 hours, and then ethyl acetate was added thereto. The resulting mixture was washed with water and saturated brine and dried over anhydrous magnesium sulfate. The solvent was evaporated, and the resulting residue was purified by silica gel column chromatography (hexane to hexane:ethyl acetate, 4:1 to 3:1, and then ethyl acetate, v/v) to give a powder (1.23 g). All this powder was dissolved in ethanol (12 mL), and then a 2 M lithium hydroxide aqueous solution (3.00 mL, 6.00 mmol) was added thereto. The resulting mixture was stirred at 60° C. for 30 minutes, and then 10% hydrochloric acid (2.1 mL) was added thereto under ice-cooling. The produced precipitate was collected by filtration, washed sequentially with water and diisopropyl ether, and then dried under reduced pressure to give 861 mg of the title compound (powder, yield: 87%).

(78b) 4-[2-(4-Chlorophenyl)ethoxy]-N-((Z)-2-[4-(difluoromethoxy)phenyl]-1-{[(2-hydroxyethyl)amino]carbonyl}vinyl)benzamide The same reaction as in Example 1 (1c) was conducted using N-{4-[2-(4-chlorophenyl)ethoxy]benzoyl}glycine (267 mg) prepared in Example 78 (78a) and 4-(difluoromethoxy)benzaldehyde (111 µL) to give the corresponding oxazolone (333 mg). Then, the same reaction as in Example 1 (1d) was conducted using 118 mg of this oxazolone to give 91 mg of the title compound (white powder).

mp: 160 to 162° C.;
$^1$H-nuclear magnetic resonance spectrum (400 MHz, DMSO-$d_6$) δ ppm:
9.71 (1H, brs), 8.00 (1H, brt, J=6 Hz), 7.92 (2H, d, J=9 Hz), 7.56 (2H, d, J=9 Hz), 7.35 (4H, s), 7.23 (1H, t, J=74 Hz), 7.16 (1H, s), 7.11 (2H, d, J=9 Hz), 7.02 (2H, d, J=9 Hz), 4.62 (1H, t, J=5 Hz), 4.26 (2H, t, J=7 Hz), 3.43 (2H, q, J=6 Hz), 3.22 (2H, q, J=6 Hz), 3.05 (2H, t, J=7 Hz).

Example 79

4-[2-(4-Chlorophenyl)ethoxy]-N-{(Z)-1-{[(2-hydroxyethyl)amino]carbonyl}-2-[4-(trifluoromethoxy)phenyl]vinyl}benzamide (Exemplary Compound No. 1-200)

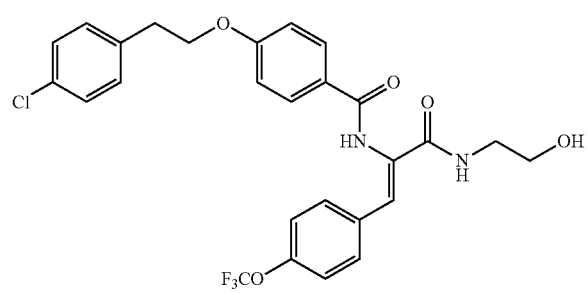 [SMILES: O=C(NCCO)/C(=C/c1ccc(OC(F)(F)F)cc1)NC(=O)c1ccc(OCCc2ccc(Cl)cc2)cc1]

The same reaction as in Example 1 (1c) was conducted using N-{4-[2-(4-chlorophenyl)ethoxy]benzoyl}glycine (234 mg) prepared in Example 78 (78a) and 4-(trifluoromethoxy)benzaldehyde (110 µL) to give the corresponding oxazolone (208 mg). Then, the same reaction as in Example 1 (1d) was conducted using all this oxazolone to give 160 mg of the title compound (white amorphous solid).

MS (FAB) m/z: 549 [M+H]$^+$;
$^1$H-nuclear magnetic resonance spectrum (400 MHz, DMSO-$d_6$) δ ppm:
9.76 (1H, s), 8.04 (1H, brt, J=5 Hz), 7.92 (2H, d, J=9 Hz), 7.61 (2H, d, J=9 Hz), 7.35 (4H, s), 7.31 (2H, d, J=9 Hz), 7.14 (1H, s), 7.02 (2H, d, J=9 Hz), 4.62 (1H, t, J=5 Hz), 4.26 (2H, t, J=7 Hz), 3.43 (2H, q, J=6 Hz), 3.22 (2H, q, J=6 Hz), 3.06 (2H, t, J=7 Hz).

Example 80

4-[2-(4-Chlorophenyl)ethoxy]-N-((Z)-2-(4-cyclopropylphenyl)-1-{[(2-hydroxyethyl)amino]carbonyl}vinyl)benzamide (Exemplary Compound No. 1-206)

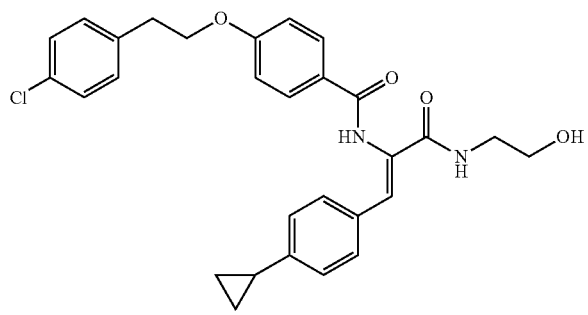

The same reaction as in Example 1 (1c) was conducted using N-{4-[2-(4-chlorophenyl)ethoxy]benzoyl}glycine (238 mg) prepared in Example 78 (78a) and 4-cyclopropylbenzaldehyde (124 mg) prepared in Example 5 to give the corresponding oxazolone (215 mg). Then, the same reaction as in Example 1 (1d) was conducted using all this oxazolone to give 173 mg of the title compound (white amorphous solid).

MS (FAB) m/z: 505 [M+H]$^+$;
$^1$H-nuclear magnetic resonance spectrum (500 MHz, DMSO-$d_6$) δ ppm:
9.69 (1H, s), 7.97-7.93 (3H, m), 7.41 (2H, d, J=8 Hz), 7.38 (4H, s), 7.17 (1H, s), 7.05 (2H, d, J=9 Hz), 7.01 (2H, d, J=8 Hz), 4.63 (1H, t, J=5 Hz), 4.28 (2H, t, J=6 Hz), 3.44 (2H, q, J=6 Hz), 3.23 (2H, q, J=6 Hz), 3.07 (2H, t, J=6 Hz), 1.89-1.84 (1H, m), 0.95-0.91 (2H, m), 0.67-0.64 (2H, m).

Example 81

4-[2-(4-Chlorophenyl)ethoxy]-N-((Z)-2-[4-(cyclopropyloxy)phenyl]-1-{[(2-hydroxyethyl)amino]carbonyl}vinyl)benzamide (Exemplary Compound No. 1-198)

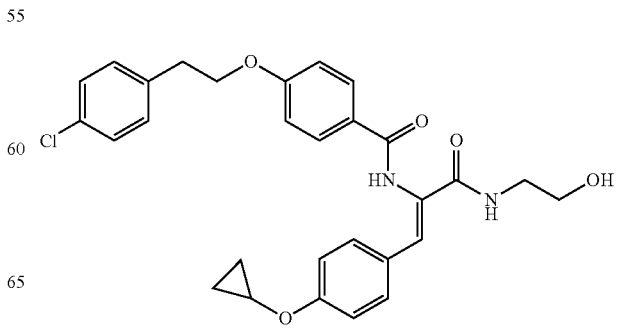

The same reaction as in Example 1 (1c) was conducted using N-{4-[2-(4-chlorophenyl)ethoxy]benzoyl}glycine (267 mg) prepared in Example 78 (78a) and 4-(cyclopropyloxy)benzaldehyde (136 mg) prepared in Example 6 (6c) to give the corresponding oxazolone (341 mg). Then, the same reaction as in Example 1 (1d) was conducted using 115 mg of this oxazolone to give 79 mg of the title compound (light yellow powder).

mp: 66 to 69° C.;
$^1$H-nuclear magnetic resonance spectrum (400 MHz, DMSO-$d_6$) δ ppm:
9.65 (1H, brs), 7.95 (2H, d, J=9 Hz), 7.89 (1H, brt, J=6 Hz), 7.47 (2H, d, J=9 Hz), 7.36 (4H, s), 7.17 (1H, s), 7.03 (2H, d, J=9 Hz), 6.97 (2H, d, J=9 Hz), 4.62 (1H, t, J=6 Hz), 4.26 (2H, t, J=7 Hz), 3.81 (1H, sept, J=3 Hz), 3.42 (2H, q, J=6 Hz), 3.21 (2H, q, J=6 Hz), 3.06 (2H, t, J=7 Hz), 0.78-0.73 (2H, m), 0.63-0.59 (2H, m).

Example 82

4-[2-(4-Chlorophenyl)ethoxy]-N-((Z)-2-(4-chlorophenyl)-1-{[(2-hydroxyethyl)amino]carbonyl}vinyl)benzamide (Exemplary Compound No. 1-212)

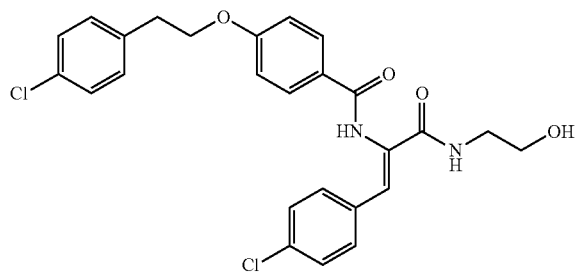

The same reaction as in Example 1 (1c) was conducted using N-{4-[2-(4-chlorophenyl)ethoxy]benzoyl}glycine (267 mg) prepared in Example 78 (78a) and 4-chlorobenzaldehyde (118 mg) to give the corresponding oxazolone (301 mg). Then, the same reaction as in Example 1 (1d) was conducted using 110 mg of this oxazolone to give 50 mg of the title compound (colorless crystalline solid).

mp: 137 to 139° C.;
$^1$H-nuclear magnetic resonance spectrum (400 MHz, DMSO-$d_6$) δ ppm:
9.72 (1H, brs), 8.04 (1H, brt, J=6 Hz), 7.91 (2H, d, J=9 Hz), 7.50 (2H, d, J=9 Hz), 7.37 (2H, d, J=9 Hz), 7.35 (4H, s), 7.11 (1H, s), 7.02 (2H, d, J=9 Hz), 4.63 (1H, t, J=5 Hz), 4.26 (2H, t, J=7 Hz), 3.43 (2H, q, J=6 Hz), 3.21 (2H, q, J=6 Hz), 3.06 (2H, t, J=7 Hz).

Example 83

4-[2-(4-Chlorophenyl)ethoxy]-N-((Z)-2-(4-ethoxyphenyl)-1-{[(2-hydroxyethyl)amino]carbonyl}vinyl)benzamide (Exemplary Compound No. 1-196)

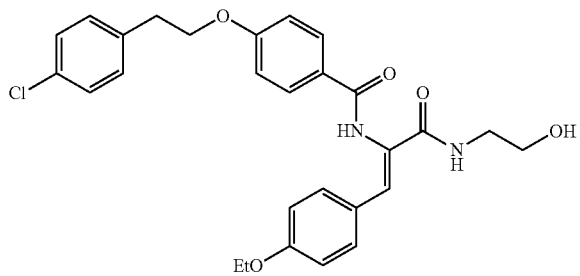 [SMILES: CCOc1ccc(/C=C(\NC(=O)c2ccc(OCCc3ccc(Cl)cc3)cc2)C(=O)NCCO)cc1]

The same reaction as in Example 1 (1c) was conducted using N-{4-[2-(4-chlorophenyl)ethoxy]benzoyl}glycine (236 mg) prepared in Example 78 (78a) and 4-ethoxybenzaldehyde (107 µL) to give the corresponding oxazolone (183 mg). Then, the same reaction as in Example 1 (1d) was conducted using all this oxazolone to give 124 mg of the title compound (white amorphous solid).

MS (FAB) m/z: 509 [M+H]$^+$;
$^1$H-nuclear magnetic resonance spectrum (400 MHz, DMSO-$d_6$) δ ppm:
9.64 (1H, s), 7.94 (2H, d, J=9 Hz), 7.87 (1H, brt, J=6 Hz), 7.45 (2H, d, J=9 Hz), 7.36 (4H, s), 7.16 (1H, s), 7.02 (2H, d, J=9 Hz), 6.85 (2H, d, J=9 Hz), 4.61 (1H, t, J=6 Hz), 4.27 (2H, t, J=7 Hz), 3.99 (2H, q, J=7 Hz), 3.42 (2H, q, J=6 Hz), 3.21 (2H, q, J=6 Hz), 3.06 (2H, t, J=7 Hz), 1.28 (3H, t, J=7 Hz).

Example 84

4-[2-(4-Cyclopropylphenyl)ethoxy]-N-((Z)-2-(4-cyclopropylphenyl)-1-{[(2-hydroxyethyl)amino]carbonyl}vinyl)benzamide (Exemplary Compound No. 1-240)

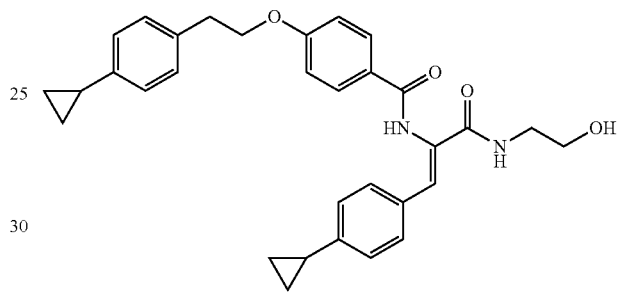

(84a) Methyl 4-[2-(4-bromophenyl)ethoxy]benzoate

Methyl 4-hydroxybenzoate (1.09 g, 7.14 mmol), 2-(4-bromophenyl)ethanol (1.44 g, 7.14 mmol), and triphenylphosphine (2.06 g, 7.86 mmol) were dissolved in THF (44 mL), and then diethyl azodicarboxylate (3.57 mL, 40% toluene solution, 7.86 mmol) was added thereto while stirring under ice-cooling. The mixture was further stirred at room temperature for 2 days, and then the reaction solution was concentrated under reduced pressure. The residue was purified by silica gel column chromatography (hexane:ethyl acetate, 19:1 to 9:1, v/v) to give 1.75 g of the title compound (white powder, yield: 73%).

$^1$H-nuclear magnetic resonance spectrum (400 MHz, CDCl$_3$) δ ppm:
7.95 (2H, d, J=9 Hz), 7.42 (2H, d, J=8 Hz), 7.14 (2H, d, J=9 Hz), 6.87 (2H, d, J=9 Hz), 4.19 (2H, t, J=7 Hz), 3.87 (3H, s), 3.06 (2H, t, J=7 Hz).

(84b) 4-[2-(4-Cyclopropylphenyl)ethoxy]benzoic acid

Cyclopropylization was conducted according to the method disclosed in Tetrahedron Lett., (2002), 43, 6987-6990. Cyclopropyl borate (298 mg, 3.46 mmol) was dissolved in a mixture solution of toluene (10 mL) and water (0.54 mL), and methyl 4-[2-(4-bromophenyl)ethoxy]benzoate (893 mg, 2.66 mmol) prepared in Example 84 (84a), tricyclohexylphosphine (15% toluene solution, 0.58 mL, 0.266 mmol), potassium phosphate (2.16 g, 9.86 mmol), and palladium acetate (45 mg, 0.200 mmol) were added thereto. The mixture was stirred at 100° C. for 2 hours and then cooled to room temperature. After the addition of ethyl acetate, the mixture was washed sequentially with water (twice) and saturated brine and dried over anhydrous sodium sulfate. Then, the solvent was evaporated. The residue was purified by silica gel column chromatography (hexane:ethyl acetate, 9:1, v/v) to give the corresponding cyclopropyl derivative (544 mg, 1.84 mmol).

All the cyclopropyl derivative was dissolved in ethanol (4.59 mL), and a 2 M lithium hydroxide aqueous solution (1.84 mL, 3.67 mmol) was added thereto. The mixture was stirred at 60° C. for 1 hour and then cooled to room temperature, and water and 1 N hydrochloric acid (3.67 mL, 3.67 mmol) were added thereto. The produced precipitate was collected by filtration and dried by heating under reduced pressure to give 448 mg of the title compound (yield: 60%).

$^1$H-nuclear magnetic resonance spectrum (400 MHz, DMSO-$d_6$) δ ppm:
12.68 (1H, brs), 7.86 (2H, d, J=9 Hz), 7.19 (2H, d, J=8 Hz), 7.01 (2H, d, J=7 Hz), 6.99 (2H, d, J=8 Hz), 4.22 (2H, t, J=7 Hz), 2.99 (2H, t, J=7 Hz), 1.88 (1H, quint, J=4 Hz), 0.93-0.89 (2H, m), 0.64-0.60 (2H, m).

(84c) N-{4-[2-(4-Cyclopropylphenyl)ethoxy]benzoyl}glycine

The same reaction as in Example 9 (9b) was conducted using 4-[2-(4-cyclopropylphenyl)ethoxy]benzoic acid (444 mg, 1.57 mmol) prepared in Example 84 (84b) to give 492 mg of the title compound (white powder, yield: 92%).

$^1$H-nuclear magnetic resonance spectrum (400 MHz, DMSO-$d_6$) δ ppm:
12.56 (1H, brs), 8.67 (1H, brt, J=6 Hz), 7.82 (2H, d, J=9 Hz), 7.20 (2H, d, J=8 Hz), 7.01 (2H, d, J=8 Hz), 7.00 (2H, d, J=8 Hz), 4.21 (2H, t, J=7 Hz), 3.88 (2H, d, J=5 Hz), 2.99 (2H, t, J=7 Hz), 1.88 (1H, quint, J=5 Hz), 0.93-0.89 (2H, m), 0.65-0.61 (2H, m).

(84d) 4-[2-(4-Cyclopropylphenyl)ethoxy]-N-((Z)-2-(4-cyclopropylphenyl)-1-{[(2-hydroxyethyl)amino]carbonyl}vinyl)benzamide The same reaction as in Example 9 (9c) was conducted using N-{4-[2-(4-cyclopropylphenyl)ethoxy]benzoyl}glycine (150 mg) prepared in Example 84 (84c) and 4-cyclopropylbenzaldehyde (68 mg) prepared in Example 5 to give the corresponding oxazolone (100 mg). Then, the same reaction as in Example 9 (9d) was conducted using 97 mg of this oxazolone to give 77 mg of the title compound (white amorphous solid).

MS (FAB) m/z: 511 [M+H]$^+$;
$^1$H-nuclear magnetic resonance spectrum (400 MHz, DMSO-$d_6$) δ ppm:
9.66 (1H, brs), 7.94-7.90 (3H, m), 7.39 (2H, d, J=8 Hz), 7.19 (2H, d, J=8 Hz), 7.14 (1H, s), 7.03-6.98 (6H, m), 4.61 (1H, t, J=5 Hz), 4.23 (2H, t, J=7 Hz), 3.42 (2H, q, J=6 Hz), 3.21 (2H, q, J=6 Hz), 3.00 (2H, t, J=7 Hz), 1.91-1.83 (2H, m), 0.95-0.89 (4H, m), 0.67-0.61 (4H, m).

Example 85

N-((Z)-2-(4-Chlorophenyl)-1-{[(2-hydroxyethyeamino]carbonyl}vinyl)-4-[2-(4-cyclopropylphenyl)ethoxy]benzamide (Exemplary Compound No. 1-246)

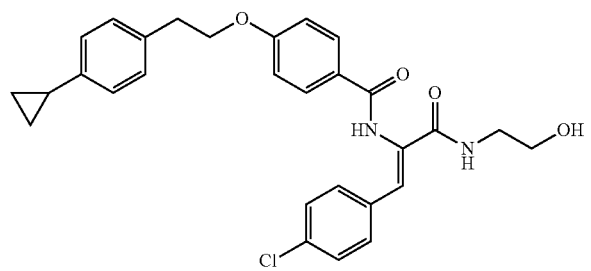 [SMILES: O=C(NCCO)/C(=C/c1ccc(Cl)cc1)NC(=O)c1ccc(OCCc2ccc(C3CC3)cc2)cc1]

The same reaction as in Example 9 (9c) was conducted using N-{4-[2-(4-cyclopropylphenyl)ethoxy]benzoyl}glycine (150 mg) prepared in Example 84 (84c) and 4-chlorobenzaldehyde (65 mg) to give the corresponding oxazolone (112 mg). Then, the same reaction as in Example 9 (9d) was conducted using 109 mg of this oxazolone to give 90 mg of the title compound (white amorphous solid).

MS (FAB) m/z: 506 [M+H]$^+$;
$^1$H-nuclear magnetic resonance spectrum (400 MHz, DMSO-$d_6$) δ ppm:
9.72 (1H, brs), 8.03 (1H, t, J=6 Hz), 7.91 (2H, d, J=9 Hz), 7.50 (2H, d, J=9 Hz), 7.37 (2H, d, J=9 Hz), 7.18 (2H, d, J=8 Hz), 7.12 (1H, s), 7.01 (2H, d, J=9 Hz), 7.00 (2H, d, J=8 Hz), 4.62 (1H, t, J=5 Hz), 4.22 (2H, t, J=7 Hz), 3.43 (2H, q, J=6 Hz), 3.22 (2H, q, J=6 Hz), 3.00 (2H, t, J=7 Hz), 1.91-1.84 (1H, m), 0.94-0.89 (2H, m), 0.65-0.61 (2H, m).

Example 86

4-{2-[3-(Dimethylamino)phenyl]ethoxy}-N-{(Z)-1-{[(2-hydroxyethyeamino]carbonyl}-2-[4-(trifluoromethoxy)phenyl]vinyl}benzamide (Exemplary Compound No. 1-183)

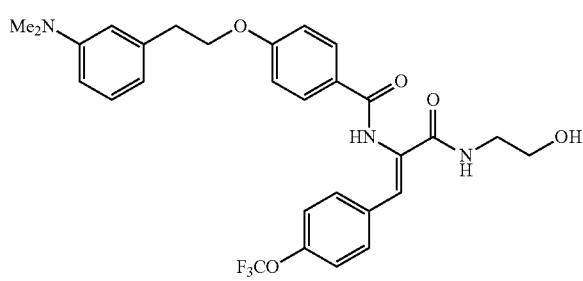 [SMILES: CN(C)c1cccc(CCOc2ccc(C(=O)N/C(=C\c3ccc(OC(F)(F)F)cc3)C(=O)NCCO)cc2)c1]

(86a) N-(4-{2-[3-(Dimethylamino)phenyl]ethoxy}benzoyl)glycine

The same reaction as in Example 78 (78a) was conducted using N-(4-hydroxybenzoyl)glycine ethyl ester (which is the compound disclosed in J. Med. Chem., (1999), 42, 1041-1052, 666 mg, 2.98 mmol) and 2-[3-(dimethylamino)phenyl]ethanol (555 mg, 3.36 mmol) to give 783 mg of the title compound (white powder, yield: 77%).

(86b) 4-{2-[3-(Dimethylamino)phenyl]ethoxy}-N-{(Z)-1-{[(2-hydroxyethyl)amino]carbonyl}-2-[4-(trifluoromethoxy)phenyl]vinyl}benzamide The same reaction as in Example 1 (1c) was conducted using N-(4-{2-[3-(dimethylamino)phenyl]ethoxy}benzoyl)glycine (242 mg) prepared in Example 86 (86a) and 4-(trifluoromethoxy)benzaldehyde (110 μL) to give the corresponding oxazolone (245 mg). The same reaction as in Example 1 (1d) was conducted using all this oxazolone to give 192 mg of the title compound (white amorphous solid).

MS (FAB) m/z: 558 [M+H]$^+$;
$^1$H-nuclear magnetic resonance spectrum (400 MHz, DMSO-$d_6$) δ ppm:
9.76 (1H, s), 8.05 (1H, brt, J=6 Hz), 7.92 (2H, d, J=9 Hz), 7.62 (2H, d, J=9 Hz), 7.31 (2H, d, J=8 Hz), 7.14 (1H, s), 7.09 (1H, t, J=8 Hz), 7.03 (2H, d, J=9 Hz), 6.68 (1H, brs), 6.60 (1H, d, =7 Hz), 6.57 (1H, dd, J=8 Hz, 2 Hz), 4.62 (1H, t, J=5 Hz), 4.25 (2H, t, J=7 Hz), 3.44 (2H, q, J=6 Hz), 3.22 (2H, q, J=6 Hz), 2.98 (2H, t, J=7 Hz), 2.88 (6H, s).

Example 87

N-((Z)-2-(4-Cyclopropylphenyl)-1-{[(2-hydroxyethyl)amino]carbonyl}vinyl)-4-{2-[3-(dimethylamino)phenyl]ethoxy}benzamide (Exemplary Compound No. 1-189)

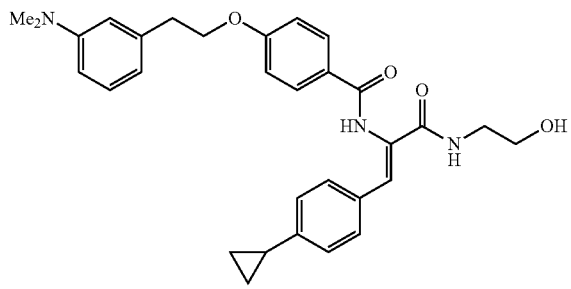 [SMILES: CN(C)c1cccc(CCOc2ccc(C(=O)N/C(=C\c3ccc(C4CC4)cc3)C(=O)NCCO)cc2)c1]

The same reaction as in Example 1 (1c) was conducted using N-(4-{2-[3-(dimethylamino)phenyl]ethoxy}benzoyl)glycine (242 mg) prepared in Example 86 (86a) and 4-cyclopropylbenzaldehyde (126 mg) prepared in Example 5 to give the corresponding oxazolone (222 mg). The same reaction as in Example 1 (1d) was conducted using all this oxazolone to give 145 mg of the title compound (light yellow amorphous solid).

MS (FAB) m/z: 514 [M+H]$^+$;
$^1$H-nuclear magnetic resonance spectrum (500 MHz, DMSO-d$_6$) δ ppm:
9.69 (1H, s), 7.97-7.93 (3H, m), 7.41 (2H, d, J=8 Hz), 7.17 (1H, s), 7.12 (1H, t, J=8 Hz), 7.05 (2H, d, J=9 Hz), 7.02 (2H, d, J=8 Hz), 6.70 (1H, brs), 6.63 (1H, d, J=7 Hz), 6.60 (1H, dd, J=8 Hz, 2 Hz), 4.62 (1H, t, J=5 Hz), 4.27 (2H, t, J=7 Hz), 3.43 (2H, q, J=6 Hz 3.22 (2H, q, J=6 Hz), 3.00 (2H, t, J=7 Hz), 2.89 (6H, s), 1.90-1.84 (1H, m), 0.95-0.91 (2H, m), 0.67-0.64 (2H, m).

Example 88

N-((Z)-2-(4-Chlorophenyl)-1-{[(2-hydroxyethyl)amino]carbonyl}vinyl)-4-{2-[3-(dimethylamino)phenyl]ethoxy}benzamide (Exemplary Compound No. 1-195)

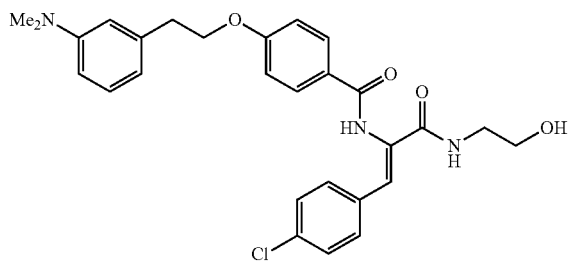 [SMILES: CN(C)c1cccc(CCOc2ccc(C(=O)N/C(=C\c3ccc(Cl)cc3)C(=O)NCCO)cc2)c1]

The same reaction as in Example 1 (1c) was conducted using N-(4-{2-[3-(dimethylamino)phenyl]ethoxy}benzoyl)glycine (241 mg) prepared in Example 86 (86a) and 4-chlorobenzaldehyde (108 mg) to give the corresponding oxazolone (227 mg). Then, the same reaction as in Example 1 (1d) was conducted using all this oxazolone to give 160 mg of the title compound (white amorphous solid).

MS (FAB) m/z: 508 [M+H]$^+$;
$^1$H-nuclear magnetic resonance spectrum (400 MHz, DMSO-d$_6$) δ ppm:
9.72 (1H, s), 8.03 (1H, brt, J=6 Hz), 7.91 (2H, d, J=9 Hz), 7.50 (2H, d, J=9 Hz), 7.37 (2H, d, J=9 Hz), 7.11 (1H, s), 7.09 (1H, t, J=7 Hz), 7.03 (2H, d, J=9 Hz), 6.67 (1H, brs), 6.60 (1H, d, J=7 Hz), 6.57 (1H, dd, J=8 Hz, 2 Hz), 4.62 (1H, t, J=6 Hz), 4.25 (2H, t, J=7 Hz), 3.43 (2H, q, J=6 Hz), 3.22 (2H, q, J=6 Hz), 2.98 (2H, t, J=7 Hz), 2.87 (6H, s).

Example 89

4-(4-Ethylphenoxy)-N-[(Z)-1-{[(2-hydroxyethyl)amino]carbonyl}-2-(4-isopropoxyphenyl)vinyl]benzamide (Exemplary Compound No. 1-335)

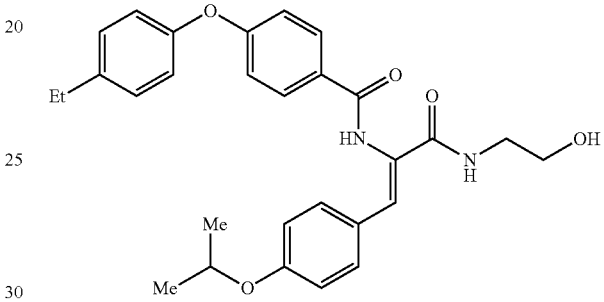

(89a) N-[4-(4-Ethylphenoxy)benzoyl]glycine

An oxidation reaction (which is the method disclosed in Tetrahedron, (1987), 43, 4767-4776) was conducted using 4-(4-ethylphenoxy)benzaldehyde (which is the compound disclosed in J. Med. Chem., (1996), 39, 3984-3997, 500 mg, 2.21 mmol). 2-Methyl-2-butene (940 µL, 8.84 mmol), sodium dihydrogen phosphate dihydrate (338 mg, 2.16 mmol), and sodium chlorite (80%, 875 mg, 7.74 mmol) were added to a mixture solution of tert-butanol (3.6 mL) and water (1.0 mL) containing 4-(4-ethylphenoxy)benzaldehyde. The resulting mixture was stirred at room temperature, and the reaction was terminated with 1 N hydrochloric acid. After the extraction with ethyl acetate, the organic layer was washed with saturated brine and dried over anhydrous sodium sulfate. The solvent was evaporated to give 622 mg of 4-(4-ethylphenoxy)benzoic acid (white powder, yield: quantitative). Then, the same reaction as in Example 9 (9b) was conducted using all this 4-(4-ethylphenoxy)benzoic acid to give 437 mg of the title compound (pale red powder, yield: 66%).

$^1$H-nuclear magnetic resonance spectrum (400 MHz, DMSO-d$_6$) δ ppm:
12.54 (1H, brs), 8.73 (1H, brt, J=6 Hz), 7.85 (2H, d, J=9 Hz), 7.25 (2H, d, J=9 Hz), 7.01 (2H, d, J=9 Hz), 6.97 (2H, d, J=9 Hz), 3.90 (2H, d, J=6 Hz), 2.61 (2H, q, J=7 Hz), 1.19 (3H, t, J=7 Hz).

(89b) (4Z)-2-[4-(4-Ethylphenoxy)phenyl]-4-(4-isopropoxybenzylidene)-1,3-oxazol-5(4H)-one A mixture of N-[4-(4-ethylphenoxy)benzoyl]glycine (200 mg, 0.668 mmol) prepared in Example 89 (89a) and acetic anhydride (0.38 mL, 4.03 mmol) was stirred at 80° C. for 20 minutes. Ethyl acetate was added to the reaction mixture, and then the mixture was cooled to room temperature. The solvent was evaporated, and then the residue was purified by silica gel column chromatography (hexane:ethyl acetate, 3:1, v/v) to give 2-[4-(4-ethylphenoxy)phenyl]-1,3-oxazol-5(4H)-one (120 mg, 0.427 mmol). All of this 2-[4-(4-ethylphenoxy)phenyl]-1,3-oxazol-5(4H)-one was dissolved in benzene (0.9 mL), and then 4-isopropoxybenzaldehyde (71 mg, 0.432 mmol) and triethylamine (24 μL, 0.172 mmol) were added thereto. The mixture was stirred at 90° C. for 2 hours. After the addition of water to the reaction solution, the mixture was extracted with a solvent mixture of hexane and ethyl acetate. The organic layers were combined, washed with saturated brine, dried over anhydrous sodium sulfate, and then concentrated to give 181 mg of the title compound (brown oil, yield: 99%).

$^1$H-nuclear magnetic resonance spectrum (400 MHz, CDCl$_3$) δ ppm:

8.13 (2H, d, J=9 Hz), 8.08 (2H, d, J=9 Hz), 7.22 (2H, d, J=9 Hz), 7.15 (1H, s), 7.03 (2H, d, J=9 Hz), 7.00 (2H, d, J=9 Hz), 6.94 (2H, d, J=9 Hz), 4.69-4.62 (1H, m), 2.67 (2H, q, J=7 Hz), 1.38 (6H, d, J=6 Hz), 1.27 (3H, t, J=7 Hz).

(89c) 4-(4-Ethylphenoxy)-N-[(Z)-1-{[(2-hydroxyethyl)amino]carbonyl}-2-(4-isopropoxyphenyl)vinyl]benzamide The same reaction as in Example 9 (9d) was conducted using (4Z)-2-[4-(4-ethylphenoxy)phenyl]-4-(4-isopropoxybenzylidene)-1,3-oxazol-5(4H)-one (181 mg, 0.422 mmol) prepared in Example 89 (89b) to give 115 mg of the title compound (light yellow amorphous solid, yield: 56%).

MS (FAB) m/z: 489 [M+H]$^+$;

$^1$H-nuclear magnetic resonance spectrum (400 MHz, DMSO-d$_6$) δ ppm:

9.73 (1H, brs), 8.00 (2H, d, J=9 Hz), 7.89 (1H, t, J=5 Hz), 7.46 (2H, d, J=9 Hz), 7.27 (2H, d, J=8 Hz), 7.18 (1H, s), 7.02 (2H, d, J=9 Hz), 7.01 (2H, d, J=8 Hz), 6.86 (2H, d, J=9 Hz), 4.64-4.58 (2H, m), 3.43 (2H, q, J=6 Hz), 3.22 (2H, q, J=6 Hz), 2.62 (2H, q, J=7 Hz), 1.23 (6H, d, J=6 Hz), 1.20 (3H, t, J=8 Hz).

Example 90

N-[(Z)-1-{[(2-Hydroxyethyl)amino]carbonyl}-2-(4-isopropoxyphenyl)vinyl]-4-(4-phenylbutoxy)benzamide (Exemplary Compound No. 1-307)

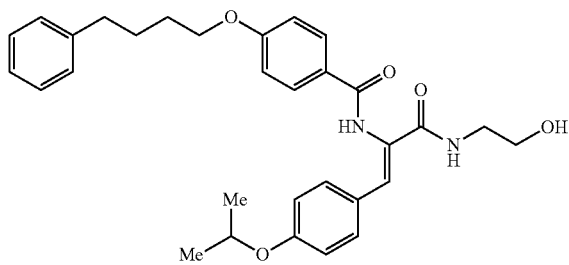 [SMILES: CC(C)Oc1ccc(/C=C(\NC(=O)c2ccc(OCCCCc3ccccc3)cc2)C(=O)NCCO)cc1]

(90a) N-[4-(4-Phenylbutoxy)benzoyl]glycine

The same reaction as in Example 1 (1b) was conducted using N-(4-hydroxybenzoyl)glycine tert-butyl ester (249 mg, 0.991 mmol) prepared in Example 1 (1a) and 4-phenylbutan-1-ol (200 μL, 1.30 mmol) to give 203 mg of the title compound (white powder, yield: 63%).

(90b) N-[(Z)-1-{[(2-Hydroxyethyl)amino]carbonyl}-2-(4-isopropoxyphenyl)vinyl]-4-(4-phenylbutoxy)benzamide The same reaction as in Example 1 (1c) was conducted using N-[4-(4-phenylbutoxy)benzoyl]glycine (203 mg) prepared in Example 90 (90a) and 4-isopropoxybenzaldehyde (108 μL) to give the corresponding oxazolone (167 mg). Then, the same reaction as in Example 1 (1d) was conducted using all this oxazolone to give 110 mg of the title compound (white amorphous solid).

MS (FAB) m/z: 517 [M+H]$^+$;

$^1$H-nuclear magnetic resonance spectrum (400 MHz, DMSO-d$_6$) δ ppm:

9.63 (1H, s), 7.94 (2H, d, J=9 Hz), 7.86 (1H, brt, J=6 Hz), 7.45 (2H, d, J=9 Hz), 7.29-7.25 (2H, m), 7.21-7.14 (4H, m), 7.01 (2H, d, J=9 Hz), 6.84 (2H, d, J=9 Hz), 4.63-4.57 (2H, m), 4.07 (2H, t, J=5 Hz), 3.42 (2H, q, J=6 Hz), 3.21 (2H, q, J=6 Hz), 2.65 (2H, t, J=7 Hz), 1.77-1.71 (4H, m), 1.22 (6H, d, J=6 Hz).

Example 91

N-[(Z)-1-{[(2-Hydroxyethyl)amino]carbonyl}-2-(4-isopropoxyphenyl)vinyl]-4-(3-phenylpropoxy)benzamide (Exemplary Compound No. 1-301)

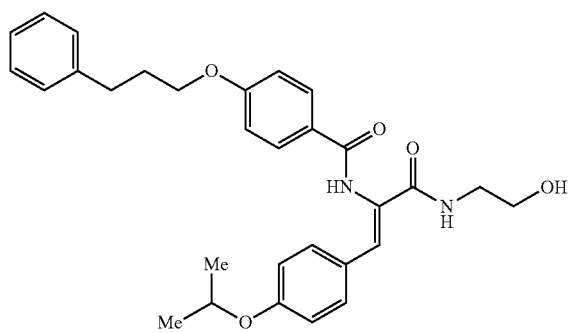 [SMILES: CC(C)Oc1ccc(/C=C(\NC(=O)c2ccc(OCCCc3ccccc3)cc2)C(=O)NCCO)cc1]

(91a) N-(4-Hydroxybenzoyl)glycine methyl ester

Oxazolyl chloride (4.0 mL, 45.9 mmol) and several drops of DMF were added to a solution of dichloromethane (5 mL) containing 4-benzyloxybenzoic acid (2.29 g, 10.0 mmol) under ice-cooling, and then dichloromethane (2.5 mL) was further added thereto. The mixture was stirred at room temperature for 2.5 hours, and the solvent was evaporated. The resulting residue was dissolved in dichloromethane (20 mL), and glycine methyl ester hydrochloride (1.39 g, 11.1 mmol) and N-ethyl-N,N-diisopropylamine (4.4 mL, 25.2 mmol) were added thereto under ice-cooling. The mixture was stirred at room temperature for 18 hours, and then water was added thereto to terminate the reaction. The mixture was extracted with dichloromethane, and the organic layers were combined and concentrated. The resulting residue was purified by silica gel column chromatography (hexane:ethyl acetate, 3:4 to 0:1, v/v) to give N-[4-(benzyloxy)benzoyl]glycine methyl ester. Then, 1.66 g of this ester was dissolved in a solvent mixture of methanol (8 mL) and THF (8 mL). To the resulting mixture, 20% palladium hydroxide-carbon (168 mg) was added. The mixture was vigorously stirred at room temperature under a hydrogen atmosphere for 4 hours. The reaction mixture was filtered through Celite and then concentrated to give 1.19 g of the title compound (white powder, yield: 85%).

$^1$H-nuclear magnetic resonance spectrum (400 MHz, DMSO-$d_6$) δ ppm:

10.0 (1H, s), 8.65 (1H, brt, J=6 Hz), 7.71 (2H, d, J=9 Hz), 6.79 (2H, d, J=9 Hz), 3.95 (2H, d, J=6 Hz), 3.63 (3H, s).

(91b) N-[4-(3-Phenylpropoxy)benzoyl]glycine

N-(4-Hydroxybenzoyl)glycine methyl ester (0.34 g, 1.63 mmol) prepared in Example 91 (91a), 3-phenylpropan-1-ol (0.23 mL, 1.70 mmol), and triphenylphosphine (457 mg, 1.74 mmol) were dissolved in THF (6.5 mL), and diethyl azodicarboxylate (0.88 mL, 40% toluene solution, 1.76 mmol) was added thereto while stirring under ice-cooling. The resulting mixture was stirred at room temperature for 3.5 hours, and then the reaction solution was diluted with ethyl acetate, washed with water and saturated brine, and dried over anhydrous magnesium sulfate. The solvent was evaporated, and the resulting residue was purified by silica gel column chromatography (hexane to hexane:ethyl acetate, 5:1, 3:1, 2:1, and 1:1, v/v) to give 490 mg of an oily substance.

All this oily substance was dissolved in ethanol (7.5 mL), and a 2 N sodium hydroxide aqueous solution (3.80 mL, 7.60 mmol) was added thereto. The mixture was stirred at 90° C. for 2 hours and then cooled with ice. This mixture was made acidic with concentrated hydrochloric acid and then concentrated. After the evaporation of ethanol, the resulting precipitate was collected by filtration, washed with water, and dried by heating under reduced pressure to give 318 mg of the title compound (yield: 63%).

$^1$H-nuclear magnetic resonance spectrum (400 MHz, DMSO-$d_6$) δ ppm:

12.6 (1H, brs), 8.67 (1H, brt, J=6 Hz), 7.83 (2H, d, J=9 Hz), 7.30-7.17 (5H, m), 7.01 (2H, d, J=9 Hz), 4.03 (2H, t, J=7 Hz), 3.90 (2H, d, J=6 Hz), 2.75 (2H, t, J=7 Hz), 2.06-2.01 (2H, m).

(91c) N-[(Z)-1-[(2-Hydroxyethyl)amino]carbonyl-2-(4-isopropoxyphenyl)vinyl]-4-(3-phenylpropoxy)benzamide The same reaction as in Example 1 (1c) was conducted using N-[4-(3-phenylpropoxy)benzoyl]glycine (227 mg) prepared in Example 91 (91b) and 4-isopropoxybenzaldehyde (125 μL) to give the corresponding oxazolone (244 mg). Then, the same reaction as in Example 1 (1d) was conducted using all this oxazolone to give 130 mg of the title compound (white amorphous solid).

MS (FAB) m/z: 503 [M+H]$^+$;

$^1$H-nuclear magnetic resonance spectrum (400 MHz, DMSO-$d_6$) δ ppm:

9.64 (1H, s), 7.95 (2H, d, J=9 Hz), 7.86 (1H, brt, J=5 Hz), 7.45 (2H, d, J=9 Hz), 7.29-7.17 (5H, m), 7.16 (1H, s), 7.02 (2H, d, J=9 Hz), 6.84 (2H, d, J=9 Hz), 4.63-4.57 (2H, m), 4.04 (2H, t, J=6 Hz), 3.42 (2H, q, J=6 Hz), 3.21 (2H, q, J=6 Hz), 2.75 (2H, t, J=7 Hz), 2.08-2.01 (2H, m), 1.23 (6H, d, J=6 Hz).

Example 92

4-(2,3-Dihydro-1H-inden-2-ylmethoxy)-N-[(Z)-1-{[(2-hydroxyethyl)amino]carbonyl}-2-(4-isopropoxyphenyl)vinyl]benzamide (Exemplary Compound No. 1-341)

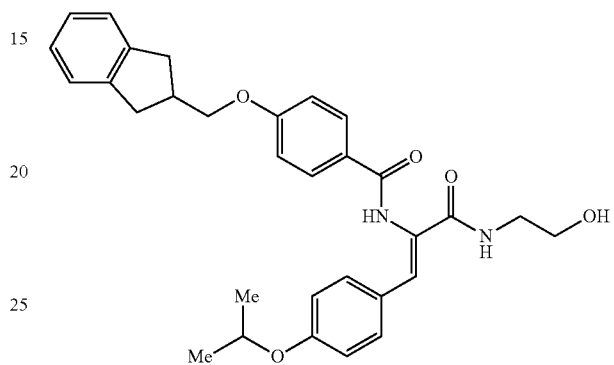

(92a) N-[4-(2,3-Dihydro-1H-inden-2-ylmethoxy)benzoyl]glycine

The same reaction as in Example 1 (1b) was conducted using N-(4-hydroxybenzoyl)glycine tert-butyl ester (250 mg, 0.995 mmol) prepared in Example 1 (1a) and 2,3-dihydro-1H-inden-2-ylmethanol (which is the compound disclosed in J. Med. Chem., (1989), 32, 1326-1334, 165 mg, 1.11 mmol) to give 263 mg of the title compound (colorless crystalline solid, yield: 85%).

(92b) 4-(2,3-Dihydro-1H-inden-2-ylmethoxy)-N-[(Z)-1-{[(2-hydroxyethyl)amino]carbonyl}-2-(4-isopropoxyphenyl)vinyl]benzamide The same reaction as in Example 1 (1c) was conducted using N-[4-(2,3-dihydro-1H-inden-2-ylmethoxy)benzoyl]glycine (258 mg) prepared in Example 92 (92a) and 4-isopropoxybenzaldehyde (138 μL) to give the corresponding oxazolone (279 mg). Then, the same reaction as in Example 1 (1d) was conducted using all this oxazolone to give 130 mg of the title compound (white amorphous solid).

MS (FAB) m/z: 515 [M+H]$^+$;

$^1$H-nuclear magnetic resonance spectrum (400 MHz, DMSO-$d_6$) δ ppm:

9.68 (1H, s), 7.98 (2H, d, J=9 Hz), 7.89 (1H, brt, J=5 Hz), 7.47 (2H, d, J=9 Hz), 7.26-7.24 (2H, m), 7.18 (1H, s), 7.15-7.12 (2H, m), 7.08 (2H, d, J=9 Hz), 6.86 (2H, d, J=9 Hz), 4.64-4.59 (2H, m), 4.08 (2H, d, J=7 Hz), 3.43 (2H, q, J=6 Hz), 3.22 (2H, q, J=6 Hz), 3.11 (2H, dd, J=16 Hz, 8 Hz), 2.94 (1H, sept, J=7 Hz), 2.81 (2H, dd, J=16 Hz, 7 Hz), 1.23 (6H, d, J=6 Hz).

Example 93

4-(2-Cyclopenta-2-en-1-ylethoxy)-N-[(Z)-1-{[(2-hydroxyethyl)amino]carbonyl}-2-(4-isopropoxyphenyl)vinyl]benzamide (Exemplary Compound No. 1-344)

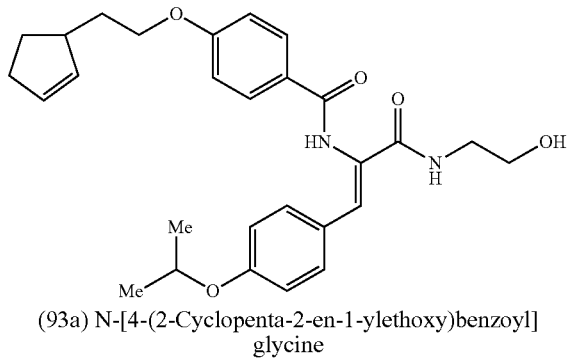

(93a) N-[4-(2-Cyclopenta-2-en-1-ylethoxy)benzoyl]glycine

The same reaction as in Example 1 (1b) was conducted using N-(4-hydroxybenzoyl)glycine tert-butyl ester (157 mg, 0.625 mmol) prepared in Example 1 (1a) and 2-cyclopenta-2-en-1-ylethanol (which is the compound disclosed in J. Org. Chem., (2000), 65, 4241-4250, 85 mg, 0.75 mmol) to give 128 mg of the title compound (white powder, yield: 72%).

(93b) 4-(2-Cyclopenta-2-en-1-ylethoxy)-N-[(Z)-1-{[(2-hydroxyethyl)amino]carbonyl}-2-(4-isopropoxyphenyl)vinyl]benzamide The same reaction as in Example 1 (1c) was conducted using N-[4-(2-cyclopenta-2-en-1-ylethoxy)benzoyl]glycine (128 mg) prepared in Example 93 (93a) and 4-isopropoxybenzaldehyde (76 mg) to give the corresponding oxazolone (90 mg). Then, the same reaction as in Example 1 (1d) was conducted using 75 mg of this oxazolone to give 77 mg of the title compound (white powder).

mp: 67 to 70° C.;
$^1$H-nuclear magnetic resonance spectrum (400 MHz, CDCl$_3$) δ ppm:
7.94 (1H, brs), 7.82 (2H, d, J=9 Hz), 7.32 (2H, d, J=9 Hz), 7.04 (1H, s), 6.91 (2H, d, J=9 Hz), 6.83 (1H, t, J=5 Hz), 6.80 (2H, d, J=9 Hz), 5.80-5.76 (1H, m), 5.74-5.71 (1H, m), 4.52 (1H, sept, J=6 Hz), 4.05 (2H, t, J=6 Hz), 3.73 (2H, t, J=5 Hz), 3.45 (2H, q; J=5 Hz), 3.33 (1H, brs), 2.88 (1H, brt, J=6 Hz), 2.43-2.26 (2H, m), 2.17-2.07 (1H, m), 1.92 (1H, sept, J=7 Hz), 1.80 (1H, sept, J=7 Hz), 1.54-1.45 (1H, m), 1.32 (6H, d, J=6 Hz).

Example 94

N-[(Z)-1-{[(2-Hydroxyethyl)amino]carbonyl}-2-(4-isopropoxyphenyl)vinyl]-4-(2-phenylpropoxy)benzamide (Exemplary Compound No. 1-347)

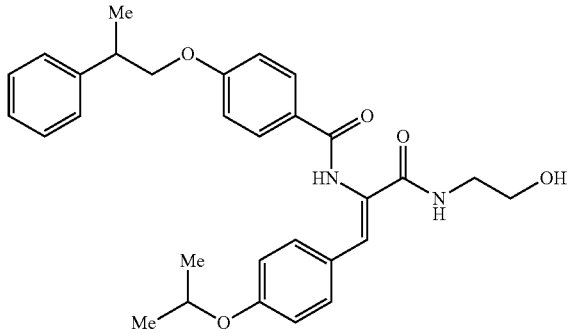 [SMILES: CC(C)Oc1ccc(/C=C(\NC(=O)c2ccc(OCC(C)c3ccccc3)cc2)C(=O)NCCO)cc1]

(94a) N-[4-(2-Phenylpropoxy)benzoyl]glycine

The same reaction as in Example 1 (1b) was conducted using N-(4-hydroxybenzoyl)glycine tert-butyl ester (247 mg, 0.983 mmol) prepared in Example 1 (1a) and 2-phenylpropan-1-ol (185 μL, 1.32 mmol) to give 221 mg of the title compound (white powder, yield: 72%).

(94b) N-[(Z)-1-{[(2-Hydroxyethyl)amino]carbonyl}-2-(4-isopropoxyphenyl)vinyl]-4-(2-phenylpropoxy)benzamide The same reaction as in Example 1 (1c) was conducted using N-[4-(2-phenylpropoxy)benzoyl]glycine (219 mg) prepared in Example 94 (94a) and 4-isopropoxybenzaldehyde (121 μL) to give the corresponding oxazolone (185 mg). Then, the same reaction as in Example 1 (1d) was conducted using all this oxazolone to give 134 mg of the title compound (white amorphous solid).

MS (FAB) m/z: 503 [M+H]$^+$;
$^1$H-nuclear magnetic resonance spectrum (400 MHz, DMSO-d$_6$) δ ppm:
9.63 (1H, s), 7.93 (2H, d, J=9 Hz), 7.85 (1H, brt, J=6 Hz), 7.44 (2H, d, J=9 Hz), 7.35-7.29 (4H, m), 7.23-7.20 (1H, m), 7.15 (1H, s), 7.01 (2H, d, J=9 Hz), 6.83 (2H, d, J=9 Hz), 4.63-4.57 (2H, m), 4.21-4.10 (2H, m), 3.41 (2H, q, J=6 Hz), 3.25-3.18 (3H, m), 1.33 (3H, d, J=7 Hz), 1.22 (6H, d, J=6 Hz).

Example 95

4-(4-Cyclopropylbutoxy)-N-[(Z)-1-{[(2-hydroxyethyl)amino]carbonyl}-2-(4-isopropoxyphenyl)vinyl]benzamide (Exemplary Compound No. 1-350)

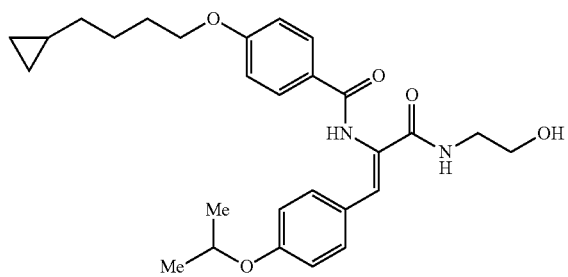 [SMILES: CC(C)Oc1ccc(/C=C(\NC(=O)c2ccc(OCCCCC3CC3)cc2)C(=O)NCCO)cc1]

(95a) N-[4-(4-Cyclopropylbutoxy)benzoyl]glycine

The same reaction as in Example 1 (1b) was conducted using N-(4-hydroxybenzoyl)glycine tert-butyl ester (251 mg, 1.00 mmol) prepared in Example 1 (1a) and 4-cyclopropylbutan-1-ol (which is the compound disclosed in J. Med. Chem., (1998), 41, 1112-1123, 137 mg, 1.20 mmol) to give 257 mg of the title compound (white powder, yield: 88%).

(95b) 4-(4-Cyclopropylbutoxy)-N-[(Z)-1-{[(2-hydroxyethyl)amino]carbonyl}-2-(4-isopropoxyphenyl)vinyl]benzamide The same reaction as in Example 1 (1c) was conducted using N-[4-(4-cyclopropylbutoxy)benzoyl]glycine (146 mg) prepared in Example 95 (95a) and 4-isopropoxybenzaldehyde (86 mg) to give the corresponding oxazolone (94 mg). Then, the same reaction as in Example 1 (1d) was conducted using all this oxazolone to give 55 mg of the title compound (white powder).

mp: 53 to 55° C.;

$^1$H-nuclear magnetic resonance spectrum (500 MHz, CDCl$_3$) δ ppm:

8.14 (1H, brs), 7.81 (2H, d, J=9 Hz), 7.30 (2H, d, J=9 Hz), 6.99 (1H, s), 6.97 (1H, t, J=5 Hz), 6.88 (2H, d, J=9 Hz), 6.77 (2H, d, J=9 Hz), 4.51 (1H, sept, J=6 Hz), 3.98 (2H, t, J=6 Hz), 3.68 (2H, t, J=5 Hz), 3.40 (2H, q, J=5 Hz), 1.88-1.77 (2H, m), 1.62-1.51 (2H, m), 1.31 (6H, d, J=6 Hz), 1.32-1.26 (2H, m), 0.73-0.65 (1H, m), 0.45-0.41 (2H, m), 0.05-0.02 (2H, m).

Example 96

N-[(Z)-1-{[(2-Hydroxyethyl)amino]carbonyl}-2-(4-isopropoxyphenyl)vinyl]-4-[2-(2-naphthyl)ethoxy]benzamide (Exemplary Compound No. 1-353)

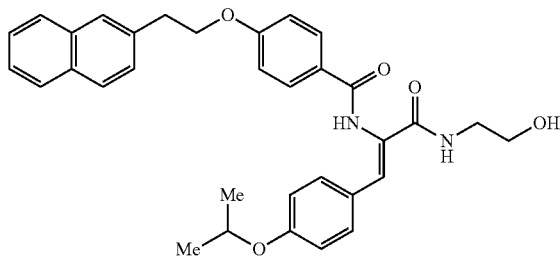 [SMILES: CC(C)Oc1ccc(/C=C(\NC(=O)c2ccc(OCCc3ccc4ccccc4c3)cc2)C(=O)NCCO)cc1]

(96a) N-{4-[2-(2-Naphthyl)ethoxy]benzoyl}glycine

The same reaction as in Example 1 (1b) was conducted using N-(4-hydroxybenzoyl)glycine tert-butyl ester (251 mg, 1.00 mmol) prepared in Example 1 (1a) and 2-(2-naphthyl)ethanol (207 mg, 1.20 mmol) to give 314 mg of the title compound (white powder, yield: 90%).

(96b) N-[(Z)-1-{[(2-Hydroxyethyl)amino]carbonyl}-2-(4-isopropoxyphenyl)vinyl]-4-[2-(2-naphthyl)ethoxy]benzamide The same reaction as in Example 1 (1c) was conducted using N-{4-[2-(2-naphthyl)ethoxy]benzoyl}glycine (140 mg) prepared in Example 96 (96a) and 4-isopropoxybenzaldehyde (69 mg) to give the corresponding oxazolone (108 mg). Then, the same reaction as in Example 1 (1d) was conducted using 81 mg of this oxazolone to give 57 mg of the title compound (white powder).

mp: 78 to 79° C.;

$^1$H-nuclear magnetic resonance spectrum (400 MHz, CDCl$_3$) δ ppm:

8.03 (1H, brs), 7.82-7.75 (5H, m), 7.69 (1H, s), 7.47-7.37 (3H, m), 7.27 (2H, d, J=9 Hz), 6.97 (1H, s), 6.88-6.86 (3H, m), 6.74 (2H, d, J=9 Hz), 4.47 (1H, sept, J=6 Hz), 4.26 (2H, t, J=6 Hz), 3.67 (2H, t, J=5 Hz), 3.39 (2H, q, J=5 Hz), 3.25 (2H, t, J=6 Hz), 1.28 (6H, d, J=6 Hz).

Example 97

N-[(Z)-1-{[(2-Hydroxyethyl)amino]carbonyl}-2-(4-isopropoxyphenyl)vinyl]-4-{2-[3-(trifluoromethyl)phenyl]ethoxy}benzamide (Exemplary Compound No. 1-356)

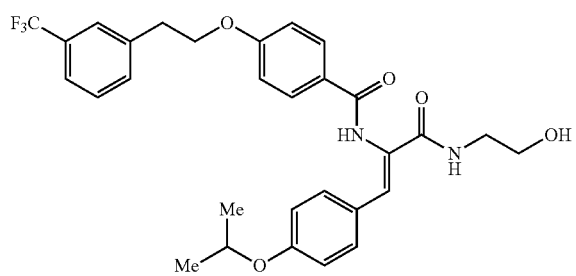 [SMILES: CC(C)Oc1ccc(/C=C(\NC(=O)c2ccc(OCCc3cccc(C(F)(F)F)c3)cc2)C(=O)NCCO)cc1]

(97a) N-(4-{2-[3-(Trifluoromethyl)phenyl]ethoxy}benzoyl)glycine

The same reaction as in Example 1 (1b) was conducted using N-(4-hydroxybenzoyl)glycine tert-butyl ester (502 mg, 2.00 mmol) prepared in Example 1 (1a) and 2-[3-(trifluoromethyl)phenyl]ethanol (330 µL, 2.20 mmol) to give 368 mg of the title compound (white powder, yield: 80%).

(97b) N-[(Z)-1-{[(2-Hydroxyethyl)amino]carbonyl}-2-(4-isopropoxyphenyl)vinyl]-4-{2-[3-(trifluoromethyl)phenyl]ethoxy}benzamide The same reaction as in Example 1 (1c) was conducted using N-(4-{2-[3-(trifluoromethyl)phenyl]ethoxy}benzoyl)glycine (368 mg) prepared in Example 97 (97a) and 4-isopropoxybenzaldehyde (174 µL) to give the corresponding oxazolone (338 mg). The same reaction as in Example 1 (1d) was conducted using all this oxazolone to give 311 mg of the title compound (white amorphous solid).

MS (FAB) m/z: 557 [M+H]$^+$;

$^1$H-nuclear magnetic resonance spectrum (400 MHz, DMSO-d$_6$) δ ppm:

9.68 (1H, s), 7.98 (2H, d, J=7 Hz), 7.89 (1H, brt, J=5 Hz), 7.74 (1H, s), 7.68 (1H, d, J=7 Hz), 7.62-7.55 (2H, m), 7.47 (2H, d, J=9 Hz), 7.18 (1H, s), 7.06 (2H, d, J=8 Hz), 6.86 (2H, d, J=8 Hz), 4.64-4.58 (2H, m), 4.34 (2H, d, J=6 Hz), 3.43 (2H, q, J=6 Hz), 3.24-3.17 (4H, m), 1.23 (6H, d, J=6 Hz).

Example 98

4-[2-(2-Fluorophenyl)ethoxy]-N-[(Z)-1-{[(2-hydroxyethyl)amino]carbonyl}-2-(4-isopropoxyphenyl)vinyl]benzamide (Exemplary Compound No. 1-359)

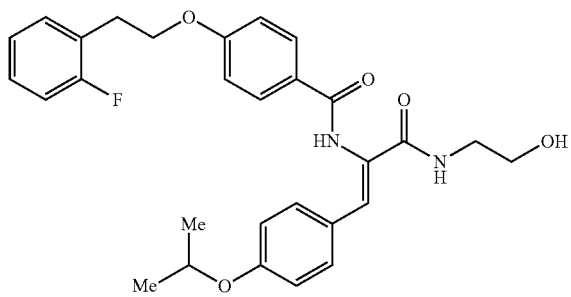 [SMILES: CC(C)Oc1ccc(/C=C(\NC(=O)c2ccc(OCCc3ccccc3F)cc2)C(=O)NCCO)cc1]

(98a) N-{4-[2-(2-Fluorophenyl)ethoxy]benzoyl}glycine

The same reaction as in Example 1 (1b) was conducted using N-(4-hydroxybenzoyl)glycine tert-butyl ester (231 mg, 0.919 mmol) prepared in Example 1 (1a) and 2-(2-fluorophenyl)ethanol (137 μL, 1.02 mmol) to give 214 mg of the title compound (white powder, yield: 73%).

(98b) 4-[2-(2-Fluorophenyl)ethoxy]-N-[(Z)-1-{[(2-hydroxyethyl)amino]carbonyl}-2-(4-isopropoxyphenyl)vinyl]benzamide The same reaction as in Example 1 (1c) was conducted using N-{4-[2-(2-fluorophenyl)ethoxy]benzoyl}glycine (214 mg) prepared in Example 98 (98a) and 4-isopropoxybenzaldehyde (118 μL) to give the corresponding oxazolone (232 mg). The same reaction as in Example 1 (1d) was conducted using all this oxazolone to give 168 mg of the title compound (white amorphous solid).

MS (FAB) m/z: 507 [M+H]$^+$;

$^1$H-nuclear magnetic resonance spectrum (400 MHz, DMSO-$d_6$) δ ppm:

9.68 (1H, s), 7.98 (2H, d, J=8 Hz), 7.90 (1H, brt, J=5 Hz), 7.48-7.42 (3H, m), 7.34-7.29 (1H, m), 7.22-7.16 (3H, m), 7.05 (2H, d, J=8 Hz), 6.86 (2H, d, J=8 Hz), 4.64-4.59 (2H, m), 4.29 (2H, t, J=7 Hz), 3.43 (2H, q, J=6 Hz), 3.22 (2H, q, J=6 Hz), 3.11 (2H, t, J=7 Hz), 1.23 (6H, d, J=6 Hz).

Example 99

4-[2-(4-Cyanophenyl)ethoxy]-N-[(Z)-1-{[(2-hydroxyethyl)amino]carbonyl}-2-(4-isopropoxyphenyl)vinyl]benzamide (Exemplary Compound No. 1-362)

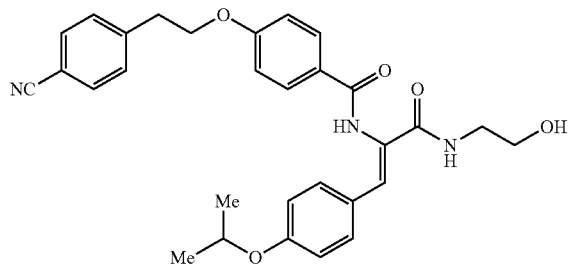 [SMILES: CC(C)Oc1ccc(/C=C(\NC(=O)c2ccc(OCCc3ccc(C#N)cc3)cc2)C(=O)NCCO)cc1]

(99a) N-{4-[2-(4-Cyanophenyl)ethoxy]benzoyl}glycine

The same reaction as in Example 1 (1b) was conducted using N-(4-hydroxybenzoyl)glycine tert-butyl ester (582 mg, 3.83 mmol) prepared in Example 1 (1a) and 4-(2-hydroxyethyl)benzonitrile (592 mg, 4.02 mmol) to give 226 mg of the title compound (white powder, yield: 46%).

$^1$H-nuclear magnetic resonance spectrum (400 MHz, DMSO-$d_6$) δ ppm:

12.5 (1H, s), 8.65 (1H, t, J=9 Hz), 7.80 (2H, d, J=9 Hz), 7.77 (2H, d, J=9 Hz), 7.53 (2H, d, J=9 Hz), 6.98 (2H, d, J=9 Hz), 4.29 (2H, t, J=7 Hz), 3.87 (2H, d, J=6 Hz), 3.15 (2H, t, J=7 Hz).

(99b) 4-[2-(4-Cyanophenyl)ethoxy]-N-[(Z)-1-{[(2-hydroxyethyl)amino]carbonyl}-2-(4-isopropoxyphenyl)vinyl]benzamide The same reaction as in Example 1 (1c) was conducted using N-{4-[2-(4-cyanophenyl)ethoxy]benzoyl}glycine (226 mg) prepared in Example 99 (99a) and 4-isopropoxybenzaldehyde (121 μL) to give the corresponding oxazolone (217 mg). Then, the same reaction as in Example 1 (1d) was conducted using all this oxazolone to give 128 mg of the title compound (white amorphous solid).

MS (FAB) m/z: 514 [M+H]$^+$;

$^1$H-nuclear magnetic resonance spectrum (400 MHz, DMSO-$d_6$) δ ppm:

9.65 (1H, s), 7.95 (2H, d, J=9 Hz), 7.87 (1H, brt, J=5 Hz), 7.78 (2H, d, J=8 Hz), 7.55 (2H, d, J=8 Hz), 7.44 (2H, d, J=9 Hz), 7.16 (1H, s), 7.02 (2H, d, J=9 Hz), 6.83 (2H, d, J=9 Hz), 4.63-4.57 (2H, m), 4.32 (2H, t, J=7 Hz), 3.42 (2H, q, J=6 Hz), 3.21 (2H, q, J=6 Hz), 3.16 (2H, t, J=7 Hz), 1.22 (6H, d, J=6 Hz).

Example 100

N-[(Z)-1-{[(2-Hydroxyethyl)amino]carbonyl}-2-(4-isopropoxyphenyl)vinyl]-4-{2-[4-(trifluoromethyl)phenyl]ethoxy}benzamide (Exemplary Compound No. 1-365)

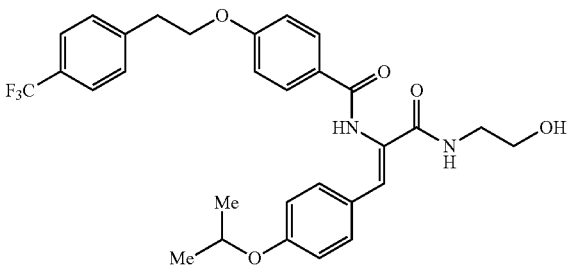 [SMILES: Cc1ccc(CCOc2ccc(C(=O)N/C(=C\c3ccc(OC(C)C)cc3)C(=O)NCCO)cc2)cc1]

(100a) N-(4-{2-[4-(Trifluoromethyl)phenyl]ethoxy}benzoyl)glycine

The same reaction as in Example 1 (1b) was conducted using N-(4-hydroxybenzoyl)glycine tert-butyl ester (251 mg, 1.00 mmol) prepared in Example 1 (1a) and 2-[4-(trifluoromethyl)phenyl]ethanol (209 mg, 1.10 mmol) prepared according to the method disclosed in the document (J. Med. Chem., (2002), 45, 4321-4335) to give 278 mg of the title compound (white powder, yield: quantitative).

(100b) N-[(Z)-1-{[(2-Hydroxyethyl)amino]carbonyl}-2-(4-isopropoxyphenyl)vinyl]-4-{2-[4-(trifluoromethyl)phenyl]ethoxy}benzamide The same reaction as in Example 1 (1c) was conducted using N-(4-{2-[4-(trifluoromethyl)phenyl]ethoxy}benzoyl)glycine (278 mg) prepared in Example 100 (100a) and 4-isopropoxybenzaldehyde (130 mg) to give the corresponding oxazolone (180 mg). Then, the same reaction as in Example 1 (1d) was conducted using all this oxazolone to give 28 mg of the title compound (white amorphous solid).

MS (FAB) m/z: 557 [M+H]$^+$;

$^1$H-nuclear magnetic resonance spectrum (400 MHz, CDCl$_3$) δ ppm:
7.79 (3H, brd, J=9 Hz), 7.57 (2H, d, J=8 Hz), 7.39 (2H, d, J=8 Hz), 7.30 (2H, d, J=9 Hz), 7.03 (1H, s), 6.89 (2H, d, J=9 Hz), 6.78 (2H, d, J=9 Hz), 6.72-6.68 (1H, m), 4.51 (1H, sept, J=6 Hz), 4.23 (2H, t, J=7 Hz), 3.74 (2H, brs), 3.46 (2H, q, J=5 Hz), 3.17 (3H, brt, J=7 Hz), 1.31 (6H, d, J=6 Hz).

Example 101

N-[(Z)-1-{[(2-Hydroxyethyl)amino]carbonyl}-2-(4-isopropoxyphenyl)vinyl]-4-[2-(4-methylphenyl)ethoxy]benzamide (Exemplary Compound No. 1-368)

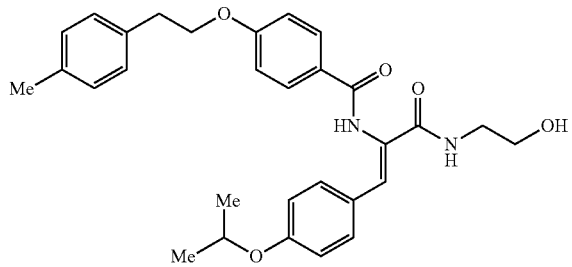

(101a) N-{4-[2-(4-Methylphenyl)ethoxy]benzoyl}glycine

The same reaction as in Example 1 (1b) was conducted using N-(4-hydroxybenzoyl)glycine tert-butyl ester (275 mg, 1.09 mmol) prepared in Example 1 (1a) and 2-(4-methylphenyl)ethanol (159 μL, 1.14 mmol) to give 306 mg of the title compound (colorless crystalline solid, yield: 90%).

(101b) N-[(Z)-1-{[(2-Hydroxyethyl)amino]carbonyl}-2-(4-isopropoxyphenyl)vinyl]-4-[2-(4-methylphenyl)ethoxy]benzamide The same reaction as in Example 1 (1c) was conducted using N-{4-[2-(4-methylphenyl)ethoxy]benzoyl}glycine (306 mg) prepared in Example 101 (101a) and 4-isopropoxybenzaldehyde (176 mg) to give the corresponding oxazolone (335 mg). Then, the same reaction as in Example 1 (1d) was conducted using all this oxazolone to give 300 mg of the title compound (light yellow amorphous solid).

MS (FAB) m/z: 503 [M+H]$^+$;

$^1$H-nuclear magnetic resonance spectrum (400 MHz, DMSO-d$_6$) δ ppm:
9.63 (1H, brs), 7.94 (2H, d, J=9 Hz), 7.86 (1H, brt, J=5 Hz), 7.44 (2H, d, J=9 Hz), 7.20 (2H, d, J=8 Hz), 7.15 (1H, s), 7.11 (2H, d, J=8 Hz), 7.02 (2H, d, J=9 Hz), 6.84 (2H, d, J=9 Hz), 4.63-4.57 (2H, m), 4.24 (2H, t, J=7 Hz), 3.42 (2H, q, J=6 Hz), 3.21 (2H, q, J=6 Hz), 3.01 (2H, t, J=7 Hz), 2.27 (3H, s), 1.22 (6H, d, J=6 Hz).

Example 102

N-{(Z)-1-{[(2-Hydroxyethyl)amino]carbonyl}-2-[4-(trifluoromethoxy)phenyl]vinyl}-4-[2-(4-isopropoxyphenyl)ethoxy]benzamide (Exemplary Compound No. 1-373)

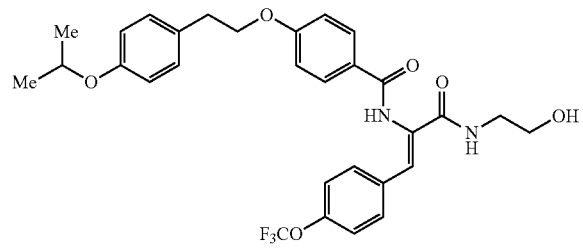 [SMILES: CC(C)Oc1ccc(CCOc2ccc(C(=O)N/C(=C\c3ccc(OC(F)(F)F)cc3)C(=O)NCCO)cc2)cc1]

(102a) N-{4-[2-(4-Isopropoxyphenyl)ethoxy]benzoyl}glycine

The same reaction as in Example 78 (78a) was conducted using N-(4-hydroxybenzoyl)glycine ethyl ester (which is the compound disclosed in J. Med. Chem., (1999), 42, 1041-1052, 397 mg, 2.20 mmol) and 2-(4-isopropoxyphenyl)ethanol (which is the compound disclosed in J. Chem. Soc. Perkin Trans. 1, (1983), 619-624, 447 mg, 2.00 mmol) to give 636 mg of the title compound (white powder, yield: 82%).

(102b) N-{(Z)-1-{[(2-Hydroxyethyl)amino]carbonyl}-2-[4-(trifluoromethoxy)phenyl]vinyl}-4-[2-(4-isopropoxyphenyl)ethoxy]benzamide The same reaction as in Example 1 (1c) was conducted using N-{4-[2-(4-isopropoxyphenyl)ethoxy]benzoyl}glycine (228 mg) prepared in Example 102 (102a) and 4-(trifluoromethoxy)benzaldehyde (96 μL) to give the corresponding oxazolone (207 mg). Then, the same reaction as in Example 1 (1d) was conducted using 204 mg of this oxazolone to give 171 mg of the title compound (white amorphous solid).

MS (FAB) m/z: 573 [M+H]$^+$;

$^1$H-nuclear magnetic resonance spectrum (400 MHz, DMSO-d$_6$) δ ppm:
9.76 (1H, brs), 8.05 (1H, t, J=6 Hz), 7.92 (2H, d, J=9 Hz), 7.62 (2H, d, J=9 Hz), 7.31 (2H, d, J=8 Hz), 7.20 (2H, d, J=9 Hz), 7.14 (1H, s), 7.02 (2H, d, J=9 Hz), 6.83 (2H, d, J=9 Hz), 4.62 (1H, t, J=5 Hz), 4.55 (1H, sept, J=6 Hz), 4.22 (2H, t, J=7

Hz), 3.44 (2H, q, J=6 Hz), 3.22 (2H, q, J=6 Hz), 2.98 (2H, t, J=7 Hz), 1.24 (6H, d, J=6 Hz).

Example 103

N-[(E)-1-{[(2-Hydroxyethyl)amino]carbonyl}-2-(4-isopropoxyphenyl)vinyl]-4-isobutoxybenzamide

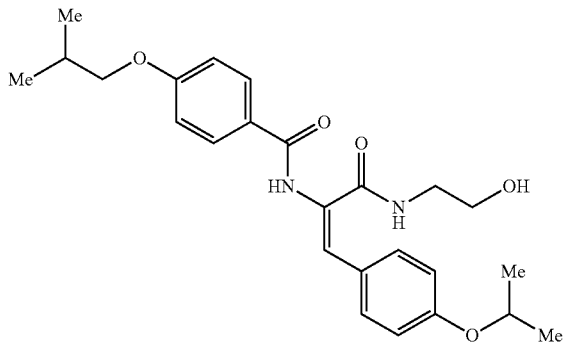 [SMILES: CC(C)COc1ccc(C(=O)N/C(=C/c2ccc(OC(C)C)cc2)C(=O)NCCO)cc1]

(103a) 2-(4-Isobutoxyphenyl)-4-(4-isopropoxybenzylidene)-1,3-oxazol-5(4H)-one

The same reaction as in Example 1 (1c) was conducted using N-(4-isobutoxybenzoyl)glycine (5.00 g) prepared in Example 30 (30a) and 4-isopropoxybenzaldehyde (3.59 g) to give the corresponding oxazolone (4.21 g). Then, 313 mg of this oxazolone was dissolved in a 33% hydrogen bromide-acetic acid solution (5.0 mL) at room temperature. The resulting solution was stirred for 0.5 hours and then poured in ice water. The precipitated crystals were collected by filtration, washed with water, and dried to give 282 mg of the title compound (yellow powder, yield: 84%, a mixture of 4E isomer/4Z isomer=4.6/1).

MS (FAB) m/z: 380 [M+H]+;

4E isomer: $^1$H-nuclear magnetic resonance spectrum (400 MHz, CDCl$_3$) δ ppm:

8.18 (2H, d, J=9 Hz), 7.99 (2H, d, J=9 Hz), 7.45 (1H, s), 6.99 (2H, d, J=9 Hz), 6.95 (2H, d, J=9 Hz), 4.66 (1H, quint, J=6 Hz), 3.80 (2H, d, J=6 Hz), 2.12 (1H, sept, J=6 Hz), 1.38 (6H, d, J=5 Hz), 1.05 (6H, d, J=7 Hz).

(103b) N-[(E)-1-{[(2-Hydroxyethyl)amino]carbonyl}-2-(4-isopropoxyphenyl)vinyl]-4-isobutoxybenzamide 2-Aminoethanol (50 μL, 0.828 mmol) was added to a solution of toluene (2.0 mL) containing 2-(4-isobutoxyphenyl)-4-(4-isopropoxybenzylidene)-1,3-oxazol-5(4H)-one (151 mg, 0.398 mmol, a mixture of 4E isomer/4Z isomer=4.6/1) prepared in Example 103 (103a). The mixture was stirred at 50° C. for 15 minutes, and then water was added to this reaction solution. The resulting mixture was extracted with ethyl acetate. The organic layers were combined, washed with water and saturated brine, and dried over anhydrous magnesium sulfate. The solvent was evaporated, and the resulting residue was purified by thin layer chromatography for separation (ethyl acetate) to give 37 mg of the title compound (white solid, yield: 21%). [In addition, 53 mg of the corresponding Z isomer of the title compound (white solid, yield: 30%) was given.]

MS (FAB) m/z: 441 [M+H]+;

$^1$H-nuclear magnetic resonance spectrum (400 MHz, CDCl$_3$) δ ppm:

8.50 (1H, s), 7.91 (1H, s), 7.82 (2H, d, J=9 Hz), 7.27 (2H, d, J=9 Hz), 6.94 (2H, d, J=9 Hz), 6.88 (2H, d, J=9 Hz), 6.17 (1H, brt, J=6 Hz), 4.56 (1H, sept, J=6 Hz), 3.77 (2H, d, J=7 Hz), 3.61 (2H, t, J=5 Hz), 3.36 (2H, q, J=5 Hz), 2.11 (1H, sept, J=7 Hz), 1.35 (6H, d, J=6 Hz), 1.04 (6H, d, J=7 Hz).

Example 104

4-(Cyclopropylmethoxy)-N-{(Z)-1-{[(2-hydroxyethyl)amino]carbonyl}-2-[4-(trifluoromethoxy)phenyl]vinyl}benzamide (Exemplary Compound No. 1-440)

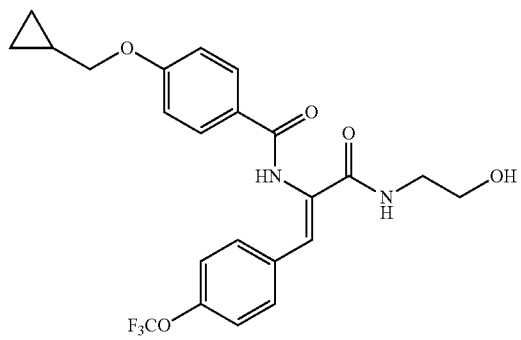 [SMILES: O=C(NCCO)/C(=C/c1ccc(OC(F)(F)F)cc1)NC(=O)c1ccc(OCC2CC2)cc1]

The same reaction as in Example 9 (9c) was conducted using N-[4-(cyclopropylmethoxy)benzoyl]glycine (499 mg) prepared by the same method as in Example 9 (9b) and 4-(trifluoromethoxy)benzaldehyde (300 μL) to give the corresponding oxazolone (668 mg). The same reaction as in Example 9 (9d) was conducted using all this oxazolone to give 698 mg of the title compound (white powder).

mp: 144 to 145° C.;

$^1$H-nuclear magnetic resonance spectrum (400 MHz, DMSO-d$_6$) δ ppm:

9.77 (1H, brs), 8.06 (1H, t, J=6 Hz), 7.93 (2H, d, J=9 Hz), 7.63 (2H, d, J=9 Hz), 7.33 (2H, d, J=9 Hz), 7.16 (1H, s), 7.02 (2H, d, J=9 Hz), 4.63 (1H, t, J=6 Hz), 3.90 (2H, d, J=7 Hz), 3.45 (2H, q, J=6 Hz), 3.23 (2H, q, J=6 Hz), 1.28-1.21 (1H, m), 0.61-0.57 (2H, m), 0.36-0.32 (2H, m).

Example 105

N-{(Z)-1-{[(2-Hydroxyethyl)amino]carbonyl}-2-[4-(trifluoromethoxy)phenyl]vinyl}-4-[(1-methylcyclopropyl)methoxy]benzamide (Exemplary Compound No. 1-443)

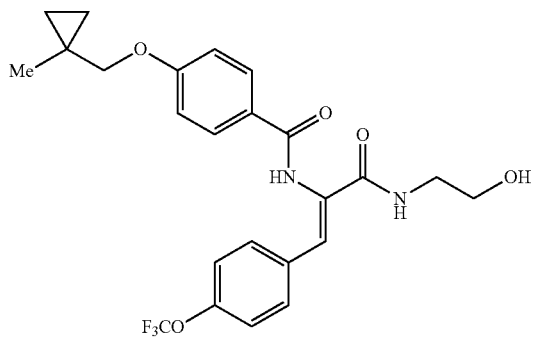 [SMILES: CC1(COc2ccc(C(=O)N/C(=C\c3ccc(OC(F)(F)F)cc3)C(=O)NCCO)cc2)CC1]

The same reaction as in Example 9 (9c) was conducted using N-{4-[(1-methylcyclopropyl)methoxy]benzoyl}glycine (363 mg) prepared by the same method as in Example 9 (9b) and 4-(trifluoromethoxy)benzaldehyde (207 μL) to give the corresponding oxazolone (532 mg). Then, the same reaction as in Example 9 (9d) was conducted using all this oxazolone to give 545 mg of the title compound (white powder)

mp: 170 to 173° C.;
$^1$H-nuclear magnetic resonance spectrum (400 MHz, DMSO-$d_6$) δ ppm:
9.77 (1H, brs), 8.06 (1H, t, J=6 Hz), 7.93 (2H, d, J=9 Hz), 7.63 (2H, d, J=9 Hz), 7.33 (2H, d, J=9 Hz), 7.15 (1H, s), 7.02 (2H, d, J=9 Hz), 4.63 (1H, t, J=6 Hz), 3.84 (2H, s), 3.45 (2H, q, J=6 Hz), 3.23 (2H, q, J=6 Hz), 1.19 (3H, s), 0.55-0.53 (2H, m), 0.42-0.40 (2H, m).

Example 106

N-{(Z)-1-{[(2-Hydroxyethyl)amino]carbonyl}-2-[4-(trifluoromethoxy)phenyl]vinyl}-4-isopropoxybenzamide (Exemplary Compound No. 1-415)

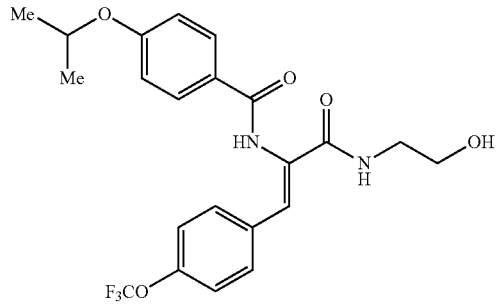 [SMILES: CC(C)Oc1ccc(C(=O)N/C(=C\c2ccc(OC(F)(F)F)cc2)C(=O)NCCO)cc1]

The same reaction as in Example 9 (9c) was conducted using N-(4-isopropoxybenzoyl)glycine (which is the compound disclosed in Tetrahedron Lett., (1995), 36, 6193-6196, 380 mg) and 4-(trifluoromethoxy)benzaldehyde (240 μL) to give the corresponding oxazolone (548 mg). Then, the same reaction as in Example 9 (9d) was conducted using all this oxazolone to give 588 mg of the title compound (white powder).

mp: 142 to 146° C.;
$^1$H-nuclear magnetic resonance spectrum (400 MHz, DMSO-$d_6$) δ ppm:
9.77 (1H, brs), 8.05 (1H, t, J=6 Hz), 7.93 (2H, d, J=9 Hz), 7.64 (2H, d, J=9 Hz), 7.34 (2H, d, J=9 Hz), 7.16 (1H, s), 7.01 (2H, d, J=9 Hz), 4.74 (1H, sept, J=6 Hz), 4.63 (1H, t, J=6 Hz), 3.44 (2H, q, J=6 Hz), 3.23 (2H, q, J=6 Hz), 1.29 (6H, d, J=6 Hz).

Example 107

N-{(Z)-1-{[(2-Hydroxyethyl)amino]carbonyl}-2-[4-(trifluoromethoxy)phenyl]vinyl}-4-(4,4,4-trifluorobutoxy)benzamide (Exemplary Compound No. 1-506)

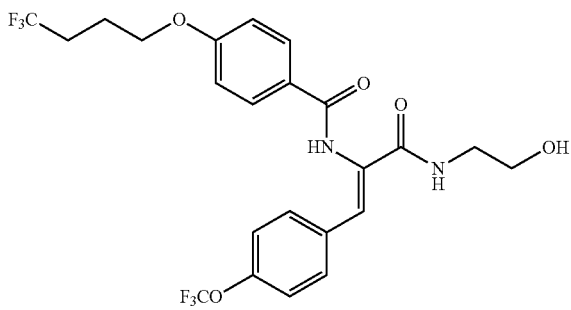 [SMILES: O=C(NCCO)/C(=C/c1ccc(OC(F)(F)F)cc1)NC(=O)c1ccc(OCCCC(F)(F)F)cc1]

The same reaction as in Example 9 (9c) was conducted using N-[4-(4,4,4-trifluorobutoxy)benzoyl]glycine (350 mg) prepared by the same method as in Example 9 (9b) and 4-(trifluoromethoxy)benzaldehyde (172 μL) to give the corresponding oxazolone (337 mg). Then, the same reaction as in Example 9 (9d) was conducted using all this oxazolone to give 297 mg of the title compound (white powder).

mp: 160 to 163° C.;
$^1$H-nuclear magnetic resonance spectrum (400 MHz, DMSO-$d_6$) δ ppm:
9.79 (1H, brs), 8.06 (1H, t, J=6 Hz), 7.95 (2H, d, J=9 Hz), 7.64 (2H, d, J=9 Hz), 7.33 (2H, d, J=9 Hz), 7.19 (1H, s), 7.05 (2H, d, J=9 Hz), 4.63 (1H, t, J=6 Hz), 4.13 (2H, t, J=6 Hz), 3.45 (2H, q, J=6 Hz), 3.23 (2H, q, J=6 Hz), 2.56-2.38 (2H, m), 2.00-1.93 (2H, m).

Example 108

N-{(Z)-1-{[(2-Hydroxyethyl)amino]carbonyl}-2-[4-(trifluoromethoxy)phenyl]vinyl}-4-(3,3,3-trifluoropropoxy)benzamide (Exemplary Compound No. 1-277)

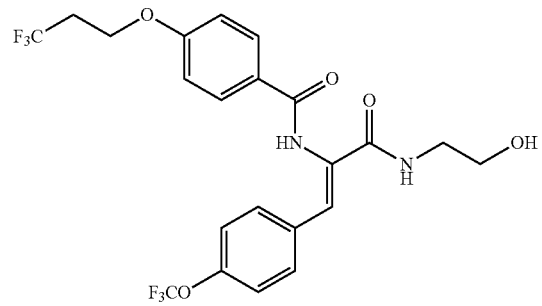 [SMILES: O=C(NCCO)/C(=C/c1ccc(OC(F)(F)F)cc1)NC(=O)c1ccc(OCCC(F)(F)F)cc1]

The same reaction as in Example 9 (9c) was conducted using N-[4-(3,3,3-trifluoropropoxy)benzoyl]glycine (291 mg) prepared by the same method as in Example 9 (9b) and 4-(trifluoromethoxy)benzaldehyde (150 μL) to give the corresponding oxazolone (390 mg). The same reaction as in Example 9 (9d) was conducted using all this oxazolone to give 349 mg of the title compound (white powder).

mp: 159 to 160° C.;
$^1$H-nuclear magnetic resonance spectrum (500 MHz, DMSO-$d_6$) δ ppm:
9.82 (1H, brs), 8.08 (1H, t, J=6 Hz), 7.97 (2H, d, J=9 Hz), 7.64 (2H, d, J=9 Hz), 7.34 (2H, d, J=9 Hz), 7.17 (1H, s), 7.08 (2H, d, J=9 Hz), 4.64 (1H, t, J=6 Hz), 4.30 (2H, t, J=6 Hz), 3.45 (2H, q, J=6 Hz), 3.23 (2H, q, J=6 Hz), 2.87-2.78 (2H, m).

Example 109

N-((Z)-2-[2-Fluoro-4-(trifluoromethyl)phenyl]-1-{[(2-hydroxyethyl)amino]carbonyl}vinyl)-4-(3,3,3-trifluoropropoxy)benzamide

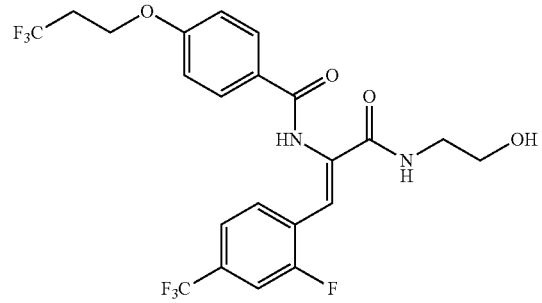 [SMILES: O=C(NCCO)/C(=C/c1ccc(C(F)(F)F)cc1F)NC(=O)c1ccc(OCCC(F)(F)F)cc1]

The same reaction as in Example 9 (9c) was conducted using N-[4-(3,3,3-trifluoropropoxy)benzoyl]glycine (300 mg) prepared by the same method as in Example 9 (9b) and 2-fluoro-4-trifluoromethylbenzaldehyde (150 μL) to give the corresponding oxazolone (265 mg). The same reaction as in Example 9 (9d) was conducted using all this oxazolone to give 286 mg of the title compound (white powder).

mp: 203 to 205° C.;

$^1$H-nuclear magnetic resonance spectrum (400 MHz, DMSO-$d_6$) δ ppm:

9.83 (1H, s), 8.26 (1H, t, J=5 Hz), 7.90 (2H, d, J=9 Hz), 7.71 (2H, d, J=9 Hz), 7.54 (1H, d, J=8 Hz), 7.07 (2H, d, J=9 Hz), 7.06 (1H, s), 4.65 (1H, t, J=5 Hz), 4.29 (2H, t, J=6 Hz), 3.46 (2H, q, J=6 Hz), 3.25 (2H, q, J=6 Hz), 2.88-2.77 (2H, m).

Example 110

N-((Z)-2-[3-Fluoro-4-(trifluoromethyl)phenyl]-1-{[(2-hydroxyethyl)amino]carbonyl}vinyl)-4-(3,3,3-trifluoropropoxy)benzamide

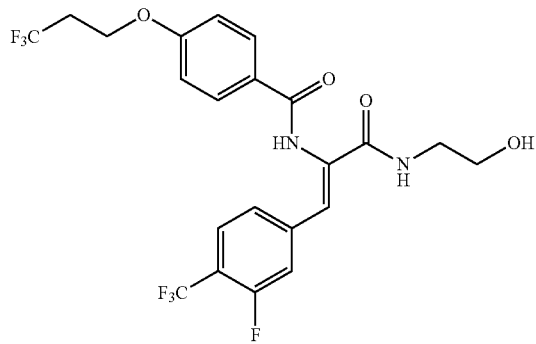 [SMILES: O=C(NCCO)/C(=C/c1ccc(C(F)(F)F)c(F)c1)NC(=O)c1ccc(OCCC(F)(F)F)cc1]

The same reaction as in Example 9 (9c) was conducted using N-[4-(3,3,3-trifluoropropoxy)benzoyl]glycine (300 mg) prepared by the same method as in Example 9 (9b) and 3-fluoro-4-trifluoromethylbenzaldehyde (208 mg) to give the corresponding oxazolone (274 mg). Then, the same reaction as in Example 9 (9d) was conducted using all this oxazolone to give 281 mg of the title compound (light yellow powder).

mp: 185 to 186° C.;
$^1$H-nuclear magnetic resonance spectrum (400 MHz, DMSO-$d_6$) δ ppm:
9.90 (1H, s), 8.23 (1H, t, J=6 Hz), 7.95 (2H, d, J=9 Hz), 7.76 (1H, t, J=8 Hz), 7.59 (1H, d, J=13 Hz), 7.52 (1H, d, J=8 Hz), 7.14 (1H, s), 7.09 (2H, d, J=9 Hz), 4.65 (1H, t, J=6 Hz), 4.30 (2H, t, J=6 Hz), 3.45 (2H, q, J=6 Hz), 3.24 (2H, q, J=6 Hz), 2.89-2.77 (2H, m).

Example 111

N-{(Z)-1-{[(2-Hydroxyethyl)amino]carbonyl}-2-[4-(trifluoromethoxy)phenyl]vinyl}-4-propoxybenzamide

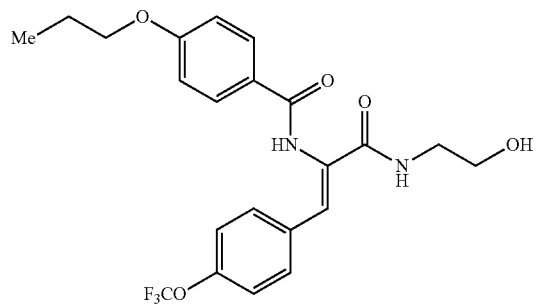 [SMILES: CCCOc1ccc(C(=O)N/C(=C\c2ccc(OC(F)(F)F)cc2)C(=O)NCCO)cc1]

The same reaction as in Example 9 (9c) was conducted using N-(4-propoxybenzoyl)glycine (which is the compound disclosed in Chem. Abstr., (1974), 80, 60167w, 403 mg) and 4-trifluoromethoxybenzaldehyde (255 μL) to give the corresponding oxazolone (461 mg). Then, the same reaction as in Example 9 (9d) was conducted using all this oxazolone to give 353 mg of the title compound (white amorphous solid).

mp: 185 to 186° C.;

$^1$H-nuclear magnetic resonance spectrum (400 MHz, DMSO-$d_6$) δ ppm:

9.79 (1H, s), 8.07 (1H, t, J=6 Hz), 7.95 (2H, d, J=9 Hz), 7.64 (2H, d, J=9 Hz), 7.34 (2H, d, J=9 Hz), 7.16 (1H, s), 7.03 (2H, d, J=9 Hz), 4.64 (1H, t, J=6 Hz), 4.02 (2H, t, J=6 Hz), 3.44 (2H, q, J=6 Hz), 3.23 (2H, q, J=6 Hz), 1.80-1.71 (2H, m), 0.99 (3H, t, J=7 Hz).

Example 112

N-{(Z)-1-{[(2-Hydroxyethyl)amino]carbonyl}-2-[4-(trifluoromethoxy)phenyl]vinyl}-4-[4-(trifluoromethyl)phenoxy]benzamide (Exemplary Compound No. 1-519)

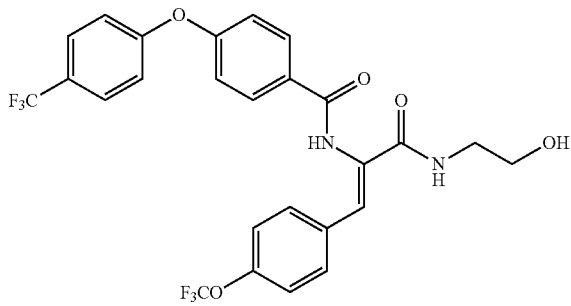 [SMILES: O=C(NCCO)/C(=C/c1ccc(OC(F)(F)F)cc1)NC(=O)c1ccc(Oc2ccc(C(F)(F)F)cc2)cc1]

The same reaction as in Example 9 (9c) was conducted using N-{-4-[4-(trifluoromethyl)phenoxy]benzoyl}glycine (382 mg) prepared by the same method as in Example 9 (9b) and 4-trifluoromethoxybenzaldehyde (169 μL) to give the corresponding oxazolone (256 mg). The same reaction as in Example 9 (9d) was conducted using all this oxazolone to give 256 mg of the title compound (white powder).

mp: 84 to 86° C.;

$^1$H-nuclear magnetic resonance spectrum (400 MHz, DMSO-$d_6$) δ ppm:

9.96 (1H, brs), 8.12 (1H, t, J=6 Hz), 8.06 (2H, d, J=9 Hz), 7.80 (2H, d, J=9 Hz), 7.66 (2H, d, J=9 Hz), 7.35 (2H, d, J=9 Hz), 7.26-7.19 (5H, m), 4.64 (1H, t, J=6 Hz), 3.45 (2H, q, J=6 Hz), 3.24 (2H, q, J=6 Hz).

Example 113

4-(4-Chlorophenoxy)-N-{(Z)-1-{[(2-hydroxyethyl)amino]carbonyl}-2-[4-(trifluoromethoxy)phenyl]vinyl}benzamide

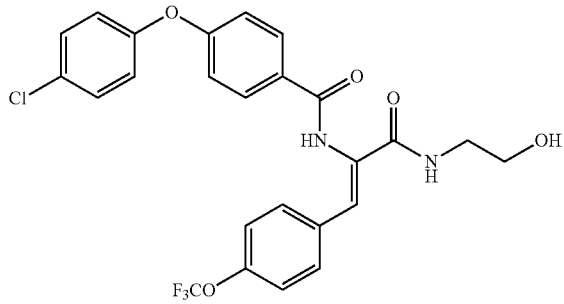 [SMILES: O=C(NCCO)/C(=C/c1ccc(OC(F)(F)F)cc1)NC(=O)c1ccc(Oc2ccc(Cl)cc2)cc1]

The same reaction as in Example 9 (9c) was conducted using N-[4-(4-chlorophenoxy)benzoyl]glycine (333 mg) prepared by the same method as in Example 9 (9b) and 4-trifluoromethoxybenzaldehyde (163 μL) to give the corresponding oxazolone (270 mg). The same reaction as in Example 9 (9d) was conducted using all this oxazolone to give 248 mg of the title compound (white powder).

mp: 77 to 82° C.;

$^1$H-nuclear magnetic resonance spectrum (400 MHz, DMSO-$d_6$) δ ppm:

9.91 (1H, brs), 8.09 (1H, t, J=6 Hz), 8.02 (2H, d, J=9 Hz), 7.65 (2H, d, J=9 Hz), 7.50 (2H, d, J=9 Hz), 7.35 (2H, d, J=9 Hz), 7.18 (1H, s), 7.13 (2H, d, J=9 Hz), 7.11 (2H, d, J=9 Hz), 4.63 (1H, t, J=6 Hz), 3.45 (2H, q, J=6 Hz), 3.23 (2H, q, J=6 Hz).

Example 114

N-{(Z)-1-{[(2,2-Difluoroethyl)amino]carbonyl}-2-[4-(trifluoromethoxy)phenyl]vinyl}-4-(3,3,3-trifluoropropoxy)benzamide

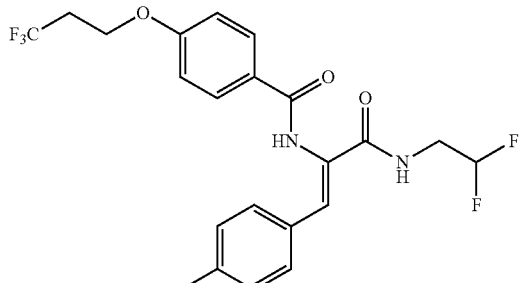

The same reaction as in Example 9 (9d) was conducted using oxazolone (223 mg) prepared in the manufacturing process of Example 108 and 2,2-difluoroethylamine (49 mg) to give 180 mg of the title compound (white powder).

mp: 142 to 143° C.;

$^1$H-nuclear magnetic resonance spectrum (500 MHz, DMSO-$d_6$) δ ppm:

9.89 (1H, s), 8.53 (1H, t, J=6 Hz), 7.98 (2H, d, J=9 Hz), 7.67 (2H, d, J=9 Hz), 7.36 (2H, d, J=9 Hz), 7.20 (1H, s), 7.09 (2H, d, J=9 Hz), 6.03 (1H, tt, J=56 Hz, 4 Hz), 4.30 (2H, t, J=6 Hz), 3.59-3.51 (2H, m), 2.87-2.78 (2H, m).

In addition to the above-mentioned Examples 1 to 114, compounds shown in Table 4 were also synthesized similarly. In Table 4, the same Exemplary Compound Numbers as those in the above-mentioned Tables 1, 2, and 3 denote the same compounds.

TABLE 4

| Exemplary Compound No. | | State | Melting point (° C.) | FABMS ([M + H]$^+$) |
|---|---|---|---|---|
| 1-6 | | colorless crystalline solid | 142-143 | |
| 1-20 | | colorless crystalline solid | 76-80 | |
| 1-21 | | colorless crystalline solid | 85-89 | |
| 1-22 | | colorless crystalline solid | 198-200 | |
| 1-23 | | colorless crystalline solid | 183-185 | |
| 1-24 | | colorless crystalline solid | 125-128 | |
| 1-25 | | colorless crystalline solid | 177-179 | |
| 1-26 | | white amorphous solid | | 465 |
| 1-27 | | white amorphous solid | | 439 |
| 1-28 | | white amorphous solid | | 477 |
| 1-29 | | light yellow crystalline solid | 107-110 | |
| 1-30 | | colorless crystalline solid | 194-197 | |
| 1-31 | | colorless crystalline solid | 154-156 | |
| 1-31 | (hydrochloride) | yellow crystalline solid | 162-165 | |
| 1-32 | | colorless crystalline solid | 138-140 | |
| 1-33 | | colorless crystalline solid | 191-193 | |
| 1-34 | | light yellow crystalline solid | 106-109 | |
| 1-35 | | light yellow crystalline solid | 93-96 | |

TABLE 4-continued

| Exemplary Compound No. | State | Melting point (° C.) | FABMS ([M + H]+) |
|---|---|---|---|
| 1-36 | light yellow crystalline solid | 110-113 | |
| 1-37 | light yellow amorphous solid | | 476 |
| 1-38 | colorless crystalline solid | 194-196 | |
| 1-39 | colorless crystalline solid | 208(dec.) | |
| 1-40 | colorless crystalline solid | 74-77 | |
| 1-41 | light yellow amorphous solid | 70-80 | |
| 1-42 | light yellow amorphous solid | | 453 |
| 1-43 | colorless crystalline solid | 143-145 | |
| 1-44 | colorless crystalline solid | 135-137 | |
| 1-45 | light yellow amorphous solid | | 495 |
| 1-46 | colorless crystalline solid | 103-107 | |
| 1-47 | colorless crystalline solid | 133-134 | |
| 1-48 | white amorphous solid | | 455 |
| 1-49 | colorless crystalline solid | 121-123 | |
| 1-50 | colorless crystalline solid | 129-130 | |
| 1-51 | light yellow amorphous solid | | 467 |
| 1-52 | light yellow amorphous solid | | 477 |
| 1-53 | white amorphous solid | | 495 |
| 1-54 | colorless crystalline solid | 166-168 | |
| 1-55 | yellow amorphous solid | 66-78 | 489 |
| 1-71 | colorless crystalline solid | 164-166 | |
| 1-73 | light yellow amorphous solid | | 471 |
| 1-110 | colorless crystalline solid | 156-158 | |
| 1-126 | colorless crystalline solid | 123-125 | |
| 1-147 | white amorphous solid | | 517 |
| 1-164 | white amorphous solid | | 530 |
| 1-168 | colorless crystalline solid | 190-192 | |
| 1-175 | white amorphous solid | | 520 |
| 1-249 | colorless crystalline solid | 73-76 | |
| 1-250 | colorless crystalline solid | 168-170 | |
| 1-254 | colorless crystalline solid | 169-171 | |
| 1-257 | colorless crystalline solid | 195-197 | |
| 1-259 | colorless crystalline solid | 180-183 | |
| 1-262 | white amorphous solid | | 465 |
| 1-263 | colorless amorphous solid | | 475 |
| 1-272 | colorless crystalline solid | 142-144 | |
| 1-273 | white amorphous solid | | 443 |
| 1-275 | colorless crystalline solid | 138-140 | |
| 1-281 | colorless crystalline solid | 170-172 | |
| 1-284 | colorless crystalline solid | 59-62 | |
| 1-290 | colorless crystalline solid | 144-146 | |
| 1-293 | white amorphous solid | | 476 |
| 1-315 | white amorphous solid | | 503 |
| 1-319 | white amorphous solid | | 513 |
| 1-320 | colorless crystalline solid | 103-105 | |
| 1-321 | colorless crystalline solid | 138-140 | |
| 1-322 | colorless crystalline solid | 158-159 | |
| 1-341 | white amorphous solid | | 501 |
| 1-372 | white amorphous solid | | 529 |
| 1-374 | colorless crystalline solid | 141-144 | |
| 1-377 | light yellow crystalline solid | 112-114 | |
| 1-380 | colorless crystalline solid | 120-122 | |
| 1-383 | white amorphous solid | | 412 |
| 1-386 | colorless crystalline solid | 82-85 | |
| 1-389 | light yellow crystalline solid | 97-100 | |
| 1-392 | colorless crystalline solid | 141-143 | |
| 1-395 | colorless crystalline solid | 205-207 | |
| 1-398 | colorless crystalline solid | 79-81 | |
| 1-401 | white amorphous solid | | 425 |
| 1-404 | white amorphous solid | | 435 |
| 1-407 | white amorphous solid | | 451 |
| 1-410 | light yellow crystalline solid | 81-84 | |
| 1-413 | light yellow crystalline solid | 92-95 | |
| 1-416 | white amorphous solid | | 441 |
| 1-419 | light yellow crystalline solid | 75-78 | |
| 1-422 | white amorphous solid | | 481 |
| 1-425 | colorless crystalline solid | 176-178 | |
| 1-428 | colorless crystalline solid | 94-97 | |
| 1-431 | white amorphous solid | | 467 |
| 1-432 | white amorphous solid | | 465 |
| 1-434 | colorless crystalline solid | 156-158 | |
| 1-435 | colorless crystalline solid | 89-92 | |
| 1-438 | white amorphous solid | | 439 |
| 1-441 | colorless crystalline solid | 90-92 | |
| 1-444 | colorless crystalline solid | 165-167 | |
| 1-447 | colorless crystalline solid | 79-81 | |

TABLE 4-continued

| Exemplary Compound No. | | State | Melting point (° C.) | FABMS ([M + H]+) |
|---|---|---|---|---|
| 1-450 | | colorless crystalline solid | 94-96 | |
| 1-451 | | white amorphous solid | | 465 |
| 1-453 | | colorless crystalline solid | 191-193 | |
| 1-454 | | colorless crystalline solid | 178-180 | |
| 1-457 | | white amorphous solid | | 495 |
| 1-460 | | white amorphous solid | | 533 |
| 1-463 | | white amorphous solid | | 495 |
| 1-466 | | light yellow amorphous solid | | 481 |
| 1-467 | | white amorphous solid | | 479 |
| 1-468 | | colorless crystalline solid | 144-145 | |
| 1-469 | | colorless crystalline solid | 165-167 | |
| 1-470 | | colorless crystalline solid | 155-156 | |
| 1-471 | | colorless crystalline solid | 179-181 | |
| 1-472 | | colorless crystalline solid | 151-153 | |
| 1-473 | | colorless crystalline solid | 60-62 | |
| 1-476 | | colorless crystalline solid | 137-139 | |
| 1-477 | | colorless crystalline solid | 70-73 | |
| 1-480 | | colorless crystalline solid | 72-74 | |
| 1-483 | | colorless crystalline solid | 89-92 | |
| 1-486 | | white amorphous solid | | 453 |
| 1-489 | | white amorphous solid | | 467 |
| 1-492 | | white amorphous solid | | 431 |
| 1-495 | | colorless crystalline solid | 84-86 | |
| 1-498 | | white amorphous solid | | 445 |
| 1-501 | | colorless crystalline solid | 86-88 | |
| 1-504 | | colorless crystalline solid | 70-73 | |
| 1-507 | | colorless crystalline solid | 71-74 | |
| 1-510 | | white amorphous solid | | 399 |
| 1-513 | | white amorphous solid | | 461 |
| 1-515 | | white amorphous solid | | 469 |
| 1-517 | | light yellow amorphous solid | | 529 |
| 1-520 | | colorless crystalline solid | 193-195 | |
| 1-523 | | yellow amorphous solid | | 501 |
| 1-526 | | light yellow amorphous solid | | 499 |
| 1-529 | | white amorphous solid | | 531 |
| 1-532 | | colorless crystalline solid | 87-88 | |
| 1-535 | | light yellow crystalline solid | 90-92 | |
| 1-538 | | white amorphous solid | | 532 |
| 1-541 | | colorless crystalline solid | 81-83 | |
| 1-544 | | light yellow amorphous solid | | 549 (ESI+) |
| 1-545 | | white amorphous solid | | 547 |
| 1-546 | | white amorphous solid | | 575 |
| 1-547 | | light yellow amorphous solid | | 557 (ESI+) |
| 1-550 | | colorless crystalline solid | 65-68 | |
| 1-553 | | white amorphous solid | | 547 |
| 1-556 | | colorless crystalline solid | 81-83 | |
| 1-559 | | white amorphous solid | | 571 |
| 1-562 | | white amorphous solid | | 563 |
| 1-565 | | white amorphous solid | | 504 |
| 1-565 | (hydrochloride) | colorless crystalline solid | 96-98 | |
| 1-568 | (hydrochloride) | colorless crystalline solid | 77-80 | |
| 1-571 | | light yellow crystalline solid | 64-68 | |
| 1-574 | | light yellow crystalline solid | 61-65 | |
| 1-577 | | light brown amorphous solid | | 510 |
| 1-580 | | colorless crystalline solid | 61-64 | |
| 1-583 | | light yellow amorphous solid | | 546 |
| 1-586 | | colorless crystalline solid | 146-148 | |
| 1-589 | | white amorphous solid | | 483 |
| 1-592 | | white amorphous solid | 165-167 | 465 |
| 1-593 | | white amorphous solid | | 471 |
| 1-596 | | white amorphous solid | | 497 |
| 1-599 | | colorless crystalline solid | 177-179 | |
| 1-600 | | colorless crystalline solid | 147 | |
| 1-603 | | white amorphous solid | | 519 |
| 1-606 | | light yellow amorphous solid | | 533 |
| 1-609 | | white amorphous solid | | 467 |
| 1-612 | | light yellow crystalline solid | 107-109 | |
| 1-618 | | colorless crystalline solid | 137-138 | |
| 1-623 | | yellow amorphous solid | | 571 |
| 1-624 | | white amorphous solid | | 531 |
| 1-625 | | white amorphous solid | | 537 |
| 1-626 | | yellow amorphous solid | | 559 |
| 1-627 | | white amorphous solid | | 525 |
| 1-629 | | brown crystalline solid | 89-93 | |
| 1-630 | | pink amorphous solid | | 584 |
| 1-631 | | colorless crystalline solid | 159-160 | |

TABLE 4-continued

| Exemplary Compound No. | | State | Melting point (° C.) | FABMS ([M + H]+) |
|---|---|---|---|---|
| 1-632 | | white amorphous solid | | 535 |
| 2-1 | | colorless crystalline solid | 129-131 | |
| 2-2 | | white amorphous solid | | 483 |
| 2-3 | | colorless crystalline solid | 89-91 | 413 |
| 2-4 | | colorless amorphous solid | | 441 |
| 2-5 | | colorless crystalline solid | 64-66 | |
| 2-6 | | colorless crystalline solid | 150-152 | |
| 2-7 | | light yellow crystalline solid | 147-149 | |
| 2-8 | | light yellow amorphous solid | | 467 |
| 2-9 | | colorless crystalline solid | 86-89 | |
| 2-10 | | colorless crystalline solid | 68-70 | |
| 2-11 | | colorless crystalline solid | 113-115 | |
| 2-12 | | white amorphous solid | 64-70 | 595 |
| 2-13 | | colorless crystalline solid | 155-158 | |
| 2-14 | | light yellow crystalline solid | 133-135 | |
| 2-15 | | colorless crystalline solid | 107-110 | |
| 2-16 | | colorless crystalline solid | 184-187 | |
| 2-17 | | colorless crystalline solid | 123-126 | |
| 2-18 | | light yellow crystalline solid | 82-84 | |
| 2-19 | | light yellow crystalline solid | 74-76 | |
| 2-20 | | colorless crystalline solid | 80-83 | |
| 2-21 | | white amorphous solid | 51-54 | 459 |
| 3-1 | | colorless crystalline solid | 156-158 | |
| 3-1 | (R isomer) | colorless crystalline solid | 75-78 | |
| 3-1 | (S isomer) | colorless crystalline solid | 75-77 | |
| 3-2 | | colorless crystalline solid | 76-78 | |
| 3-3 | | colorless crystalline solid | 144-146 | |
| 3-4 | | colorless crystalline solid | 182-184 | |
| 3-5 | | colorless crystalline solid | 88-90 | |
| 3-6 | (R isomer) | colorless crystalline solid | 82-85 | |
| 3-6 | (S isomer) | colorless crystalline solid | 82-84 | |
| 3-7 | | colorless crystalline solid | 85-87 | |
| 3-8 | | light yellow amorphous solid | 70-75 | 455 |
| 3-9 | | colorless crystalline solid | 135-137 | |
| 3-10 | | colorless crystalline solid | 156-159 | |
| 3-11 | | light yellow crystalline solid | 151-153 | |
| 3-12 | | colorless crystalline solid | 123-125 | |
| 3-13 | | white amorphous solid | | 481 |
| 3-14 | | colorless crystalline solid | 156-158 | |
| 3-15 | | yellow crystalline solid | 147-149 | |
| 3-16 | | colorless crystalline solid | 103-105 | |
| 3-17 | | light yellow crystalline solid | 101-103 | |
| 3-18 | | colorless crystalline solid | 112-115 | |
| 3-19 | | colorless crystalline solid | 186-190 | |
| 3-20 | | white amorphous solid | | 477 |
| 3-21 | | colorless crystalline solid | | 488 |
| 3-22 | | brown crystalline solid | 229-232 | |
| 3-23 | | colorless crystalline solid | 96-99 | |
| 3-24 | | colorless crystalline solid | 74-76 | |
| 3-25 | | colorless crystalline solid | 60-62 | |
| 3-26 | | colorless crystalline solid | 179-180 | |
| 3-27 | | colorless crystalline solid | 93-95 | |
| 3-28 | | light yellow crystalline solid | 195-197 | |
| 3-29 | | colorless crystalline solid | 176-177 | |
| 3-30 | | colorless crystalline solid | 83-85 | |
| 3-31 | | colorless crystalline solid | 240-241 | |
| 3-32 | | yellow crystalline solid | 208-211 | |
| 3-33 | | colorless crystalline solid | 98-101 | |
| 3-34 | | light yellow crystalline solid | 107-109 | |
| 3-35 | | white amorphous solid | 87-91 | 540 |
| 3-36 | | colorless crystalline solid | 134-136 | |
| 3-37 | | light yellow crystalline solid | 153-155 | |
| 3-38 | | colorless crystalline solid | 101-103 | |
| 3-39 | | light yellow amorphous solid | 86-101 | 467 |
| 3-40 | | white amorphous solid | 108-110 | 566 |
| 3-41 | | colorless crystalline solid | 224-226 | |
| 3-42 | | colorless amorphous solid | | 426 |
| 3-43 | | white amorphous solid | | 442 |
| 3-44 | | white amorphous solid | | 441 |
| 3-45 | | white amorphous solid | | 457 |

In Table 4, "dec." means decomposition temperature.

Test Example 1

Evaluation of Blood Calcium Concentration-Decreasing Activity

The blood calcium concentration in a living body is strictly controlled and constantly maintained by intestinal absorption and urinary excretion and release (bone resorption) and adhesion (bone formation) in bone tissues. In an immature rat, which is very active in bone resorption and bone formation, the blood calcium concentration is significantly decreased by strongly suppressing bone resorption. The bone resorption-suppressing activity of compounds according to the present invention was evaluated by administering the compounds to immature rats and observing decreases in blood calcium concentration as an index of the activity.

The test was conducted using 4-week old male Wistar rats fasted for 12 to 24 hours. Each compound to be tested was suspended in 0.5% methyl cellulose (MC). The suspension was orally administered to the rats at a dose of 5 mL/kg. Similarly, rats of a normal control group were administered with 0.5% MC alone. Then, blood was drawn from rat jugular vein under ether anesthesia 6 hours after the administration of each test compound or 0.5% MC. The blood was immediately centrifuged (10000 rpm, 5 minutes) at room temperature to separate serum. The calcium concentration of each serum was measured by an autoanalyzer (JEOL, JCA-BM2250). Five rats were used for each test group.

The test results are shown in Table 5 below. The evaluation was conducted by a comparative test with the normal control group and based on the serum calcium concentration-decreasing rate (%) calculated according to the following formula:

Serum calcium concentration-decreasing rate (%)=
(([serum calcium concentration in normal control group]−[serum calcium concentration in test compound administration group])/[serum calcium concentration in normal control group])×100.

TABLE 5

| Test compound | Administration dose (mg/kg) | Serum calcium concentration-decreasing rate (%) |
|---|---|---|
| Example 5 | 10 | 27.6 |
| Example 9 | 20 | 29.3 |
| Example 11 | 20 | 30.6 |
| Example 14 | 10 | 33.2 |
| Example 16 | 10 | 27.2 |

In general, a constant blood calcium concentration should be strictly maintained, but the blood calcium concentrations were decreased by administering the compounds according to the present invention. This result suggests that the blood calcium concentration-decreasing activity of the compounds according to the present invention is high.

Test Example 2

Evaluation of Bone Density Decrease-Suppressing Activity and Anti-Arthritic Activity In rheumatoid arthritis, not only swelling and pain caused by arthritis but also systemic bone mass decrease and articular destruction caused by a significant increase in bone resorption are observed. The effects of the compounds according to the present invention in suppressing the bone mass decrease and the paw volume increase caused by arthritis were evaluated using adjuvant arthritis model rats, which exhibit arthritis similar to human rheumatoid arthritis.

The test was conducted using 8-week old female Lewis rats. Mycobacterium butyricum cells which were killed by heat were ground in an agate mortar, suspended in liquid paraffin sterilized by dry heat to a concentration of 2 mg/mL, and treated with ultrasound to prepare an adjuvant. Under ether anesthesia, rats in a control group other than a normal control group and rats in a test compound administration group were intradermally injected with 0.05 mL of this adjuvant each time (0.1 mL/rat in total) at two portions of the base of the tail. Starting from 14 days after the injection of the adjuvant, each rat was orally administered with 5 mL/kg of a test compound suspended in 0.5% MC once a day for 7 days. Similarly, the rats of the control group were administered with 0.5% MC alone. On the 21st day after the adjuvant injection, hind paw volumes were measured by using a paw edema volume determining device (MUROMACHI KIKAI, TK-101CMP). Then, the thighbone was biopsied. The thighbone was, after removing soft tissues, sufficiently fixed, dehydrated, and dried using ethanol. The bone density of the thighbone was measured with a bone density analyzer (Aloka, DOS-600 EX-IIIR). Five rats were used for each test group.

The test results are shown in Table 6 below.

The evaluation was conducted by comparison tests with the normal control group and the control group and based on the bone density decrease-suppressing rate (%) and the paw edema-suppressing rate (%) calculated according to the following formulae:

Bone density decrease-suppressing rate (%)=(1−([thighbone bone density in normal control group]−[thighbone bone density in test compound administration group])/([thighbone bone density in normal control group]−[thighbone bone density in control group]))×100

Paw edema-suppressing rate (%)=(1−([paw volume of test compound administration group]−[paw volume in normal control group])/([paw volume in control group]−[paw volume in normal control group]))×100

TABLE 6

| Test compound | Administration dose (mg/kg) | Bone density decrease-suppressing rate (%) | Paw edema-suppressing rate (%) |
|---|---|---|---|
| Example 3 | 10 | 57 | 22 |
| Example 5 | 10 | 54 | 25 |
| Example 9 | 10 | 37 | 11 |
| Example 11 | 10 | 40 | 29 |
| Example 14 | 10 | 86 | 12 |
| Example 16 | 10 | 70 | 35 |

The bone density decrease and the paw volume increase were significantly suppressed by administering the compounds according to the present invention. Thus, advantageous effects of the compounds according to the present invention as prophylactic or therapeutic drugs for bone metabolic diseases and inflammation were confirmed.

INDUSTRIAL APPLICABILITY

The drugs according to the present invention have blood calcium concentration-decreasing effect and bone mass decrease-suppressing effect due to their excellent bone resorption-suppressing effects and are low in toxicity. Therefore, the drugs are useful as prophylactic or therapeutic drugs for bone metabolic diseases, for example, osteoporosis, hypercalcemia, bone metastasis of cancer, periodontal disease, bone Paget's disease, and osteoarthrosis, in mammals (such as human, ape, dog, cat, horse, and hog, in particular, human).

The invention claimed is:
1. A compound having Formula (I') or a pharmacologically acceptable salt thereof:

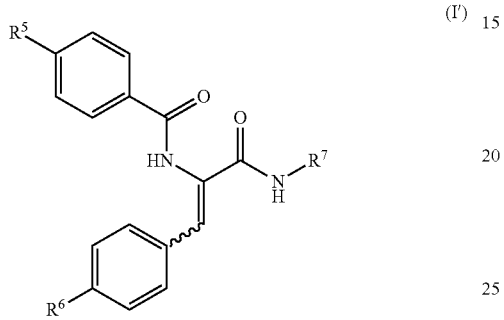

wherein,
R⁵ represents an isobutyloxy group, a cyclopropylmethoxy group, a 2-cyclopropylethoxy group, a 1-methylcyclopropylmethoxy group, a 3,3,3-trifluoropropyloxy group, a 4,4,4-trifluorobutyloxy group, a 2-phenylethoxy group, a 2-(4-methoxyphenyl)ethoxy group, a 2-(3-methoxyphenyl)ethoxy group, a 2-(4-chlorophenyl)ethoxy group, a 2-(4-(N,N-dimethylamino)phenyl)ethoxy group, a 4-chlorophenoxy group, or a 4-trifluoromethylphenoxy group;
R⁶ represents a substituent independently selected from an ethoxy group, a trifluoromethyl group, a cyclopropyl group, a cyclopropyloxy group, a difluoromethoxy group, a trifluoromethoxy group, and a 2,2-difluoroethoxy group; and
R⁷ is selected from a $C_2$-$C_3$ haloalkyl group, a $C_2$-$C_3$ hydroxyalkyl group which may be protected by a hydroxyl protecting group, and a $C_1$-$C_3$ alkyl group substituted with 1-hydroxycyclopropyl group.

2. The compound or a pharmacologically acceptable salt thereof according to claim 1, wherein R⁷ is a 2-fluoroethyl group, a 2,2-difluoroethyl group, a 2-hydroxyethyl group, a 2-hydroxypropyl group, a 1-hydroxycyclopropylmethyl group, a 2-acetoxyethyl group, a 2-(morpholin-4-ylacetoxy)ethyl group, or a 2-(3-carboxypropionyloxy)ethyl group.

3. The compound or pharmacologically acceptable salt thereof according to claim 1, wherein the chemical structure regarding the position of the acrylamide moiety of Formula (I') is Z.

4. A pharmaceutical composition comprising a compound or a pharmacologically acceptable salt thereof according to claim 1 as an active ingredient.

5. A compound or a pharmacologically acceptable salt thereof, the compound being selected from the followings:
4-(2-cyclopropylethoxy)-N-(2-(4-ethoxyphenyl)-1-{[(2-hydroxyethyl)amino]carbonyl}vinyl)benzamide,
4-(2-cyclopropylethoxy)-N-(2-[4-(cyclopropyloxy)phenyl]-1-{[(2-hydroxyethyl)amino]carbonyl}vinyl)benzamide,
4-(2-cyclopropylethoxy)-N-(2-[4-(difluoromethoxy)phenyl]-1-{[(2-hydroxyethyl)amino]carbonyl}vinyl)benzamide,
4-(2-cyclopropylethoxy)-N-{1-{[(2-hydroxyethyl)amino]carbonyl}-2-[4-(trifluoromethoxy)phenyl]vinyl}benzamide,
4-(2-cyclopropylethoxy)-N-(2-[4-(2,2-difluoroethoxy)phenyl]-1-{[(2-hydroxyethyl)amino]carbonyl}vinyl)benzamide,
4-(2-cyclopropylethoxy)-N-(2-(4-cyclopropylphenyl)-1-{[(2-hydroxyethyl)amino]carbonyl}vinyl)benzamide,
2-{[(2Z)-2-{[4-(2-cyclopropylethoxy)benzoyl]amino}-3-(4-cyclopropylphenyl)propen-2-oyl]amino}ethyl acetate,
2-{[(2Z)-2-{[4-(2-cyclopropylethoxy)benzoyl]amino}-3-(4-cyclopropylphenyl)propen-2-oyl]amino}ethyl succinate,
4-(2-cyclopropylethoxy)-N-{1-{[(2-hydroxyethyl)amino]carbonyl}-2-[4-(trifluoromethyl)phenyl]vinyl}benzamide,
4-(2-cyclopropylethoxy)-N-{1-{[(2-hydroxyethyl)amino]carbonyl}-2-[4-(1H-pyrrol-1-yl)phenyl]vinyl}benzamide,
N-(2-(4-chlorophenyl)-1-{[(2-hydroxyethyl)amino]carbonyl}vinyl)-4-(2-cyclopropylethoxy)benzamide,
N-[1-{[(2-hydroxyethyl)amino]carbonyl}-2-(4-isopropoxyphenyl)vinyl]-4-[2-(4-methoxyphenyl)ethoxy]benzamide,
N-(2-[4-(cyclopropyloxy)phenyl]-1-{[(2-hydroxyethyl)amino]carbonyl}vinyl)-4-[2-(4-methoxyphenyl)ethoxy]benzamide,
N-{1-{[(2-hydroxyethyl)amino]carbonyl}-2-[4-(trifluoromethoxy)phenyl]vinyl}-4-[2-(4-methoxyphenyl)ethoxy]benzamide,
N-(2-(4-cyclopropylphenyl)-1-{[(2-hydroxyethyl)amino]carbonyl}vinyl)-4-[2-(4-methoxyphenyl)ethoxy]benzamide,
N-{1-{[(2-hydroxyethyl)amino]carbonyl}-2-[4-(methylthio)phenyl]vinyl}-4-[2-(4-methoxyphenyl)ethoxy]benzamide,
N-(2-(4-chlorophenyl)-1-{[(2-hydroxyethyl)amino]carbonyl}vinyl)-4-[2-(4-methoxyphenyl)ethoxy]benzamide,
4-{2-[4-(dimethylamino)phenyl]ethoxy}-N-[1-{[(2-hydroxyethyl)amino]carbonyl}-2-(4-isopropoxyphenyl)vinyl]benzamide,
4-{2-[4-(dimethylamino)phenyl]ethoxy}-N-{1-{[(2-hydroxyethyl)amino]carbonyl}-2-[4-(trifluoromethoxy)phenyl]vinyl}benzamide,
N-(2-(4-cyclopropylphenyl)-1-{[(2-hydroxyethyl)amino]carbonyl}vinyl)-4-{2-[4-(dimethylamino)phenyl]ethoxy}benzamide,
4-[2-(4-chlorophenyl)ethoxy]-N-(2-(4-ethoxyphenyl)-1-{[(2-hydroxyethyl)amino]carbonyl}vinyl)benzamide,
4-[2-(4-chlorophenyl)ethoxy]-N-(2-[4-(cyclopropyloxy)phenyl]-1-{[(2-hydroxyethyl)amino]carbonyl}vinyl)benzamide,
4-[2-(4-chlorophenyl)ethoxy]-N-(2-[4-(difluoromethoxy)phenyl]-1-{[(2-hydroxyethyl)amino]carbonyl}vinyl)benzamide,
4-[2-(4-chlorophenyl)ethoxy]-N-{1-{[(2-hydroxyethyl)amino]carbonyl}-2-[4-(trifluoromethoxy)phenyl]vinyl}benzamide,
4-[2-(4-chlorophenyl)ethoxy]-N-(2-(4-cyclopropylphenyl)-1-{[(2-hydroxyethyl)amino]carbonyl}vinyl)benzamide, 4-[2-(4-chlorophenyl)ethoxy]-N-(2-(4-chlorophenyl)-1-{[(2-hydroxyethyl)amino]carbonyl}vinyl)benzamide, 4-(cyclopropylmethoxy)-N-{1-{[(2-hydroxyethyl)amino]carbonyl}-2-[4-(trifluoromethoxy)phenyl]vinyl}benzamide, 4-(cyclopropylmethoxy)-N-{1-{[(2-hydroxyethyl)amino]carbonyl}-2-[4-(trifluoromethyl)phenyl]vinyl}benzamide, N-{1-{[(2-hydroxyethyl)amino]carbonyl}-2-[4-(trifluoromethoxy)phenyl]vinyl}-4-(4,4,4-trifluorobutoxy)benzamide, N-{1-{[(2-hydroxyethyl)amino]carbonyl}-2-[4-(trifluoromethyl)phenyl]vinyl}-4-(4,4,4-trifluorobutoxy)benzamide, N-{1-{[(2-hydroxyethyl)amino]carbonyl}-2-[4-(trifluoromethoxy)phenyl]vinyl}-4-(3,3,3-trifluoropropoxy)benzamide, N-{1-{[(2-hydroxyethyl)amino]carbonyl}-2-[4-(trifluoromethyl)phenyl]vinyl}-4-(3,3,3-trifluoropropoxy)benzamide, N-{1-{[(2,2-difluoroethyl)amino]carbonyl}-2-[4-(trifluoromethoxy)phenyl]vinyl}-4-(3,3,3-trifluoropropoxy)benzamide, N-{1-({[(2S)-2-hydroxypropyl]amino}carbonyl)-2-[4-(trifluoromethoxy)phenyl]vinyl}-4-(3,3,3-trifluoropropoxy)benzamide, N-(2-[4-(difluoromethoxy)phenyl]-1-{[(2-hydroxyethyl)amino]carbonyl}vinyl)-4-[4-(trifluoromethyl)phenoxy]benzamide, N-{1-{[(2-hydroxyethyl)amino]carbonyl}-2-[4-(trifluoromethoxy)phenyl]vinyl}-4-[4-(trifluoromethyl)phenoxy]benzamide, N-{1-{[(2-hydroxyethyl)amino]carbonyl}-2-[4-(trifluoromethyl)phenyl]vinyl}-4-[4-(trifluoromethyl)phenoxy]benzamide, 4-(4-chlorophenoxy)-N-{1-{[(2-hydroxyethyl)amino]carbonyl}-2-[4-(trifluoromethoxy)phenyl]vinyl}benzamide, and 4-(4-chlorophenoxy)-N-{1-{[(2-hydroxyethyl)amino]carbonyl}-2-[4-(trifluoromethyl)phenyl]vinyl}benzamide.

6. The compound or a pharmacologically acceptable salt thereof according to claim 5, wherein the chemical structure regarding the position of the acrylamide moiety is Z.

7. A pharmaceutical composition comprising a compound or a pharmacologically acceptable salt thereof according to claim 5 as an active ingredient.

8. The composition according to claim 7, the composition being a bone resorption-suppressing agent.

9. A method of decreasing blood calcium concentration, comprising administering the composition according to claim 7 to a mammal.

10. A method of suppressing a decrease in bone mass, comprising administering the composition according to claim 7 to a mammal.

11. A method of suppressing bone metastasis of cancer, comprising administering the composition according to claim 7 to a mammal.

12. The bone resorption-suppressing agent according to claim 8, the agent significantly decreasing the serum calcium concentration of a mammal administered with the agent.

13. The bone resorption-suppressing agent according to claim 12, wherein the dose of the agent as an active ingredient is from 0.001 mg/kg to 100 mg/kg.

* * * * *